(12) United States Patent
Kutchan et al.

(10) Patent No.: US 9,534,227 B2
(45) Date of Patent: Jan. 3, 2017

(54) METHODS FOR HIGH YIELD PRODUCTION OF TERPENES

(71) Applicant: Donald Danforth Plant Science Center, St. Louis, MO (US)

(72) Inventors: Toni Kutchan, St. Louis, MO (US); Yasuhiro Higashi, Yokohama Kanagawa (JP); Xiaohong Feng, Ladue, MO (US)

(73) Assignee: Donald Danforth Plant Science Center, St. Louis, MO (US)

( * ) Notice: Subject to any disclaimer, the term of this patent is extended or adjusted under 35 U.S.C. 154(b) by 383 days.

(21) Appl. No.: 13/893,105

(22) Filed: May 13, 2013

(65) Prior Publication Data

US 2014/0081058 A1 Mar. 20, 2014

Related U.S. Application Data

(60) Provisional application No. 61/645,877, filed on May 11, 2012.

(51) Int. Cl.
| | |
|---|---|
| *A01H 5/10* | (2006.01) |
| *C12N 9/88* | (2006.01) |
| *C07C 11/02* | (2006.01) |
| *C07C 11/21* | (2006.01) |
| *C12N 15/82* | (2006.01) |
| *C12N 9/10* | (2006.01) |
| *C07C 13/47* | (2006.01) |

(Continued)

(52) U.S. Cl.
CPC ............. *C12N 15/8257* (2013.01); *A01H 5/10* (2013.01); *C07C 11/02* (2013.01); *C07C 11/21* (2013.01); *C07C 13/20* (2013.01); *C07C 13/47* (2013.01); *C07C 15/02* (2013.01); *C12N 9/1085* (2013.01); *C12N 9/88* (2013.01); *C12N 15/8243* (2013.01); *C07C 2101/16* (2013.01); *C07K 2319/08* (2013.01)

(58) Field of Classification Search
CPC ...... C12N 15/82; C12N 15/8243; C07C 13/47
See application file for complete search history.

(56) References Cited

U.S. PATENT DOCUMENTS 6,291,745 B1 * 9/2001 Meyer ................... A01N 27/00
435/418
2008/0201796 A1 8/2008 Chappell et al.
(Continued)

OTHER PUBLICATIONS

Buttery, Ron G., Louisa C. Ling, and Bock G. Chan. "Volatiles of corn kernels and husks: Possible corn ear worm attractants." Journal of Agricultural and Food Chemistry 26.4 (1978): 866-869.*
(Continued)

*Primary Examiner* — Amjad Abraham
*Assistant Examiner* — Fan Weihua
(74) *Attorney, Agent, or Firm* — Erica A. Fishel

(57) ABSTRACT

Provided are enhanced high yield production systems for producing terpenes in plants via the expression of fusion proteins comprising various combinations of geranyl diphosphate synthase large and small subunits and limonene synthases. Also provided are engineered oilseed plants that accumulate monoterpene and sesquiterpene hydrocarbons in their seeds, as well as methods for producing such plants, providing a system for rapidly engineering oilseed crop production platforms for terpene-based biofuels.

10 Claims, 40 Drawing Sheets

(51) Int. Cl.
*C07C 13/20* (2006.01)
*C07C 15/02* (2006.01)

(56) References Cited

U.S. PATENT DOCUMENTS

| | | |
|---|---|---|
| 2008/0281135 A1 | 11/2008 | Tissier et al. |
| 2009/0123984 A1 | 5/2009 | Chappell et al. |
| 2010/0138954 A1 | 6/2010 | Sallaud et al. |

OTHER PUBLICATIONS

Blank, I., and W. Grosch. "Evaluation of potent odorants in dill seed and dill herb (*Anethum graveolens* L.) by aroma extract dilution analysis." Journal of food science 56.1 (1991): 63-67.*

Rodriguez-Concepción, Manuel, and Albert Boronat. "Elucidation of the methylerythritol phosphate pathway for isoprenoid biosynthesis in bacteria and plastids. A metabolic milestone achieved through genomics." Plant physiology 130.3 (2002): 1079-1089.*

Le, Brandon H., et al. "Global analysis of gene activity during Arabidopsis seed development and identification of seed-specific transcription factors." Proceedings of the National Academy of Sciences 107.18 (2010): 8063-8070.* van Wijk, K. J., and S. Baginsky, 2011. "Plastid proteomics in higher plants: current state and future goals." Plant physiology 155.(4): 1578-1588.*

Emanuelsson O, Nielsen H, von Heijne G., 1999, ChloroP, a neural network-based method for predicting chloroplast transit peptides and their cleavage sites Protein Sci. 8(5):978-84.*

Zavala-Páramo, Guadalupe, et al. "Isolation of an elicitor-stimulated 5-epi-aristolochene synthase gene (gPEAS1) from chili pepper (*Capsicum annuum*)." Physiologia Plantarum 110.3 (2000): 410-418.*

Okada, Kazunori, et al. "Five geranylgeranyl diphosphate synthases expressed in different organs are localized into three subcellular compartments in Arabidopsis." Plant physiology 122.4 (2000): 1045-1056.*

Charles, Denys J., and James E. Simon. "Comparison of extraction methods for the rapid determination of essential oil content and composition of basil." Journal of the American Society for Horticultural Science 115.3 (1990): 458-462.*

Wu, Shuiqin, et al. "Redirection of cytosolic or plastidic isoprenoid precursors elevates terpene production in plants." Nature biotechnology 24.11 (2006): 1441-1447.*

Morris, Wayne L., et al. "Overexpression of a bacterial 1-deoxy-D-xylulose 5-phosphate synthase gene in potato tubers perturbs the isoprenoid metabolic network: implications for the control of the tuber life cycle." Journal of Experimental Botany 57.12 (2006): 3007-3018.*

Augustin, Jörg M., et al. "Production of mono-and sesquiterpenes in Camelina sativa oilseed." Planta 242.3 (2015): 693-708.*

International Search Report for PCT/US2013/040791.

* cited by examiner

Figure 1
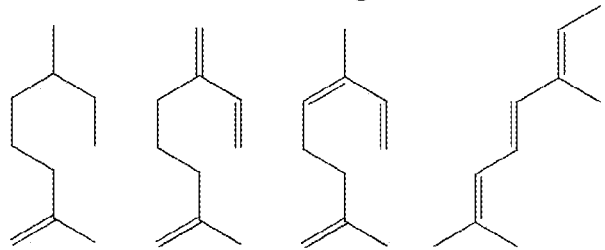
2,6-dimethyloctane    alpha myrcene    cis - alpha ocimene    4-trans -6-trans-alloocimene
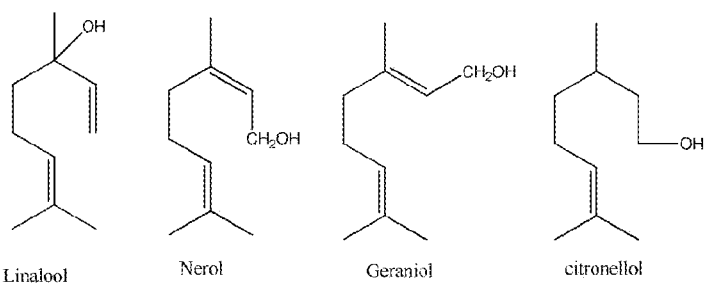
Linalool    Nerol    Geraniol    citronellol
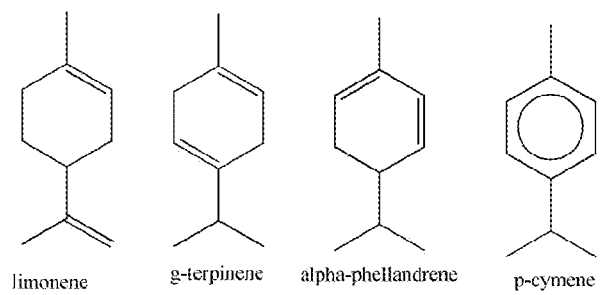
limonene    g-terpinene    alpha-phellandrene    p-cymene
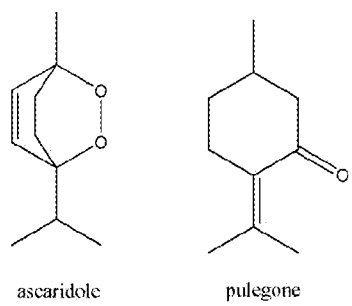
ascaridole    pulegone
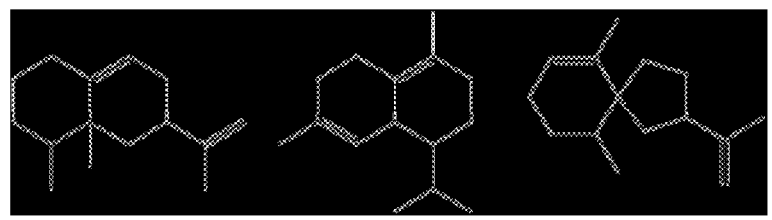

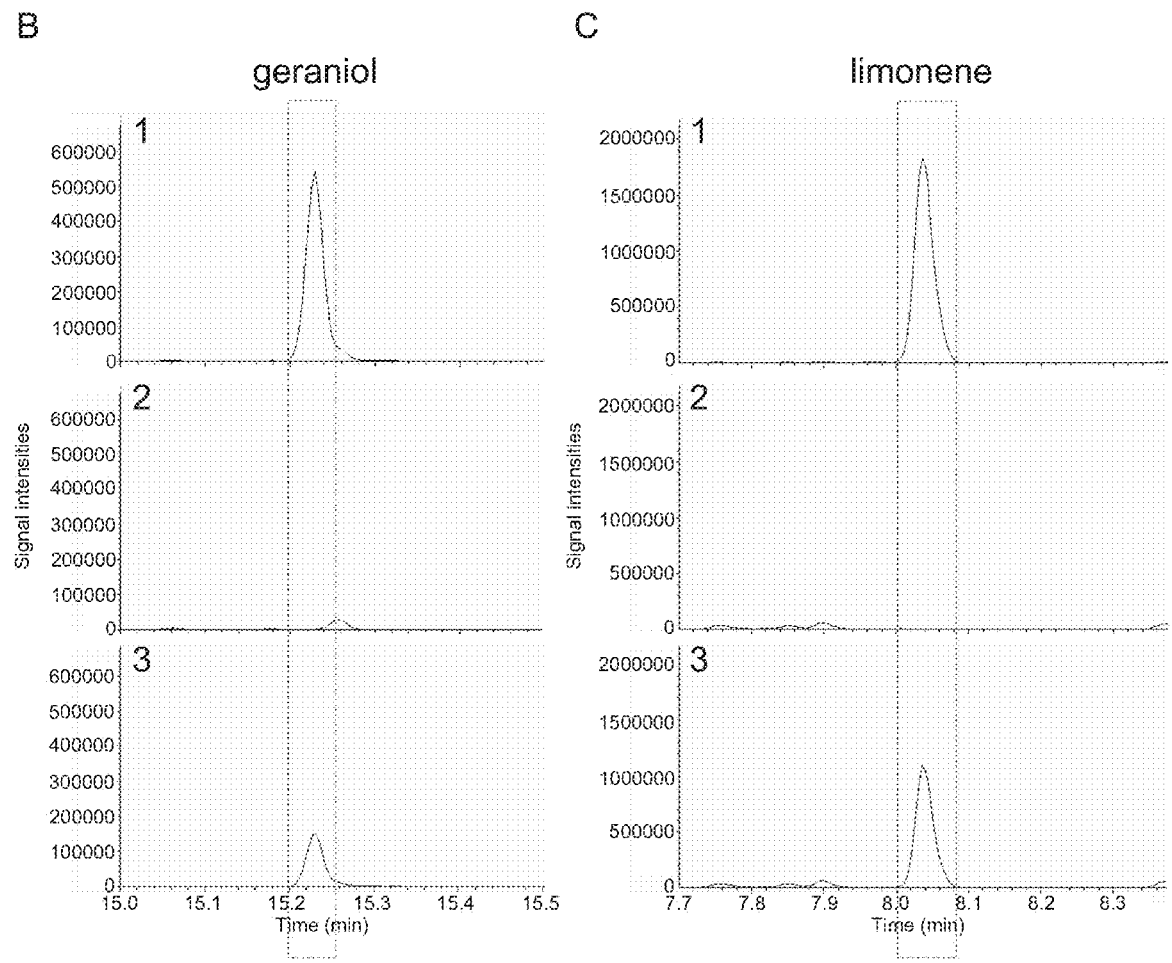
Figure 3B, C

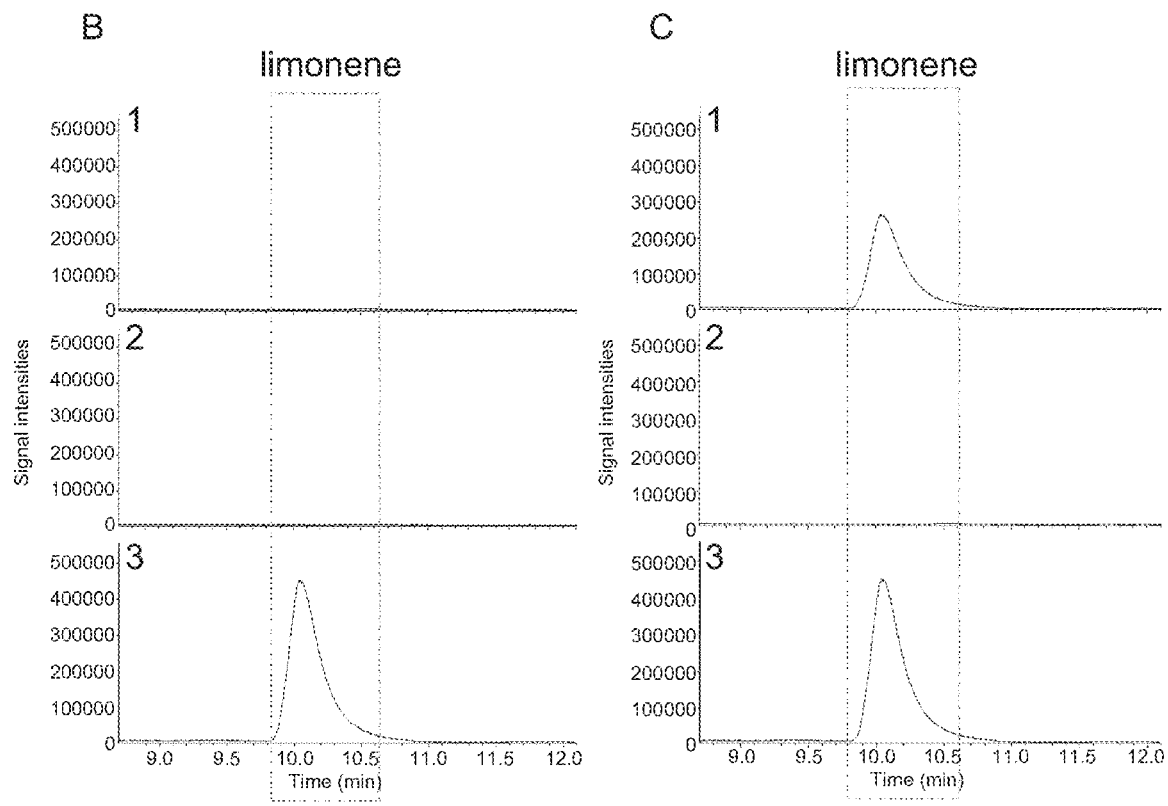
Figure 9B, C

Figure 32
a
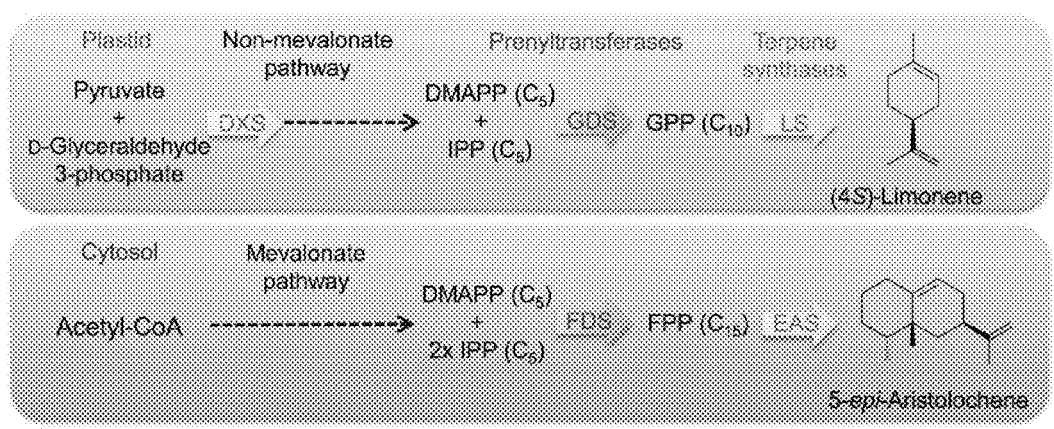
b
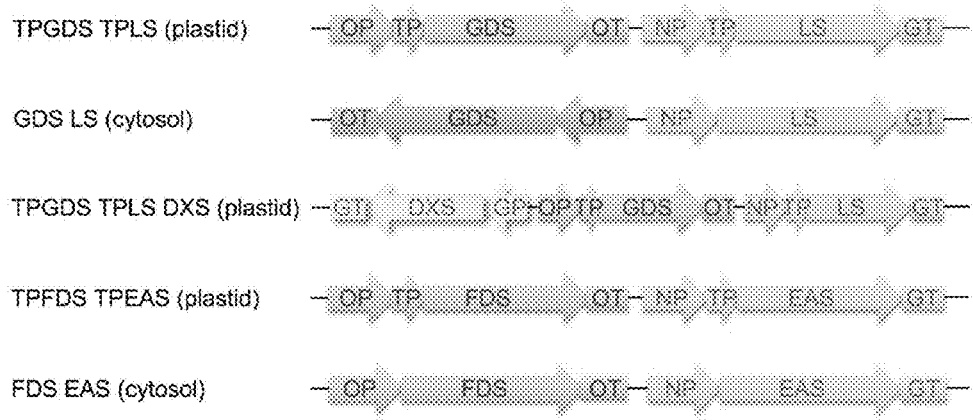

Figure 33
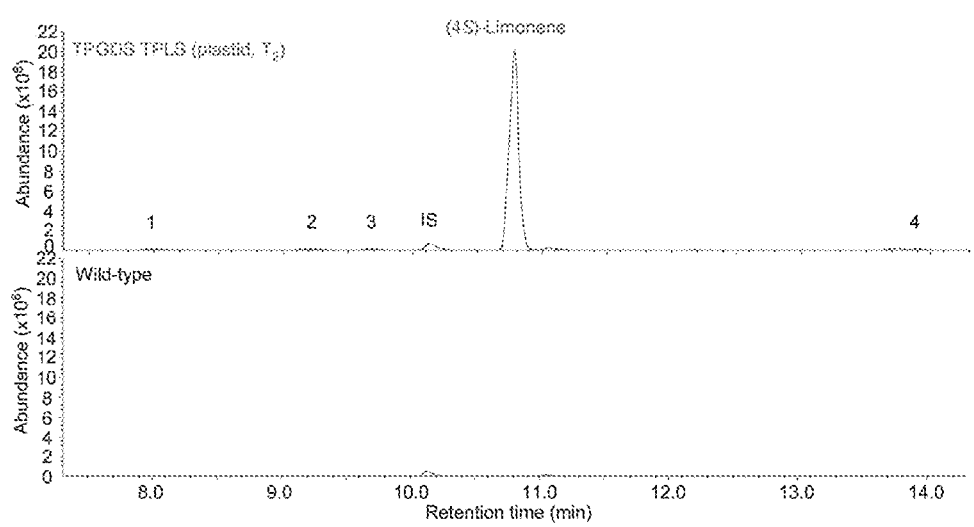
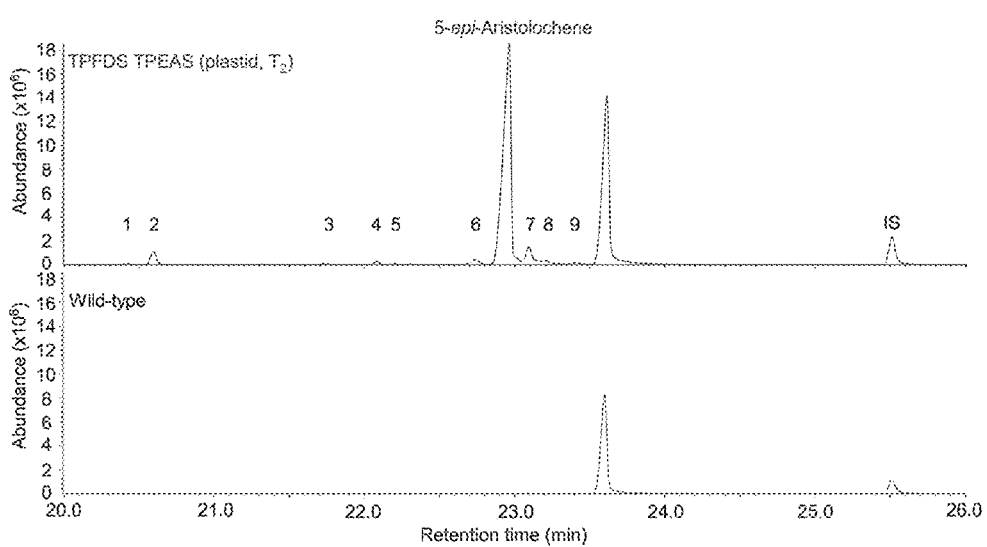

Figure 36
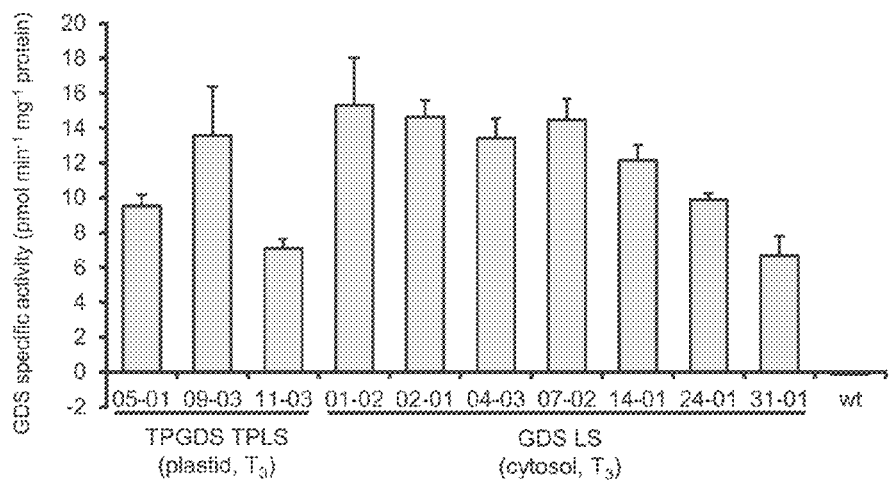
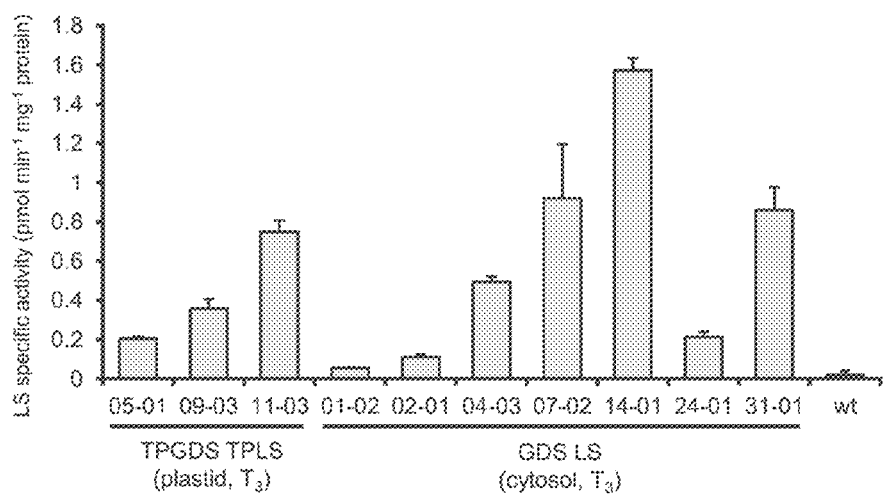
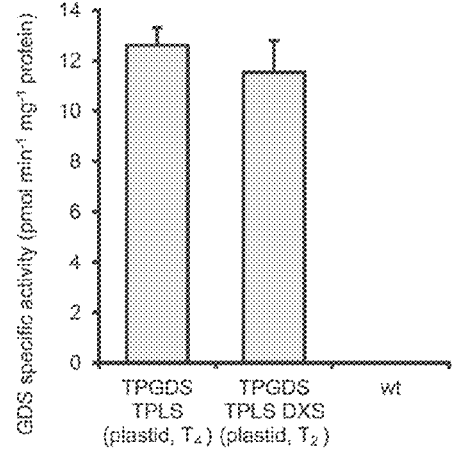
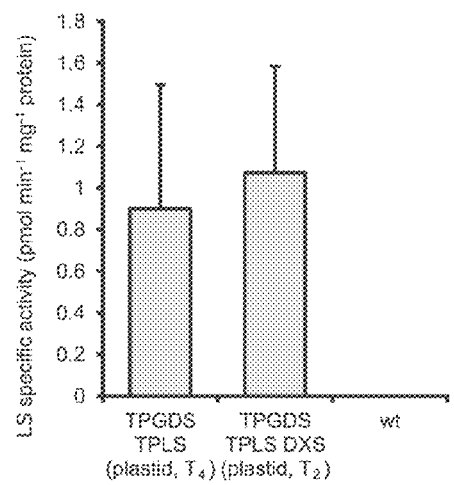

METHODS FOR HIGH YIELD PRODUCTION OF TERPENES

CROSS REFERENCE TO RELATED APPLICATIONS

This application claims the benefit of priority of U.S. Provisional Application Ser. No. 61/645,877, filed May 11, 2012, the contents of which are herein incorporated by reference in their entirety.

STATEMENT REGARDING FEDERALLY SPONSORED RESEARCH OR DEVELOPMENT

This invention was made with government support under DOE grant # DE-SC0001295 awarded by the Department of Energy. The government has certain rights in the invention.

BACKGROUND OF THE INVENTION

1. Field of the Invention

The present invention relates to the enhanced production and accumulation of terpenes in plants via the expression of fusion proteins comprising various combinations of geranyl diphosphate synthase large and small subunits with limonene synthase. The present invention also relates to engineering of oilseed plants, exemplified by *camelina*, to accumulate monoterpene and sesquiterpene hydrocarbons, exemplified herein by the cyclic monoterpene hydrocarbon (4S)-limonene and the bicyclic sesquiterpene hydrocarbon 5-epi-aristolochene. This establishes a framework for the rapid engineering of oilseed crop production platforms for terpene-based biofuels.

2. Description of Related Art

Jet fuel is a mixture of many different hydrocarbons. Modern analytical techniques indicate that there may be a thousand or more. The range of their sizes (carbon numbers) is restricted by specific physical requirements of a specific jet fuel product. Kerosine-type jet fuel has a carbon number distribution between about 8 and 16 carbons. Most of the hydrocarbons in jet fuel are members of the paraffin, naphthene and aromatic classes. The compounds that boil near the middle of the kerosine-type jet fuel boiling-range are C10 aromatics, C11 naphthenes, and C12 waxes. Given the decline in oil based natural resources, and potential for environmental disasters associated with oil extraction and transport, there is renewed interest in identifying renewable sources of jet fuels and related industrial hydrocarbon based products.

Plants synthesize a wide repertoire of cyclic and linear low molecular weight hydrocarbon compounds, which have the potential to be readily converted into jet fuel and industrial solvents. For example, the cyclic monoterpene, limonene, (4S)-1-methyl-4-(prop-1-en-2-yl)cyclohex-1-ene) occurs naturally in various ethereal oils, particularly oils of lemon, orange, caraway, dill and bergamot, and is a valuable industrial chemical. Some limonene is prepared by extraction from plants of the mint family, a large quantity is obtained from citrus oils, which are typically 80-90% limonene, and some is obtained from pine oil. It is also synthesized chemically and finds use as a solvent and cleaning agent (in the manufacture of synthetic pine oil), as an expectorant, as a wetting and dispersing agent, as a monomer in the manufacture of various polymeric resins, as a flavorant and a precursor in the synthesis of the flavorant carvone, and as a polymerization inhibitor in storage of the tetrafluoreoethylene monomer used in the manufacture of polytetrafluoroethylene (PTFE).

In principal the introduction of relatively few low molecular weight metabolite biosynthetic genes into a heterologous host such as an oilseed plant, or an alga could result in the production and accumulation of a variety of hydrocarbons that could serve as chemical precursors to wide range of industrial aromatic hydrocarbons including, C10 aromatics, C11 aromatics which are widely used as solvents and fuels.

In planta, C-10 terpenes (monoterpenes) are synthesized in plastids of specialized gland cells (Turner et al., (1999). Plant Physiology 120: 879-886) from precursors derived via the non-mevalonate pathway from pyruvate and glyceraldehyde-3-phosphate (Rohdich et al., Current Opinion in Chemical Biology 5: 535-540). C-15 terpenes (sesquiterpenes) are synthesized in the cytosol via the mevalonate pathway from acetyl-CoA (Chappell, J (2004) Trends in Plant Science. 9: 266-269). The volatile products of mono- and sesquiterpene biosynthesis in most plants are either secreted into specialized storage cavities or are released to the atmosphere.

The first committed step of monoterpene (see FIG. 2) biosynthesis is mediated Geranyl diphosphate synthase (GDS) which catalyzes the condensation of dimethylallyl diphosphate (DMAPP) and isopentenyl diphosphate (IPP) to form GPP, the immediate acyclic precursor of monoterpenes. GPP is converted to (−)-4S-limonene by the catalytic action of (−)-4S-limonene synthase (cyclase), which represents the primary precursor of various monoterpenes including its downstream metabolites (−)-trans-carveol and carvone; as well as the precursor of S-linalool. See FIG. 1; Wise et al. (1997) In "Comprehensive Natural Products Chemistry: Isoprenoids, Vol. 2" (Cane, D. E., ed.), Elsevier Science, Oxford (1998).

Both GPP synthase and 4S-limonene synthase has been isolated from several plant sources, including grape, geranium, sage (Croteau et al. (1989) Arch. Biochem. Biophys. 271:524-535; Heide et al. (1989) Arch. Biochem. Biophys. 273:331-338; Suga et al. (1991) Phytochemistry 30:1757-1761; Clastre et al. (1993) Plant Physiol. 102:205-211); and spearmint (Colby et al., (1993) J. Biol. Chem. 268(31) 23016-23024) and various cDNA clones are publicly available.

Despite the availability of these clones, previous systems for the production of Limonene and other downstream metabolites of related monoterpenes have primarily focused on the use of such systems for insect control. (See for example, U.S. Pat. No. 6,291,745). In this case, the emphasis was on producing sufficient amounts Limonene in plant tissues such as root to provide effective insect resistance, which was reported to be in the range of 200 ppm, rather than the high level stable production and stable accumulation of mg quantities of terpenes in plant seeds. *Camelina sativa* is an oilseed plant that has been little exploited in agriculture. It is similar in appearance to oilseed rape and similar in genetic characteristics to *Arabidopsis thaliana*. As *Arabidopsis*, it can be readily transformed by floral dip. *Camelina* is not a foodstuff plant and grows on marginal lands (e.g. Montana) that are generally considered unsuitable for large scale food production. *Camelina* is being investigated as a winter crop for southern Missouri and could potentially be double-cropped with soy. These characteristics make *Camelina* an ideal candidate plant to be developed as a chemical factory, particularly if high level production and accumulation of chemicals can be demonstrated in seeds. It is believed, however that the successful large scale biosynthesis and production of terpenes in *Camelina* seed has not been previously reported.

The current invention is based, at least in part, on the surprising discovery that the over expression of fusion proteins comprising either the GPP synthase large and small subunits, and limonene synthase, or one or more of these subunits fused to limonene synthase, in *Camelina* seeds results in the high level production and stable accumulation of various terpenes within the seeds. The present invention also surprisingly demonstrates that plants, in particular oil seed crops, can produce and accumulate monoterpene and sesquiterpene hydrocarbons in seeds. The resulting transgenic plants provide for the first time a viable approach for the large scale commercial production of commercially important terpenes in plants, with the potential to directly provide a renewable source of aromatic hydrocarbons, suitable for use for the production of jet fuel, organic solvents, plastics and high value industrial raw materials.

SUMMARY OF THE INVENTION

In one embodiment, the invention includes a transgenic plant comprising a heterologous nucleic acid sequence comprising a method for the production of a monoterpene, comprising the steps of:
  i) transforming a plant cell with a first nucleotide sequence encoding a fusion protein comprising a geranyl diphosphate synthase small subunit fused in frame to a geranyl diphosphate synthase large subunit, operatively linked to a first set of expression control sequences that drive expression of the geranyl diphosphate fusion protein in the plant cell;
  ii) transforming a plant cell with a second nucleotide sequence encoding a limonene synthase, operatively linked to a second set of expression control sequences that drive expression of the limonene synthase in the plant cell;
    wherein the fusion protein and limonene synthase are expressed primarily in the plant cell plastids.

In certain embodiments, the geranyl diphosphate synthase small subunit comprises an amino acid sequence selected from Table D1. In certain embodiments, the geranyl diphosphate synthase large subunit comprises an amino acid sequence selected from Table D2. In certain embodiments, the limonene synthase comprises an amino acid sequence selected from Table D3.

In certain embodiments, the method further comprises regenerating stably transformed transgenic plants. In some embodiments, the terpene is limonene. In some embodiments, the plant cell is co-transformed. In some embodiments, the first and second expression control sequences comprise constitutive promoters. In some embodiments, first and second expression control sequences comprise cell type specific promoters. In some embodiments, the first and second expression control sequences comprise seed specific promoters. In some embodiments, the first set of expression control sequences comprises the soybean oleosin promoter, and soybean oleosin terminator. In some embodiments, the second set of expression control sequences comprises the rapeseed napin promoter and soybean glycinin terminator. In some embodiments, the first and second set of expression control sequences comprises the RuBisCo small subunit transit peptide. In some embodiments, the plant cell is derived from a monocotyledonous plant. In some embodiments, the plant cell is derived from a dicotyledonous plant. In some embodiments the plant cell is derived from a plant that naturally produces a terpene. In some embodiments, the plant cell is derived from *Camelina sativa*. In some embodiments, the method further comprises the step of growing the transgenic plant, and harvesting the seeds. In some embodiments, the plant has a seed terpene content of at least 1.0 mg/g dry weight.

In another embodiment, the current invention includes a method for the production of a terpene, comprising the step of:
  transforming a plant cell with a first nucleotide sequence encoding a fusion protein comprising a geranyl diphosphate synthase small subunit or a geranyl diphosphate synthase large subunit fused in frame to a limonene synthase, operatively linked to a first set of expression control sequences that drive expression of the geranyl diphosphate fusion protein in the plant cell;
  wherein the fusion protein is expressed primarily in the plant cell plastids.

In certain embodiments, the geranyl diphosphate synthase small subunit comprises an amino acid sequence selected from Table D1. In certain embodiments, the geranyl diphosphate synthase large subunit comprises an amino acid sequence selected from Table D2. In certain embodiments, the limonene synthase comprises an amino acid sequence selected from Table D3.

In certain embodiments, the method further comprises regenerating stably transformed transgenic plants. In some embodiments, the terpene is limonene. In some embodiments, the plant cell is co-transformed. In some embodiments, the first and second expression control sequences comprise constitutive promoters. In some embodiments, first and second expression control sequences comprise cell type specific promoters. In some embodiments, the first and second expression control sequences comprise seed specific promoters. In some embodiments, the first set of expression control sequences comprises the soybean oleosin promoter, and soybean oleosin terminator. In some embodiments, the second set of expression control sequences comprises the rapeseed napin promoter and soybean glycinin terminator. In some embodiments, the first and second set of expression control sequences comprises the RuBisCo small subunit transit peptide. In some embodiments, the plant cell is derived from a monocotyledonous plant. In some embodiments, the plant cell is derived from a dicotyledonous plant. In some embodiments the plant cell is derived from a plant that naturally produces a terpene. In some embodiments, the plant cell is derived from *Camelina sativa*. In some embodiments, the method further comprises the step of growing the transgenic plant, and harvesting the seeds. In some embodiments, the plant has a seed terpene content of at least 1.0 mg/g dry weight.

Certain embodiments include a fusion protein comprising geranyl diphosphate synthase large subunit fused in frame to geranyl diphosphate synthase small subunit. In some aspects, the geranyl diphosphate synthases are selected from an amino acid sequence as set forth in Tables D1 or D2. In some aspects, the fusion protein is characterized by an improved rate of geranyl diphosphate production in vivo compared to the separate expression of the geranyl diphosphate synthase large and small subunits under comparable expression levels and incubation conditions.

Certain embodiments include a fusion protein comprising a geranyl diphosphate synthase large or small subunit is fused in frame to limonene synthase. In some aspects, the fusion protein is characterized by an improved rate of limonene synthesis compared to a mixture of geranyl diphosphate synthase and limonene synthases at the same molar concentration, and incubated under comparable reaction conditions. In some aspects, the geranyl diphosphate synthase is selected from an amino acid sequence as set forth in Tables D1 or D2, and the limonene synthase is selected from an amino acid sequence as set forth in Table D3.

Certain embodiments include a comprising a geranyl diphosphate synthase large subunit fused in frame to a geranyl diphosphate synthase small subunit fused in frame to limonene synthase. In some aspects, the fusion protein is characterized by an improved rate of limonene synthesis compared to a mixture of geranyl diphosphate synthase and limonene synthases at the same molar concentration, and incubated under comparable reaction conditions. In some aspects, the geranyl diphosphate synthase is selected from an amino acid sequence as set forth in Tables D1 or D2, and the limonene synthase is selected from an amino acid sequence as set forth in Table D3.

Certain embodiments include an expression vector comprising a polynucleotide sequence encoding a fusion protein of any of foregoing fusion proteins.

Certain embodiments include a transgenic plant comprising within its genome,
i) a first nucleotide sequence encoding a fusion protein comprising a geranyl diphosphate synthase small subunit fused in frame to a geranyl diphosphate synthase large subunit, operatively linked to a first set of expression control sequences that drive expression of the geranyl diphosphate fusion protein in the plant cell;
ii) a second nucleotide sequence encoding a limonene synthase, operatively linked to a second set of expression control sequences that drive expression of the limonene synthase in the plant cell;
wherein the fusion protein and limonene synthase are expressed primarily in the plant cell plastids.

In certain embodiments, the geranyl diphosphate synthase small subunit comprises an amino acid sequence selected from Table D1. In certain embodiments, the geranyl diphosphate synthase large subunit comprises an amino acid sequence selected from Table D2. In certain embodiments, the limonene synthase comprises an amino acid sequence selected from Table D3. In some aspects of the transgenic plant, the terpene is limonene. In some aspects of the transgenic plant, the first and second expression control sequences comprise constitutive promoters. In some aspects of the transgenic plant, the first and second expression control sequences comprise cell type specific promoters. In some aspects of the transgenic plant, the first and second expression control sequences comprise seed specific promoters. In some aspects of the transgenic plant, the first set of expression control sequences comprises the soybean oleosin promoter, and soybean oleosin terminator. In some aspects of the transgenic plant, the second set of expression control sequences comprises the rapeseed napin promoter and soybean glycinin terminator. In some aspects of the transgenic plant, the first and second set of expression control sequences comprises the RuBisCo small subunit transit peptide. In some aspects of the transgenic plant, the plant cell is derived from a monocotyledonous plant. In some aspects of the transgenic plant, the plant cell is derived from a dicotyledonous plant. In some aspects of the transgenic plant, the plant cell is derived from a plant that naturally produces a terpene. In some aspects of the transgenic plant, the plant cell is derived from the genus *Camelina*. In some aspects of the transgenic plant, the transgenic plant has a seed monoterpene content of at least 1.0 mg/g dry weight.

Certain embodiments include a transgenic plant comprising within its genome, a first nucleotide sequence encoding a fusion protein comprising a geranyl diphosphate synthase small subunit or a geranyl diphosphate synthase large subunit fused in frame to a limonene synthase, operatively linked to a first set of expression control sequences that drive expression of the geranyl diphosphate fusion protein in the plant cell;
wherein the fusion protein is expressed primarily in the plant cell plastids.

In certain embodiments, the geranyl diphosphate synthase small subunit comprises an amino acid sequence selected from Table D1. In certain embodiments, the geranyl diphosphate synthase large subunit comprises an amino acid sequence selected from Table D2. In certain embodiments, the limonene synthase comprises an amino acid sequence selected from Table D3.

In some aspects of the transgenic plant, the terpene is limonene. In some aspects of the transgenic plant, the first and second expression control sequences comprise constitutive promoters. In some aspects of the transgenic plant, the first and second expression control sequences comprise cell type specific promoters. In some aspects of the transgenic plant, the first and second expression control sequences comprise seed specific promoters. In some aspects of the transgenic plant, the first set of expression control sequences comprises the soybean oleosin promoter, and soybean oleosin terminator. In some aspects of the transgenic plant, the second set of expression control sequences comprises the rapeseed napin promoter and soybean glycinin terminator. In some aspects of the transgenic plant, the first and second set of expression control sequences comprises the RuBisCo small subunit transit peptide. In some aspects of the transgenic plant, the plant cell is derived from a monocotyledonous plant. In some aspects of the transgenic plant, the plant cell is derived from a dicotyledonous plant. In some aspects of the transgenic plant, the plant cell is derived from a plant that naturally produces a terpene. In some aspects of the transgenic plant, the plant cell is derived from the genus *Camelina*. In some aspects of the transgenic plant, the transgenic plant has a seed monoterpene content of at least 1.0 mg/g dry weight. In some aspects of the transgenic plant, the transgenic plant has a seed monoterpene content of at least 1.2 mg/g dry weight. In some aspects of the transgenic plant, the transgenic plant has a seed monoterpene content of at least 1.4 mg/g dry weight. In some aspects of the transgenic plant, the transgenic plant has a seed monoterpene content of at least 1.6 mg/g dry weight. In some aspects of the transgenic plant, the transgenic plant has a seed monoterpene content of at least 1.8 mg/g dry weight. In some aspects of the transgenic plant, the transgenic plant has a seed monoterpene content of at least 2.0 mg/g dry weight.

More particularly, among its various aspects, the present invention provides the following:
1. A method for the production of a terpene, comprising the steps of:
   i) transforming a plant cell with a first nucleotide sequence encoding a fusion protein comprising a geranyl diphosphate synthase small subunit comprising an amino acid sequence selected from Table D1 fused in frame to a geranyl diphosphate synthase large subunit comprising an amino acid sequence selected from Table D2, operatively linked to a first set of expression control sequences that drive expression of the geranyl diphosphate fusion protein in the plant cell;
   ii) transforming a plant cell with a second nucleotide sequence encoding a limonene synthase comprising a sequence selected from Table D3, operatively linked to a second set of expression control sequences that drive expression of the limonene synthase in the plant cell;
wherein the fusion protein and limonene synthase are expressed primarily in the plant cell plastids.

2. The method of 1, further comprising regenerating stably transformed transgenic plants.

3. The method of 2, wherein the terpene is limonene.

4. The method of 3, wherein the plant cell is co-transformed.

5. The method of any of 1-4, wherein the first and second expression control sequences comprise constitutive promoters.

6. The method of any of 1-4, wherein the first and second expression control sequences comprise cell type specific promoters.

7. The method of 6, wherein the first and second expression control sequences comprise seed specific promoters.

8. The method of 7, wherein the first set of expression control sequences comprises the soybean oleosin promoter, and soybean oleosin terminator.

9. The method of 7, wherein the second set of expression control sequences comprises the rapeseed napin promoter and soybean glycinin terminator.

10. The method of 7, wherein the first and second set of expression control sequences comprises the RuBisCo small subunit transit peptide.

11. The method 7, wherein the plant cell is derived from a monocotyledonous plant.

12. The method of 7, wherein the plant cell is derived from a dicotyledonous plant.

13. The method of 7, wherein the plant cell is derived from a plant that naturally produces a terpene.

14. The method of any of 7 to 10, wherein the plant cell is derived from *Camelina sativa*.

15. The method of 14, further comprising the step of growing the transgenic plant, and harvesting the seeds.

16. The method of 7, wherein the plant has a seed terpene content of at least 1.0 mg/g dry weight.

17. A method for the production of a terpene, comprising the step of:
transforming a plant cell with a nucleotide sequence encoding a fusion protein comprising geranyl diphosphate synthase fused in frame to limonene synthase,
wherein the fusion protein is operatively linked to a set of expression control sequences that drive expression of the fusion protein in the plant cell; and
wherein the fusion protein is primarily expressed in a plastid of the plant cell.

18. The method of 16, further comprising regenerating stably transformed plants.

19. The method of 17, wherein the terpene is limonene.

20. The method of 18, wherein the geranyl diphosphate synthase is selected from an amino acid sequence as set forth in Table D1, and the limonene synthase is selected from an amino acid sequence as set forth in Table D2.

21. The method of any of 16-19, wherein the expression control sequences comprise constitutive promoters.

22. The method of any of 16-19, wherein the expression control sequences comprise cell type specific promoters.

23. The method of 21, wherein the expression control sequences comprises a seed specific promoter.

24. The method of 22, wherein the expression control sequences comprise the soybean oleosin promoter, and soybean oleosin terminator.

25. The method of 22, wherein the expression control sequences comprise the rapeseed napin promoter and soybean glycinin terminator.

26. The method of 22, wherein the expression control sequences comprise the RuBisCo small subunit transit peptide.

27. The method 22, wherein the plant cell is from monocotyledonous plant.

28. The method 22, wherein the plant cell is from a dicotyledonous plant.

29. The method of 22, wherein the plant cell is derived from a plant that naturally produces a terpene.

30. The method of any of 23 to 26, wherein the plant cell is derived from plant from the genus *Camelina*.

31. The method of 30, further comprising the step of growing the transgenic plant, and harvesting the seeds.

32. The method of 31, wherein the plant has a seed terpene content of at least 1 mg/g dry weight.

33. A fusion protein comprising geranyl diphosphate synthase large subunit fused in frame to geranyl diphosphate synthase small subunit.

34. The fusion protein of 33, wherein the geranyl diphosphate synthases are selected from an amino acid sequence as set forth in Tables D1 or D2.

35. The fusion protein of 34, wherein the fusion protein is characterized by an improved rate of geranyl diphosphate production in vivo compared to the separate expression of the geranyl diphosphate synthase large and small subunits under comparable expression levels and incubation conditions.

36. A fusion protein comprising a geranyl diphosphate synthase large or small subunit fused in frame to limonene synthase.

37. The fusion protein of 36, wherein the fusion protein is characterized by an improved rate of limonene synthesis compared to a mixture of geranyl diphosphate synthase and limonene synthases at the same molar concentration, and incubated under comparable reaction conditions.

38. The fusion protein of 37, wherein the geranyl diphosphate synthase is selected from an amino acid sequence as set forth in Tables D1 or D2, and the limonene synthase is selected from an amino acid sequence as set forth in Table D3.

39. A fusion protein comprising a geranyl diphosphate synthase large subunit fused in frame to a geranyl diphosphate synthase small subunit fused in frame to limonene synthase.

40. The fusion protein of 39, wherein the fusion protein is characterized by an improved rate of limonene synthesis compared to a mixture of geranyl diphosphate synthase and limonene synthases at the same molar concentration, and incubated under comparable reaction conditions.

41. The fusion protein of 40, wherein the geranyl diphosphate synthase is selected from an amino acid sequence as set forth in Tables D1 or D2, and the limonene synthase is selected from an amino acid sequence as set forth in Table D3.

42. An expression vector comprising a polynucleotide sequence encoding a fusion protein of any of 33 to 41.

43. The expression vector of 42, wherein the geranyl diphosphate synthase is selected from an amino acid sequence as set forth in Tables D1 or D2, and the limonene synthase is selected from an amino acid sequence as set forth in Table D3.

44. A transgenic plant comprising within its genome,
i) a first nucleotide sequence encoding a fusion protein comprising a geranyl diphosphate synthase small subunit comprising an amino acid sequence selected from Table D1 fused in frame to a geranyl diphosphate synthase large subunit comprising an amino acid sequence selected from Table D2, operatively linked to a first set of expression control sequences that drive expression of the geranyl diphosphate fusion protein in the plant cell;
  ii) a second nucleotide sequence encoding a limonene synthase comprising a sequence selected from Table D3, operatively linked to a second set of expression control sequences that drive expression of the limonene synthase in the plant cell;
  wherein the fusion protein and limonene synthase are expressed primarily in the plant cell plastids.

45. The transgenic plant of 44, wherein the terpene is limonene.

46. The transgenic plant of any of 44 or 45, wherein the first and second expression control sequences comprise constitutive promoters.

47. The transgenic plant of any of 44 or 45, wherein the first and second expression control sequences comprise cell type specific promoters.

48. The transgenic plant of 47, wherein the first and second expression control sequences comprise seed specific promoters.

49. The transgenic plant of 47, wherein the first set of expression control sequences comprises the soybean oleosin promoter, and soybean oleosin terminator.

50. The transgenic plant of 47, wherein the second set of expression control sequences comprises the rapeseed napin promoter and soybean glycinin terminator.

51. The transgenic plant of 47, wherein the first and second set of expression control sequences comprises the RuBisCo small subunit transit peptide.

52. The transgenic plant 47, wherein the plant cell is derived from a monocotyledonous plant.

53. The transgenic plant 47, wherein the plant cell is derived from a dicotyledonous plant.

54. The transgenic plant of 47, wherein the plant cell is derived from a plant that naturally produces a terpene.

55. The transgenic plant of any of 47 to 54, wherein the plant cell is derived from the genus *Camelina*.

56. The transgenic plant of 55, wherein the transgenic plant has a seed terpene content of at least 1.0 mg/g dry weight.

57. A transgenic plant comprising within its genome,
  a first nucleotide sequence encoding a fusion protein comprising a geranyl diphosphate synthase small subunit comprising an amino acid sequence selected from Table D1 or a geranyl diphosphate synthase large subunit comprising an amino acid sequence selected from Table D2 fused in frame to a limonene synthase comprising an amino acid sequence selected from Table D3, operatively linked to a first set of expression control sequences that drive expression of the geranyl diphosphate fusion protein in the plant cell;
  wherein the fusion protein is expressed primarily in the plant cell plastids.

58. The transgenic plant of 57, wherein the terpene is limonene.

59. The transgenic plant of any of 57 or 58, wherein the first and second expression control sequences comprise constitutive promoters.

60. The transgenic plant of any of 57 or 58, wherein the first and second expression control sequences comprise cell type specific promoters.

61. The transgenic plant of 59, wherein the first and second expression control sequences comprise seed specific promoters.

62. The transgenic plant of 60, wherein the first set of expression control sequences comprises the soybean oleosin promoter, and soybean oleosin terminator.

63. The transgenic plant of 60, wherein the second set of expression control sequences comprises the rapeseed napin promoter and soybean glycinin terminator.

64. The transgenic plant of 60, wherein the first and second set of expression control sequences comprises the RuBisCo small subunit transit peptide.

65. The transgenic plant 60, wherein the plant cell is derived from a monocotyledonous plant.

66. The transgenic plant 60, wherein the plant cell is derived from a dicotyledonous plant.

67. The transgenic plant of 60, wherein the plant cell is derived from a plant that naturally produces a terpene.

68. The transgenic plant of any of 60 to 67, wherein the plant cell is derived from *Camelina sativa*.

69. The transgenic plant of 68, wherein the transgenic plant has a seed terpene content of at least 1.2 mg/g dry weight.

70. A method of producing and accumulating a monoterpene hydrocarbon of interest, a sesquiterpene hydrocarbon of interest, or a combination thereof, in a plant, comprising coexpressing in cells of said plant nucleotide sequences encoding all, or a biosynthetically appropriate combination of, enzymes selected from the group consisting of a geranyl diphosphate synthase, a monoterpene synthase that catalyzes the formation of said monoterpene hydrocarbon of interest, a farnesyl diphosphate synthase, and a sesquiterpene synthase that catalyzes the formation of said sesquiterpene hydrocarbon of interest, or a biosynthetically appropriate combination of said nucleotide sequences, wherein each of said nucleotide sequences is operably linked for expression to a seed-specific promoter.

71. The method of 70, wherein said biosynthetically appropriate combination of enzymes comprises a combination selected from the group consisting of:
  i) a geranyl diphosphate synthase and a monoterpene synthase that catalyzes the formation of said monoterpene hydrocarbon of interest, and
  ii) a farnesyl diphosphate synthase and a sesquiterpene synthase that catalyzes the formation of said sesquiterpene hydrocarbon of interest.

72. The method of 71 or 72, wherein said monoterpene hydrocarbon of interest is (4S)-limonene, said sesquiterpene hydrocarbon of interest is 5-epi-aristolochene, and said nucleotide sequences encoding all, or a biosynthetically appropriate combination of, enzymes are selected from the group consisting of a geranyl diphosphate synthase, a (4S)-limonene synthase, a farnesyl diphosphate synthase, and an epi-aristolochene synthase, wherein each of said nucleotide sequences is operably linked for expression to a seed-specific promoter.

73. The method of 72, wherein said biosynthetically appropriate combination of enzymes comprises a combination of a geranyl diphosphate synthase and a (4S)-limonene synthase, or a combination of a farnesyl diphosphate synthase and a 5-epi-aristolochene synthase.

74. The method of any one of 70-73, wherein:
  i) each of said nucleotide sequences comprises its own naturally occurring plastid transit peptide, or
  ii) in the case where any of said enzyme-encoding nucleotide sequences lacks a plastid transit peptide, a nucleotide sequence encoding a plastid transit peptide is added to said enzyme-encoding nucleotide sequences, or
  iii) in the case where any of said enzyme-coding nucleotide sequences comprises a nucleotide sequence encoding a non-plastid transit peptide, said nucleotide sequence encoding said non-plastid transit peptide is replaced with a nucleotide sequence encoding a plastid transit peptide.

75. The method of any one of 70 to 74, wherein said geranyl diphosphate synthase is expressed as a heterodimeric fusion protein.

76. The method of any one of 70-75, wherein said seed-specific promoter is selected from the group consisting of an oleosin promoter, a napin promoter, and a glycinin promoter.

77. The method of any one of 74-76, further comprising coexpressing a nucleotide sequence encoding an enzyme that catalyzes the biosynthesis of isopentenyl diphosphate and dimethylallyl diphosphate via the non-mevalonate pathway in plastids, wherein said nucleotide sequence comprises a sequence encoding a plastid transit peptide.

78. The method of 77, wherein said enzyme encoding nucleotide sequence encodes a 1-deoxy-xylulose 5-phosphate synthase enzyme comprising a plastid transit peptide.

79. The method of 77 or 78, wherein said enzyme encoding nucleotide sequence is overexpressed.

80. The method of any one of 70-79, further comprising expressing a nucleotide sequence encoding a selectable marker or a screenable marker that facilitates identification of transgenic seed, under the control of an operably linked, seed-specific promoter.

81. The method of 80, wherein said screenable marker is DsRed fluorescent protein.

82. The method of any one of 70-81, wherein said plant is an oil crop plant.

83. The method of 82, wherein said oil crop plant is selected from the group consisting of a plant of the genus *Camelina*, coconut, cotton, peanut, rapeseed (canola), safflower, sesame, soybean, wheat, flax, sunflower, olive, corn, palm, sugarcane, castor bean, switchgrass, *Miscanthus*, and *Jatropha*.

84. The method of 83, wherein said oil crop plant is *camelina*.

85. The method of 84, wherein said *camelina* is transformed by floral dip.

86. The method of any one of 70-85, further comprising recovering said monoterpene hydrocarbon of interest, said sesquiterpene hydrocarbon of interest, or combination thereof, from seeds of said plant.

87. The method of any one of 70-86, wherein said plant coexpresses a geranyl diphosphate synthase enzyme and a (4S)-limonene synthase enzyme, and accumulates monoterpene hydrocarbons including (4S)-limonene.

88. The method of 87, wherein said plant is *camelina*, and seeds thereof comprise about 1.5 to about 3 mg of (4S)-limonene per gram seed.

89. The method of any one of 70-86, wherein said plant coexpresses a farnesyl diphosphate synthase enzyme and an epi-aristolochene synthase enzyme, and accumulates sesquiterpenes including 5-epi-aristolochene.

90. The method of 89, wherein said plant is *camelina*, and seeds thereof comprise about 0.2 to about 1.4 mg of 5-epi-aristolochene per gram seed.

91. The method of any one of 72-90, further comprising recovering said (4S)-limonene, said 5-epi-aristolochene, or combination thereof, from seeds of said plant.

92. A plant that produces and accumulates a monoterpene hydrocarbon of interest, a sesquiterpene hydrocarbon of interest, or a combination thereof, by the method of any one of 70-.

93. The plant of 92, which is an oil crop plant.

94. The plant of 93, wherein said oil crop plant is selected from the group consisting of plants of the genus *Camelina*, coconut, cotton, peanut, rapeseed (canola), safflower, sesame, soybean, wheat, flax, sunflower, olive, corn, palm, sugarcane, castor bean, switchgrass, *Miscanthus*, and *Jatropha*.

95. The plant of 94, wherein said oil crop plant is *camelina*.

96. A part of said plant of any one of 70-95.

97. The part of 96, which is selected from the group consisting of a protoplast, a cell, a tissue, an organ, a cutting, and an explant.

98. The part of 96, which is selected from the group consisting of an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

99. Progeny of said plant of any one of 70-95.

100. Seed of said plant of any one of 70-95.

101. A transgenic plant, cells of which comprise in their genome nucleotide sequences encoding all, or a biosynthetically appropriate combination of, enzymes selected from the group consisting of a geranyl diphosphate synthase, a monoterpene synthase that catalyzes the formation of a monoterpene hydrocarbon of interest, a farnesyl diphosphate synthase, and a sesquiterpene synthase that catalyzes the formation of a sesquiterpene hydrocarbon of interest, or a biosynthetically appropriate combination of said nucleotide sequences,
    wherein each of said nucleotide sequences is operably linked for expression to a seed-specific promoter,
    wherein said nucleotide sequences are coexpressed, and
    wherein said monoterpene hydrocarbon of interest, said sesquiterpene hydrocarbon of interest, or a combination thereof, accumulates in seeds of said transgenic plant.

102. The transgenic plant of 101, wherein said biosynthetically appropriate combination of enzymes comprises a combination selected from the group consisting of:
    i) a geranyl diphosphate synthase and a monoterpene synthase that catalyzes the formation of said monoterpene hydrocarbon of interest, and
    ii) a farnesyl diphosphate synthase and a sesquiterpene synthase that catalyzes the formation of said sesquiterpene hydrocarbon of interest.

103. The transgenic plant of 101 or 102, wherein said monoterpene hydrocarbon of interest is (4S)-limonene, said sesquiterpene hydrocarbon of interest is 5-epi-aristolochene, and said nucleotide sequences encoding all, or a biosynthetically appropriate combination of, enzymes are selected from the group consisting of a geranyl diphosphate synthase, a (4S)-limonene synthase, a farnesyl diphosphate synthase, and an epi-aristolochene synthase, wherein each of said nucleotide sequences is operably linked for expression to a seed-specific promoter.

104. The transgenic plant of 103, wherein said biosynthetically appropriate combination of enzymes comprises a combination of a geranyl diphosphate synthase and a (4S)-limonene synthase, or a combination of a farnesyl diphosphate synthase and a 5-epi-aristolochene synthase.

105. The transgenic plant of 103 or 104, which produces (4S)-limonene, 5-epi-aristolochene, or a combination thereof.

106. The transgenic plant of any one of 101-105, wherein:
   i) each of said nucleotide sequences comprises its own naturally occurring plastid transit peptide, or
   ii) in the case where any of said enzyme-encoding nucleotide sequences lacks a plastid transit peptide, a nucleotide sequence encoding a plastid transit peptide is added to said enzyme-encoding nucleotide sequences, or
   iii) in the case where any of said enzyme-coding nucleotide sequences comprises a nucleotide sequence encoding a non-plastid transit peptide, said nucleotide sequence encoding said non-plastid transit peptide is replaced with a nucleotide sequence encoding a plastid transit peptide.

107. The transgenic plant of any one of 101-106, wherein said geranyl diphosphate synthase is expressed as a heterodimeric fusion protein.

108. The transgenic plant of any one of 101-107, wherein said seed-specific promoter is selected from the group consisting of an oleosin promoter, a napin promoter, and a glycinin promoter.

109. The transgenic plant of any one of 101-108, which coexpresses a nucleotide sequence encoding an enzyme that catalyzes the biosynthesis of isopentenyl diphosphate and dimethylallyl diphosphate via the non-mevalonate pathway in plastids, wherein said nucleotide sequence comprises a nucleotide sequence encoding a plastid transit peptide.

110. The transgenic plant of 109, wherein said enzyme encoding nucleotide sequence encodes a 1-deoxy-xylulose 5-phosphate synthase enzyme comprising a plastid transit peptide.

111. The transgenic plant of 109 or 110, wherein said enzyme encoding nucleotide sequence is overexpressed.

112. The transgenic plant of any one of 101-111, further comprising a nucleotide sequence encoding a selectable marker or a screenable marker that facilitates identification of transgenic seed, under the control of an operably linked, seed-specific promoter.

113. The transgenic plant of 112, wherein said screenable marker is DsRed fluorescent protein.

114. The transgenic plant of any one of 101-113, which is an oil crop plant.

115. The transgenic plant of 114, wherein said oil crop plant is selected from the group consisting of a plant of the genus *Camelina*, coconut, cotton, peanut, rapeseed (canola), safflower, sesame, soybean, wheat, flax, sunflower, olive, corn, palm, sugarcane, castor bean, switchgrass, *Miscanthus*, and *Jatropha*.

116. The transgenic plant of 115, wherein said oil crop plant is *camelina*.

117. A part of said transgenic plant of any one of 101-116.

118. The part of 117, which is selected from the group consisting of a protoplast, a cell, a tissue, an organ, a cutting, and an explant.

119. The part of 117, which is selected from the group consisting of an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

120. Progeny of said transgenic plant of any one of 101-116.

121. Seed of said transgenic plant of any one of 101-116.

122. A monoterpene hydrocarbon of interest, a sesquiterpene hydrocarbon of interest, or a combination thereof, produced by the method of any one of 70-91, obtained from seed of said plant of any one of 92-100, or obtained from seed of said transgenic plant of any one of 101-116.

Further scope of the applicability of the present invention will become apparent from the detailed description and drawing(s) provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

A better understanding of the features and advantages of the present invention can be obtained by reference to the following detailed description that sets forth illustrative embodiments, in which the principles of the invention are utilized, and the accompanying drawings of which:

FIG. 1. Shows some representative exemplary terpenes of the invention.

FIG. 3B, shows GDS in vitro enzyme reactions analyzed by GS-MS. Substrates IPP and DMAPP were incubated with, *E. coli* recombinant GDS extract (spectra 1), boiled *E. coli* recombinant GDS extract (spectra 2), and geranyl diphosphate (GPP) (spectra 3); then the resulting GPP was hydrolyzed by alkaline phosphatase to produce geraniol.

FIG. 3C shows, LS in vitro enzyme reactions which were analyzed by GS-MS. Substrate GPP was incubated with, *E. coli* recombinant LS extract (spectra 1), boiled *E. coli* recombinant LS extract (spectra 2), and limonene (spectra 3).

FIG. 9. FIG. 9B shows *E. coli* recombinant GDS and LS in vitro coupling enzyme reactions which were analyzed by GS-MS. Substrates IPP and DMAPP were incubated with, *E. coli* recombinant GDS9aaLS extract (spectra 1), boiled *E. coli* recombinant GDS9aaLS extract (spectra 2), and limonene (spectra 3). FIG. 9C Shows the results of GS-MS analysis of samples of, *E. coli*-expressed recombinant proteins incubated with substrates IPP and DMAPP. The results with LS9aaGDS extract (spectra 1), boiled *E. coli* recombinant LS9aaGDS extract (spectra 2), and limonene (spectra 3).

FIG. 32. Shows a graphical representation of terpene metabolic pathway directed to producing (4S)-limonene and 5-epi-aristolochene. GDS and FDS are prenyltransferases; LS and EAS are terpene synthases. (a) Peppermint (4S)-limonene is produced in plastid via the non-mevalonate pathway. Tobacco 5-epi-aristolochene is produced in cytosol via the mevalonate pathway. (b) Binary vectors harboring the genes for (4S)-limonene and 5-epi-aristolochene production in *camelina* transgenic seeds. Expression of the transgenes was controlled by seed-specific promoters. GDS, geranyl diphosphate synthase; LS, (4S)-limonene synthase; FDS, farnesyl diphosphate synthase; EAS, 5-epi-aristolochene synthase; DXS, 1-deoxy-D-xylulose-5-phosphate synthase with its own transit peptide; TP, Rubisco small subunit transit peptide; OP, oleosin promoter; NP, napin promoter; GP, glycinin promoter; OT, oleosin terminator; GT, glycinin terminator.

FIG. 33. Shows detection of (4S)-limonene and 5-epi-aristolochene in the transgenic *camelina* seeds. Diethyl ether extract from *camelina* seed was analyzed by GC-MS. Each extract was prepared from 10 mature seeds. (a) Total ion chromatogram of TPGDS TPLS (plastid) T2 seed and wild-type seed. The peak of (4S)-limonene was detected at the retention time of 10.8 min. Four peaks (represented as 1, 2, 3 and 4) showed mass fragmentation pattern similar to that of monoterpene compounds. (4S)-Limonene constituted 97% of the total monoterpenes calculated from the signal intensities. (b) Total ion chromatogram of TPFDS TPEAS (plastid) T2 seed and wild-type seed. The peak of 5-epi-aristolochene was detected at the retention time of 22.9 min and constituted 83% of the total sesquiterpenes. At least 9 peaks (represented as 1 to 9) showed mass fragmentation pattern similar to that of sesquiterpene compounds. The peak at 25.5 min is the internal standard hexadecane; the peak at 23.6 min in butylated hydroxytoluene from the solvent. IS, internal standard.

Figure 34:
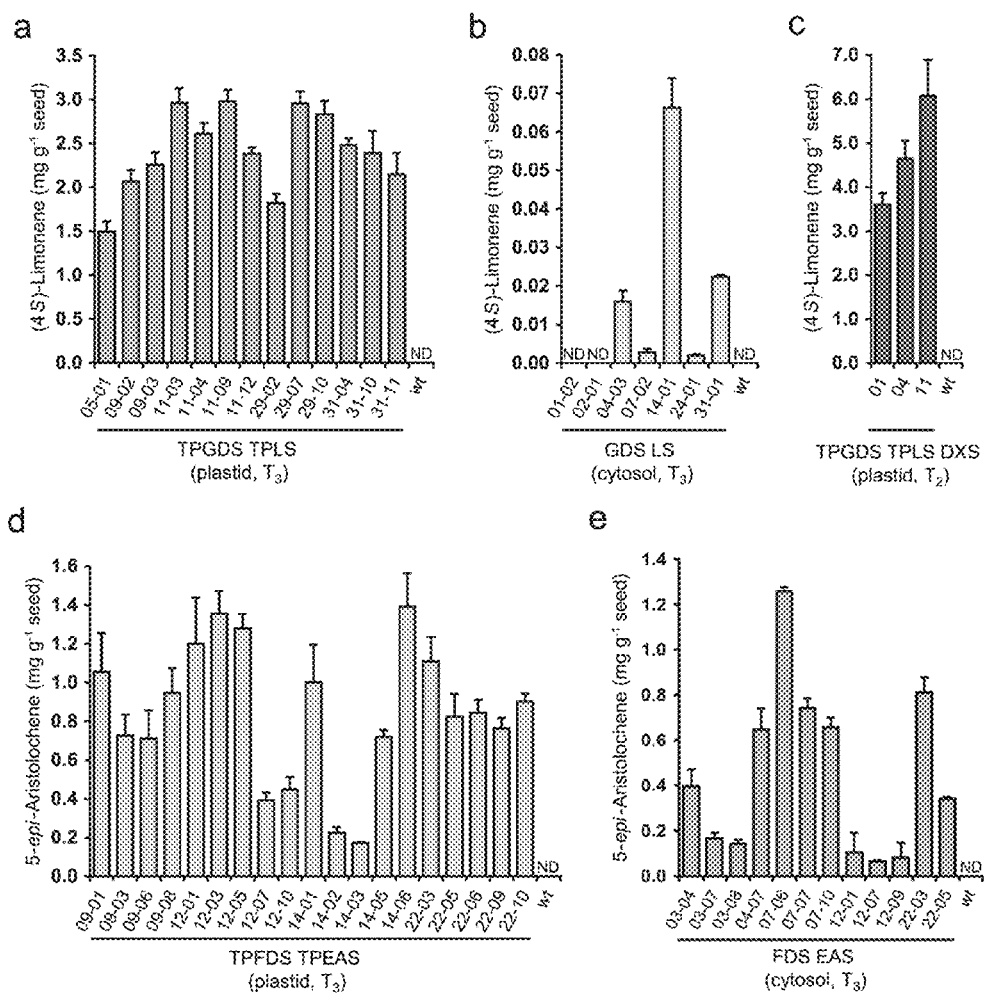

FIG. 34. Shows (4S)-limonene and 5-epi-aristolochene in the transgenic camelina seeds. The (4S)-limonene content was calculated by GC-MS with standard (4S)-limonene. (a) TPGDS TPLS (plastid) $T_3$ seed, (b) GDS LS (cytosol) $T_3$ seed, (c) TPGDS TPLS DXS (plastid) $T_2$ seed. The 5-epi-aristolochene content was calculated by GC-MS with standard valencene (analog of 5-epi-aristrolochene). (d) TPFDS TPEAS (plastid) $T_3$ seed and (e) FDS EAS (cytosol) $T_3$ seed. ND, not detected; wt, wild-type plant. Data are means±SD from analysis of at least 3 independent seed batches containing 10 seeds.

Figure 35:
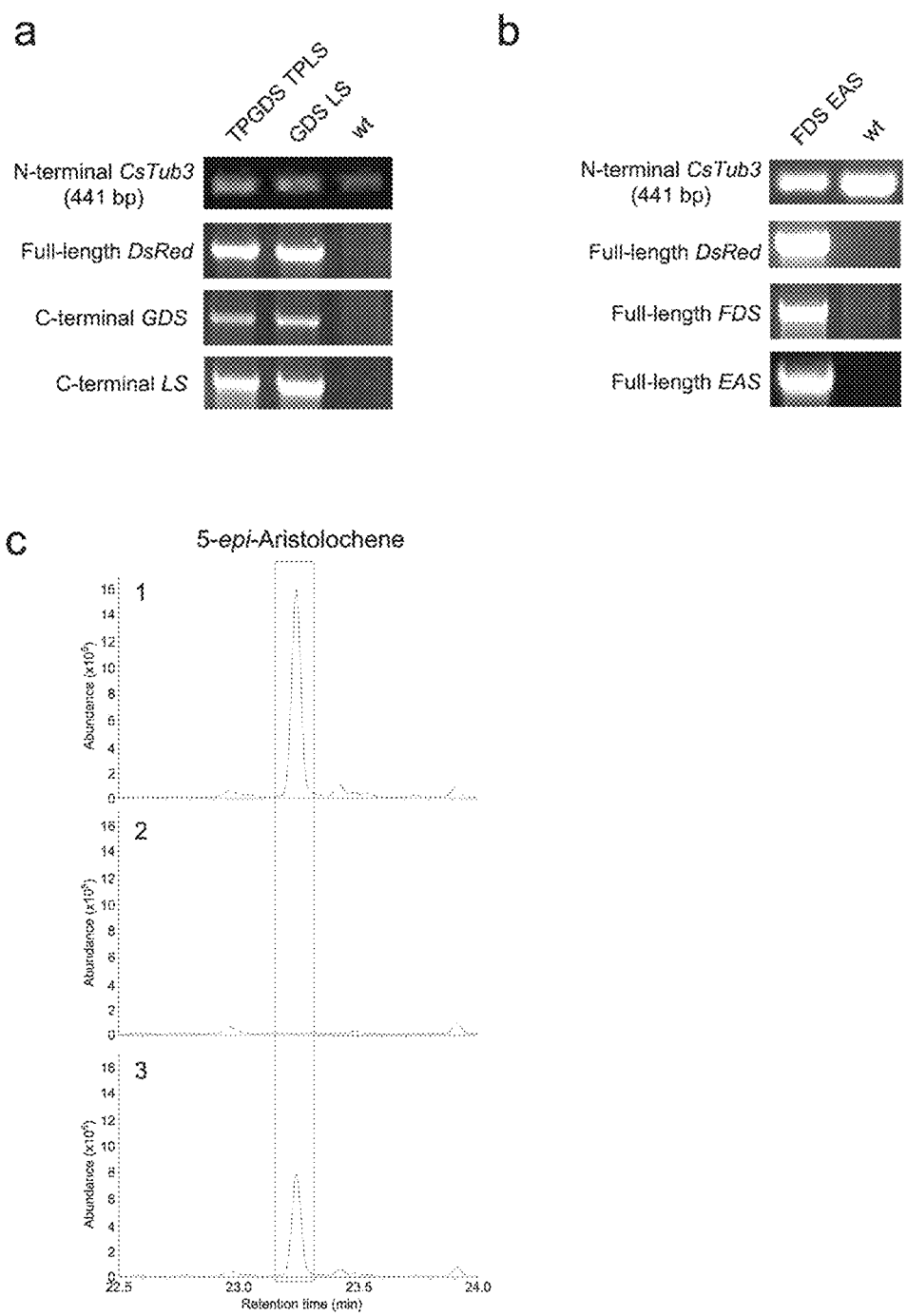

FIG. 35. Shows confirmation of transgene expression in Example 2. (a) Gene expression of GDS and LS were detected from transgenic camelina developing seed by RT-PCR analysis. Camelina β-tubulin 3 gene (accession number: FN811150.1) and DsRed were used as controls. (b) Gene expression of FDS and EAS was detected from transgenic camelina developing seed by RT-PCR analysis. (c) The FDS and EAS activities were determined by GC-MS in vitro. Crude protein of the transgenic camelina mature seeds was incubated with substrates of DMAPP and IPP. Enzymatically produced 5-epi-aristolochene was detected by GC-MS. 1, FDS EAS (cytosol) T2 seed; 2, wild-type camelina seed; 3, the mixture of purified E. coli recombinant proteins of FDS and EAS. wt, wild-type plant.

FIG. 36. Shows enzyme assay of the transgenes in Example 2. The specific activities of GDS and LS were determined by GC-MS. Crude protein of the transgenic camelina mature seeds was incubated with substrates. (a) GDS reaction was started by adding DMAPP and IPP as substrates. The reaction mixture contained LS recombinant protein (50 μg) purified from E. coli. (b) LS reaction was started with GPP as substrate. Enzymatically produced (4S)-limonene amount was quantified by GC-MS. (c, d) The activities of GDS and LS were detected from TPGDS TPLS (plastid) $T_4$ homozygous seed and TPGDS TPLS DXS (plastid) $T_2$ seed. wt, wild-type plant. Data are means±SD from analysis of 3 reactions from 2-3 independent seed batches containing ca. 22 seeds.

Figure 2:
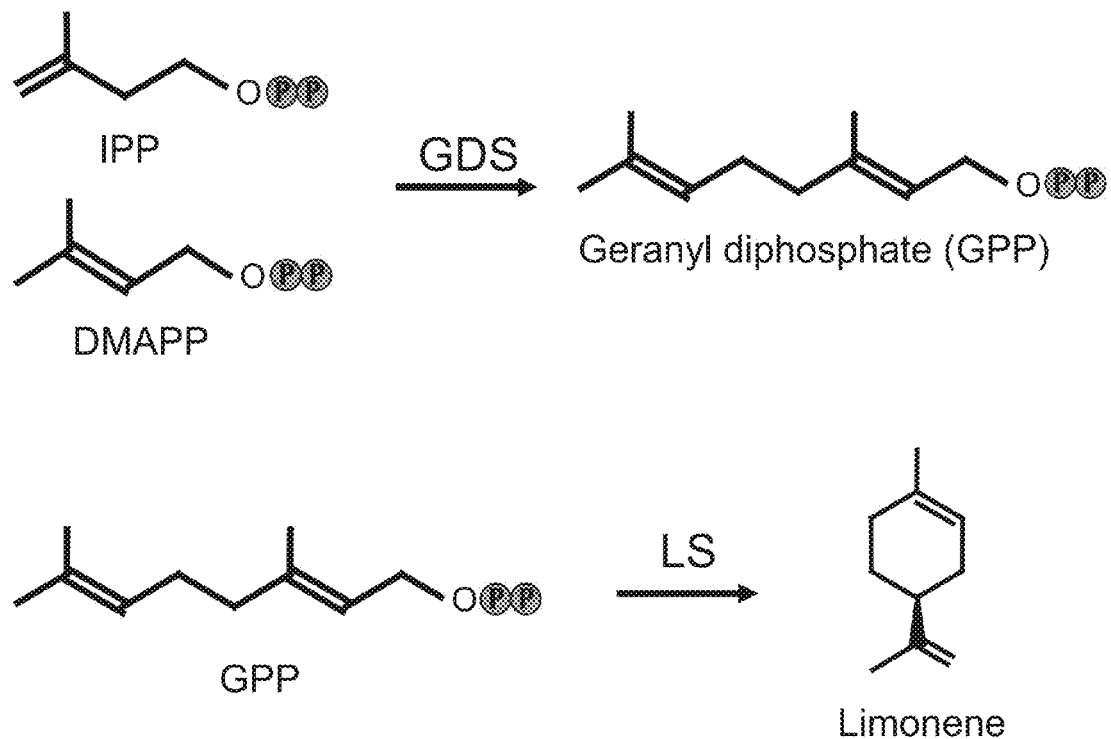
FIG. 2 Shows the synthetic scheme through which geranyl diphosphate synthase (GDS) and limonene synthase (LS) catalyze the production of Limonene from IPP and DMAPP.
Figure 37:
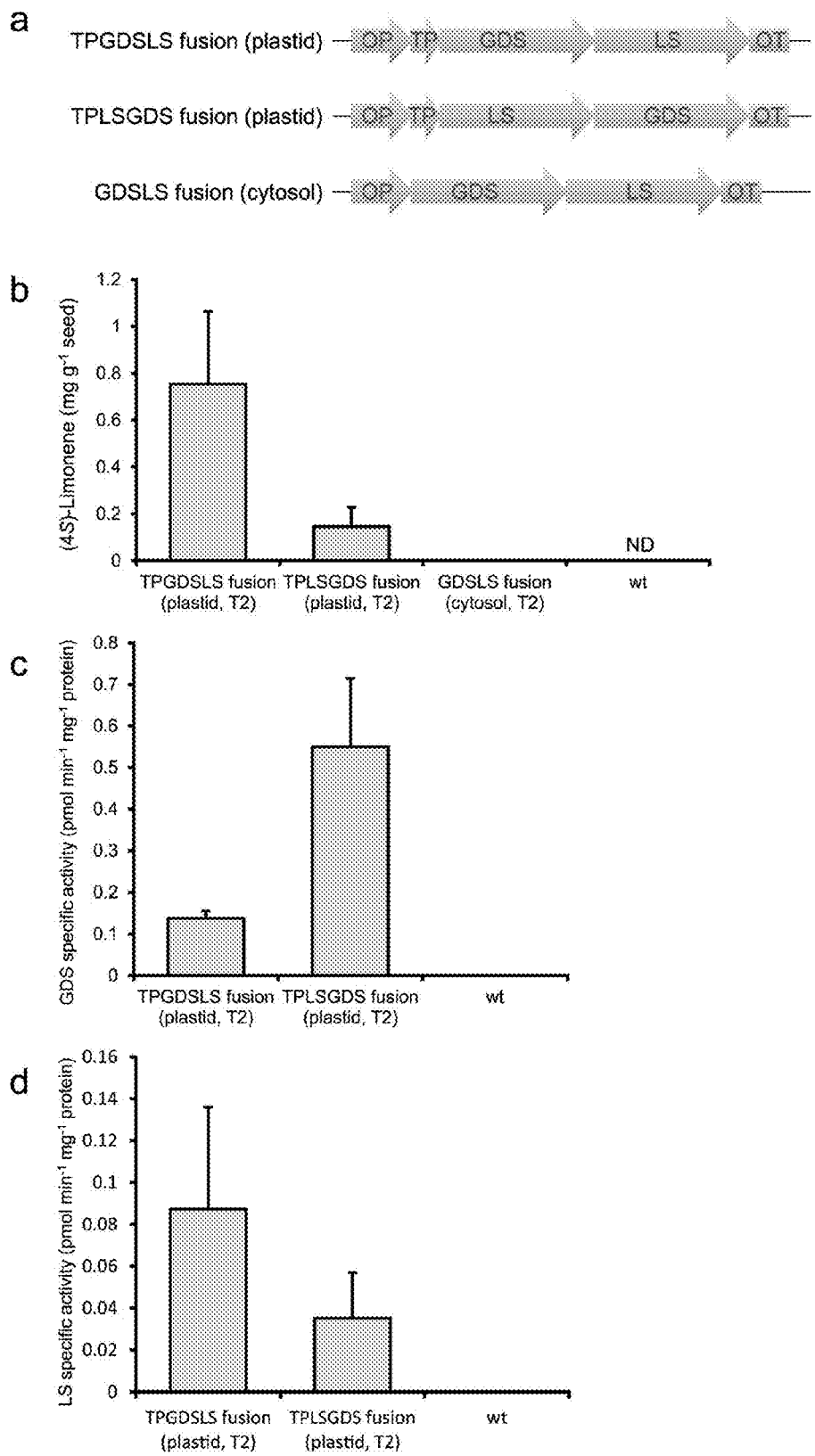

FIG. 37. Shows camelina transgenic lines expressing a fusion protein of GDS and LS. (a) The TPGDSLS fusion (plastid) binary vector contains a fusion protein comprised of a transit peptide (TP), GDS, a 9 amino acid linker and LS. The TPLSGDS fusion (plastid) binary vector contains a fusion protein comprised of a transit peptide (TP), LS, a 9 amino acid linker and GDS. The GDSLS fusion (cytosol) binary vector contains a fusion protein comprised of GDS, a 9 amino acid linker and LS. The gene expression was controlled by the seed-specific oleosin promoter (OP). OT, oleosin terminator. (b) The (4S)-limonene content, (c) GDS enzyme activity, and (d) LS enzyme activity were determined using the same methods as those of the unfused gene expression lines described in FIG. 3 and supplementary FIG. 2. ND, not detected; wt, wild-type plant.

Figure 38:
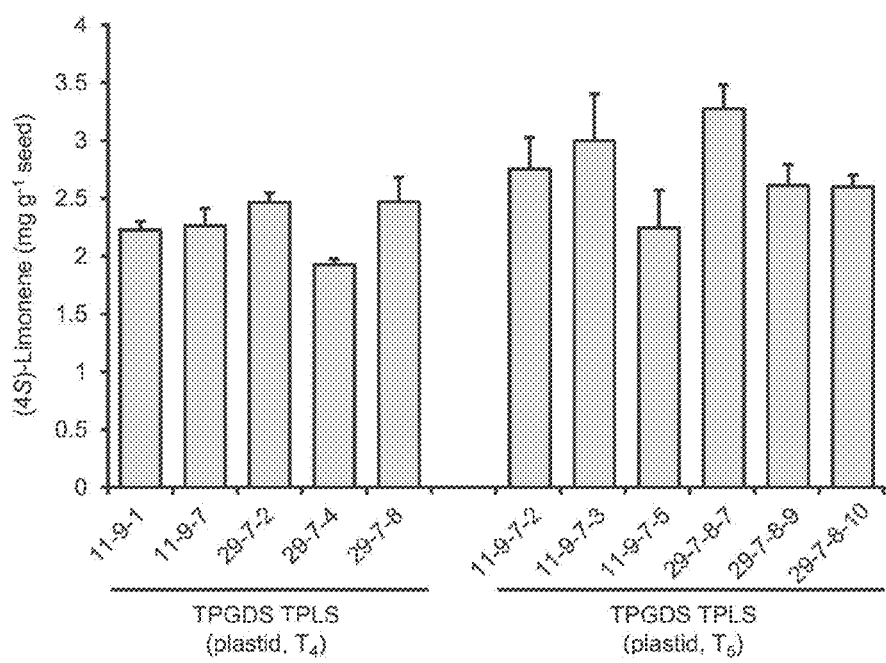

FIG. 38. Shows (4S)-limonene in TPGDS TPLS plastid type $T_4$ and $T_5$ seeds. The (4S)-limonene content was calculated from TPGDS TPLS (plastid) $T_4$ and $T_5$ seed (lines #11 and 29) by GC-MS with standard (4S)-limonene. Data are means±SD from analysis of at least 3 independent seed batches containing 10 seeds.

DETAILED DESCRIPTION OF THE INVENTION

Definitions

In order that the present disclosure may be more readily understood, certain terms are first defined. Additional definitions are set forth throughout the detailed description.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges can independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The terms "about" or "approximately" means within an acceptable error range for the particular value as determined by one of ordinary skill in the art, which will depend in part on how the value is measured or determined, i.e., the limitations of the measurement system. For example, "about" can mean within 1 or 2 standard deviations, from the mean value. Alternatively, "about" can mean plus or minus a range of up to 20%, preferably up to 10%, more preferably up to 5%.

As used herein, the terms "cell," "cells," "cell line," "host cell," and "host cells," are used interchangeably and, encompass animal cells and include plant, invertebrate, non-mammalian vertebrate, insect, algal, and mammalian cells. All such designations include cell populations and progeny. Thus, the terms "transformants" and "transfectants" include the primary subject cell and cell lines derived therefrom without regard for the number of transfers.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids can be defined where amino acids within a group exchange preferentially with each other, and therefore resemble each other most in their impact on the overall protein structure (Schulz, G. E. and R. H. Schirmer, Principles of Protein Structure, Springer-Verlag).

Examples of amino acid groups defined in this manner include: a "charged/polar group," consisting of Glu, Asp, Asn, Gln, Lys, Arg and His; an "aromatic, or cyclic group,"

consisting of Pro, Phe, Tyr and Trp; and an "aliphatic group" consisting of Gly, Ala, Val, Leu, Ile, Met, Ser, Thr and Cys.

Within each group, subgroups can also be identified, for example, the group of charged/polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gln. The aromatic or cyclic group can be sub-divided into the sub-groups consisting of the "nitrogen ring sub-group," consisting of Pro, His and Trp; and the "phenyl sub-group" consisting of Phe and Tyr. The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala.

Examples of conservative mutations include substitutions of amino acids within the sub-groups above, for example, Lys for Arg and vice versa such that a positive charge can be maintained; Glu for Asp and vice versa such that a negative charge can be maintained; Ser for Thr such that a free —OH can be maintained; and Gln for Asn such that a free —$NH_2$ can be maintained.

The term "expression" as used herein refers to transcription and/or translation of a nucleotide sequence within a host cell. The level of expression of a desired product in a host cell may be determined on the basis of either the amount of corresponding mRNA that is present in the cell, or the amount of the desired polypeptide encoded by the selected sequence. For example, mRNA transcribed from a selected sequence can be quantified by Northern blot hybridization, ribonuclease RNA protection, in situ hybridization to cellular RNA or by PCR. Proteins encoded by a selected sequence can be quantified by various methods including, but not limited to, e.g., ELISA, Western blotting, radioimmunoassays, immunoprecipitation, assaying for the biological activity of the protein, or by immunostaining of the protein followed by FACS analysis.

"Expression control sequences" are regulatory sequences of nucleic acids, or the corresponding amino acids, such as promoters, leaders, enhancers, introns, recognition motifs for RNA, or DNA binding proteins, polyadenylation signals, terminators, internal ribosome entry sites (IRES), secretion signals, subcellular localization signals, and the like, that have the ability to affect the transcription or translation, or subcellular, or cellular location of a coding sequence in a host cell. Exemplary expression control sequences are described in Goeddel; Gene Expression Technology: Methods in Enzymology 185, Academic Press, San Diego, Calif. (1990).

A "gene" is a sequence of nucleotides which code for a functional gene product. Generally, a gene product is a functional protein. However, a gene product can also be another type of molecule in a cell, such as RNA (e.g., a tRNA or an rRNA). A gene may also comprise expression control sequences (i.e., non-coding) sequences as well as coding sequences and introns. The transcribed region of the gene may also include untranslated regions including introns, a 5'-untranslated region (5'-UTR) and a 3'-untranslated region (3'-UTR).

The term "heterologous" refers to a nucleic acid or protein which has been introduced into an organism (such as a plant, animal, or prokaryotic cell), or a nucleic acid molecule (such as chromosome, vector, or nucleic acid construct), which are derived from another source, or which are from the same source, but are located in a different (i.e. non native) context.

The term "homologous" refers to a nucleic acid or protein which is naturally occurring within an organism (such as a plant, animal, or prokaryotic cell) and is in its native context or location, or a nucleic acid molecule (such as chromosome, vector, or nucleic acid construct) which is derived from the same source, and which is in its native context.

The term "homologous" can also refer to the relationship between two proteins that possess a "common evolutionary origin", including proteins from superfamilies (e.g., the immunoglobulin superfamily) in the same species of animal, as well as homologous proteins from different species of animal (for example, myosin light chain polypeptide, etc.; see Reeck et al., (1987) Cell, 50:667). Such proteins (and their encoding nucleic acids) have sequence homology, as reflected by their sequence similarity, whether in terms of percent identity or by the presence of specific residues or motifs and conserved positions.

The term "homology" describes a mathematically based comparison of sequence similarities which is used to identify genes or proteins with similar functions or motifs. The nucleic acid and protein sequences of the present invention can be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention.

To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used.

As used herein, the term "increase" or the related terms "increased", "enhance" or "enhanced" refers to a statistically significant increase. For the avoidance of doubt, the terms generally refer to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control value.

The term "isolated," when used to describe a protein or nucleic acid, means that the material has been identified and separated and/or recovered from a component of its natural environment. Contaminant components of its natural environment are materials that would typically interfere with research, diagnostic or therapeutic uses for the protein or nucleic acid, and may include enzymes, hormones, and other proteinaceous or non-proteinaceous solutes. In some embodiments, the protein or nucleic acid will be purified to at least 95% homogeneity as assessed by SDS-PAGE under non-reducing or reducing conditions using Coomassie blue or, preferably, silver stain. Isolated protein includes protein in situ within recombinant cells, since at least one component of the protein of interest's natural environment will not be present. Ordinarily, however, isolated proteins and nucleic acids will be prepared by at least one purification step.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, (Altschul, S. F. et al., J. Molec. Biol. 215: 403-410 (1990) and Altschul et al. Nuc. Acids Res. 25: 3389-3402 (1997)).

One example of an algorithm that is suitable for determining percent sequence identity and sequence similarity is the BLAST algorithm, which is described in (Altschul, S., et al., NCBI NLM NIH Bethesda, Md. 20894; & Altschul, S., et al., J. Mol. Biol. 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when the −27 cumulative alignment score falls off by the quantity X from its maximum achieved value, the cumulative score goes to zero or below due to the accumulation of one or more negative-scoring residue alignments, or the end of either sequence is reached. The BLAST algorithm parameters W. T. and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

The term "terpene" refers to any organic derived molecule formed directly from one or more isoprene, ($C_5H_8$) units. The term "hemiterpenes" refers to any cyclic or acyclic terpene containing one isoprene units. The term "monoterpene" refers to any cyclic or acyclic terpene containing two isoprene units. The term "sesquiterpene" refers to any cyclic or acyclic terpene containing three isoprene units. Terpenes and terpenoids are the primary constituents of the essential oils of many types of plants and flowers. Exemplary terpenes are provided for example in CRC Handbook of Terpenoids: Acyclic, Monocyclic, Bicyclic, Tricyclic, and Tetracyclic Terpenoids (1989) by S. Dev. ISBN 9780849336119; HANDBOOK OF TERPENOIDS, VOLUME 1 by DEV S. and NAGASAMPAGI ISBN: 0849336112; Chapter 13. Terpenoids and steroids of *Annu. Rep. Prog. Chem., Sect. B: Org. Chem.*, 1985, 82, 353-375 by J. R. Hanson and in Degenhardt et al., Phytochemistry (2009) 70 1621-1637, all of which are incorporated by reference in their entirety. Representative exemplary terpenes are provided by way of illustration, but not limitation, in FIG. 1.

The term "oilseed plant" or "oil crop" refers to plants that produce seeds or fruit with a high oil content, e.g., greater than about 10%. Exemplary oil seed or oil crop plants include, for example, plants of the genus *Camelina*, coconut, cotton, peanut, rapeseed (canola), safflower, sesame, soybean, wheat, flax, sunflower, olive, corn, palm, sugarcane, castor bean, switchgrass, *Miscanthus*, and *Jatropha*.

The terms "operably linked", "operatively linked," or "operatively coupled" as used interchangeably herein, refer to the positioning of two or more nucleotide sequences or sequence elements in a manner which permits them to function in their intended manner. In some embodiments, a nucleic acid molecule according to the invention includes one or more DNA elements capable of opening chromatin and/or maintaining chromatin in an open state operably linked to a nucleotide sequence encoding a recombinant protein. In other embodiments, a nucleic acid molecule may additionally include one or more DNA or RNA nucleotide sequences chosen from: (a) a nucleotide sequence capable of increasing translation; (b) a nucleotide sequence capable of increasing secretion of the recombinant protein outside a cell; (c) a nucleotide sequence capable of increasing the mRNA stability, and (d) a nucleotide sequence capable of binding a trans-acting factor to modulate transcription or translation, where such nucleotide sequences are operatively linked to a nucleotide sequence encoding a recombinant protein. Generally, but not necessarily, the nucleotide sequences that are operably linked are contiguous and, where necessary, in reading frame. However, although an operably linked DNA element capable of opening chromatin and/or maintaining chromatin in an open state is generally located upstream of a nucleotide sequence encoding a recombinant protein; it is not necessarily contiguous with it. Operable linking of various nucleotide sequences is accomplished by recombinant methods well known in the art, e.g. using PCR methodology, by ligation at suitable restrictions sites or by annealing. Synthetic oligonucleotide linkers or adaptors can be used in accord with conventional practice if suitable restriction sites are not present.

The term "organism that naturally produces monoterpenes" refers to any plant, algae, or fungi that produces detectable levels of any terpene. Representative examples of "plants that naturally produce terpenes" include for example, *Pinus taeda*, loblolly pine, Pinaceae, forest, *Juniperus virginiana*, cedar, Cupressaceae, tree, *Magnolia grandiflora*, magnolia, Magnoliaceae, flower and fruit, *Umbellularia californica*, California bay laurel, Lauraceae, branches with fruit, *Cinnamomum camphora*, camphor tree, Lauraceae, branch with flowers, *Cananga odorata*, ylang-ylang, Annonaceae, branch with flower, *Citrus limon*, lemon, Rutaceae, branch with fruits, *Bursera gummifera*, Burseraceae, tree, *Rosa damascena*, rose, Rosaceae, plant with flower, *Pelargonium* sp., geranium, Geraniaceae, plant with flowers, *Cannabis sativa*, marijuana, Cannabaceae, plants, *Mentha piperita*, peppermint, Lamiaceae, plant with flowers, *Lavandula officinalis*, lavender, Lamiaceae, flowers, *Salvia officinalis*, sage, Lamiaceae, plants with flowers, *Eucalyptus kondinensis*, Myrtaceae, trees, *Eucalyptus globulus*, Myrtaceae, flowers, *Anethum graveolens*, dill, Apiaceae, plants and fruits, *Coriandrum sativum*, coriander, cilantro, Apiaceae, plant and inflorescences, *Chrysactinia mexicana*, Asteraceae, plant with flowers, *Artemisia* sp., sage brush, Asteraceae, pasture with plants, *Ambrosia bidentata*, ragweed, Asteraceae, plants in bloom, *Reboulia hemisphaerica*, liverwort, *Salvia leucophylla*, Lamiaceae, allelopathic zones in the chaparral, *Pyrethrum* sp., Asteraceae, plants in field and harvest (irregular monoterpenes).

The terms "polynucleotide," "nucleotide sequence" and "nucleic acid" are used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, a polynucleotide includes not only naturally occurring bases such as A, T, U, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease S1) can be found within a promoter sequence, as well as protein binding domains (consensus sequences) responsible for the binding of RNA polymerase. Prokaryotic promoters contain Shine-Dalgarno sequences in addition to the −10 and −35 consensus sequences.

A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters active in plants include, for example nopaline synthase (nos) promoter and octopine synthase (ocs) promoters carried on tumor-inducing plasmids of *Agrobacterium tumefaciens* and the caulimovirus promoters such as the Cauliflower Mosaic Virus (CaMV) 19S or 35S promoter (U.S. Pat. No. 5,352,605), CaMV 35S promoter with a duplicated enhancer (U.S. Pat. Nos. 5,164,316; 5,196,525; 5,322,938; 5,359,142; and 5,424,200), the Figwort Mosaic Virus (FMV) 35S promoter (U.S. Pat. No. 5,378,619), the cassava vein mosaic virus (U.S. Pat. No. 7,601,885). These promoters and numerous others have been used in the creation of constructs for transgene expression in plants or plant cells. Other useful promoters are described, for example, in U.S. Pat. Nos. 5,391,725; 5,428,147; 5,447,858; 5,608,144; 5,614,399; 5,633,441; 6,232,526; and 5,633,435, all of which are incorporated herein by reference.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell. Methods for purification are well-known in the art. As used herein, the term "substantially free" is used operationally, in the context of analytical testing of the material. Preferably, purified material substantially free of contaminants is at least 50% pure; more preferably, at least 75% pure, and more preferably still at least 95% pure. Purity can be evaluated by chromatography, gel electrophoresis, immunoassay, composition analysis, biological assay, and other methods known in the art. The term "substantially pure" indicates the highest degree of purity, which can be achieved using conventional purification techniques known in the art.

The term "sequence similarity" refers to the degree of identity or correspondence between nucleic acid or amino acid sequences that may or may not share a common evolutionary origin. However, in common usage and in the instant application, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 85%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

In particular embodiments of the invention, two amino acid sequences are "substantially homologous" or "substantially similar" when greater than 90% of the amino acid residues are identical. Two sequences are functionally identical when greater than about 95% of the amino acid residues are similar. Preferably the similar or homologous polypeptide sequences are identified by alignment using, for example, the GCG (Genetics Computer Group, Version 7, Madison, Wis.) pileup program, or using any of the programs and algorithms described above. The program may use the local homology algorithm of Smith and Waterman with the default values: Gap creation penalty=−(1+1/k), k being the gap extension number, Average match=1, Average mismatch=−0.333.

As used herein, a "transgenic plant" is one whose genome has been altered by the incorporation of heterologous genetic material, e.g. by transformation as described herein. The term "transgenic plant" is used to refer to the plant produced from an original transformation event, or progeny from later generations or crosses of a transgenic plant, so long as the progeny contains the heterologous genetic material in its genome.

The term "transformation" or "transfection" refers to the transfer of one or more nucleic acid molecules into a host cell or organism. Methods of introducing nucleic acid molecules into host cells include, for instance, calcium phosphate transfection, DEAE-dextran mediated transfection, microinjection, cationic lipid-mediated transfection, electroporation, scrape loading, ballistic introduction, or infection with viruses or other infectious agents.

"Transformed", "transduced", or "transgenic", in the context of a cell, refers to a host cell or organism into which a recombinant or heterologous nucleic acid molecule (e.g., one or more DNA constructs or RNA, or siRNA counterparts) has been introduced. The nucleic acid molecule can be stably expressed (i.e. maintained in a functional form in the cell for longer than about three months) or non-stably maintained in a functional form in the cell for less than three months i.e. is transiently expressed. For example, "transformed," "transformant," and "transgenic" cells have been through the transformation process and contain foreign nucleic acid. The term "untransformed" refers to cells that have not been through the transformation process.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Buchanan et al., Biochemistry and Molecular Biology of Plants, Courier Companies, USA, 2000; Miki and Iyer, Plant Metabolism, $2^{nd}$ Ed. D. T. Dennis, D H Turpin, D D Lefebrve, D G Layzell (eds) Addison Wesly, Langgmans Ltd. London (1997); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein.

The publications discussed above are provided solely for their disclosure before the filing date of the present application. Nothing herein is to be construed as an admission that the invention is not entitled to antedate such disclosure by virtue of prior invention.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Overview

The present invention includes methods, DNA constructs, and transgenic plants that exhibit enhanced rates of terpene production and improved terpene content. In one aspect such methods and transgenic plants are created through the over expression of fusion proteins comprising either the GPP synthase large and small subunits, and limonene synthase, or one or more of these subunits fused to limonene synthase. In certain embodiments the enzymes are expressed with plastids of seed tissues.

Accordingly, in one aspect the current invention includes a method for the production of a terpene, comprising the steps of:

transforming a plant cell with a first nucleotide sequence encoding a fusion protein comprising a geranyl diphosphate synthase small subunit fused in frame to a geranyl diphosphate synthase large subunit, operatively linked to a first set of expression control sequences that drive expression of the geranyl diphosphate fusion protein in the plant cell;

transforming a plant cell with a second nucleotide sequence encoding a limonene synthase, operatively linked to a second set of expression control sequences that drive expression of the limonene synthase in the plant cell;

wherein the fusion protein and limonene synthase are expressed primarily in the plant cell plastids.

In another aspect, the invention includes a method for the production of a monoterpene, comprising the step of:

transforming a plant cell with a first nucleotide sequence encoding a fusion protein comprising a geranyl diphosphate synthase small subunit or a geranyl diphosphate synthase large subunit fused in frame to a limonene synthase, operatively linked to a first set of expression control sequences that drive expression of the geranyl diphosphate fusion protein in the plant cell;

wherein the fusion protein is expressed primarily in the plant cell plastids.

In certain embodiments of either of these methods the fusion protein is expressed primarily in the seeds of the plant.

I. Exemplary Geranyl Diphosphate Synthase Genes

In any of these methods, fusion proteins, DNA constructs, and transgenic organisms, the terms "geranyl diphosphate synthase" or "GDP synthase" or "GDS" refers to all naturally-occurring and synthetic genes encoding a geranyl diphosphate synthase large or small subunit. In one aspect, the geranyl diphosphate synthase is from a plant. In one aspect the geranyl diphosphate synthase is from plant that naturally produces terpenes.

Representative species and Gene bank accession numbers for various species of geranyl diphosphate synthase large and small subunits are listed below in Table D1.

TABLE D1

Exemplary geranyl diphosphate synthases small subunits

| Organism | Sequence | Gene Bank Accession No. | SEQ ID NO: |
|---|---|---|---|
| Mentha x piperita | MAINLSHINSKTCFPLKTRSDLSRSSSARCMPTA AAAAFPTIATAAQSQPYWAAIEADIERYLKKSI TIRPPETVFGPMHHLTFAAPATAASTLCLAACE LVGGDRSQAMAAAAAIHLVHAAAYVHEHLPL TDGSRPVSKPAIQHKYGPNVELLTGDGIVPFGF ELLAGSVDPARTDDPDRILRVIIEISRAGGPEGM ISGLHREEEIVDGNTSLDFIEYVCKKKYGEMHA CGAACGAILGGAAEEEIQKLRNFGLYQGTLRG MMEMKNSHQLIDENIIGKLKELALEELGGFHG KNAELMSSLVAEPSLYAA | AF182827 | 1 |
| Antirrhinum majus | MAHGLTHFNT KSGLFPSITK SKTTRPSTRP VILAMTRTQT YRATIESDIE SYLKKAIPIR APESVFEPMH HLTFAAPRTS ASALCVAACE LVGGDRSDAM AAAAAVHLMH VAAYTHENLP LTDGPMSKSE IQHKFDPNIE LLTGDGIIPF GLELMARSMD PTRNNPDRIL RAIIELTRVM GSEGIVEGQY HELGLNQLND LELIEYVCKK KEGTLHACGA ACGAILGGCD EDKIEKLRRF GLYVGTVQGL LGKNRSGFEG RIKELKELAV KELESFGGEK IELIRGVFEL EHSLAGV | AAS82859.1 | 2 |
| Ricinus communis | MAGALPYIPG NPVGRGVFRR SFGYGRGGAL FSRRPVACVM SNSSKIDYWT CINADIETHL KEAIPVRPPV VVFEPMHHLT FAAPRSFAPA LCIAACELVG GSRDQALAAA SALRLMIAAA FTHENIPLTD RPRPSARPMF HHTFGPNIEL LTGDGMIPFA FELLAQLNNP AQDNSDRILR VMIEISRAMG SQGMVEGQYN EFQYDQSVGD ELFHVAWLRD VCKKKEGASH ACAGACGAIL GGGNEEEIEK LRRYGLYVGT IQGIYNKVEG NEEWSLKEVN KLRDLALKEL KDFNEEEKVR AICSLVEN | XP_002532570.1 | 3 |
| Populus trichocarpa | SYWTSVNDEI DAHLKQAIPI RPPLSVFEPM HHLTFAAPRT TAPALCIAAC ELVGGNRDQA MAAASALRLM HAAALTHEHI LSTGNRARIG HSFGSNIELL TGDGMVPFGL ELLAKSDDLT QNNSERILRV IIEITQAMGS QGMALGQYNQ FQHGQSDYID HVCKKKEGEL HSCAGAVGAI LGGGTEEEIE KLRRYGLYVG LMQGVLSNWV ERKEEVSMEK VLNELENLAL KELEGF | XP_002322072.1 | 4 |
| Hevea brasiliensis | MAGALSSTIH GNLIARAVSS SNPKHPLFSH RPMVVAMSTD QSYWSSVNAD LDTHLKQAIP IRQPLAVFEP MRHLILSAPQ TSAPALCIAA CELVGGHRNQ AMAAASALRL VHASASTHEN LPLTDRPRPM PRTRPTLYGP NIELLIADGI IPYGFELLAR DDDAAENNSN RVLRAIIEIS RAMGSQGVIE GQYNESQYEE SEGEEIFHVG WLQNVCRKKE GTLHACAGAC GAILGGGSED EIEKLRRYGL YVGMVQGILS KVDERKEWPV KEVNKLRDLA LKELKDFNQA KVKTISILVE TRFCNL | BAF98300.1 | 5 |
| Humulus lupulus | MSRTHENHHV PTSTSIVVSA SITADIEAHL KQSITLKPPL SVHEPMYNLV FSAPPNSAPS LCVAACELVG GHRSKAIAAA SALRLLHAAN FTHEHLPLTD SPSPSPVIHN SYDPSIQLLM PDAILPLGFE LLAQSYNPAQ NNSDRVLRVI VEFARAFGSK GILDGQYRQR VVSISNGDEV | ACQ90681.1 | 6 |

TABLE D1-continued

Exemplary geranyl diphosphate synthases small subunits

| Organism | Sequence | Gene Bank Accession No. | SEQ ID NO: |
|---|---|---|---|
| | DNAERVDCSG REKEGKMHAC AAACGAILGD ANEEETEKLR TFGLYVGMIQ GYSIKFMRER EEEKEAERTI KELRNLALKE LEHFHGRKLE PISSFIYCL | | |
| Glycine max | MLGALLLNAN FKIHFSLISC QARVPLPVKP APLRMPSPHY PHWASLQADI EAHLKQTIPL KEPLEVFEPM LHLAFSAPRT TVPALCLAAC ELVGGHRQQA MAAASALLLN LANAHAHEHL TDGPMYGPNI ELLTGDGIVP FGFELLARPD GPASASPERV LRVMIEISRA VGSVGLQDAQ YVKKTLWDGG EEVQNVESMQ RFVLEKRDGG LHACGAASGA ILGGGSEDQI ERLRNFGFHV GMMRGMLQMG FMEKHVQEER HLALKELQFF MDRDVHVISS FIY | ABY90133.1 | 7 |

TABLE D2

Exemplary geranyl diphosphate synthases large subunits

| Organism | Sequence | Gene Bank Accession No. | SEQ ID NO: |
|---|---|---|---|
| Mentha x piperita | MSALVNPVAK WPQTIGVKDV HGGRRRRSRS TLFQSHPLRT EMPFSLYFSS PLKAPATFSV SAVYTKEGSE IRDKDPAPST SPAFDFDGYM LRKAKSVNKA LEAAVQMKEP LKIHESMRYS LLAGGKRVRP MLCIAACELV GGDESTAMPA ACAVEMIHTM SLMHDDLPCM DNDDLRRGKP TNHMAFGESV AVLAGDALLS FAFEHVAAAT KGAPPERIVR VLGELAVSIG SEGLVAGQVV DVCSEGMAEV GLDHLEFIHH HKTAALLQGS VVLGAILGGG KEEEVAKLRK FANCIGLLFQ VVDDILDVTK SSKELGKTAG KDLVADKTTY PKLIGVEKSK EFADRLNREA QEQLLHFHPH RAAPLIALAN YIAYRDN | AAF08793.1 | 8 |
| Mentha haplocalyx var. piperascens | MSALVNPVAK WPQTIGIKDV HGGRRRRSRS TLFLSHPLRT EMPFSLYFSS PLKAPATFSV SAVYTKEGSE IRDKDPAPST SPAFDFDGYM LRKAKSVNKA LEAAVQMKEP LKIHESMRYS LLAGGKRVRP MLCIAACELV GGDESTAMPA ACAVEMIHTM SLMHDDLPCM DNDDLRRGKP TNHMAFGESV AVLAGDALLS FAFEHVAAAT KGAPPERIVR VLGELAVSVG SEGLVAGQVV DVCSEGMAEV GLDHLEFIHH HKTAALLQGS VVLGAILGGG NEEEVAKLRK FANCIGLLFQ VVDDILDVTK SSKELGKKAG KDLVADKTTY PKLIGVEKSM EFADRLNREA QEQLLHFHPH RAAPLIALAN YIAYRDN | ABR15420.1 | 9 |
| Catharanthus roseus | MRSNLCHPLK NQLPISFFLS GTIRKPIFSC SRLSISAIIT KEQTQEESES KSKKEVAFSS SSSFDFKAYM IGKANSVNKA LEDAVLVREP LKIHESMRYS LLAGGKRVRP MLCIAACELF GGTESVAMPS ACAVEMIHTM SLMHDDLPCM DNDDLRRGKP TNHKVFGEDV AVLAGDALLA FAFEHIATAT KGVSSERIVR VVGELAKCIG SEGLVAGQVV DVCSEGIADV GLEHLEFIHI HKTAALLEGS VVLGAIVGGA NDEQISKLRK FARCIGLLFQ VVDDILDVTK SSQELGKTAG KDLVADKVTY PKLLGIDKSR EFAEKLNREA QEQLAEFDPE KAAPLIALAN YIAYRDN | CAA63486.1 | 10 |
| Picrorhiza kurrooa | MSLVNSITWS QTSSILNIQS NISKKLTPFS ILPHPLTNNL PISLFPNPKS NISNSNTPLS AILTKDQKPQ NPPTTPTFDF KSYMLQKADS VNKALDDSIP LTEPLKIQES MRYSLLAGGK RIRPMLCIAA CELVGGDEST AMPAACAVEM VHTMSLMHDD LPCMDNDDLR RGKPTNHKVF | AAW66658.1 | 11 |

TABLE D2-continued

Exemplary geranyl diphosphate synthases large subunits

| Organism | Sequence | Gene Bank Accession No. | SEQ ID NO: |
|---|---|---|---|
| | TEDVAVLAGD AMLAFSFEHV ASLTKGVCSE RIVRVIYELA KCVGCEGLVA GQVVDICSEG MDEVGLEHLE FIHLNKTAAL LEGSVVLGAI LGGGSDEEVE KLRNFARCIG LLFQVVDDIL DVTKSSKELG KTAGKDLVAD KTTYPKLIGI EKSKEFAERL NREAKEHLAG FDQNKAAPLI ALADYIAYRD N | | |
| Ipomoea sp. Kenyan | MSLANPSTTW AKTHSFCGRF RSRSLIRNNE FSINLSSFPT SIRKPLYYHS CSAILTKEQT GVPQEESESE SEKKPAAAKL DFTAYVLGKA KSVNKALEGA VLVKEPLRIH ESMRYSLLAG GKRIRPMLCI AACELVGGDE ETAMPAACAV EMIHTMSLMH DDLPCMDNDD LRRGKPTNHK VYGEDVAVLA GDALLAFAFE HIATATKGAS SEKIVRVVGE LAKSIGAEGL VAGQVVDICS EGISNVGLEH LEFIHLHKTA ALLEGSVVLG AILGGGTEEE IAKLRKFARN IGLLFQVVDD ILDVTKSSKE LGKTAGKDLV ADKVTYPKLL GIQKSREFAE QLNNEAQAQL SGFDQEKAAP LIALANYIAY RDN | BAI47571.1 | 12 |
| Scoparia dulcis | MSLVNPVSTW PNPTRSSVFR PKPAILNTTH LPISPLFAGK PISAVLTKEY SHQTSSTFDF KKYMLEKASS VNKALESAVS LKEPLKIHES MRYSLLAGGK RVRPMLCLAA CELVGGHPST AMPAACSIEM IHTMSLMHDD LPCMDNDHLR RGHPTNHIVF GEDVAVLAGD ALLAYSFEYL ATATEGVLPE RIVRVIAELA KCIRSEGLLA GQVVDICSEG VSEIGLEHLE YIHLHKTAAL LEGSVVLGAI LGGGNDEEVE RLRKFARCIG LLFQVVDDIL DVTKTSVELG KTAGKDLVAD KTTYPKLIGI EKSREFAEKL NREAQEQLVG FDSDKAAPLI ALANYIAYRE N | BAA86285.1 | 13 |
| Antirrhinum majus | MSLVNPITTW STTTTSKSPK NVQTTTRSRS IILPHKISLF PSNPKSKSKT HLRFSISSIL TKNPQESSQK TSKDPTFTLD FKTYMLEKAS SVNKALEQAV LLKEPLKIHE SMRYSLLAGG KRVRPMLCIA ACELVGGLES TAMPSACAVE MIHTMSLIHD DLPCMDNDDL RRGKPTNHKI YGEDVAVLAG DALLAFSFEH VAKSTKGVSS DRIVRVIGEL AKCIGSEGLV AGQVVDISSE GMTEVGLEHL EFIHVHKTAA LLEASVVLGA IVGGADDEDV EKLRKFARCI GLLFQVVDDI LDVTKSSQEL GKTAGKDLVA DKTTYPKLLG IEKSREFAEK LNREAQEQLE GFDSVKAAPL IALANYIAYR DN | AAS82860.1 | 14 |
| Arabidopsis thaliana | MLFTRSVARISSKFLRNRSFYGSSQSLASHRFAII PDQGHSCSDSPHKGYVCRTTYSLKSPVFGGFSH QLYHQSSSLVEEELDPFSLVADELSLLSNKLREM VLAEVPKLASAAEYFFKRGVQGKQFRSTILLLM ATALNVRVPEALIGESTDIVTSELRVRQRGIAEIT EMIHVASLLHDDVLDDADTRRGVGSLNVVMG NKMSVLAGDFLLSRACGALAALKNTEVVALLA TAVEHLVTGETMEITSSTEQRYSMDYYMQKTY YKTASLISNSCKAVAVLTGQTAEVAVLAFEYGR NLGLAFQLIDDILDFTGTSASLGKGSLSDIRHGVI TAPILFAMEEFPQLREVVDQVEKDPRNVDIALE YLGKSKGIQRARELAMEHANLAAAAIGSLPETD NEDVKRSRRALIDLTHRVITRNK | NM_001036406.2 | 15 |
| Chlamydomon as reinhardtii | MSLKHALRQA GGLISAVASS SSSTGAVSLF LNGALDVRPA LHRLFLTAAV PQGYIQTWAE VHDRRVEPFS VVQQEVDVVS ERLRHSVTTG IPALKTAAEY FFRRGIEGKR LRPTLALLMS SALSPAAPSP EYLQVDTRPA AEHPHEMRRR QQRLAEIAEL IHVASLLHDD VIDDAQTRRG VLSLNTSVGN KTAILAGDFL LARASVTLAS LRNSEIVELM SQVLEHLVSG EIMQMTATSE QLLDLEHYLA KTYCKTASLM ANSSRSVAVL AGAAPEVCDM AWSYGRHLGI AFQVVDDLLD LTGSSSVLGK PALNDMRSGL ATAPVLFAAQ | XP_001691069.1 | 16 |

TABLE D2-continued

Exemplary geranyl diphosphate synthases large subunits

| Organism | Sequence | Gene Bank Accession No. | SEQ ID NO: |
|---|---|---|---|
| | EEPALQALIL RRFKHDGDVT KAMSLIERTQ GLRRAEELAA QHAKAAADMI RCLPTAQSDH AEIAREALIQ ITHRVLTRKK | | |

It is well established that the genetic code is degenerate and that some amino acids have multiple codons, and accordingly, multiple polynucleotides can encode the geranyl diphosphate synthases of the invention. Moreover, the polynucleotide sequence can be manipulated for various reasons. Examples include, but are not limited to, the incorporation of preferred codons to enhance the expression of the polynucleotide in various organisms (see generally Nakamura et al., Nuc. Acid. Res. (2000) 28 (1): 292). In addition, silent mutations can be incorporated in order to introduce, or eliminate restriction sites, remove cryptic splice sites, or manipulate the ability of single stranded sequences to form stem-loop structures: (see, e.g., Zuker M., Nucl. Acid Res. (2003); 31(13): 3406-3415). In addition, expression can be further optimized by including consensus sequences at and around the start codon.

Such codon optimization can be completed by standard analysis of the preferred codon usage for the host organism in question, and the synthesis of an optimized nucleic acid via standard DNA synthesis. A number of companies provide such services on a fee for services basis and include for example, DNA2.0, (CA, USA) and Operon Technologies. (CA, USA).

The geranyl diphosphate synthase subunits may be in their native form, i.e., as different apo forms, or allelic variants as they appear in nature, which may differ in their amino acid sequence, for example, by proteolytic processing, including by truncation (e.g., from the N- or C-terminus or both) or other amino acid deletions, additions, insertions, substitutions.

Naturally-occurring chemical modifications including post-translational modifications and degradation products of the geranyl diphosphate synthase subunits, are also specifically included in any of the methods of the invention including for example, pyroglutamyl, iso-aspartyl, proteolytic, phosphorylated, glycosylated, reduced, oxidatized, isomerized, and deaminated variants of the geranyl diphosphate synthase.

The geranyl diphosphate synthase subunits which may be used in any of the methods, DNA constructs, and plants of the invention may have amino acid sequences which are substantially homologous, or substantially similar to any of the native geranyl diphosphate synthase sequences, for example, to any of the native geranyl diphosphate synthase gene sequences listed in Tables D1 and D2.

Alternatively, the geranyl diphosphate synthase may have an amino acid sequence having at least 30% preferably at least 40, 50, 60, 70, 75, 80, 85, 90, 95, 98, or 99% identity with a geranyl diphosphate synthase listed in Tables D1 or D2.

In certain aspects, the geranyl diphosphate synthase small subunit for use in any of the methods and plants of the present invention is at least 80% identical to the mature geranyl diphosphate synthase (shown without the native transit peptide below) small subunit from Menthaxpiperita:

(SEQ ID NO: 17)
MQPYWAAIEADIERYLKKSITIRPPETVFGPMHHLTFAAPATAASTLCLA

ACELVGGDRSQAMAAAAAIHLVHAAAYVHEHLPLTDGSRPVSKPAIQ

HKYGPNVELLTGDGIVPFGFELLAGSVDPARTDDPDRILRVIIEISRAG

GPEGMISGLHREEEIVDGNTSLDFIEYVCKKKYGEMHACGAACGAIL

GGAAEEEIQKLRNFGLYQGTLRGMMEMKNSHQLIDENIIGKLKELALE

ELGGFHGKNAELMSSLVAEPSLYAA.

In certain aspects, the geranyl diphosphate synthase large subunit for use in any of the methods and plants of the present invention is at least 80% identical to the mature geranyl diphosphate synthase (shown without the native transit peptide below) large subunit from Menthaxpiperita:

(SEQ ID NO: 18)
MFDFDGYMLRKATSVNTALEAAVEMKEPLKIHESMRYSLLAGGKRVRPI

LCIAACELVGGDETTAMPAACAVEMIHTMSLMHDDLPCMDNDDLRRGK

PTNHKVFGESTAVLAGDALLSFAFEHVAATTRGAPTERIVRVLGELAVSI

GSEGLVAGQVVDICSEGMAEVGLEHLEYIHHHKTAALLQGSVVLGAILG

GGGEEEVARLRKFANCIGLLFQVVDDILDVTKSSKELGKTAGKDLVADKT

TYPKLIGVEKSKEFADRLKREAVEQLLHFHPHRAAPLIALANYIAYRDN.

Additionally in some embodiments, the geranyl diphosphate synthase subunits and fusion proteins thereof can include modified forms in which the native transit peptide has been removed, or replaced with another synthetic, or naturally occurring, transit peptide sequence.

Such transit sequences are joined to the coding sequence of an expressed gene, and are removed post-translationally from the initial translation product. Various transit peptides which function as described herein are well known in the art, and are described in, for example, Johnson et al. The Plant Cell (1990) 2:525-532; Sauer et al. EMBO J. (1990) 9:3045-3050; Mueckler et al. Science (1985) 229:941-945; Von Heijne, Eur. J. Biochem. (1983) 133:17-21; Yon Heijne, J. Mol. Biol. (1986) 189:239-242; Iturriaga et al. The Plant Cell (1989) 1:381-390; McKnight et al., Nucl. Acid Res. (1990) 18:4939-4943; Matsuoka and Nakamura, Proc. Natl. Acad. Sci. USA (1991) 88:834-838. Such transit peptides can be identified in the primary amino acid sequences of the preproteins by those ordinarily skilled in the art. For example, see Colby et al. (1993) J. Biol. Chem. 268(31): 23016-23024, for the transit peptide sequence of limonene synthase.

In certain embodiments, the transit peptide may comprise the pea RuBisCO small subunit transit peptide:

(SEQ ID NO: 19)
(MASMISSSAVTTVSRASTVQSAAVAPFGGLKSMTGFPVKKVNTDITSI

TSNGGRVKC).

II. Exemplary Limonene Synthase Genes

In any of these methods, fusion proteins, DNA constructs, and transgenic organisms, the term "limonene synthase", or "LS" refers to all naturally-occurring and synthetic genes encoding a limonene synthase. One of skill in the art will appreciate that such limonene synthases may exist in two forms; The (S) or (−) forms producing the (−)-(4S)-limonene enantiomer and the (R) or (+) forms producing the (+)-(4R)-limonene enantiomer. In one aspect, the limonene synthase is from a plant. In one aspect the limonene synthase is from plant that naturally produces terpenes. In certain embodiments, the limonene synthase is the (−) or (S) form. In certain embodiments, the limonene synthase is the (+) or (R) form.

Representative species and Gene bank accession numbers for various species of are listed below in Table D3.

TABLE D3

Exemplary limonene synthases

| Organism | Sequence | Gene Bank Accession No. | SEQ ID NO: |
|---|---|---|---|
| Mentha x piperita | MALKVFSGAM QMPIPSKLTT YLQPSHLNSS PKLLSNTKGT SRSRLRVSCS SSQLTTERRS GNYNPSRWDV DFIQTLHSDY KDEKHARRAS ELVTLVKMEL EKETDQIRQL ELIDDLQRMG LSDHFQNEFK EILSSVYLDH GYYKNPDDKE ERDLYSTSLA FRLLREHGFQ VAQEVFDSFK NEEGEFKESL SDDTRGLLQL YEASFLLTEG ETTLESAREF ATKFLEERVN EGGGDENLLT RIAYSLEIPL HWRIKRPNAP VWIDSYRKRP NMNPVVLDLA ILDLNIVQAH FQQELKESFR WWRNTGFVEK LPFARDRLVE CYFWNTGIIE PRQHASARIM MGKVNALITV IDDIYDVYGT LEELEHFTDL IRRWDIDSID QLPDYMQLCF LALNNFVDET SYDVMKEKGV NVIPYLRQSW VDLADKYMVE ARWFYGGHKP SLEEYLENSW MSISGPCMLT HIFFRVTDSF TKETVDSLYK YHDLVRWSSF VLRLADDLGT SVEEVSRGDV PKSLQCYMSD YNASEAEARK HVKWLIAEVW KKMNAERVSK DSPFGKDFIG CAVDLGRMAQ LMYHNGDGHG TQHPIIHQQM TATLFEPFA | ABW86881.1 | 20 |
| Cannabis sativa | MQCIAFHQFA SSSSLPIWSS IDNRFTPKTS ITSISKPKPK LKSKSNLKSR SRSSTCYSIQ CTVVDNPSST ITNNSDRRSA NYGPPIWSFD FVQSLPIQYK GESYTSRLNK LEKDVKRMLI GVENSLAQLE LIDTIQRLGI SYRFENEIIS ILKEKFTNNN DNPNPNYDLY ATALQFRLLR QYGFEVPQEI FNNFKNHKTG EFKANISNDI MGALGLYEAS FHGKKGESIL EEARIFTTKC LKKYKLMSSS NNNNMTLISL LVNHALEMPL QWRITRSEAK WFIEEIYERK QDMNPTLLEF AKLDFNMLQS TYQEELKVLS RWWKDSKLGE KLPFVRDRLV ECFLWQVGVR FEPQFSYFRI MDTKLYVLLT IIDDMHDIYG TLEELQLFTN ALQRWDLKEL DKLPDYMKTA FYFTYNFTNE LAFDVLQEHG FVHIEYFKKL MVELCKHHLQ EAKWFYSGYK PTLQEYVENG WLSVGGQVIL MHAYFAFTNP VTKEALECLK DGHPNIVRHA SIILRLADDL GTLSDELKRG DVPKSIQCYM HDTGASEDEA REHIKYLISE SWKEMNNEDG NINSFFSNEF VQVCQNLGRA SQFIYQYGDG HASQNNLSKE RVLGLIITPI PM | ABI21837.1 | 21 |
| Mentha longifolia | MALKVFSVAT QMAIPSKLTR CLQPSHLKSS PKLLSSTNSS SRSRLRVYCS SSQLTTERRS GNYNPSRWDV EFIQSLHSDY EEDKHAIRAS ELVTLVKMEL EKETDHIRQL ELIDDLQRMG LSDHFQNEFK EILSSIYLDH HYYKNPFPKE ERDLYSTSLA FRLLREHGFQ VAQEVFDSFK NEEGEFKESL SDDTRGLLQL YEASFLLTEG ETTLESAREF ATKFLEERVN EGGVDGDLLT RIAYSLDIPL HWRIKRPNAP AWIEWYRKRP DMNPVVLELA ILDLNIVQAQ FQEELKESFR WWRNTGFVEK LPFARDRLVE CYFWNTGIIE PRQHASARIM MGKVNALITV IDDIYDVYGT LEELEQFTDL IRRWDINSID QLPDYMQLCF | AAD50304.1 | 22 |

TABLE D3-continued

Exemplary limonene synthases

| Organism | Sequence | Gene Bank Accession No. | SEQ ID NO: |
|---|---|---|---|
| | LALNNFVDDT SYDVMKEKGV NVIPYLRQSW VDLADKYMVE ARWFYGGHKP SLEEYLENSW QSISGPCMLT HIFFRVTDSF TKETVDSLYK YHDLVRWSSF VLRLADDLGT SVEEVSRGDV PKSLQCYMSD YNASEAEARK HVKWLIAEVW KKMNAERVSK DSPFGKDFIG CAADLGRMAQ LMYHNGDHG TQHPIIHQQM TRTLFEPFA | | |
| Picea sitchensis | MSPVSAIPLA YKLCLPRSLI SSSRELNPLH ITIPNLGMCR RGKSMAPASM SMILTAAVSD DDRVQRRRGN YHSNLWDDDF IQSLSTPYGE PSYRESAERL KGEIKKMFRS MSKEDEELIT PLNDLIQRLW MVDSVERLGI DRHFKNEIKS ALDYVYSYWN EKGIGCGRDS VVADLNSTAL GFRTLRLHGY NVSSEVLKVF EDQNGQFACS PSKTEGEIRS ALNLYRASLI AFPGEKVMED AEIFSSRYLK EAVQKIPDCS LSQEIAYALE YGWHTNMPRL EARNYMDVFG HPSSPWLKKN KTQYMDGEKL LELAKLEFNI FHSLQQEELQ YISRWWKDSG LPKLAFSRHR HVEYYTLGSC IATDPKHRAF RLGFVKTCHL NTVLDDIYDT FGTMDEIELF TEAVRRWDPS ETESLPDYMK GVYMVLYEAL TEMAQEAEKT QGRDTLNYAR KAWEIYLDSY IQEAKWIASG YLPTFQEYFE NGKISSAYRA AALTPILTLD VPLPEYILKG IDFPSRFNDL ASSFLRLRGD TRCYKADRAR GEEASCISCY MKDNPGSTEE DALNHINSMI NEIIKELNWE LLRPDSNIPM PARKHAFDIT RALHHLYKYR DGFSVATKET KSLVSRMVLE PVTL | ABA86248.1 | 23 |
| Perilla frutescens var. frutescens | 1 MYTGVIMHMA IPIKPAHYLH NSGRSYASQL CGFSSTSTRA AIARLPLCLR PRCSLQASDQ RRSGNYSPSF WNADYILSLN NHYKEESRHM KRAGELIVQV KMVMGKETDP VVQLELIDDL HKLALSHHFE KEIKEILFNI SIYDHKIMVE RDLYSTALAF RLLRQYGFKV PQEVFDCFKN DNGEFKRSLS SDTKGLLQLY EASFLLTEGE MTLELAREFA TIFLQEKLND KTIDDDDDAD TNLISCVRHS LDIPIHWRIQ RPNASWWIDA YKRRSHMNPL VLELAKLDLN IFQAQFQQEL KQDLGWWKNT CLAEKLPFTR DRLVECYFWC TGIIQPLQHE NARVTLAKVN ALITTLDDIY DVYGTLEELE LFTEAIRRWD VSSIDHLPNY MQLCFLALNN FVDDTAYDVM KEKDINIIPY LRKSWLDLAE TYLVEAKWFY SGHKPNMEEY LNNAWISISG PVMLCHVFFR VTDSITRETV ESLFKYHDLI RYSSTILRLA DDLGTSLEEV SRGDVPKSIQ CYMNDNNASE EEARRHVRWL IAETWKKINE EVWSADSPFC KDFIACAADM GRMAQFMYHN GDGHGIQNPQ IHQQMTDILF EQWL | AAK06663.1 | 24 |
| Rosmarinus officinalis | MFTIMTSMAI PMKPVKHVHN FAARRDPKLR LASPTCWRQS CSLKLTTDYP CDQLQSTRRS GNYKPTLWDF ERIQSLNSVY TEEKYTTRAS ELVVQVKKLL LLESNWFLQL ELIDDLQKLG VSYRFNHEIN QILNRIYLEQ KYCNNSERDL YSTALAFRLL RQHGLKVSQD VFDFFKNDEG EFEPNLGDNT KGLLQLYEAS FLLTEGEMSL EQARVFSTNL QKKLDDGIM DEYLSSLVRR SLELPLHWSV QRPNSRWLID AYTNRSDVNP ILIELAKLDF NIVQASYHEE LKEVSRWWKE TELAEKLPFA RDRVVENYIW NVGLLFQPQY GYPRIMTTKL FILITVIDDV FDVYGTLEET ELFKKAILSW DVEVLDQLPN YMQICYMALD SFINEMAYHV LKEQGVLIIQ DLRKFWADLC VAYAKEAEWY HTGHKPTMEE YIDVAWISIS AHLILAHVFF LITNPIGKEA AESLRNYDDI IRNSAMILRL ADDLGTSSYE MQRGDVPKAV ECYMNEMGAS VEEAREHVKC | ABD77416.1 | 25 |

TABLE D3-continued

Exemplary limonene synthases

| Organism | Sequence | Gene Bank Accession No. | SEQ ID NO: |
|---|---|---|---|
| | MIREAWMKTS AERFKESPFS KDFIRSAADL GRHAQYMYQH GDGHGIRNPQ MEERISTLIF QPID | | |
| Citrus jambhiri | MSSCINPSTL VTSVNAFKCL PLATNKAAIR IMAKYKPVQC LISAKYDNLT VDRRSANYQP SIWDHDFLQS LNSNYTDEAY KRRAEELRGK VKIAIKDVIE PLDQLELIDN LQRLGLAHRF ETEIRNILNN IYNNNKDYNW RKENLYATSL EFRLLRQHGY PVSQEVFNGF KDDQGGFICD DFKGILSLHE ASYYSLEGES IMEEAWQFTS KHLKEVMISK NMEEDVFVAE QAKRALELPL HWKVPMLEAR WFIHIYERRE DKNHLLLELA KMEFNTLQAI YQEELKEISG WWKDTGLGEK LSFARNRLVA SFLWSMGIAF EPQFAYCRRV LTISIALITV IDDIYDVYGT LDELEIFTDA VERWDINYAL KHLPGYMKMC FLALYNFVNE FAYYVLKQQD FDLLLSIKNA WLGLIQAYLV EAKWYHSKYT PKLEEYLENG LVSITGPLII TISYLSGTNP IIKKELEFLE SNPDIVHWSS KIFRLQDDLG TSSDEIQRGD VPKSIQCYMH ETGASEEVAR QHIKDMMRQM WKKVNAYTAD KDSPLTGTTT EFLLNLVRMS HFMYLHGDGH GVQNQETIDV GFTLLFQPIP LEDKHMAFTA SPGTKG | BAF73932.1 | 26 |

(R) OR (+) SYNTHASES

| Organism | Sequence | Gene Bank Accession No. | SEQ ID NO: |
|---|---|---|---|
| Toona sinensis (+synthase) | MASHVLASLR SASARISTRL QSRSCILATA TSFSNGFVSA SLVQSMSTTT QCDESVARRS ANYEPPIWTY DYVQSLRNPY AGGSYAKRIE KLKGDVRVML QKLVDLDPLH QLEFIDTLQR LGVSYHYQEG IKGILDTVYN NYMQKQESLY AVALGFRLFR QHGYHIPADI FSSFRDDKGN LKSCLGDDCR GILALYEAAH LLVEEERDIF YEIVNFTTAY LKEYVKHDND EYLSALVNHS LEIPLHWRVL RLEARWFIGA YERAPNTHPI LLEFAKLDFN DVQATHQEDL KFMSRWWKNT GLDREKMNFA RDRIVQNVLW SLGIIFEPQF AYCRRMSVKA YAFITLIDDV YDVYGTLDEL ELFTDAVDRW DATAIEKLPD YMKPIFRTLY TSINDMALDA RKDRGVDTRP FLHKAWSTLF NYYLMEAKWF SNGYMPTYKE YMDIAWFSVG GPVMIVHSYC AIANPATKEN MEFFQEYYDI IRLCSTILRF KDDMGTSSDE LKRGDNPKSI QCYMHESGVS EKEARQHLGN LITETWMKVN KNRAENPHLS DVYMGIAINM ARMALCMYQF GDGHAVEAHS KDRVLSLLIN PIPCP | BAH03282.1 | 27 |
| Citrus limon | MSSCINPSTL VTSVNAFKCL PLATNKAAIR IMAKYKPVQC LISAKYDNLT VDRRSANYQP SIWDHDFLQS LNSNYTDEAY KRRAEELRGK VKIAIKDVIE PLDQLELIDN LQRLGLAHRF ETEIRNILNN IYNNNKDYNW RKENLYATSL EFRLLRQHGY PVSQEVFNGF KDDQGGFICD DFKGILSLHE ASYYSLEGES IMEEAWQFTS KHLKEVMISK NMEEDVFVAE QAKRALELPL HWKVPMLEAR WFIHIYERRE DKNHLLLELA KMEFNTLQAI YQEELKEISG WWKDTGLGEK LSFARNRLVA SFLWSMGIAF EPQFAYCRRV LTISIALITV IDDIYDVYGT LDELEIFTDA VERWDINYAL KHLPGYMKMC FLALYNFVNE FAYYVLKQQD FDLLLSIKNA WLGLIQAYLV EAKWYHSKYT PKLEEYLENG LVSITGPLII TISYLSGTNP IIKKELEFLE SNPDIVHWSS KIFRLQDDLG TSSDEIQRGD VPKSIQCYMH ETGASEEVAR QHIKDMMRQM WKKVNAYTAD KDSPLTGTTT EFLLNLVRMS HFMYLHGDGH GVQNQETIDV GFTLLFQPIP LEDKHMAFTA SPGTKG | Q8L5K3.1 | 28 |

TABLE D3-continued

Exemplary limonene synthases

| Organism | Sequence | Gene Bank Accession No. | SEQ ID NO: |
|---|---|---|---|
| Ricinus communis | MEIVFSSSLS STLTVTKILR SPRHATTGNM QDYSRFPLFF TIASRSNASQ AKHRRSANYH PTIWDPKAIE CLRTPYTYDG VHGARLQKLK DEVRSLLTTF TKEPCGQLKL IDSMQRLGVS YHFREEIEEI LNLVELDSDS DLYTTALHFR LLRQHGFTIS KEVFEKFRNE DGKFKDSLKE DILGLLSLYD ASYLGMHGEH ILEEAKDFST EQLKSLLGRS QGDIVTYQVK QALDVPLHWR MQRIENRNYI NIYQKEDTNN LALLELAKLD YNLVQSVYQI ELKELARWWI ALGFREKLHF SRDRLMENYL WSMGMIFEPH FSKCRIYLTK FICILSSIDD MYDIYGSLDE LELFTSALKR WDPMALEELP DYMKICYLAI LNFASELVYD VLKEEGLYTL PFIRDEWVKL CQAYLVEARW FNSGYTPTFD EYLENAWISV GGHEAIVHAC ALLGHTSTED FQNFLKHGFE LIYWSSLLVR LNDDLGTSQA EIKRGDVVKS IQCYMIEKGV SEKEAKDHVK GLISHAWKVL NEESVKCSLS RSFVNVCLNM TRTAQCIFQY GDGIGTSIGV TKDRLEFLIV KPIL | EEF46639.1 | 29 |

It is well established that the genetic code is degenerate and that some amino acids have multiple codons, and accordingly, multiple polynucleotides can encode the limonene synthase of the invention. Moreover, the polynucleotide sequence can be manipulated for various reasons. Examples include, but are not limited to, the incorporation of preferred codons to enhance the expression of the polynucleotide in various organisms (see generally Nakamura et al., Nuc. Acid. Res. (2000) 28 (1): 292). In addition, silent mutations can be incorporated in order to introduce, or eliminate restriction sites, remove cryptic splice sites, or manipulate the ability of single stranded sequences to form stem-loop structures: (see, e.g., Zuker M., Nucl. Acid Res. (2003); 31(13): 3406-3415). In addition, expression can be further optimized by including consensus sequences at and around the start codon.

Such codon optimization can be completed by standard analysis of the preferred codon usage for the host organism in question, and the synthesis of an optimized nucleic acid via standard DNA synthesis. A number of companies provide such services on a fee for services basis and include for example, DNA2.0, (CA, USA) and Operon Technologies. (CA, USA).

The limonene synthase may be in its native form, i.e., as different apo forms, or allelic variants as they appear in nature, which may differ in their amino acid sequence, for example, by proteolytic processing, including by truncation (e.g., from the N- or C-terminus or both) or other amino acid deletions, additions, insertions, substitutions.

Naturally-occurring chemical modifications including post-translational modifications and degradation products of the limonene synthase, are also specifically included in any of the methods of the invention including for example, pyroglutamyl, iso-aspartyl, proteolytic, phosphorylated, glycosylated, reduced, oxidatized, isomerized, and deaminated variants of the limonene synthase.

The limonene synthase which may be used in any of the methods, fusion proteins, DNA constructs, and plants of the invention may have amino acid sequences which are substantially homologous, or substantially similar to any of the native limonene synthase sequences, for example, to any of the native limonene synthase gene sequences listed in Table D3.

Alternatively, the limonene synthase may have an amino acid sequence having at least 30% preferably at least 40, 50, 60, 70, 75, 80, 85, 90, 95, 98, or 99% identity with a limonene synthase listed in Table D3. In certain embodiments, the limonene synthase for use in any of the methods and plants of the present invention is at least 80% identical to the mature limonene synthase from Mentha×piperita (shown both with and without the native transit peptide):

(SEQ ID NO: 30)
MALKVFSGAMQMPIPSKLTTYLQPSHLNSSPKLLSNTKGTSRSRLRVSCS
SSQLTTERRSGNYNPSRWDVDFIQTLHSDYKDEKHARRASELVTLVKME
LEKETDQIRQLELIDDLQRMGLSDHFQNEFKEILSSVYLDHGYYKNPDPK
EERDLYSTSLAFRLLREHGFQVAQEVFDSFKNEEGEFKESLSDDTRGLLQ
LYEASFLLTEGETTLESAREFATKFLEERVNEGGGDENLLTRIAYSLEIP
LHWRIKRPNAPVWIDSYRKRPNMNPVVLDLAILDLNIVQAHFQQELKESF
RWWRNTGFVEKLPFARDRLVECYFWNTGIIEPRQHASARIMMGKVNALIT
VIDDIYDVYGTLEELEHFTDLIRRWDIDSIDQLPDYMQLCFLALNNFVDE
TSYDVMKEKGVNVIPYLRQSWVDLADKYMVEARWFYGGHKPSLEEYLEN
SWMSISGPCMLTHIFFRVTDSFTKETVDSLYKYHDLVRWSSFVLRLADDL
GTSVEEVSRGDVPKSLQCYMSDYNASEAEARKHVKWLIAEVWKKMNA
ERVSKDSPFGKDFIGCAVDLGRMAQLMYHNGDGHGTQHPIIHQQMTAT
LFEPFA.

(SEQ ID NO: 31)
MQLTTERRSGNYNPSRWDVDFIQTLHSDYKDEKHARRASELVTLVKME
LEKETDQIRQLELIDDLQRMGLSDHFQNEFKEILSSVYLDHGYYKNPDP
KEERDLYSTSLAFRLLREHGFQVAQEVFDSFKNEEGEFKESLSDDTR
GLLQLYEASFLLTEGETTLESAREFATKFLEERVNEGGGDENLLTRIAY
SLEIPLHWRIKRPNAPVWIDSYRKRPNMNPVVLDLAILDLNIVQAHFQQ
ELKESFRWWRNTGFVEKLPFARDRLVECYFWNTGIIEPRQHASARIMM
GKVNALITVIDDIYDVYGTLEELEHFTDLIRRWDIDSIDQLPDYMQLCFL
ALNNFVDETSYDVMKEKGVNVIPYLRQSWVDLADKYMVEARWFYGG
HKPSLEEYLENSWMSISGPCMLTHIFFRVTDSFTKETVDSLYKYHDLV
RWSSFVLRLADDLGTSVEEVSRGDVPKSLQCYMSDYNASEAEARK
HVKWLIAEVWKKMNAERVSKDSPFGKDFIGCAVDLGRMAQLMYHNG
DGHGTQHPIIHQQMTATLFEPFA.

Additionally in some embodiments, the limonene synthase, and fusion proteins thereof, can include modified forms in which the native transit peptide has been removed, or replaced with another synthetic, or naturally occurring, transit peptide sequence derived from another well characterized chloroplast localized proteins. Such transit sequences are joined to the coding sequence of an expressed gene, and are removed post-translationally from the initial translation product. Various transit peptides which function as described herein are well known in the art, and are described in, for example, Johnson et al. The Plant Cell (1990) 2:525-532; Sauer et al. EMBO J. (1990) 9:3045-3050; Mueckler et al. Science (1985) 229:941-945; Von Heijne, Eur. J. Biochem. (1983) 133:17-21; Yon Heijne, J. Mol. Biol. (1986) 189:239-242; Iturriaga et al. The Plant Cell (1989) 1:381-390; McKnight et al., Nucl. Acid Res. (1990) 18:4939-4943; Matsuoka and Nakamura, Proc. Natl. Acad. Sci. USA (1991) 88:834-838. Such transit peptides can be identified in the primary amino acid sequences of the preproteins by those ordinarily skilled in the art. For example, see Colby et al. (1993) J. Biol. Chem. 268(31): 23016-23024, for the transit peptide sequence of limonene synthase.

In certain embodiments, the transit peptide may comprise the pea RuBisCO small subunit transit peptide:

(SEQ ID NO: 32)
(MASMISSSAVTTVSRASTVQSAAVAPFGGLKSMTGFPVKKVNTDITSI

TSNGGRVKC), as shown fused to the 5' region of the LS gene below:

(SEQ ID NO: 33)
MASMISSSAVTTVSRASTVQSAAVAPFGGLKSMTGFPVKKVNTDITSI

TSNGGRVKCMDPQLTTERRSGNYNPSRWDVDFIQTLHSDYKDEKHA

RRASELVTLVKMELEKETDQIRQLELIDDLQRMGLSDHFQNEFKEILS

SVYLDHGYYKNPDPKEERDLYSTSLAFRLLREHGFQVAQEVFDSFKN

EEGEFKESLSDDTRGLLQLYEASFLLTEGETTLESAREFATKFLEERVN

EGGGDENLLTRIAYSLEIPLHWRIKRPNAPVWIDSYRKRPNMNPVVLDL

AILDLNIVQAHFQQELKESFRWWRNTGFVEKLPFARDRLVECYFWNTG

IIEPRQHASARIMMGKVNALITVIDDIYDVYGTLEELEHFTDLIRRWDID

SIDQLPDYMQLCFLALNNFVDETSYDVMKEKGVNVIPYLRQSWVDLA

DKYMVEARWFYGGHKPSLEEYLENSWMSISGPCMLTHIFFRVTDSF

TKETVDSLYKYHDLVRWSSFVLRLADDLGTSVEEVSRGDVPKSLQC

YMSDYNASEAEARKHVKWLIAEVWKKMNAERVSKDSPFGKDFIGC

AVDLGRMAQLMYHNGDGHGTQHPIIHQQMTATLFEPFA

IV. Auxiliary Enzymes

In certain embodiments of any of the methods, fusion proteins, transgenic plants and DNA constructs disclosed herein, the invention includes the further expression, or introduction of further synthetic enzymes to promote the formation of distinct classes of terpenes. Representative exemplary enzymes include for example, the enzymes listed in Table D4.

TABLE D4

Exemplary Auxiliary Enzymes

| Species | Name | GeneBank Accession No. | Type of Synthase |
|---|---|---|---|
| Mentha x piperita | farnesyl diphosphate synthase | AAK63847.1 | Prenyl-transferases: |
| Salvia officinalis | Sabinene synthase | AAC26018.1 | monoterpene synthases |

TABLE D4-continued

Exemplary Auxiliary Enzymes

| Species | Name | GeneBank Accession No. | Type of Synthase |
|---|---|---|---|
| Arabidopsis thaliana | Sabinene synthase | BAA95770.1 | monoterpene synthases |
| Picea sitchensis | Pinene synthase | AAP72020.1 | monoterpene synthases |
| Aspergillus oryzae RIB40 | Anstolochene synthase | XP_001825789 | sesquiterpene synthases |
| Helianthus annuus | Cadinene synthase | ACA33926.1 | sesquiterpene synthases |
| Solanum lycopersicum | Vetispiradiene synthase | AAG09950.1 | sesquiterpene synthases |

Those of skill in the art will appreciate that the foregoing list represents only representative exemplary enzymes that could be additionally expressed with the GDP synthase and limonene fusion proteins to enhance the relative production of a specific terpene, or class of terpene, for example to increase the relative production of specific sesquiterpene terpenes.

V. Fusion Proteins

In certain embodiments, the invention includes fusion proteins of either the GDP synthase large and small subunits, or one or more of these subunits fused to limonene synthase. In certain embodiments these fusion proteins may increase the relative enzymatic specific activity and/or efficiency of terpene synthesis.

Examples of such fusion proteins include, i) the fusion of the GDP synthase large subunit to the GDP synthase small subunit; ii) the fusion GDP synthase large subunit to limonene synthase; iii) the fusion of the GDP synthase small subunit to limonene synthase. It will be appreciated that any of such fusion proteins can be arranged in a number of different of relative orientations. Specific embodiments contemplated herein include:

5' TP-GDP synthase (large subunit)-GDP synthase (small subunit) 3'
5' TP-GDP synthase (small subunit)-GDP synthase (large subunit) 3'
5' TP-GDP synthase (large subunit)-limonene synthase 3'
5' TP-GDP synthase (small subunit)-limonene synthase 3'
5' TP-limonene synthase-GDP synthase (large subunit) 3'
5' TP-limonene synthase-GDP synthase (small subunit) 3'
5' TP-limonene synthase-GDP synthase (large subunit)-GDP synthase (small subunit) 3'
5' TP-limonene synthase-GDP synthase (small subunit)-GDP synthase (large subunit) 3'
5' TP-GDP synthase (large subunit)-GDP synthase (small subunit)-limonene synthase 3'
5' TP-GDP synthase (small subunit)-GDP synthase (large subunit)-limonene synthase 3'
5' TP-GDP synthase (large subunit)-limonene synthase-GDP synthase (small subunit) 3'
5' TP-GDP synthase (small subunit)-limonene synthase-GDP synthase (large subunit) 3'

Where "-" represents an optional linker, and "TP" represents a transit peptide.

It will be appreciated that a flexible molecular linker (or spacer) optionally may be interposed between, and covalently join, any of the transit peptides, GPP synthase subunits and limonene synthases disclosed herein. Any such fusion protein may be used in any of the methods, proteins, polynucleotides and host cells of the present invention.

Exemplary Fusion Protein Sequences Include:
5' TP-GDP Synthase (Small Subunit)-GDP Synthase (Large Subunit) 3'.

The construct shown includes a 10 amino acid linker (SSNNLGIEGR (SEQ ID NO:34)), with the native transit peptide sequences removed from the GDS large and small subunits, and with a 5' transit peptide from the pea RuBisCO small subunit.

(SEQ ID NO: 34)
MASMISSSAVTTVSRASTVQSAAVAPFGGLKSMTGFPVKKVNTDITSI

TSNGGRVKCMDPQPYWAAIEADIERYLKKSITIRPPETVFGPMHHLTF

AAPATAASTLCLAACELVGGDRSQAMAAAAAIHLVHAAAYVHEHLP

LTDGSRPVSKPAIQHKYGPNVELLTGDGIVPFGFELLAGSVDPARTD

DPDRILRVIIEISRAGGPEGMISGLHREEEIVDGNTSLDFIEYVCKKKYG

EMHACGAACGAILGGAAEEEIQKLRNFGLYQGTLRGMMEMKNSHQL

IDENIIGKLKELALEELGGFHGKNAELMSSLVAEPSLYAASSNNLGIE

GRFDFDGYMLRKATSVNTALEAAVEMKEPLKIHESMRYSLLAGGKR

VRPILCIAACELVGGDETTAMPAACAVEMIHTMSLMHDDLPCMDND

DLRRGKPTNHKVFGESTAVLAGDALLSFAFEHVAATTRGAPTERIVR

VLGELAVSIGSEGLVAGQVVDICSEGMAEVGLEHLEYIHHHKTAALL

QGSVVLGAILGGGEEEVARLRKFANCIGLLFQVVDDILDVTKSSKE

LGKTAGKDLVADKTTYPKLIGVEKSKEFADRLKREAVEQLLHFHPHR

AAPLIALANYIAYRDN

5' TP-Limonene Synthase-GDP Synthase (Small Subunit)-GDP Synthase (Large Subunit) 3'

The construct shown includes a 9 amino acid linker (SGGSGGSGG (SEQ ID NO:36)), linking the limonene synthase to the GDS (small subunit), with the native transit peptide sequences removed from the GDS subunit and limonene synthase, and with the transit peptide from the pea RuBisCO small subunit added to the N-terminus of limonene synthase.

(SEQ ID NO: 37)
MASMISSSAVTTVSRASTVQSAAVAPFGGLKSMTGFPVKKVNTDITSI

TSNGGRVKCMDPQLTTERRSGNYNPSRWDVDFIQTLHSDYKDEKHA

RRASELVTLVKMELEKETDQIRQLELIDDLQRMGLSDHFQNEFKEILS

SVYLDHGYYKNPDPKEERDLYSTSLAFRLLREHGFQVAQEVFDSFK

NEEGEFKESLSDDTRGLLQLYEASFLLTEGETTLESAREFATKFLEERVN

EGGGDENLLTRIAYSLEIPLHWRIKRPNAPVWIDSYRKRPNMNPVVLD

LAILDLNIVQAHFQQELKESFRWWRNTGFVEKLPFARDRLVECYFWNT

GIIEPRQHASARIMMGKVNALITVIDDIYDVYGTLEELEHFTDLIRRWDI

DSIDQLPDYMQLCFLALNNFVDETSYDVMKEKGVNVIPYLRQSWVD

LADKYMVEARWFYGGHKPSLEEYLENSWMSISGPCMLTHIFFRVTD

SFTKETVDSLYKYHDLVRWSSFVLRLADDLGTSVEEVSRGDVPKS

LQCYMSDYNASEAEARKHVKWLIAEVWKKMNAERVSKDSPFGKD

FIGCAVDLGRMAQLMYHNGDGHGTQHPIIHQQMTATLFEPFASGGS

GGSGGMQPYWAAIEADIERYLKKSITIRPPETVFGPMHHLTFAAPATA

ASTLCLAACELVGGDRSQAMAAAAAIHLVHAAAYVHEHLPLTDGSRPV

SKPAIQHKYGPNVELLTGDGIVPFGFELLAGSVDPARTDDPDRILRVIIE

ISRAGGPEGMISGLHREEEIVDGNTSLDFIEYVCKKKYGEMHACGAAC

GAILGGAAEEEIQKLRNFGLYQGTLRGMMEMKNSHQLIDENIIGKLKEL

ALEELGGFHGKNAELMSSLVAEPSLYAASSNNLGIEGRFDFDGYMLR

KATSVNTALEAAVEMKEPLKIHESMRYSLLAGGKRVRPILCIAACELV

GGDETTAMPAACAVEMIHTMSLMHDDLPCMDNDDLRRGKPTNHKV

FGESTAVLAGDALLSFAFEHVAATTRGAPTERIVRVLGELAVSIGSE

GLVAGQVVDICSEGMAEVGLEHLEYIHHHKTAALLQGSVVLGAILGG

GGEEEVARLRKFANCIGLLFQVVDDILDVTKSSKELGKTAGKDLVADK

TTYPKLIGVEKSKEFADRLKREAVEQLLHFHPHRAAPLIALANYIAYRDN

5' TP-GDP Synthase (Small Subunit)-GDP Synthase (Large Subunit)-Limonene Synthase The construct shown also includes a 9 amino acid linker (SGGSGGSGG (SEQ ID NO:36)) linking GDS (large) to limonene synthase. Here the native transit peptide sequences have been removed from the GDS large and small subunits, and limonene synthase, and the 5' transit peptide from the pea RuBisCO small subunit added to the N-terminus.

(SEQ ID NO: 38)
MASMISSSAVTTVSRASTVQSAAVAPFGGLKSMTGFPVKKVNTDITSI

TSNGGRVKCMDPQPYWAAIEADIERYLKKSITIRPPETVFGPMHHLTFA

APATAASTLCLAACELVGGDRSQAMAAAAAIHLVHAAAYVHEHLPLT

DGSRPVSKPAIQHKYGPNVELLTGDGIVPFGFELLAGSVDPARTDDP

DRILRVIIEISRAGGPEGMISGLHREEEIVDGNTSLDFIEYVCKKKYG

EMHACGAACGAILGGAAEEEIQKLRNFGLYQGTLRGMMEMKNSHQL

IDENIIGKLKELALEELGGFHGKNAELMSSLVAEPSLYAASSNNLGIE

GRFDFDGYMLRKATSVNTALEAAVEMKEPLKIHESMRYSLLAGGKR

VRPILCIAACELVGGDETTAMPAACAVEMIHTMSLMHDDLPCMDND

DLRRGKPTNHKVFGESTAVLAGDALLSFAFEHVAATTRGAPTERIVR

VLGELAVSIGSEGLVAGQVVDICSEGMAEVGLEHLEYIHHHKTAALL

QGSVVLGAILGGGEEEVARLRKFANCIGLLFQVVDDILDVTKSSKE

LGKTAGKDLVADKTTYPKLIGVEKSKEFADRLKREAVEQLLHFHPHR

AAPLIALANYIAYRDNSGGSGGSGGMQLTTERRSGNYNPSRWDVDFI

QTLHSDYKDEKHARRASELVTLVKMELEKETDQIRQLELIDDLQRMGL

SDHFQNEFKEILSSVYLDHGYYKNPDPKEERDLYSTSLAFRLLREHGF

QVAQEVFDSFKNEEGEFKESLSDDTRGLLQLYEASFLLTEGETTLES

AREFATKFLEERVNEGGGDENLLTRIAYSLEIPLHWRIKRPNAPVWID

SYRKRPNMNPVVLDLAILDLNIVQAHFQQELKESFRWWRNTGFVEK

LPFARDRLVECYFWNTGIIEPRQHASAREVIMGKVNALITVIDDIYDVYG

TLEELEHFTDLIRRWDIDSIDQLPDYMQLCFLALNNFVDETSYDVMKEK

GVNVIPYLRQSWVDLADKYMVEARWFYGGHKPSLEEYLENSWMSISG

-continued

PCMLTHIFFRVTDSFTKETVDSLYKYHDLVRWSSFVLRLADDLGTSVE

EVSRGDVPKSLQCYMSDYNASEAEARKHVKWLIAEVWKKMNAERVS

KDSPFGKDFIGCAVDLGRMAQLMYHNGDGHGTQHPIIHQQMTATLFEPFA

VI. DNA Constructs

In some embodiments, the DNA constructs, and expression vectors of the invention include separate expression vectors each including either the isolated geranyl diphosphate synthase or limonene synthase, or the previously described fusion proteins thereof.

In one aspect the DNA constructs and expression vectors for the GDS and limonene fusion proteins comprise polynucleotide sequences encoding any of the previously described fusion proteins operatively coupled to a promoter, transit peptide sequence and transcriptional terminator for efficient expression in the organism of interest. In one aspect of any of these expression vectors, the geranyl diphosphate synthase is codon optimized for expression in the organism of interest.

In some embodiments, the geranyl diphosphate synthase DNA constructs and expression vectors of the invention further comprise polynucleotide sequences encoding one or more of the following elements i) a selectable marker gene to enable antibiotic selection, ii) a screenable marker gene to enable visual identification of transformed cells, and iii) T-element DNA sequences to enable *Agrobacterium tumefaciens* mediated transformation. Exemplary expression cassettes are described in the Examples.

In certain embodiments, the DNA constructs and expression vectors for the limonene synthase, comprise polynucleotide sequences encoding any of the previously described limonene synthase, genes (Table D2) operatively coupled to a promoter, and transcriptional terminator for efficient expression in the organism of interest. In one aspect of any of these expression vectors, the limonene synthase is codon optimized for expression in the photosynthetic organism of interest. In one aspect the limonene synthase gene encodes a limonene synthase of *Mentha×piperita*.

In some embodiments, the limonene synthase DNA constructs and expression vectors of the invention further comprise polynucleotide sequences encoding one or more of the following elements i) a selectable marker gene to enable antibiotic selection, ii) a screenable marker gene to enable visual identification of transformed cells, and iii) T-element DNA sequences to enable *Agrobacterium tumefaciens* mediated transformation. Exemplary expression cassettes are described in the Examples.

In another embodiment, the DNA constructs, and expression vectors of the invention include expression vectors comprising nucleic acid sequences encoding i) the GDS large and small subunit fusion protein and ii) a limonene synthase gene. Exemplary expression cassettes are described in the Examples.

Those of skill in the art will appreciate that the foregoing descriptions of expression cassettes represents only illustrative examples of expression cassettes that could be readily constructed, and is not intended to represent an exhaustive list of all possible DNA constructs or expression cassettes that could be constructed.

Moreover expression vectors suitable for use in expressing the claimed DNA constructs in plants, and methods for their construction are generally well known, and need not be limited. These techniques, including techniques for nucleic acid manipulation of genes such as subcloning a subject promoter, or nucleic acid sequences encoding a gene of interest into expression vectors, labeling probes, DNA hybridization, and the like, and are described generally in Sambrook, et al., *Molecular Cloning—A Laboratory Manual* (2nd Ed.), Vol. 1-3, Cold Spring Harbor Laboratory, Cold Spring Harbor, N.Y., 1989, which is incorporated herein by reference. For instance, various procedures, such as PCR, or site directed mutagenesis can be used to introduce a restriction site at the start codon of a heterologous gene of interest. Heterologous DNA sequences are then linked to a suitable expression control sequences such that the expression of the gene of interest are regulated (operatively coupled) by the promoter. DNA constructs comprising an expression cassette for the gene of interest can then be inserted into a variety of expression vectors. Such vectors include expression vectors that are useful in the transformation of plant cells. Many other such vectors useful in the transformation of plant cells can be constructed by the use of recombinant DNA techniques well known to those of skill in the art as described above.

Exemplary expression vectors for expression in protoplasts or plant tissues include pUC 18/19 or pUC 118/119 (GIBCO BRL, Inc., MD); pBluescript SK (+/−) and pBluescript KS (+/−) (STRATAGENE, La Jolla, Calif.); pT7Blue T-vector (NOVAGEN, Inc., WI); pGEM-3Z/4Z (PROMEGA Inc., Madison, Wis.), and the like vectors, such as is described herein Exemplary vectors for expression using *Agrobacterium tumefaciens*-mediated plant transformation include for example, pBin 19 (CLONETECH), Frisch et al, *Plant Mol. Biol.,* 27:405-409, 1995; pCAMBIA 1200 and pCAMBIA 1201 (Center for the Application of Molecular Biology to International Agriculture, Canberra, Australia); pGA482, An et al, *EMBO J.,* 4:277-284, 1985; pCGN1547, (CALGENE Inc.) McBride et al, *Plant Mol. Biol.,* 14:269-276, 1990, and the like vectors, such as is described herein.

Expression Control Sequences:

DNA constructs will typically include expression control sequences comprising promoters to drive expression of the limonene synthase and geranyl diphosphate synthase within the plastids of the photosynthetic organism. Promoters may provide ubiquitous, cell type specific, constitutive promoter or inducible promoter expression. Basal promoters in plants typically comprise canonical regions associated with the initiation of transcription, such as CAAT and TATA boxes. The TATA box element is usually located approximately 20 to 35 nucleotides upstream of the initiation site of transcription. The CAAT box element is usually located approximately 40 to 200 nucleotides upstream of the start site of transcription. The location of these basal promoter elements result in the synthesis of an RNA transcript comprising nucleotides upstream of the translational ATG start site. The region of RNA upstream of the ATG is commonly referred to as a 5' untranslated region or 5' UTR. It is possible to use standard molecular biology techniques to make combinations of basal promoters, that is, regions comprising sequences from the CAAT box to the translational start site, with other upstream promoter elements to enhance or otherwise alter promoter activity or specificity. In some aspects promoters may be altered to contain "enhancer DNA" to assist in elevating gene expression. As is known in the art certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are particularly useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (U.S. Pat. No. 5,593,874), the maize shrunken 1 gene, the light sensitive 1 gene of *Solanum tuberosum*, and the heat shock protein 70 gene of *Petunia hybrida* (U.S. Pat. No. 5,659,122).

Depending upon the host cell system utilized, any one of a number of suitable promoters can be used. Promoter selection can be based on expression profile and expression level. The following are representative non-limiting examples of promoters that can be used in the expression cassettes.

Constitutive Expression:

Constitutive promoters typically provide for the constant and substantially uniform production of proteins in all tissues. Exemplary constitutive promoters include for example, the core promoter of the Rsyn7 (U.S. patent application Ser. No. 08/661,601), the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. patent application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Tissue Specific Expression:

Tissue-specific promoters include those described in Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc. Natl. Acad. Sci. U.S.A. 90(20):9586-9590; and Guevara-Garcia et al. (1993) Plant J. 4(3):495-505. Root specific promoters include, for example, those disclosed in Hire, et al (1992) Plant Mol. Biology, 20(2): 207-218; Keller and Baumgartner, (1991) The Plant Cell, 3(10): 1051-1061; Sanger et al. (1990) Plant Mol. Biology, 14(3): 433-443; Miao et al. (1991) The Plant Cell, 3(1): 11-22; Bogusz et al. (1990) The Plant Cell, 2(7): 633-641. Seed-preferred promoters includes both seed-specific promoters (those promoters active during seed development) as well as seed-germinating promoters (those promoters active during seed germination). Such promoters include Cim1 (cytokinin-induced message); cZ19B1 (maize 19 KDa zein); milps (myo-inositol-1-phosphate synthase); celA (cellulose synthase); end1 (Hordeum verlgase mRNA clone END1); and imp3 (myo-inositol monophosphate-3). For dicots, particular promoters include phaseolin, napin, β-conglycinin, soybean lectin, and the like. For monocots, particular promoters include maize 15 Kd zein, 22 KD zein, 27 kD zein, waxy, shrnmken 1, shrunken 2, globulin 1, etc. In certain embodiments the DNA constructs, transgenic plants and methods use the oleosin promoter and/or napin promoter.

Inducible Expression:

Chemically Inducible PR-la Promoter. The double 35S promoter in pCGN1761ENX can be replaced with any other promoter of choice that will result in suitably high expression levels. By way of example, one of the chemically regulatable promoters described in U.S. Pat. Nos. 5,614,395 and 5,880,333 can replace the double 35S promoter. The promoter of choice is preferably excised from its source by restriction enzymes, but can alternatively be PCR-amplified using primers that carry appropriate terminal restriction sites. The selected target gene coding sequence can be inserted into this vector, and the fusion products (i.e., promoter-gene-terminator) can subsequently be transferred to any selected transformation vector, including those described below. Various chemical regulators can be employed to induce expression of the selected coding sequence in the plants transformed according to the presently disclosed subject matter, including the benzothiadiazole, isonicotinic acid, salicylic acid and Ecdysone receptor ligands compounds disclosed in U.S. Pat. Nos. 5,523,311, 5,614,395, and 5,880,333 herein incorporated by reference.

Transcriptional Terminators:

A variety of transcriptional terminators are available for use in the DNA constructs of the invention. These are responsible for the termination of transcription beyond the transgene and its correct polyadenylation.

Appropriate transcriptional terminators are those that are known to function in the relevant plant system. Representative plant transcriptional terminators include the CaMV 35S terminator, the tml terminator, the nopaline synthase terminator (NOS ter), and the pea rbcS E9 terminator. In certain embodiments, the inventions utilize the oleosin terminator and/or napin terminator. With regard to RNA polymerase III terminators, these terminators typically comprise a -52 run of 5 or more consecutive thymidine residues. In one embodiment, an RNA polymerase III terminator comprises the sequence TTTTTTT. These can be used in both monocotyledons and dicotyledons.

Transit Peptide (TP) Sequences:

Various transit peptides which function as described herein are well known in the art, and are described in, for example, Johnson et al. The Plant Cell (1990) 2:525-532; Sauer et al. EMBO J. (1990) 9:3045-3050; Mueckler et al. Science (1985) 229:941-945; Von Heijne, Eur. J. Biochem. (1983) 133:17-21; Yon Heijne, J. Mol. Biol. (1986) 189: 239-242; Iturriaga et al. The Plant Cell (1989) 1:381-390; McKnight et al., Nucl. Acid Res. (1990) 18:4939-4943; Matsuoka and Nakamura, Proc. Natl. Acad. Sci. USA (1991) 88:834-838. Such transit peptides can be identified in the primary amino acid sequences of the preproteins by those ordinarily skilled in the art. For example, see Colby et al. (1993) J. Biol. Chem. 268(31):23016-23024, for the transit peptide sequence of limonene synthase. In certain embodiments, the transit peptide sequence form the RuBisCO small subunit transit peptide is used.

Sequences for the Enhancement or Regulation of Expression:

Numerous sequences have been found to enhance the expression of an operatively lined nucleic acid sequence, and these sequences can be used in conjunction with the nucleic acids of the presently disclosed subject matter to increase their expression in transgenic plants.

Various intron sequences have been shown to enhance expression, particularly in monocotyledonous cells. For example, the introns of the maize Adbl gene have been found to significantly enhance the expression of the wild-type gene under its cognate promoter when introduced into maize cells. Intron 1 was found to be particularly effective and enhanced expression in fusion constructs with the chloramphenicol acetyltransferase gene. In the same experimental system, the intron from the maize bronzes gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMY) have been shown to be effective in enhancing expression.

Selectable Markers:

For certain target species, different antibiotic or herbicide selection markers can be included in the DNA constructs of the invention. Selection markers used routinely in transformation include the npt II gene (Kan), which confers resistance to kanamycin and related antibiotics, the bar gene, which confers resistance to the herbicide phosphinothricin, the hph gene, which confers resistance to the antibiotic hygromycin, the dhfr gene, which confers resistance to methotrexate, and the EPSP synthase gene, which confers resistance to glyphosate (U.S. Pat. Nos. 4,940,935 and 5,188,642).

Screenable Markers:

Screenable markers may also be employed in the DNA constructs of the present invention, including for example the β-glucuronidase or uidA gene (the protein product is commonly referred to as GUS), isolated from E. coli, which encodes an enzyme for which various chromogenic substrates are known; an R-locus gene, which encodes a product that regulates the production of anthocyanin pigments (red color) in plant tissues; a β-lactamase gene, which encodes an enzyme for which various chromogenic substrates are known (e.g., PADAC, a chromogenic cephalosporin); a xylE gene, which encodes a catechol dioxygenase that can convert chromogenic catechols; an α-amylase gene; a tyrosinase gene which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene, which allows for bioluminescence detection; an aequorin gene, which may be employed in calcium-sensitive bioluminescence detection; or a gene encoding for green fluorescent protein (PCT Publication WO 97/41228). Screenable markers also include fluorescent proteins, such as DsRed, that facilitate identification of transgenic seed. Expression of such screenable markers can be under the control of a seed-specific promoter.

The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. Thus, an R gene introduced into such cells will cause the expression of a red pigment and, if stably incorporated, can be visually scored as a red sector. If a maize line carries dominant alleles for genes encoding for the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which has the genotype r-g, b, Pl. Alternatively, any genotype of maize can be utilized if the C1 and R alleles are introduced together.

In some aspects, screenable markers provide for visible light emission or fluorescence as a screenable phenotype. Suitable screenable markers contemplated for use in the present invention include firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for population screening for bioluminescence, such as on tissue culture plates, or even for whole plant screening.

Many naturally fluorescent proteins including red and green fluorescent proteins and mutants thereof, from jelly fish and coral are commercially available (for example from CLONTECH, Palo Alto, Calif.) and provide convenient visual identification of plant transformation.

VII. Methods of Transformation

Techniques for transforming a wide variety of plant species are well known and described in the technical and scientific literature. See, for example, Weising et al, (1988) Ann. Rev. Genet., 22:421-477. As described herein, the DNA constructs of the present invention typically contain a marker gene which confers a selectable phenotype on the plant cells. For example, the marker may encode biocide resistance, particularly antibiotic resistance, such as resistance to kanamycin, G418, bleomycin, hygromycin, or herbicide resistance, such as resistance to chlorsulfuron or Basta. Such selective marker genes are useful in protocols for the production of transgenic plants.

DNA constructs can be introduced into the genome of the desired plant host by a variety of conventional techniques. For example, the DNA construct may be introduced directly into the DNA of the plant cell using techniques such as electroporation and microinjection of plant cell protoplasts. Alternatively, the DNA constructs can be introduced directly to plant tissue using biolistic methods, such as DNA microparticle bombardment. In addition, the DNA constructs may be combined with suitable T-DNA flanking regions and introduced into a conventional Agrobacterium tumefaciens host vector. The virulence functions of the Agrobacterium tumefaciens host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al, (1984) EMBO J., 3:2717-2722. Electroporation techniques are described in Fromm et al, (1985) Proc. Natl. Acad. Sci. USA, 82:5824. Biolistic transformation techniques are described in Klein et al, (1987) Nature 327:70-7. The full disclosures of all references cited are incorporated herein by reference.

A variation involves high velocity biolistic penetration by small particles with the nucleic acid either within the matrix of small beads or particles, or on the surface (Klein et al, (1987) Nature, 327:70-73,). Although typically only a single introduction of a new nucleic acid segment is required, this method particularly provides for multiple introductions.

Agrobacterium tumefaciens-meditated transformation techniques are well described in the scientific literature. See, for example Horsch et al, (1984) Science, 233:496-498, and Fraley et al, (1983) Proc. Natl. Acad. Sci. USA, 90:4803.

More specifically, a plant cell, an explant, a meristem or a seed is infected with Agrobacterium tumefaciens transformed with the segment. Under appropriate conditions known in the art, the transformed plant cells are grown to form shoots, roots, and develop further into plants. The nucleic acid segments can be introduced into appropriate plant cells, for example, by means of the Ti plasmid of Agrobacterium tumefaciens. The Ti plasmid is transmitted to plant cells upon infection by *Agrobacterium tumefaciens*, and is stably integrated into the plant genome (Horsch et al, (1984) Science, 233:496-498; Fraley et al, (1983) Proc. Nat'l. Acad. Sci. U.S.A., 80:4803.

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without its transferring ability being affected. By removing the tumor-causing genes so that they no longer interfere, the modified Ti plasmid can then be used as a vector for the transfer of the gene constructs of the invention into an appropriate plant cell, such being a "disabled Ti vector".

All plant cells which can be transformed by *Agrobacterium* and whole plants regenerated from the transformed cells can also be transformed according to the invention so as to produce transformed whole plants which contain the transferred foreign nucleic acid sequence. There are various ways to transform plant cells with *Agrobacterium*, including: (1) co-cultivation of *Agrobacterium* with cultured isolated protoplasts, (2) co-cultivation of cells or tissues with *Agrobacterium*, or (3) transformation of seeds, apices or meristems with *Agrobacterium*. Method (1) requires an established culture system that allows culturing protoplasts and plant regeneration from cultured protoplasts. Method (2) requires (a) that the plant cells or tissues can be transformed by *Agrobacterium* and (b) that the transformed cells or tissues can be induced to regenerate into whole plants. Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids. After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

The present invention embraces use of the claimed DNA constructs in transformation of any plant, including both dicots and monocots. Transformation of dicots is described in references above. Transformation of monocots is known using various techniques including electroporation (e.g., Shimamoto et al, (1992) Nature, 338:274-276; ballistics (e.g., European Patent Application 270,356); and *Agrobacterium* (e.g., Bytebier et al, (1987) Proc. Nat'l Acad. Sci. USA, 84:5345-5349).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium typically relying on a biocide and/or herbicide marker which has been introduced together with the nucleotide sequences. Plant regeneration from cultured protoplasts is described in Evans et al, Handbook of Plant Cell Culture, pp. 124-176, MacMillan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally by Klee et al, Ann. Rev. Plant Phys., 38:467-486, 1987. Additional methods for producing a transgenic plant useful in the present invention are described in U.S. Pat. Nos. 5,188,642; 5,202,422; 5,384,253; 5,463,175; and 5,639,947. The methods, compositions, and expression vectors of the invention have use over a broad range of types of plants, including the creation of transgenic plant species belonging to virtually any species.

Selection:

Typically DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin, G418 and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA. Using the techniques disclosed herein, greater than 40% of bombarded embryos may yield transformants.

One example of a herbicide which is useful for selection of transformed cell lines in the practice of the invention is the broad spectrum herbicide glyphosate. Glyphosate inhibits the action of the enzyme EPSPS, which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, PCT Publication WO 97/04103. The best characterized mutant EPSPS gene conferring glyphosate resistance comprises amino acid changes at residues 102 and 106, although it is anticipated that other mutations will also be useful (PCT Publication WO 97/04103). Furthermore, a naturally occurring glyphosate resistant EPSPS may be used, e.g., the CP4 gene isolated from *Agrobacterium* encodes a glyphosate resistant EPSPS (U.S. Pat. No. 5,627,061).

To use the bar-bialaphos or the EPSPS-glyphosate selective systems, tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is believed that ranges of 0.1-50 mg/l bialaphos or 0.1-50 mM glyphosate will find utility in the practice of the invention. Bialaphos and glyphosate are provided as examples of agents suitable for selection of transformants, but the technique of this invention is not limited to them.

Another herbicide which constitutes a desirable selection agent is the broad spectrum herbicide bialaphos. Bialaphos is a tripeptide antibiotic produced by Streptomyces hygroscopicus and is composed of phosphinothricin (PPT), an analogue of L-glutamic acid, and two L-alanine residues. Upon removal of the L-alanine residues by intracellular peptidases, the PPT is released and is a potent inhibitor of glutamine synthase (GS), a pivotal enzyme involved in ammonia assimilation and nitrogen metabolism. Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in Streptomyces hygroscopicus and the pat gene in Streptomyces viridochromogenes. The use of the herbicide resistance gene encoding phosphinothricin acetyl transferase (PAT) is referred to in DE 3642 829 A, wherein the gene is isolated from Streptomyces viridochromogenes. In the bacterial source organism, this enzyme acetylates the free amino group of PPT preventing auto-toxicity. The bar gene has been cloned and expressed in transgenic tobacco, tomato, potato, Brassica and maize (U.S. Pat. No. 5,550,318). In previous reports, some transgenic plants which expressed the resistance gene were completely resistant to commercial formulations of PPT and bialaphos in greenhouses.

It further is contemplated that the herbicide dalapon, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (U.S. Pat. No. 5,780,708).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468 and U.S. Pat. No. 6,118,047.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. In a similar fashion, the introduction of the C1 and B genes will result in pigmented cells and/or tissues.

The enzyme luciferase may be used as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells that are expressing luciferase and manipulate cells expressing in real time. Another screenable marker which may be used in a similar fashion is the gene coding for green fluorescent protein (GFP) or a gene coding for other fluorescing proteins such as DSRED® (Clontech, Palo Alto, Calif.).

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase or GFP would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene (WO 99/60129).

Regeneration and Seed Production:

Cells that survive the exposure to the selective agent, or cells that have been scored positive in a screening assay, may be cultured in media that supports regeneration of plants. In an exemplary embodiment, MS and N6 media may be modified by including further substances such as growth regulators. Preferred growth regulators for plant regeneration include cytokines such as 6-benzylamino pelerine, peahen or the like, and abscise acid. Media improvement in these and like ways has been found to facilitate the growth of cells at specific developmental stages. Tissue may be maintained on a basic media with axing type growth regulators until sufficient tissue is available to begin plant regeneration efforts, or following repeated rounds of manual selection, until the morphology of the tissue is suitable for regeneration, then transferred to media conducive to maturation of embroils. Cultures are transferred every 1-4 weeks, preferably every 2-3 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets were transferred to soilless plant growth mix, and hardened off, e.g., in an environmentally controlled chamber at about 85% relative humidity, 600 pap $CO_2$, and 25-250 microeinsteins $m^{-2} s^{-1}$ of light, prior to transfer to a greenhouse or growth chamber for maturation. Plants are preferably matured either in a growth chamber or greenhouse. Plants are regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing. Plants may be pollinated using conventional plant breeding methods known to those of skill in the art and seed produced.

Progeny may be recovered from transformed plants and tested for expression of the exogenous expressible gene. Note however, that seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

Characterization:

To confirm the presence of the exogenous DNA or "transgene(s)" in the regenerating plants, a variety of assays, known in the art may be performed. Such assays include, for example, "molecular biological" assays, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

DNA Integration, RNA Expression and Inheritance:

Genomic DNA may be isolated from callus cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined by polymerase chain reaction (PCR). Using this technique discreet fragments of DNA are amplified and detected by gel electrophoresis. This type of analysis permits one to determine whether a gene is present in a stable transformant, but does not necessarily prove integration of the introduced gene into the host cell genome. Typically, DNA has been integrated into the genome of all transformants that demonstrate the presence of the gene through PCR analysis. In addition, it is not possible using PCR techniques to determine whether transformants have exogenous genes introduced into different sites in the genome, i.e., whether transformants are of independent origin. Using PCR techniques it is possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition, it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

It is contemplated that using the techniques of dot or slot blot hybridization, which are modifications of Southern hybridization techniques, one could obtain the same information that is derived from PCR, e.g., the presence of a gene.

Both PCR and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR techniques, referred to as RT-PCR, also may be used for detection and quantification of RNA produced from introduced genes. In this application of PCR it is first necessary to reverse transcribe RNA into DNA, using enzymes such as reverse transcriptase, and then through the use of conventional PCR techniques amplify the DNA. In most instances PC techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

It is further contemplated that TAQMAN® technology (Applied Biosystems, Foster City, Calif.) may be used to quantitate both DNA and RNA in a transgenic cell.

Gene Expression:

While Southern blotting and PCR may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following an increase in fluorescence as anthranilate is produced, to name two.

Very frequently the expression of a gene product is determined by evaluating the phenotypic results of its expression. These assays also may take many forms, including but not limited to, analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

Event Specific Transgene Assay:

Southern blotting, PCR and RT-PCR techniques can be used to identify the presence or absence of a given transgene but, depending upon experimental design, may not specifically and uniquely identify identical or related transgene constructs located at different insertion points within the recipient genome. To more precisely characterize the presence of transgenic material in a transformed plant, one skilled in the art could identify the point of insertion of the transgene and, using the sequence of the recipient genome flanking the transgene, develop an assay that specifically and uniquely identifies a particular insertion event. Many methods can be used to determine the point of insertion such as, but not limited to, Genome Walker™ technology (CLONTECH, Palo Alto, Calif.), Vectorette™ technology (Sigma, St. Louis, Mo.), restriction site oligonucleotide PCR, uneven PCR (Chen and Wu, 1997) and generation of genomic DNA clones containing the transgene of interest in a vector such as, but not limited to, lambda phage.

Once the sequence of the genomic DNA directly adjacent to the transgenic insert on either or both sides has been determined, one skilled in the art can develop an assay to specifically and uniquely identify the insertion event. For example, two oligonucleotide primers can be designed, one wholly contained within the transgene and one wholly contained within the flanking sequence, which can be used together with the PCR technique to generate a PCR product unique to the inserted transgene. In one embodiment, the two oligonucleotide primers for use in PCR could be designed such that one primer is complementary to sequences in both the transgene and adjacent flanking sequence such that the primer spans the junction of the insertion site while the second primer could be homologous to sequences contained wholly within the transgene. In another embodiment, the two oligonucleotide primers for use in PCR could be designed such that one primer is complementary to sequences in both the transgene and adjacent flanking sequence such that the primer spans the junction of the insertion site while the second primer could be homologous to sequences contained wholly within the genomic sequence adjacent to the insertion site. Confirmation of the PCR reaction may be monitored by, but not limited to, size analysis on gel electrophoresis, sequence analysis, hybridization of the PCR product to a specific radiolabeled DNA or RNA probe or to a molecular beacon, or use of the primers in conjugation with a TAQMAN probe and technology (Applied Biosystems, Foster City, Calif.).

Site Specific Integration or Excision of Transgenes:

It is specifically contemplated by the inventors that one could employ techniques for the site-specific integration or excision of transformation constructs prepared in accordance with the instant invention. An advantage of site-specific integration or excision is that it can be used to overcome problems associated with conventional transformation techniques, in which transformation constructs typically randomly integrate into a host genome and multiple copies of a construct may integrate. This random insertion of introduced DNA into the genome of host cells can be detrimental to the cell if the foreign DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the inserted DNA, often only desiring the insertion of a single copy of the DNA sequence. Site-specific integration can be achieved in plants by means of homologous recombination (see, for example, U.S. Pat. No. 5,527, 695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the host cell. Once the DNA enters the cell, the two homologous sequences can interact to insert the introduced DNA at the site where the homologous genomic DNA sequences were located. Therefore, the choice of homologous sequences contained on the introduced DNA will determine the site where the introduced DNA is integrated via homologous recombination. For example, if the DNA sequence of interest is linked to DNA sequences sharing homology to a single copy gene of a host plant cell, the DNA sequence of interest will be inserted via homologous recombination at only that single specific site. However, if the DNA sequence of interest is linked to DNA sequences sharing homology to a multicopy gene of the host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example, if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. Thus random integration of transgenes is more common in plants. To maintain control over the copy number and the location of the inserted DNA, randomly inserted DNA sequences can be removed. One manner of removing these random insertions is to utilize a site-specific recombinase system (U.S. Pat. No. 5,527,695). A number of different site specific recombinase systems could be employed in accordance with the instant invention, including, but not limited to, the Cre/lox system of bacteriophage P1 (U.S. Pat. No. 5,658,772, specifically incorporated herein by reference in its entirety), the FLP/FRT system of yeast, the Gin recombinase of phage Mu, the Pin recombinase of *E. coli*, and the R/RS system of the pSR1 plasmid. The bacteriophage P1 Cre/lox and the yeast FLP/FRT systems constitute two particularly useful systems for site specific integration or excision of transgenes. In these systems, a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors.

The FLP/FRT recombinase system has been demonstrated to function efficiently in plant cells. Experiments on the performance of the FLP/FRT system in both maize and rice protoplasts indicate that FRT site structure, and amount of the FLP protein present, affects excision activity. In general, short incomplete FRT sites leads to higher accumulation of excision products than the complete full-length FRT sites. The systems can catalyze both intra- and intermolecular reactions in maize protoplasts, indicating its utility for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage P1, recombination between lox sites occurs in the presence of the Cre recombinase (see, e.g., U.S. Pat. No. 5,658,772, specifically incorporated herein by reference in its entirety). This system has been utilized to excise a gene located between two lox sites which had been introduced into a yeast genome (Sauer, 1987). Cre was expressed from an inducible yeast GAL1 promoter and this Cre gene was located on an autonomously replicating yeast vector.

Since the lox site is an asymmetrical nucleotide sequence, lox sites on the same DNA molecule can have the same or opposite orientation with respect to each other. Recombination between lox sites in the same orientation results in a deletion of the DNA segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region.

Deletion of Sequences Located within the Transgenic Insert:

During the transformation process it is often necessary to include ancillary sequences, such as selectable marker or reporter genes, for tracking the presence or absence of a desired trait gene transformed into the plant on the DNA construct. Such ancillary sequences often do not contribute to the desired trait or characteristic conferred by the phenotypic trait gene. Homologous recombination is a method by which introduced sequences may be selectively deleted in transgenic plants.

It is known that homologous recombination results in genetic rearrangements of transgenes in plants. Repeated DNA sequences have been shown to lead to deletion of a flanked sequence in various dicot species, e.g. *Arabidopsis thaliana* and *Nicotiana tabacum*. One of the most widely held models for homologous recombination is the double-strand break repair (DSBR) model.

Deletion of sequences by homologous recombination relies upon directly repeated DNA sequences positioned about the region to be excised in which the repeated DNA sequences direct excision utilizing native cellular recombination mechanisms. The first fertile transgenic plants are crossed to produce either hybrid or inbred progeny plants, and from those progeny plants, one or more second fertile transgenic plants are selected which contain a second DNA sequence that has been altered by recombination, preferably resulting in the deletion of the ancillary sequence. The first fertile plant can be either hemizygous or homozygous for the DNA sequence containing the directly repeated DNA which will drive the recombination event.

The directly repeated sequences are located 5' and 3' to the target sequence in the transgene. As a result of the recombination event, the transgene target sequence may be deleted, amplified or otherwise modified within the plant genome. In the preferred embodiment, a deletion of the target sequence flanked by the directly repeated sequence will result.

Alternatively, directly repeated DNA sequence mediated alterations of transgene insertions may be produced in somatic cells. Preferably, recombination occurs in a cultured cell, e.g., callus, and may be selected based on deletion of a negative selectable marker gene, e.g., the periA gene isolated from *Burkholderia caryolphilli* which encodes a phosphonate ester hydrolase enzyme that catalyzes the hydrolysis of glyceryl glyphosate to the toxic compound glyphosate (U.S. Pat. No. 5,254,801).

VIII. Transgenic Organisms

In certain embodiments, the invention contemplates a transgenic organism comprising within its genome:

a first nucleotide sequence encoding a fusion protein comprising a geranyl diphosphate synthase small subunit fused in frame to a geranyl diphosphate synthase large subunit, operatively linked to a first set of expression control sequences that drive expression of the geranyl diphosphate fusion protein in the plant cell;

a second nucleotide sequence encoding a limonene synthase, operatively linked to a second set of expression control sequences that drive expression of the limonene synthase in the plant cell;

wherein the fusion protein and limonene synthase are expressed primarily in the plant cell plastids.

In certain embodiments, the invention contemplates a transgenic organism comprising within its genome:

a first nucleotide sequence encoding a fusion protein comprising a geranyl diphosphate synthase small subunit or a geranyl diphosphate synthase large subunit fused in frame to a limonene synthase, operatively linked to a first set of expression control sequences that drive expression of the geranyl diphosphate fusion protein in the plant cell;

wherein the fusion protein is expressed primarily in the plant cell plastids.

The transgenic organisms therefore contain one or more DNA constructs as defined herein as a part of the organism, the DNA constructs having been introduced by transformation of the organism.

In certain embodiments, the geranyl diphosphate synthase small subunit comprises an amino acid sequence selected from Table D1. In certain embodiments, the geranyl diphosphate synthase large subunit comprises an amino acid sequence selected from Table D2. In certain embodiments, the limonene synthase comprises an amino acid sequence selected from Table D3.

In one aspect such transgenic organisms are characterized by having a terpene content which is at least about 10% higher, at least about 20% higher, at least about 30% higher, at least about 40% higher, at least about 60% higher, at least about 80% higher, or at least about 100% higher than corresponding wild type organism.

In another aspect such transgenic organisms are characterized by having a monoterpene content of at least 1 mg/g dry weight, or about 1.2 mg/g dry weight, or about 1.4 mg/g dry weight, or about 1.6 mg/g dry weight, or about 1.8 mg/g dry weight, or about 2.0 mg/g dry weight, or greater then about or about 2.0 mg/g dry weight of seed.

In some embodiments of these transgenic organisms the monoterpene produced is selected from the group consisting of limonene, gamma-terpinene and alpha phellandrene, p-cymene, ascaridole and pulegone. In some embodiments the monoterpene is primarily limonene. In some embodiments the monoterpene is a mixture of any of the monoterpenes disclosed herein.

In any of these transgenic characteristics, it will be understood that the transgenic organism will be grown using standard growth conditions as disclosed in the Examples, and compared to the equivalent wild type species.

In one aspect of these transgenic organisms, the transgenic organism is a plant. In some embodiments the plant naturally produces a terpene. In some embodiments the transgenic plant is from the genus *Camelina*. In different aspect, the transgenic plant is selected from *Camelina alyssum, Canelina microcarpa, Camelina runelica* and *Camelina sativa*.

In certain embodiments of the transgenic plants, the geranyl diphosphate synthase fusion protein and limonene synthase, are expressed primarily in the seed tissue of the transgenic plant. In this context, the term "primarily" means that the relative expression of these proteins is at least about 150%, or at least about 200%, or at least about 300%, or at least about 400%, or at least about 500% higher in the seed tissue (on a dry weight by dry weight basis) compared to any other plant tissue, in the mature full developed plant, when grown under standard growth conditions.

In certain embodiments, the transgenic plant further expresses an auxillary enzyme as listed in Table D4.

The following examples describe various aspects of the present invention, and are merely intended to be illustrative rather than limiting of the compounds, compositions, and methods useful therein.

Example 1

Experimental Procedures

Plant Materials:

Wild-type *Camelina sativa* was grown in the green house at Donald Danforth Plant Science Center. Peppermint *Mentha piperita* leaves were harvested from a garden in St. Louis, Mo. in September, 2009.

Cloning of Peppermint Geranyl Diphosphate Synthase and Limonene Synthase cDNAs

Figure 10:
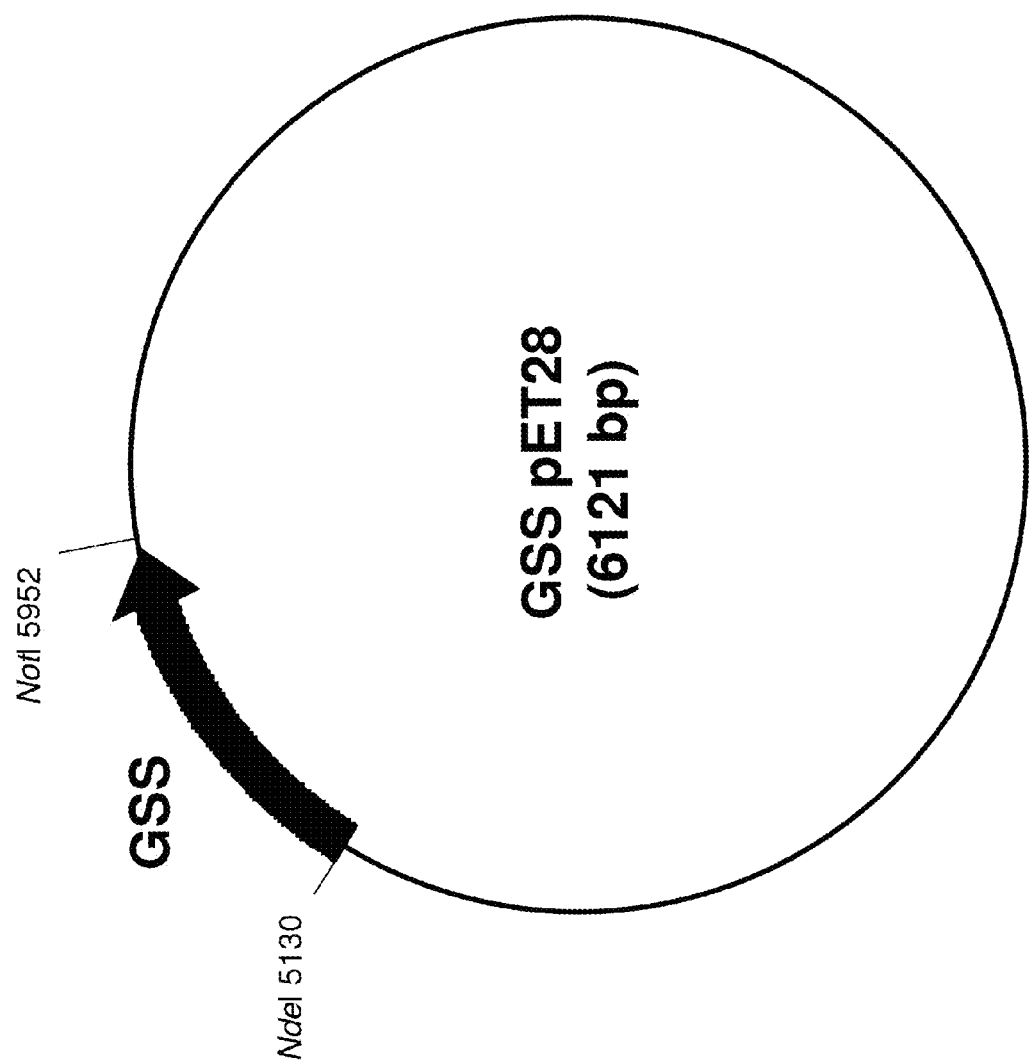
FIG. 10. Shows an exemplary *E. coli* expression vector (GSS pET28) for geranyl diphosphate synthase small subunit (GSS).
Figure 11:
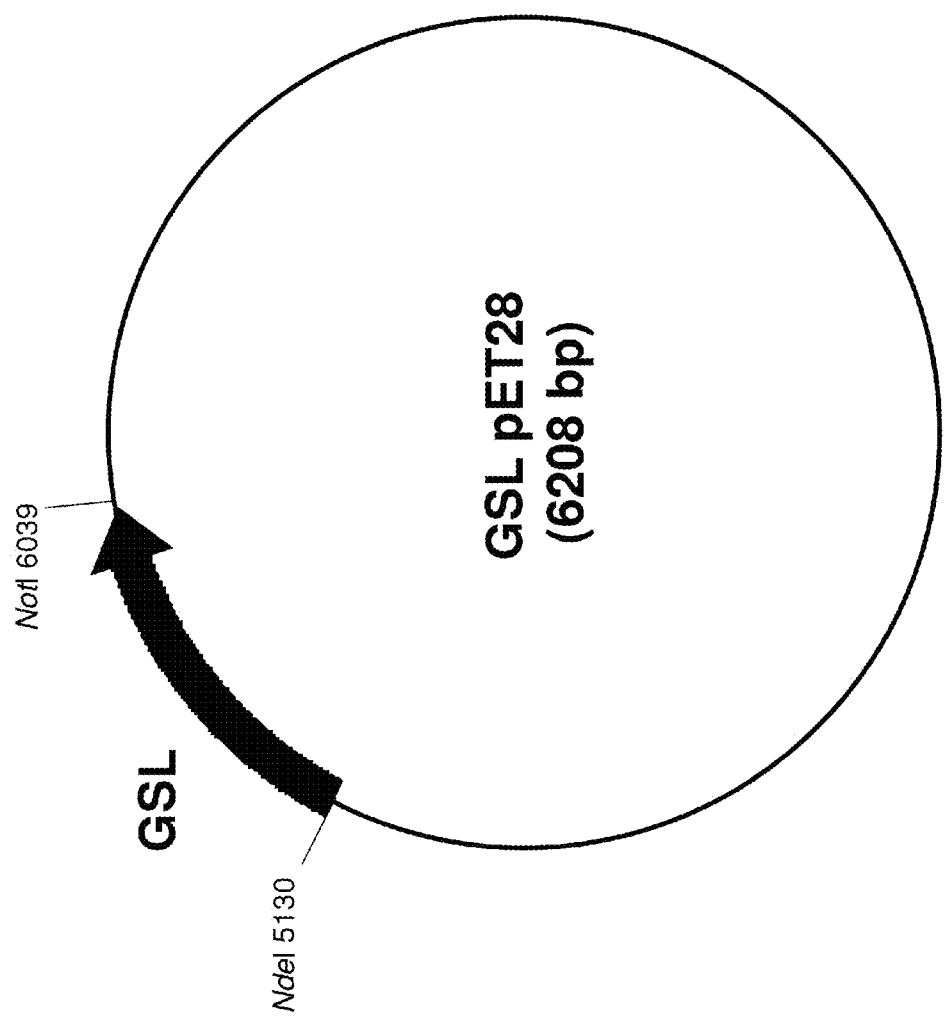
FIG. 11. Shows an exemplary *E. coli* expression vector (GSL pET28) for geranyl diphosphate synthase large subunit (GSL).
Figure 12:
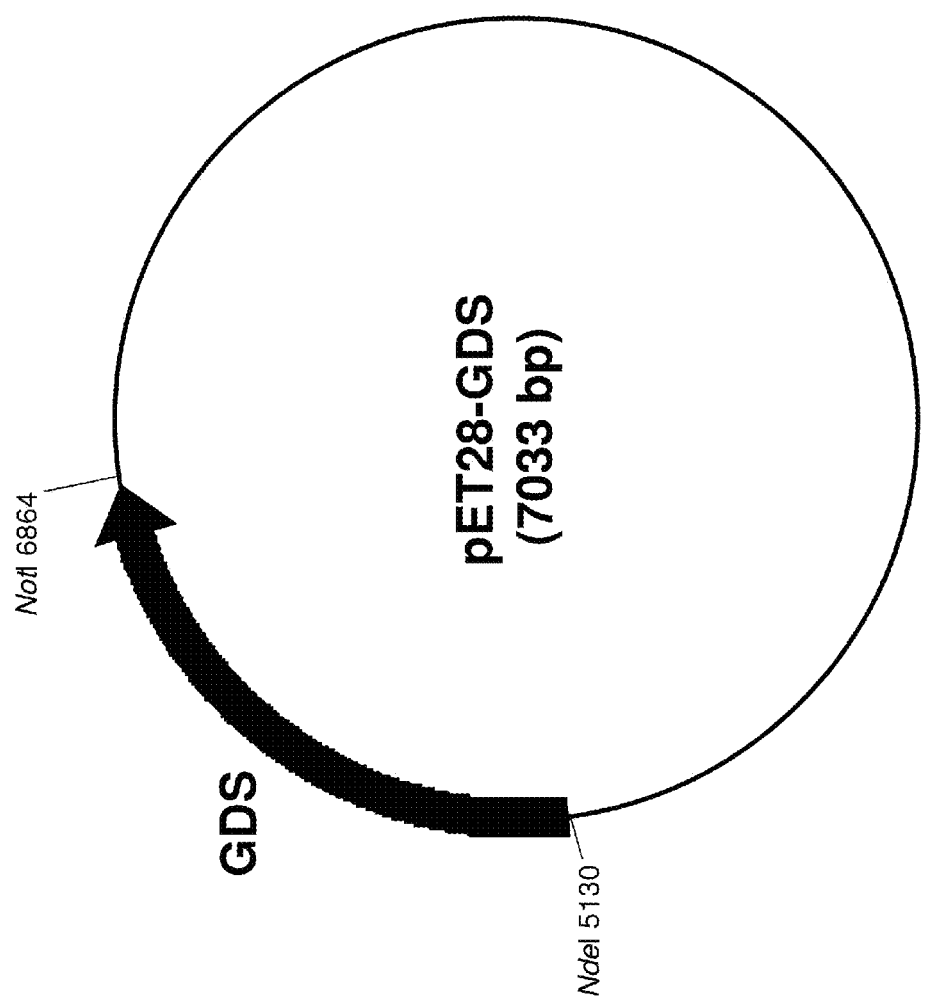
FIG. 12. Shows an exemplary *E. coli* expression vector (pET28-GDS) for geranyl diphosphate synthase (GDS) expressing a fusion protein of small subunit (GSS) and large subunit (GSL).
Figure 13:
FIG. 13. Shows an exemplary *E. coli* expression vector (LSfull pET28) for limonene synthase (LS) full-length cDNA.
Figure 14:
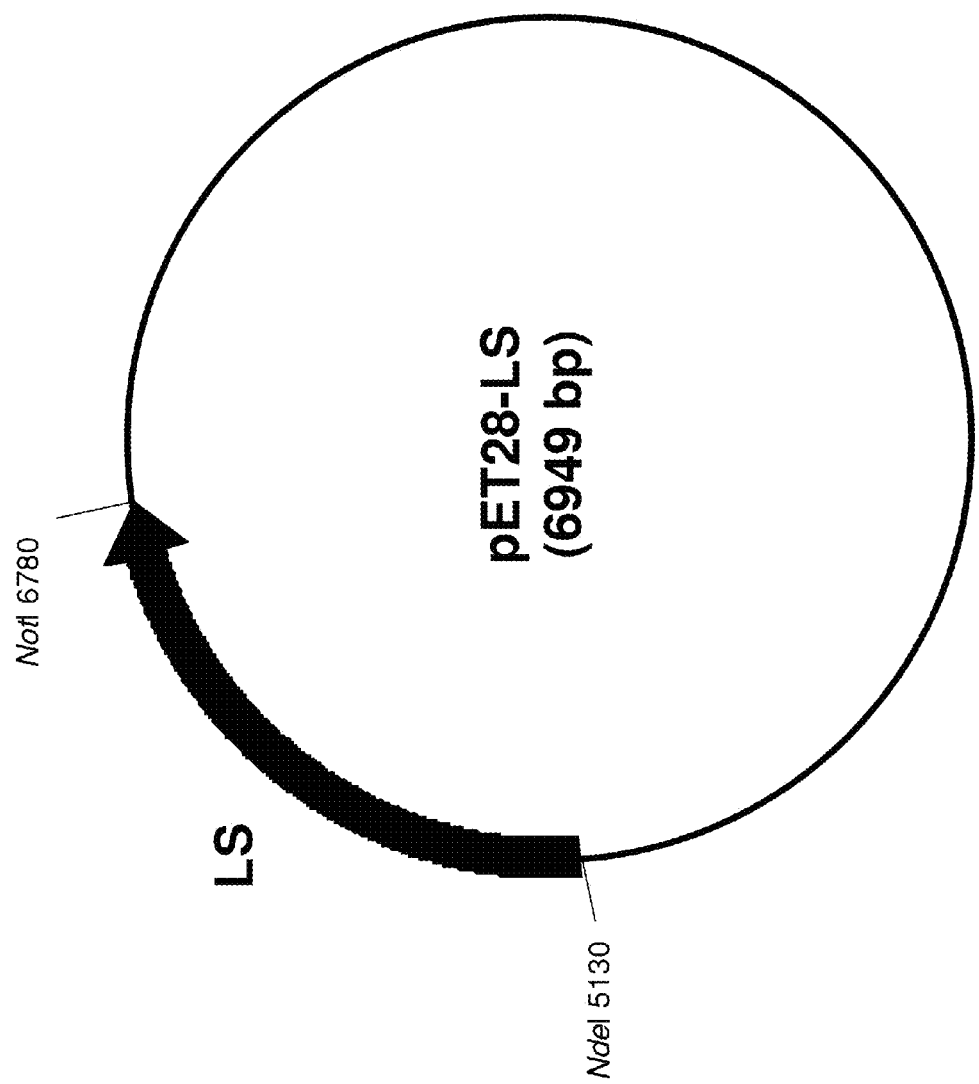
FIG. 14. Shows an exemplary *E. coli* expression vector (pET28-LS) for limonene synthase (LS).

Total RNA was extracted from peppermint leaves using RNeasy plant mini kit (Qiagen). First-strand cDNAs was synthesized using SuperScript III (Invitrogen). References and nucleotide sequences (Burke et al. (1999) *Arch. Biochem. Biophys.*, 422, 52-60; Alonso et al. (1992) J Biol Chem., 267, 7582-7; Colby et al. (1993) J Biol Chem., 268, 23016-24. NCBI accession numbers: AF182827, AJ249453, EU108697, AW255818) were used to design cloning primers. Geranyl diphosphate synthase small subunit without predicted chloroplast transit peptide has been cloned from the peppermint cDNAs with primers: GSSfC and GSSr4 (Table E1) (FIG. 10). Geranyl diphosphate synthase large subunit without predicted chloroplast transit peptide has been cloned from the peppermint cDNAs with primers: GSLfC and GSLr2 (FIG. 11). Geranyl diphosphate synthase (GDS) fusion protein was generated by a 2-step PCR method (Burke et al. 2004, *Arch. Biochem. Biophys.*, 422, 52-60. Ho et al. 1989 Gene, 77, 51-9) using the subunit clones as template by Phusion polymerase (Finnzymes) with primers: GSSfC, GSSr10aa, 10aaGSLfC and GSLr2, which is comprised of the small subunit, a 10 amino acid linker and the large subunit in this order (FIG. 12). The entire coding sequence of limonene synthase (LS) has been cloned from the peppermint cDNAs with primers: LSuf and LSr (Table E1) (FIG. 13). LS without predicted chloroplast transit peptide was amplified by PCR using the entire LS clone as template with primers: fwdLSfC3 and LSr (FIG. 14). The resulting GDS and LS PCR fragments were inserted into an NdeI/NotI-digested pET28a expression vector (Novagen) and sequenced, yielding pET28-GDS (FIG. 12) and pET28-LS (FIG. 14), respectively. Both enzyme activities were detected from partially purified *E. coli* recombinant proteins.

Figure 15:
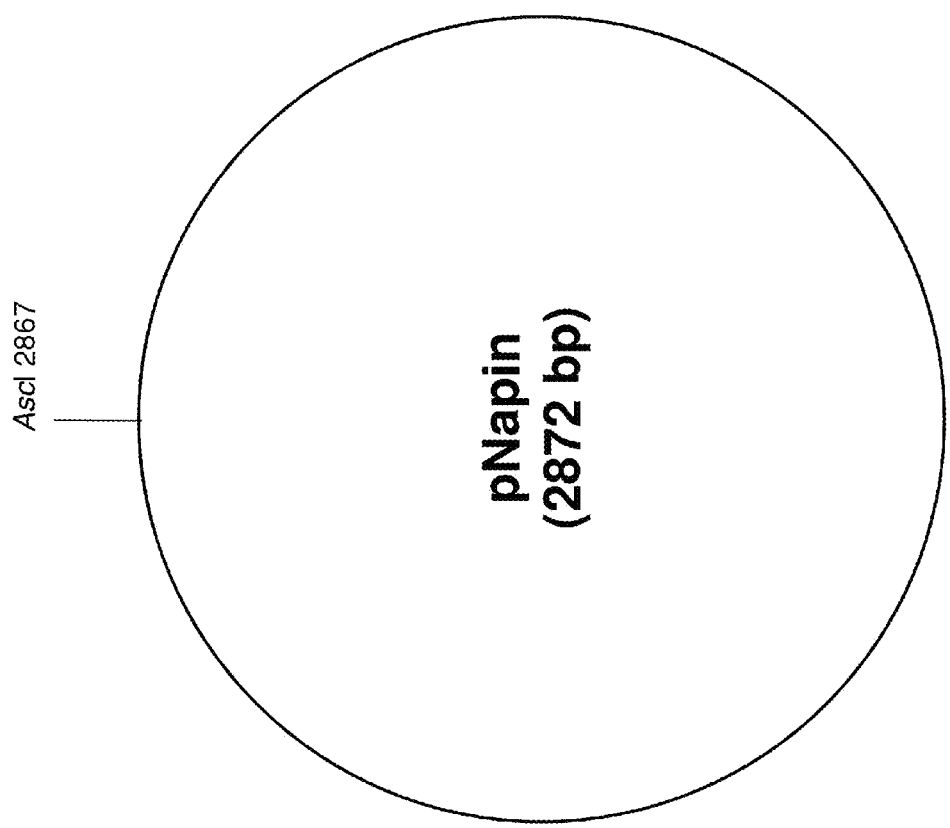
FIG. 15. Shows an exemplary *E. coli* cloning vector (pNapin) with an AscI site for preparing binary vectors as described herein.
Figure 16:
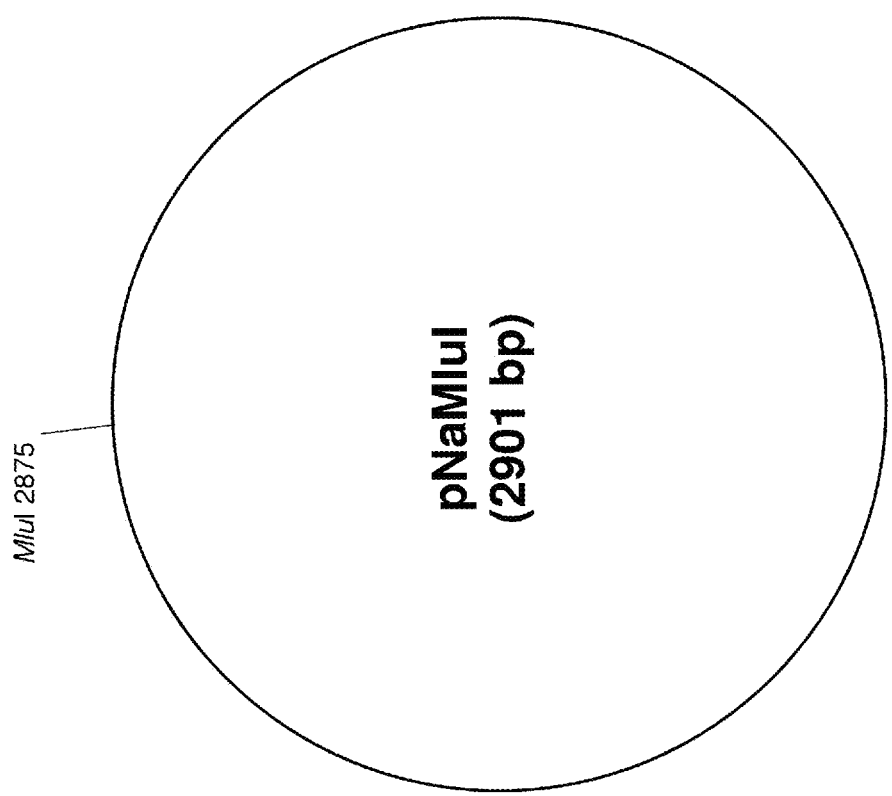
FIG. 16. Shows an exemplary *E. coli* cloning vector (pNaMluI) with a MluI site for preparing binary vectors as described herein.
Figure 17:
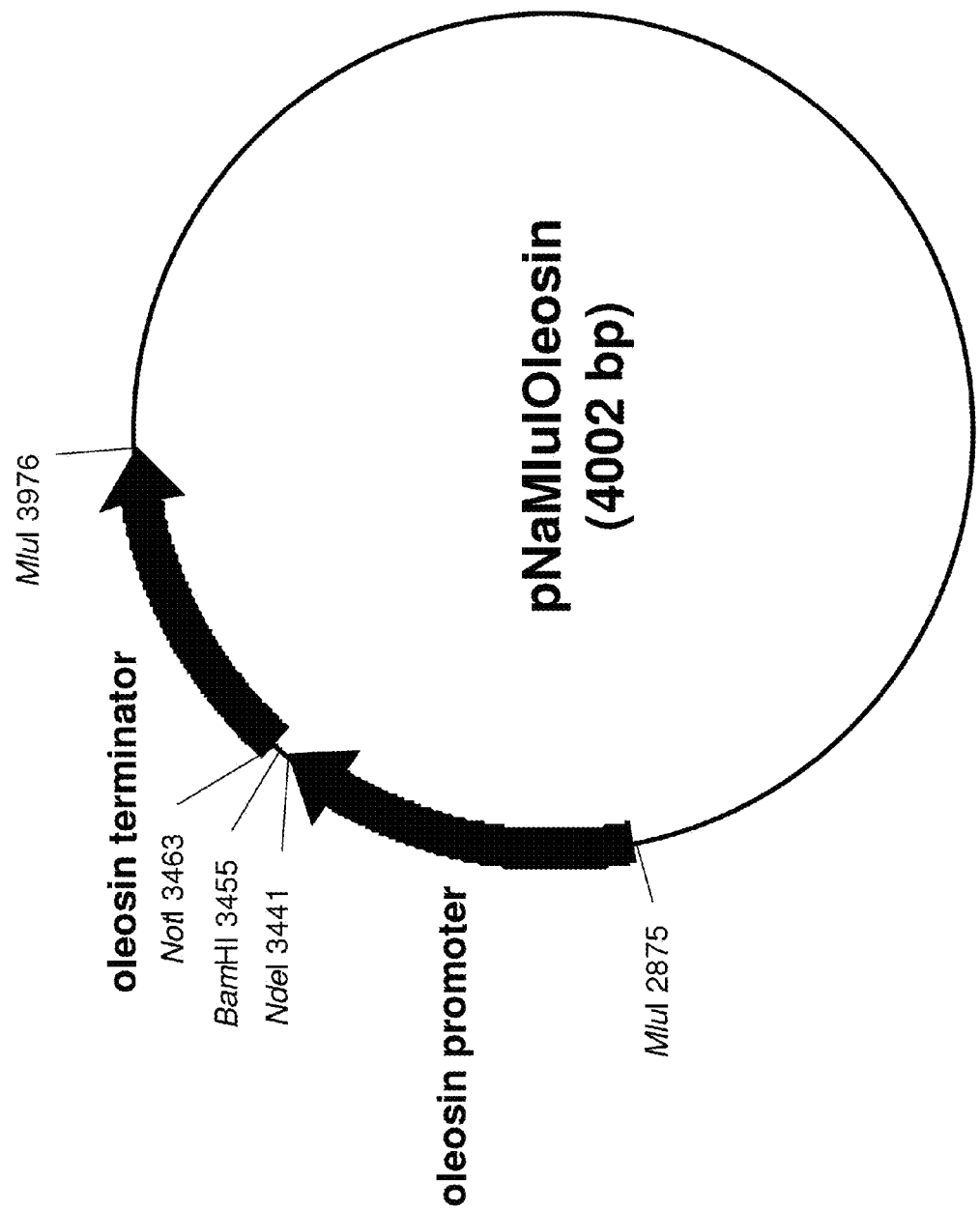
FIG. 17. Shows an exemplary *E. coli* cloning vector (pNaMluIOleosin) with an oleosin promoter and an oleosin terminator.
Figure 18:
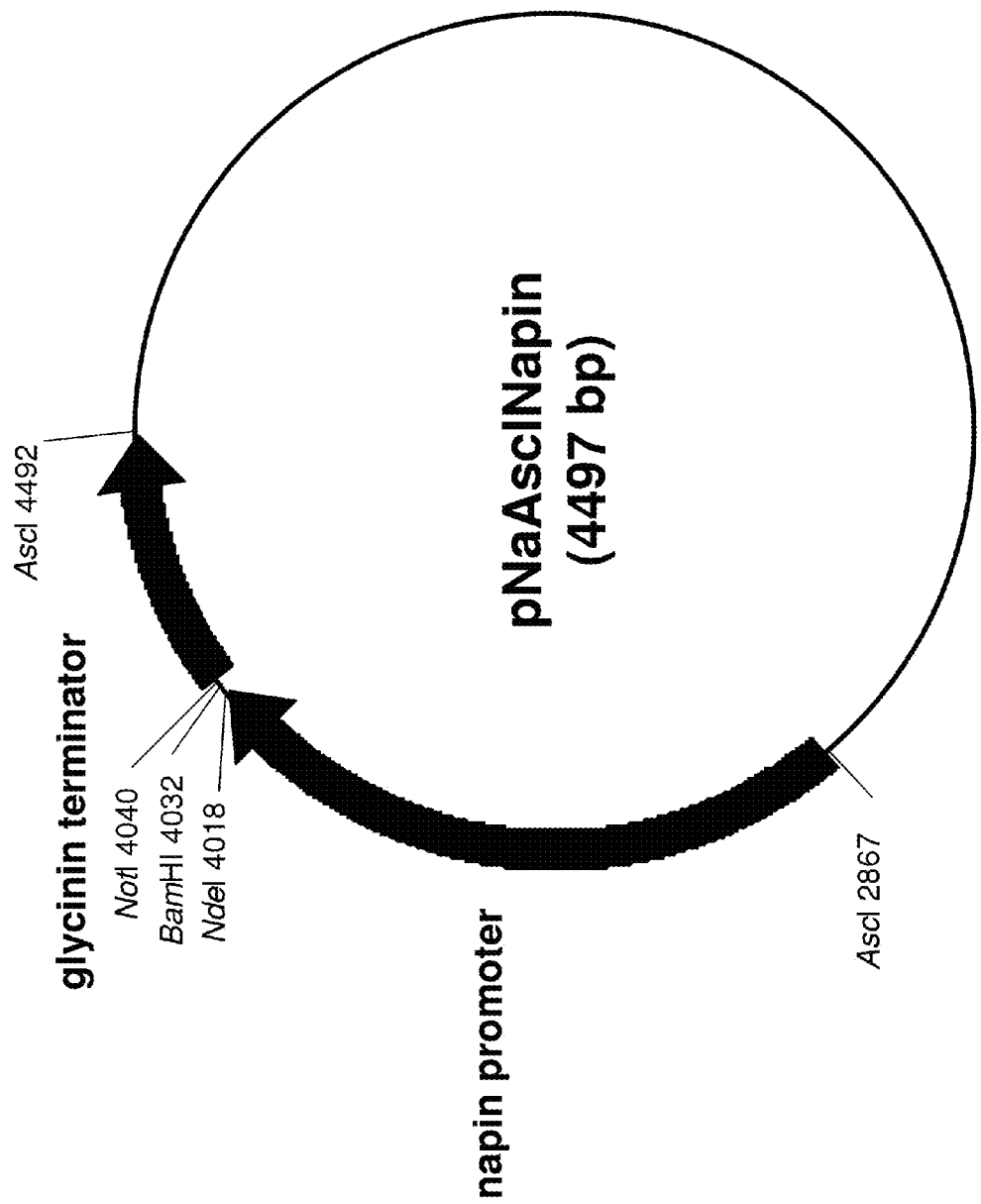
FIG. 18. Shows an exemplary *E. coli* cloning vector (pNaAscINapin) with a napin promoter and a glycinin terminator.
Figure 19:
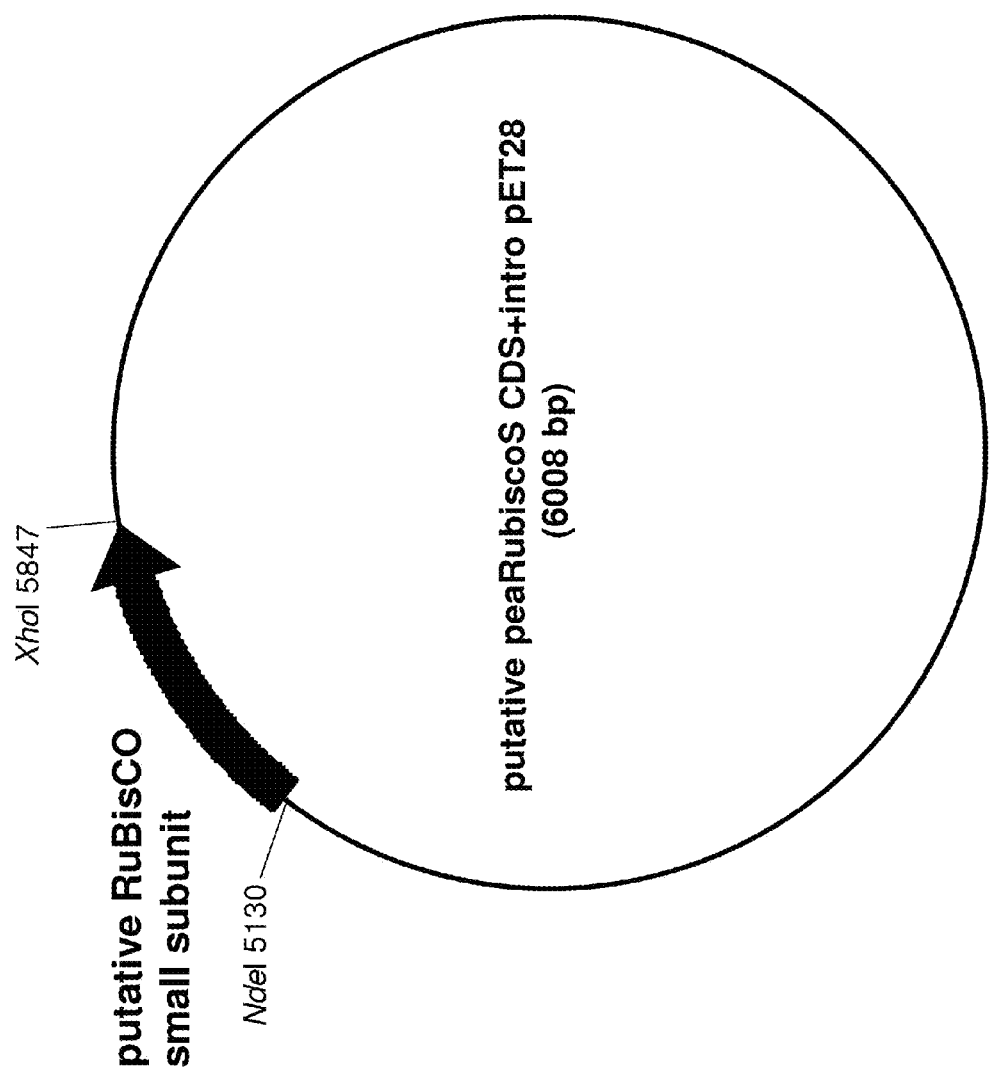
FIG. 19. Shows an exemplary *E. coli* cloning vector (putative peaRubiscoS CDS+intro pET28) with a putative RuBisCO small subunit.
Figure 20:
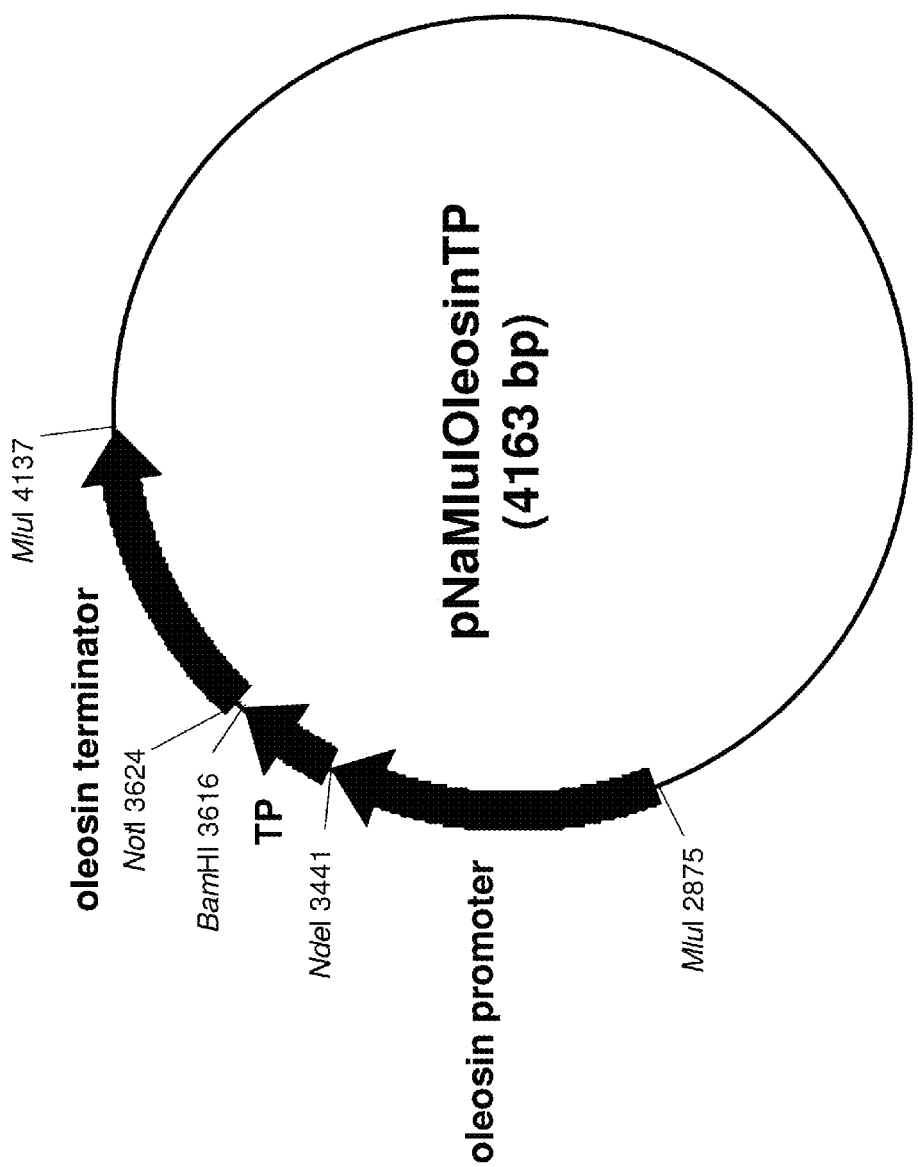
FIG. 20. Shows an exemplary *E. coli* cloning vector (pNaMluIOleosinTP) with an oleosin promoter, a RuBisCO transit peptide and an oleosin terminator.
Figure 21:
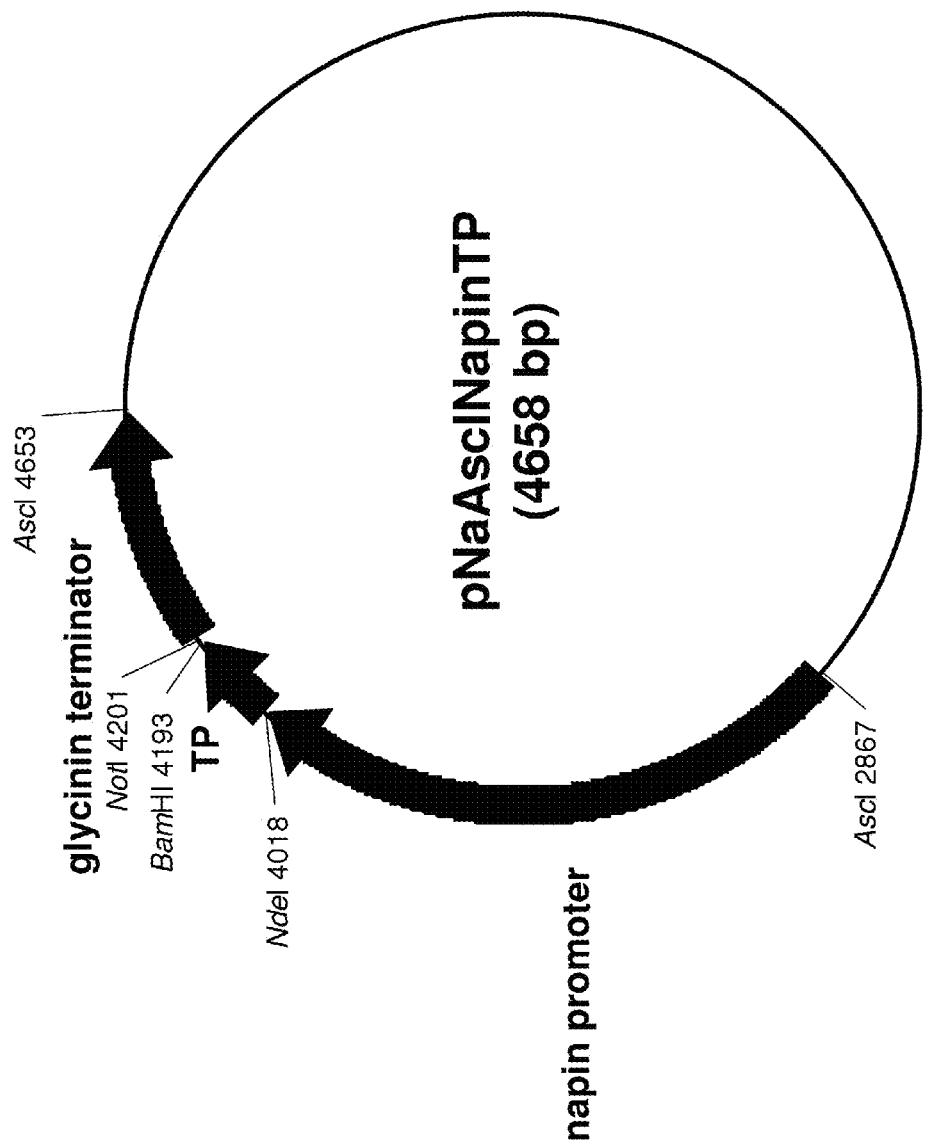
FIG. 21. Shows an exemplary *E. coli* cloning vector (pNaAscINapinTP) with a napin promoter, a RuBisCO transit peptide and a glycinin terminator.

Vector Construction:

Two *E. coli* plasmid vectors, pNapin (FIG. 15) and pABC were obtained from Dr. Jaworski (DDPSC). To insert MluI site, pNapin was digested by SacI and ligated with oligo nucleotides: fwdSacIMluISacI and revSacIMluISacI, (Table E1) yielding pNaMluI (FIG. 16). The soybean oleosin promoter and soybean oleosin terminator were amplified by the 2-step PCR method using pABC as template with primers: fwdMluIOP, revNotIBamHINdeIOP, fwdNdeIBamHINotIOT and revMluIOT (Table E1). The resulting promoter/terminator fusion DNA fragment was inserted into MluI-digested pNaMluI (FIG. 16) and sequenced, yielding pNaMluIOleosin (FIG. 17). Rapeseed napin promoter and soybean glycinin terminator were amplified by the 2-step PCR method using pNapin as template with primers: fwdAscINP, revNotIBamHINdeINP, fwdNdeIBamHINotIGT and revAscIGT (Table E1). The resulting napin promoter/glycinin terminator fusion DNA fragment was inserted into AscI-digested pNapin and sequenced, yielding pNaAscINapin (FIG. 18). The entire coding sequence of RuBisCO small subunit has been cloned from sweet pea siliques with primers: RuSfwd and RuSrev (Table E1) (FIG. 19). The RuBisCO small subunit transit peptide was amplified by PCR using the entire RuBisCO clone as template with primers: RuSfwd and revBamHIRuTP (Table E1). The resulting PCR product was inserted into NdeI/BamHI-digested pNaMluIOleosin (FIG. 17) and pNaAscINapin (FIG. 18), and sequenced, yielding two entry vectors: pNaMluIOleosinTP (FIG. 20) and pNaAscINapinTP (FIG. 21), respectively. The pNaMluIOleosinTP vector (FIG. 20) contains MluI, the oleosin promoter, the transit peptide, BamHI, NotI, the oleosin terminator and MluI in this order. The pNaAscINapinTP vector (FIG. 21) contains AscI, the napin promoter, the transit peptide, BamHI, NotI, the glycinin terminator and AscI in this order.

Figure 22:
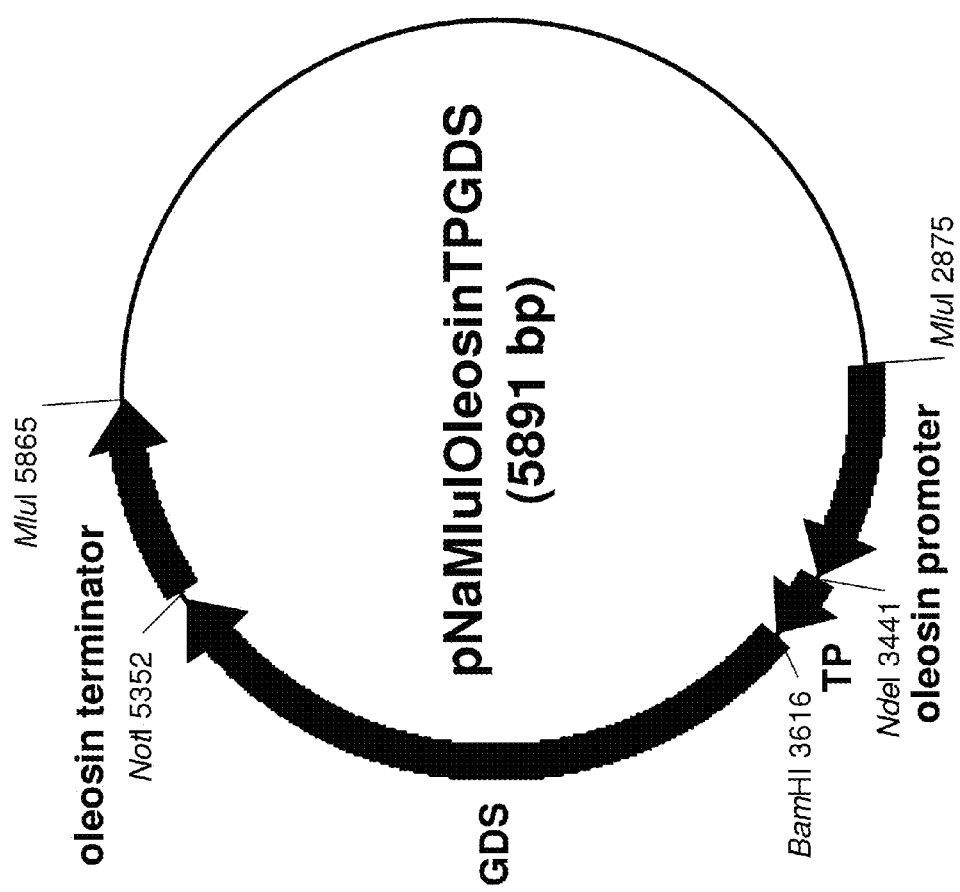
FIG. 22. Shows an exemplary *E. coli* cloning vector (pNaMluIOleosinTPGDS) with an oleosin promoter, a RuBisCO transit peptide, GDS and an oleosin terminator.
Figure 23:
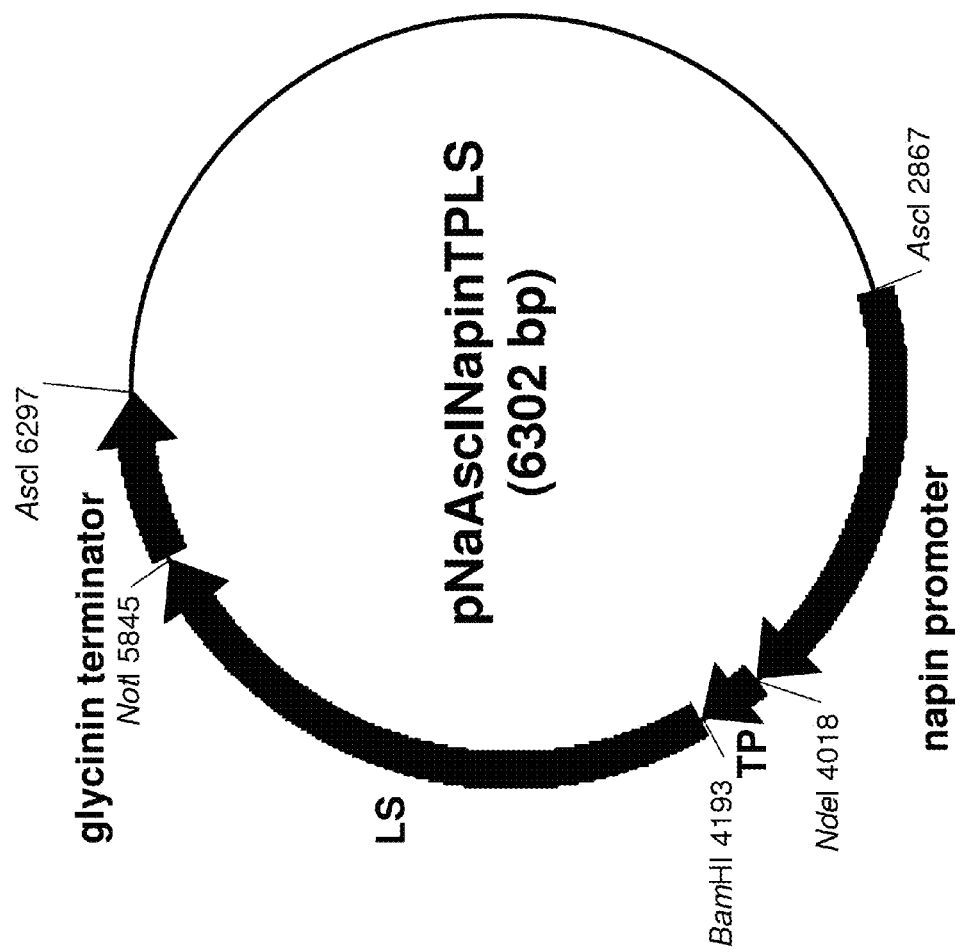
FIG. 23. Shows an exemplary *E. coli* cloning vector (pNaAscINapinTPLS) with a napin promoter, a RuBisCO transit peptide, LS and a glycinin terminator.

The GDS sequence with BamHI/NotI sites was amplified by PCR using pET28-GDS (FIG. 12) as template with primers: fwdBamHIGDS and GSLr2 (Table E1). The resulting PCR product was inserted into BamHI/NotI-digested pNaMluIOleosinTP (FIG. 20), yielding pNaMluIOleosinTPGDS (FIG. 22). The LS sequence with BamHI/NotI sites was amplified by PCR using pET28-LS (FIG. 14) as template with primers: fwdBamHILS and LSr. The resulting PCR product was inserted into BamHI/NotI digested pNaAscINapinTP (FIG. 21), yielding pNaAscINapinTPLS (FIG. 23).

Figure 24:
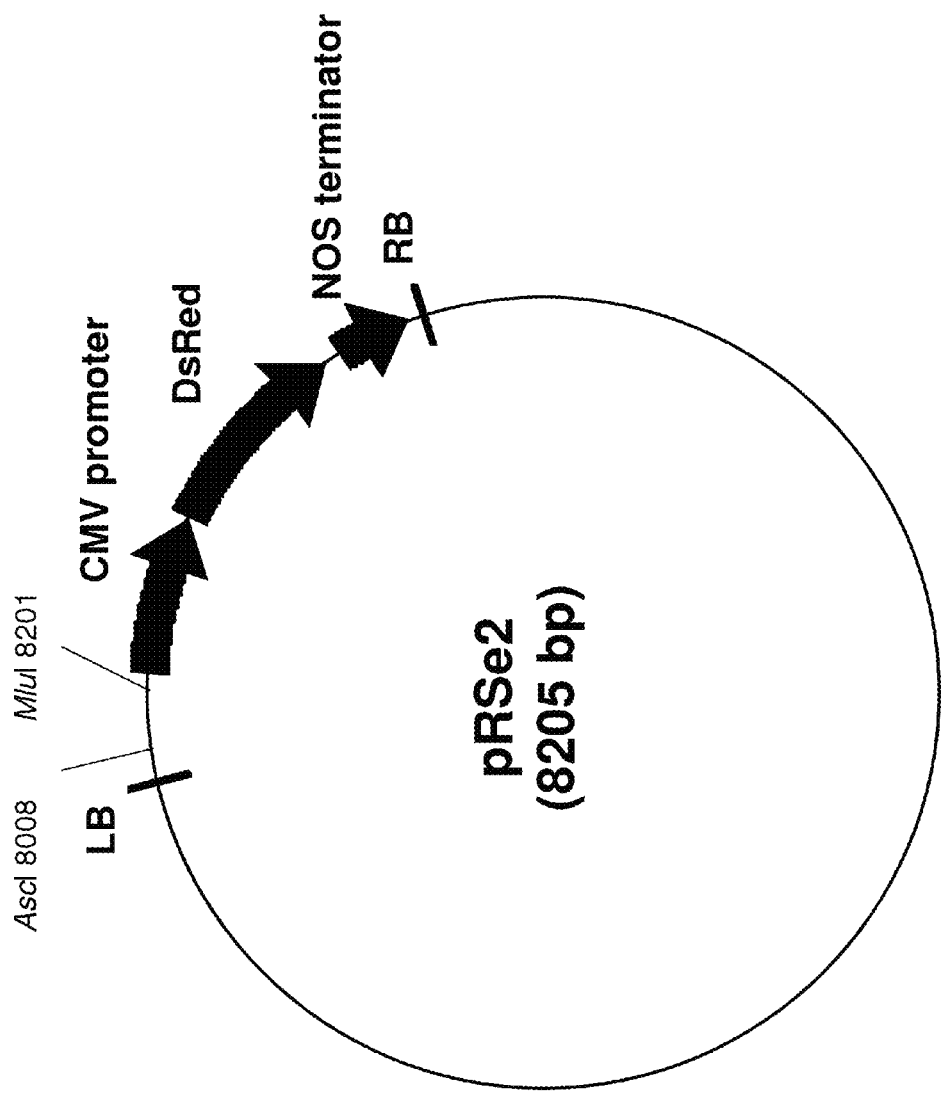
FIG. 24. Shows an exemplary plant expression vector (pRSe2) with a cytomegalovirus (CMV) promoter, a *Discosoma* red fluorescent protein (DsRed) and a nopaline synthase (NOS) terminator.
Figure 25:
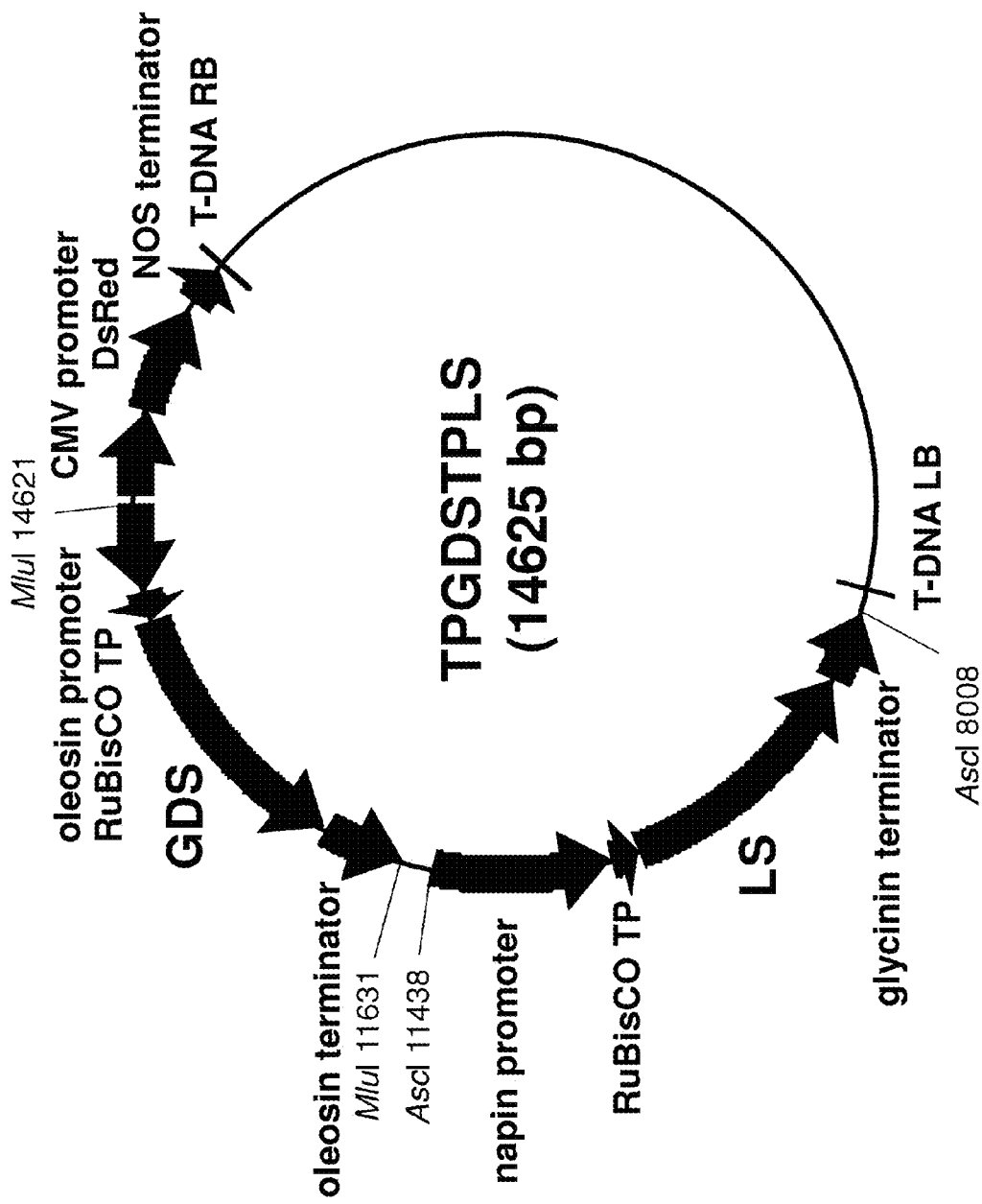
FIG. 25. Shows an exemplary plant expression vector (TPGDSTPLS) for co-expressing geranyl diphosphate synthase (GDS) and limonene synthase (LS) in plastid.

A pRS binary vector was obtained from Dr. Jan Jaworski, which contains a *Discosoma* red fluorescent protein (DsRed) as a selection marker, and AscI/MluI restriction enzyme sites between the left border and right border T-DNA repeat sequences. To eliminate a glycinin promoter and a glycinin terminator, pRS was digested by BamHI/HindIII and ligated with oligo nucleotides: fwdBamHIEcoRIHindIII and revHindIIIEcoRIBamHI (Table E1), yielding pRSe2 (FIG. 24). MluI-digested GDS from pNaMluIOleosinTPGDS (FIG. 22) and AscI-digested LS from pNaAscINapinTPLS (FIG. 23) were inserted into pRSe2 (FIG. 24) and sequenced, yielding a TPGDSTPLS *Camelina* transformation vector (FIG. 25).

Figure 26:
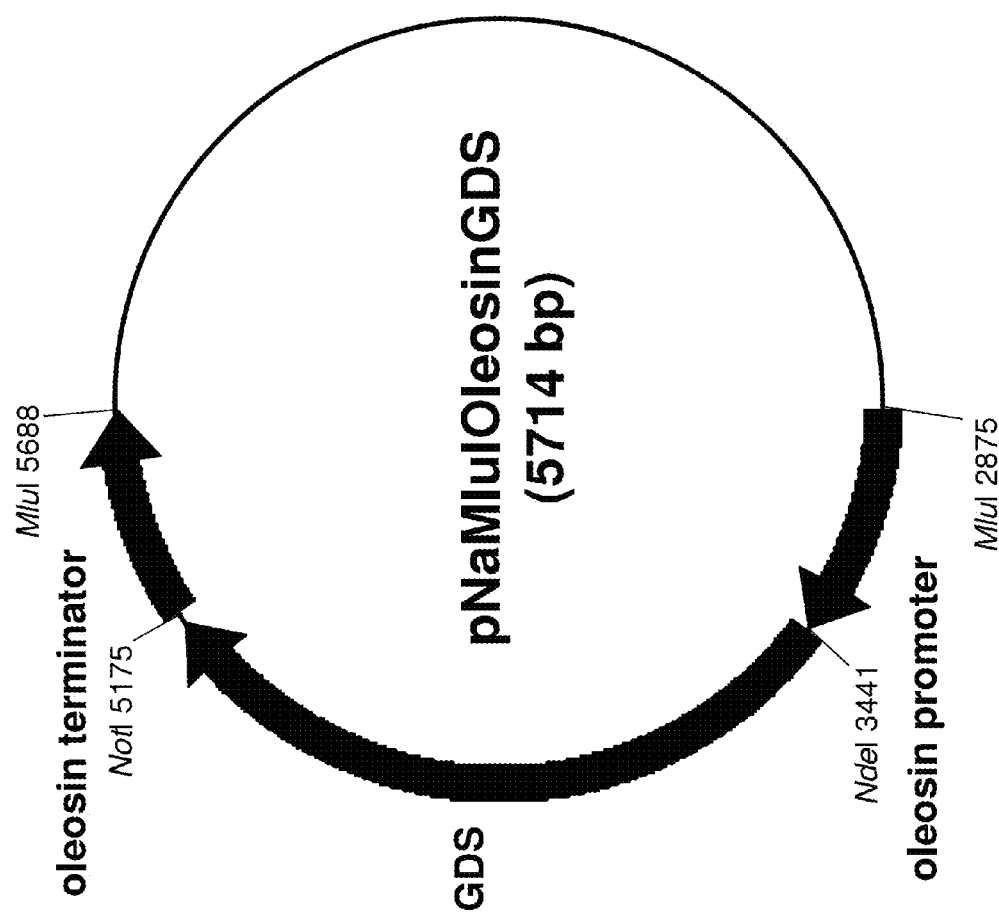
FIG. 26. Shows an exemplary *E. coli* cloning vector (pNaMluIOleosinGDS) with an oleosin promoter, GDS and an oleosin terminator.
Figure 27:
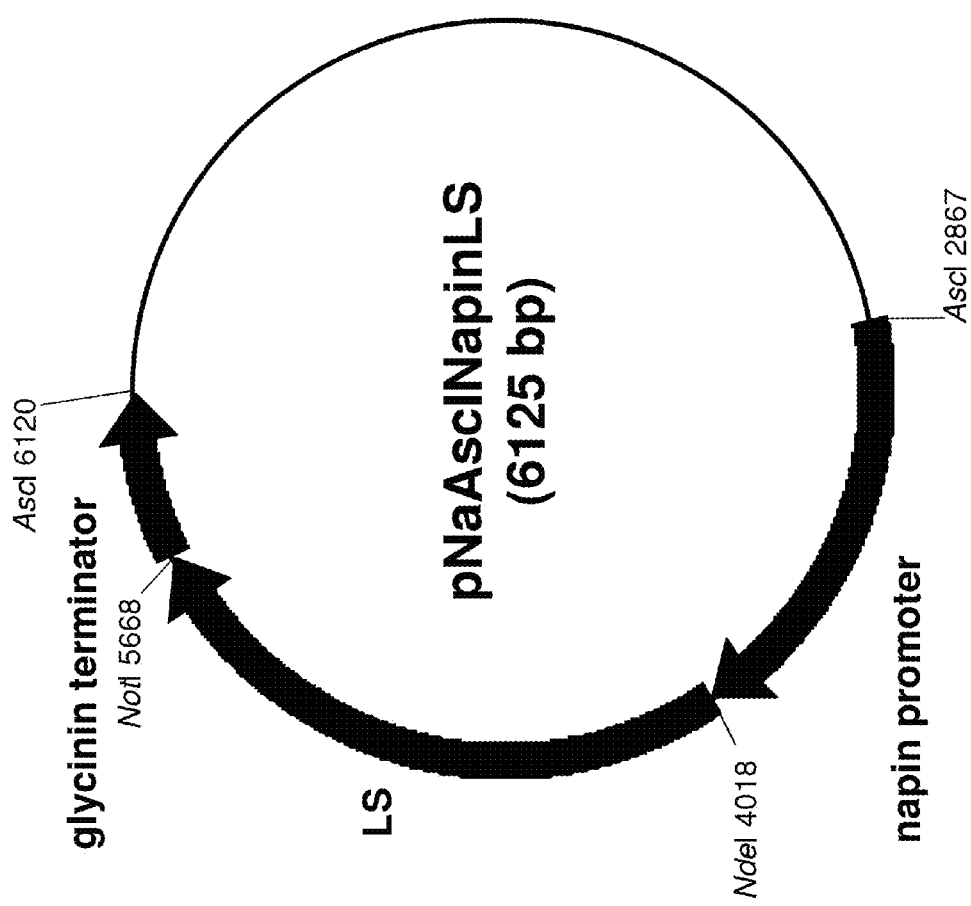
FIG. 27. Shows an exemplary *E. coli* cloning vector (pNaAscINapinLS) with a napin promoter, LS and a glycinin terminator.
Figure 28:
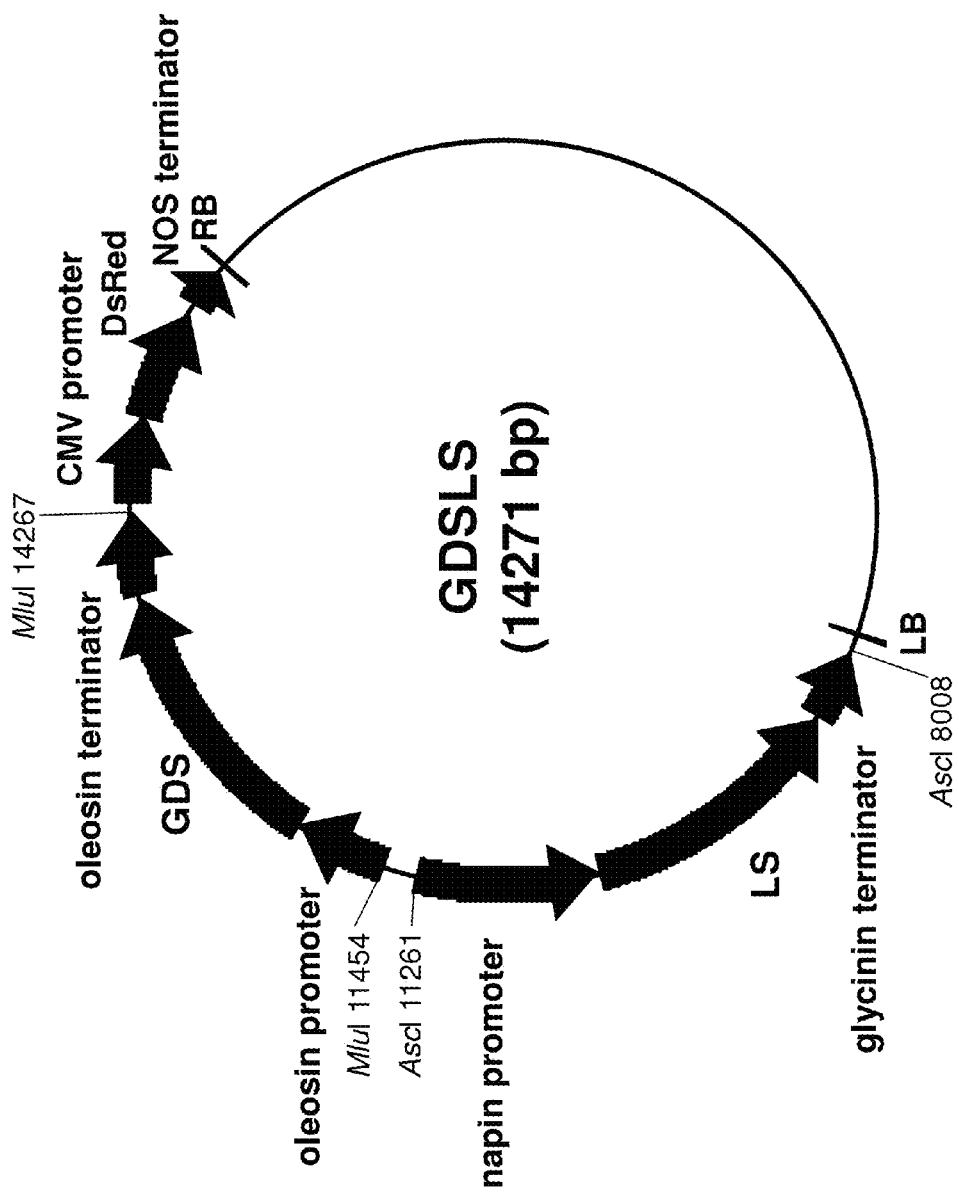
FIG. 28. Shows an exemplary plant expression vector (GDSLS) for co-expressing geranyl diphosphate synthase (GDS) and limonene synthase (LS) in cytosol.
Figure 29:
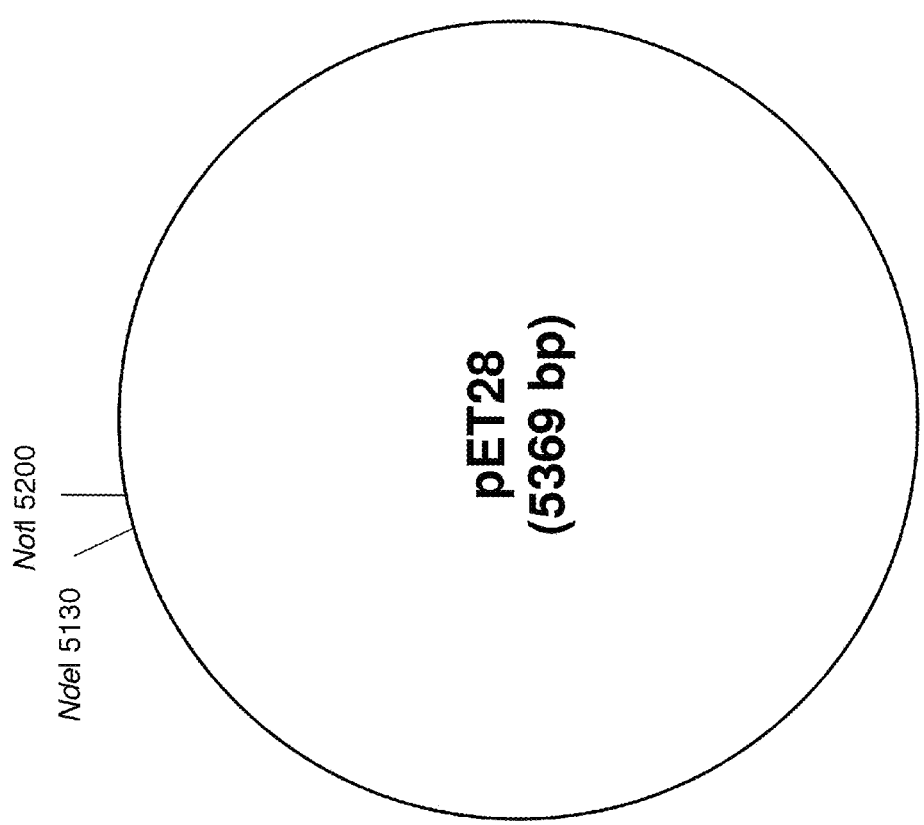
FIG. 29. Shows an exemplary *E. coli* expression vector (pET28)
Figure 30:
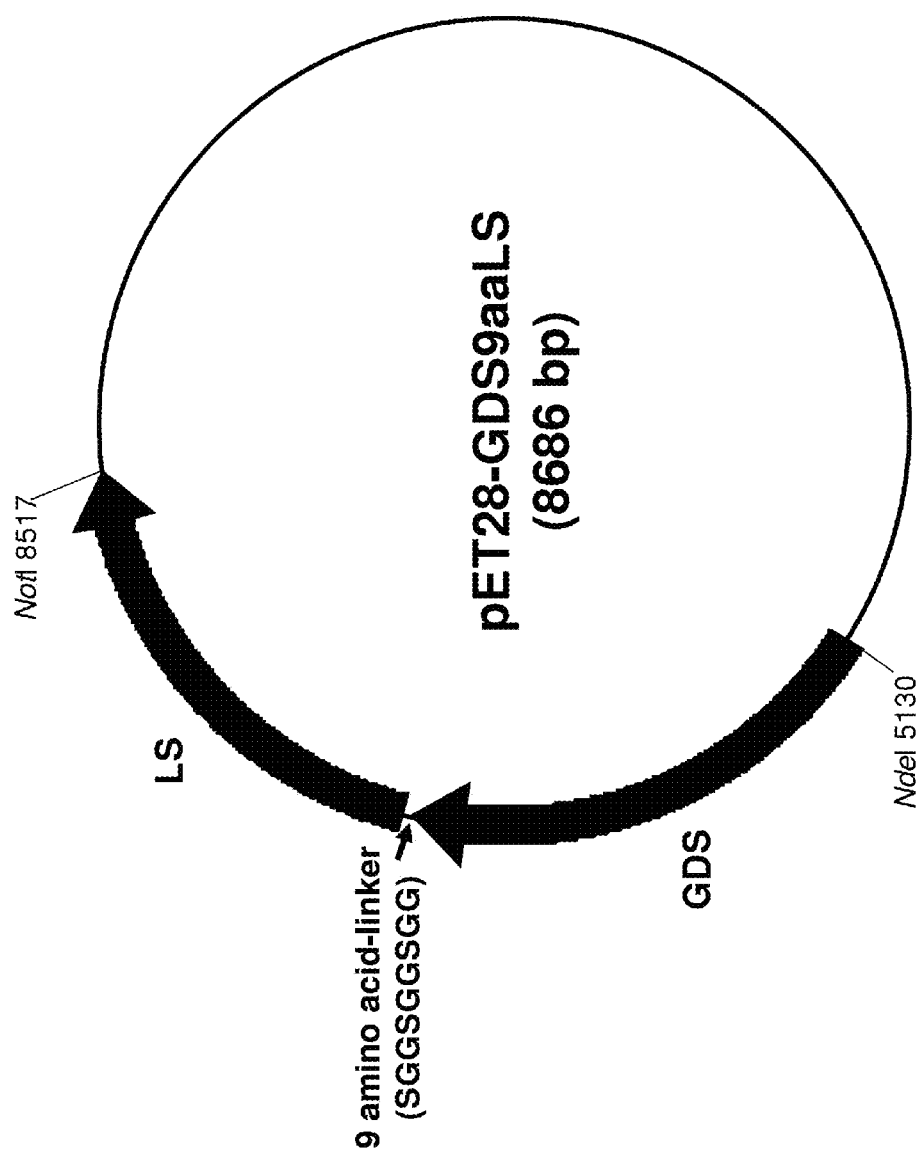
FIG. 30. Shows an exemplary *E. coli* expression vector (pET28-GDS9aaLS) for a fusion protein of geranyl diphosphate synthase (GDS) and limonene synthase (LS).
Figure 31:
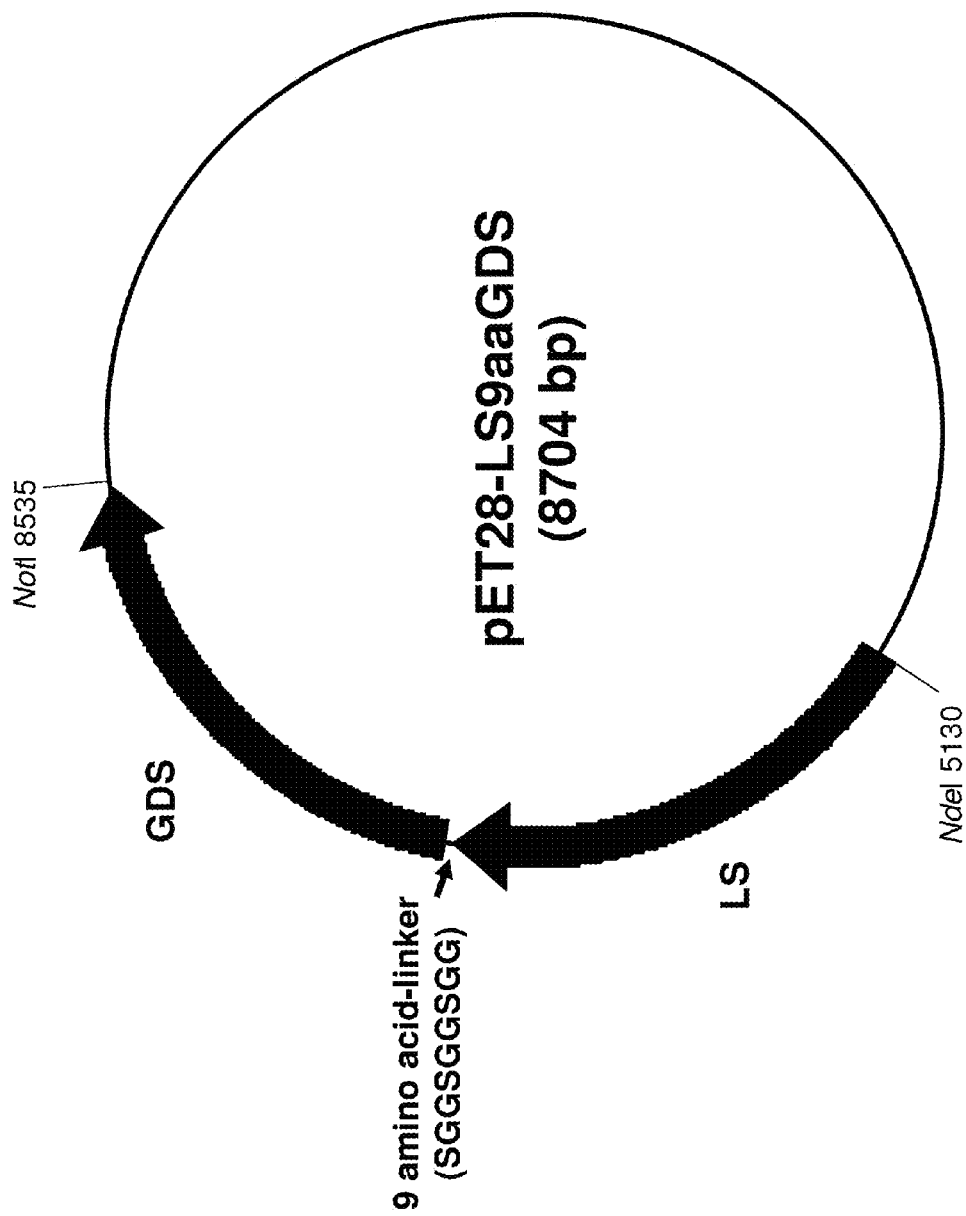
FIG. 31. Shows an exemplary *E. coli* expression vector (pET28-LS9aaGDS) for a fusion protein of limonene synthase (LS) and geranyl diphosphate synthase (GDS).

A GDSLS *Camelina* transformation vector (GDSLS) for cytosolic expression was prepared with pNaMluIOleosin (FIG. 17) and pNaAscINapin (FIG. 18). These entry vectors differ only in the absence of the sequence for TP from pNaMluIOleosinTP (FIG. 20) and pNaAscINapinTP (FIG. 21), respectively. NdeI/NotI-digested GDS and LS from the pET28-GDS (FIG. 12) and pET28-LS (FIG. 14) were inserted into pNaMluIOleosin (FIG. 17) and pNaAscINalin (FIG. 18), yielding pNaMluOleosinGDS (FIG. 26) and pNaAscINapinLS (FIG. 27). The subsequent procedures to make the binary vector (GDSLS) were identical to those of TPGDSTPLS, i.e. MluI-digested GDS from pNaMluIOleosinGDS (FIG. 26) and AscI-digested LS from pNaAscINapinLS (FIG. 27) were inserted into pRSe2 (FIG. 24) and sequenced, yielding a GDSLS *Camelina* transformation vector (FIG. 28). GDS9aaLS nucleotide sequence with NdeI/NotI sites was amplified by the 2-step PCR method using the TPGDSTPLS plasmid (FIG. 25) as template with primers: GSSfC, rev9aaGSLr2, fwd9aaLSfC3 and LSr (Table E1). The resulting PCR product was inserted into NdeI/NotI-digested pET28 (FIG. 29), yielding pET28-GDS9aaLS (FIG. 30). LS9aaGDS nucleotide sequence with NdeI/NotI sites was amplified by the 2-step PCR method using the TPGDSTPLS plasmid (FIG. 25) as template with primers: fwdLSfC3, rev9aaLSr, fwd9aaGSSfC and GSLr2. The resulting PCR product was inserted into NdeI/NotI-digested pET28 (FIG. 29), yielding pET28-LS9aaGDS (FIG. 31).

Plant Transformation:

The TPGDSTPLS vector (FIG. 25) and the GDSLS vector (FIG. 28) were transformed into *Agrobacterium tumefaciens* strain GV3101 (pMP90) using a freeze-thaw method (Weigel and Glazebrook (2006) *Cold Spring Harb Protoc.*, doi:10.1101/pdb.prot4666). Selection of transformed bacteria was carried out on YEP medium containing 10 g/l peptone, 5 g/l yeast extract and 5 g/l NaCl at pH 6.8 with 25 mg/l rifampicin, 40 mg/l gentamicin and 50 mg/l kanamycin. Overnight culture of the transformed bacteria was transferred into 2 l flask containing 300 ml YEP medium with 50 mg/l kanamycin and incubated at 28° C. for 24 hours. Cells were harvested by centrifugation for 20 min at root temperature at 5000 g and then resuspended in an infiltration medium containing half strength Murashige and Skoog Basal Medium, 50 g/l sucrose and 0.05% (v/v) Silwet L77 (Lehle Seeds, Round Rock, Tex.) to a final $OD_{600}$ of between 1.0 to 1.5.

*Camelina* transformation was performed using a floral dip method (Lu and Kang (2008) *Plant Cell Rep.*, 27, 273-8.). *Camelina* plants were inoculated with the *Agrobacterium* suspension prepared as described above. A flowering *Camelina* plant was placed into a vacuum desiccator and the inflorescences were immersed into the suspension in a 500 ml beaker. The suspension with the inflorescences was degassed under vacuum for 5 min. The inoculated plants were covered with plastic trays for 24 hours before returned to normal growth in greenhouse. Transgenic fluorescent mature seeds were illuminated by a green LED flashlight, and visually detected using a red-lens screen.

GC-MS Analysis of the Transgenic Seeds

Ten transgenic mature seeds were ground with a glass rod and then soaked overnight in diethyl ether at room temperature, and then shook every 15 minutes for two hours. Fifty nanomoles of iso-butylbenzene were added as internal standard for limonene analysis. The extract was concentrated under nitrogen and analyzed by GC-MS. GC-MS analyses were performed on an Agilent 5975C inert XL MSD equipped with a 7683B injector and a 7890A GC system, under the following conditions: EI, 70 eV; column, Phenomenex ZB-5MSi (32.5 m×250 μm×0.25 μm); oven temperature program, 50° C. for 3 min, and then raised to 65° C. at a rate of 5° C. $min^{-1}$, and then raised again to 75° C. at 1° C. $min^{-1}$, and then raised to 300° C. at 40° C. $min^{-1}$, held for 3 min; injector temperature 220° C.; source temperature 230° C.; interface temperature 250° C.; carrier gas, He; flow rate 1.0 ml/min; splitless injection; injected volume, 1.0 μL. Limonene accumulation was calculated using authentic limonene standard (Sigma). Other monoterpenes were identified by comparison of their EI-MS spectra with those of the NIST library (V 2.0).

Figure 3A:
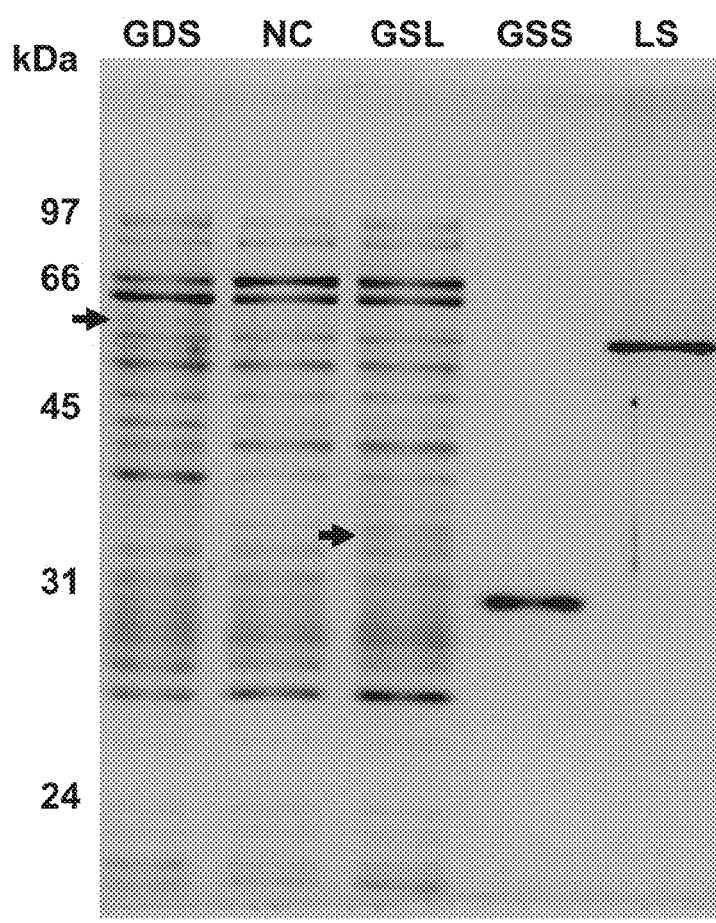
FIG. 3A. Shows the SDS PAGE analysis of the recombinant production of geranyl diphosphate synthase (GDS) and limonene synthase (LS) in *E. coli*. NC, vector control; GSL, geranyl diphosphate synthase large subunit; GSS, geranyl diphosphate synthase small subunit; LS, limonene synthase.
Figure 4:
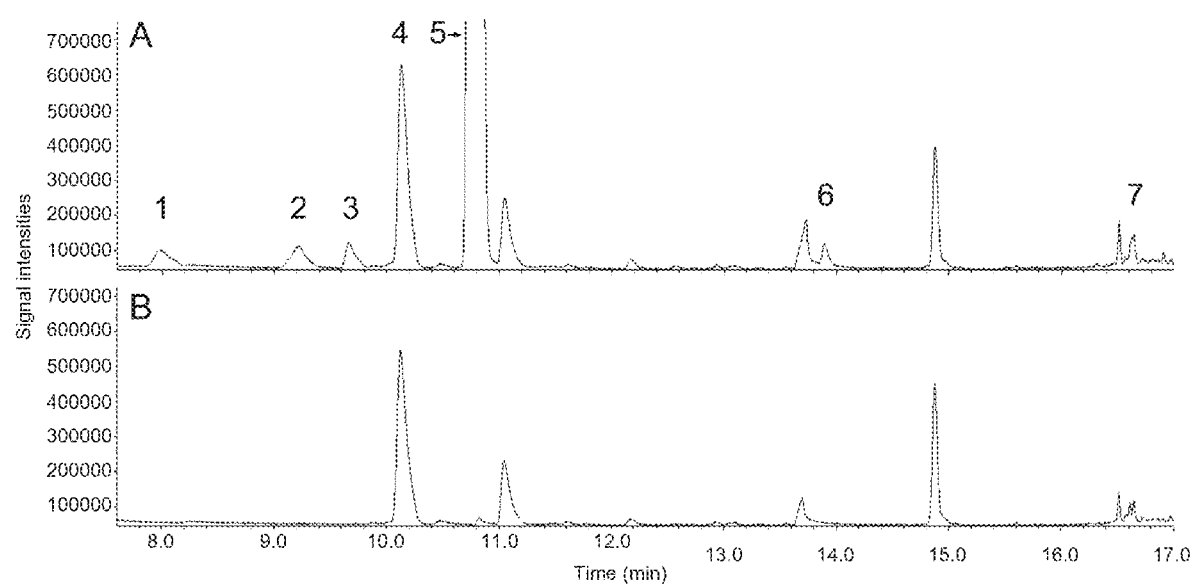
FIG. 4. Shows the accumulation of limonene detected by GC-MS. A, T2 *Camelina* seed extract expressing the individual enzymes GDS and LS in plastids using the TPGD-STPLS vector (#3-5), B, wild-type *Camelina* seed extract. Peak 1, $C_{10}H_{16}$; Peak 2, $C_{10}H_{16}$; Peak 3, $C_{10}H_{16}$; Peak 4, internal standard; Peak 5, limonene ($C_{10}H_{16}$); Peak 6, $C_{10}H_{16}O$; Peak 7, $C_{10}H_{14}O$.

The expressed and purified *E. coli* recombinant GDS, GSL, GSS and LS were observed on SDS-PAGE (FIG. 3A). Functional activity of the GDS protein was detected using isopentenyl diphosphate (IPP) and dimethylallyl diphosphate (DMAPP) as substrates to produce geranyl diphosphate (GPP) which was hydrolyzed to geraniol (FIG. 3B). Also, functional activity of the LS protein was detected using GPP as substrate to produce limonene (FIG. 3C). GC-MS separated limonene, three hydrocarbons ($C_{10}H_{16}$) and two oxidized monoterpenes ($C_{10}H_{16}O$, $C_{10}H_{14}O$) from the T2 seeds (FIG. 4). Limonene constituted 97.3% of the total monoterpenes calculated from the signal intensities.

Figure 5:
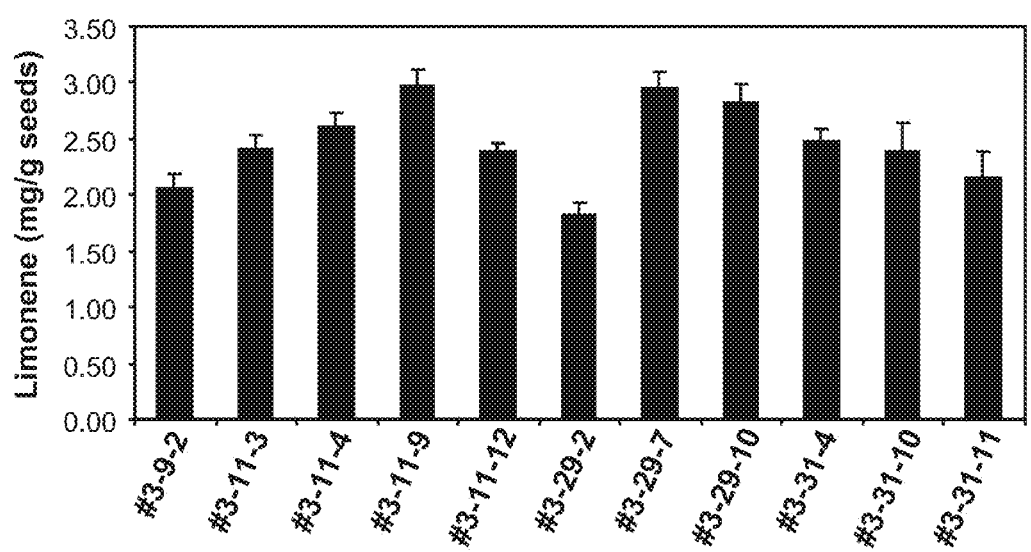
FIG. 5. Shows the limonene contents of T3 homozygous seeds expressing the individual enzymes GDS and LS in plastids using TPGDSTPLS vector. Ten seeds from each T3 line were analyzed by GC-MS. Bars show SD values from 3 to 6 extractions.

The limonene content of the T3 homozygous seeds ranged from 1.8 to 3 mg/g seeds (FIG. 5).

Figure 6:
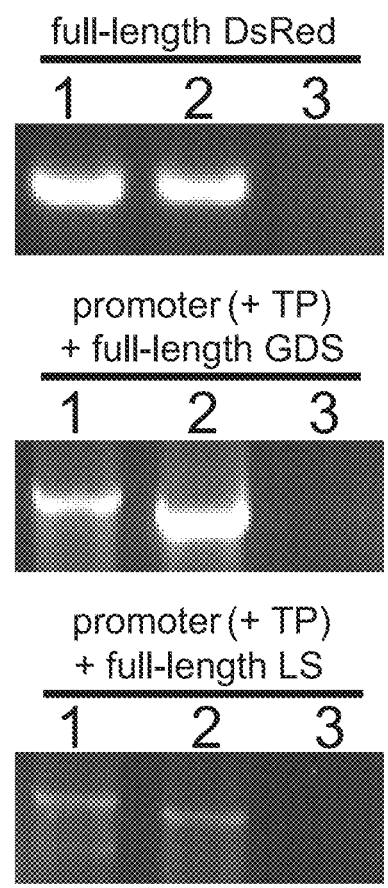
FIG. 6. Shows the results of Genomic DNA PCR analysis for the monoterpene genes from 10-day-old T2 leaves. PCR templates: Lane 1, genomic DNA extracted from T2 plants expressing the individual enzymes GDS and LS in plastid using TPGDSTPLS vector; Lane 2, genomic DNA extracted from T2 plants expressing the individual enzymes GDS and LS in cytosol using GDSLS vector; Lane 3, wild-type *Camelina* genomic DNA.
Figure 7:
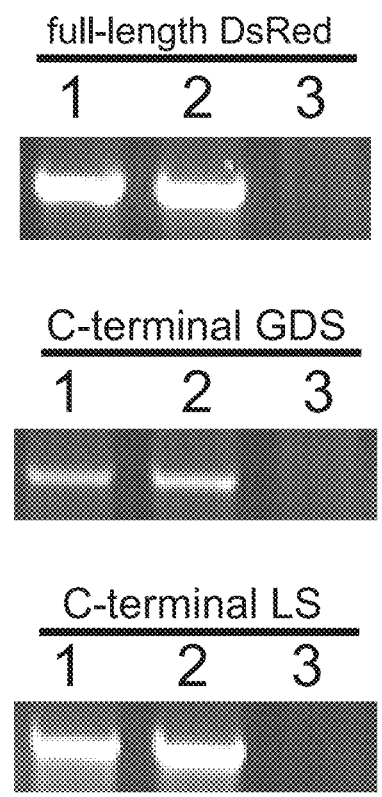
FIG. 7. Shows the results of Expression analysis (RT-PCR) for the monoterpene genes in T2 developing seeds. PCR templates: Lane 1, genomic DNA extracted from T2 seeds expressing the individual enzymes GDS and LS in plastid using TPGDSTPLS vector; Lane 2, genomic DNA extracted from T2 seeds expressing the individual enzymes GDS and LS in cytosol using GDSLS vector; Lane 3, wild-type *Camelina* genomic DNA.
Figure 8:
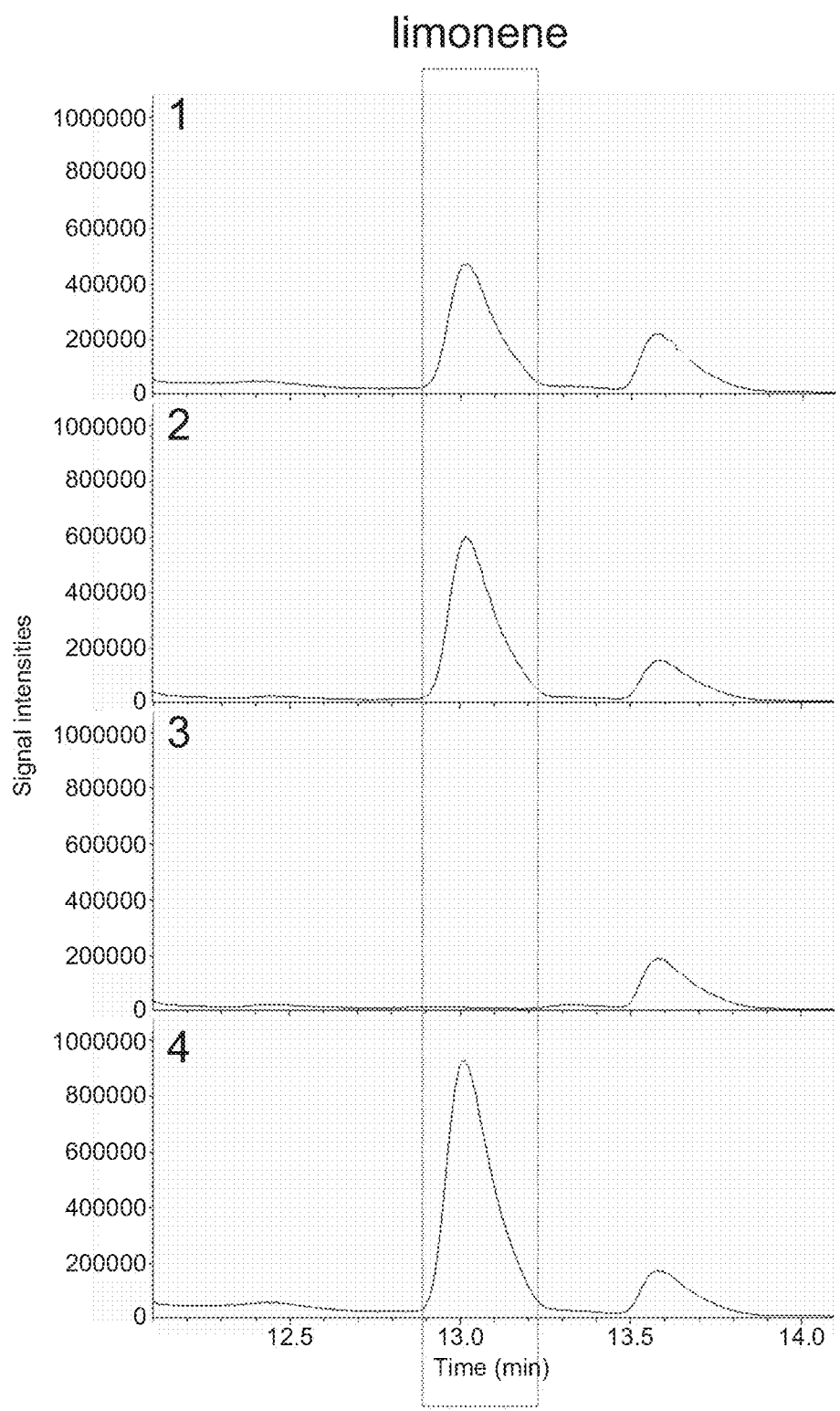
FIG. 8. Shows the results of GS-MS analysis of samples from T2 mature seeds transformed with GDS and LS after in vitro coupling enzyme reactions. Substrates IPP and DMAPP were incubated with, seed extract expressing the individual enzymes GDS and LS in plastid using TPGDST-PLS vector (spectra 1), seed extract expressing the individual enzymes GDS and LS in cytosol using GDSLS vector (spectra 2), wild-type seed extract (spectra 3), wild-type seed extract and both *E. coli* recombinant GDS and LS (spectra 4).
Figure 9A:
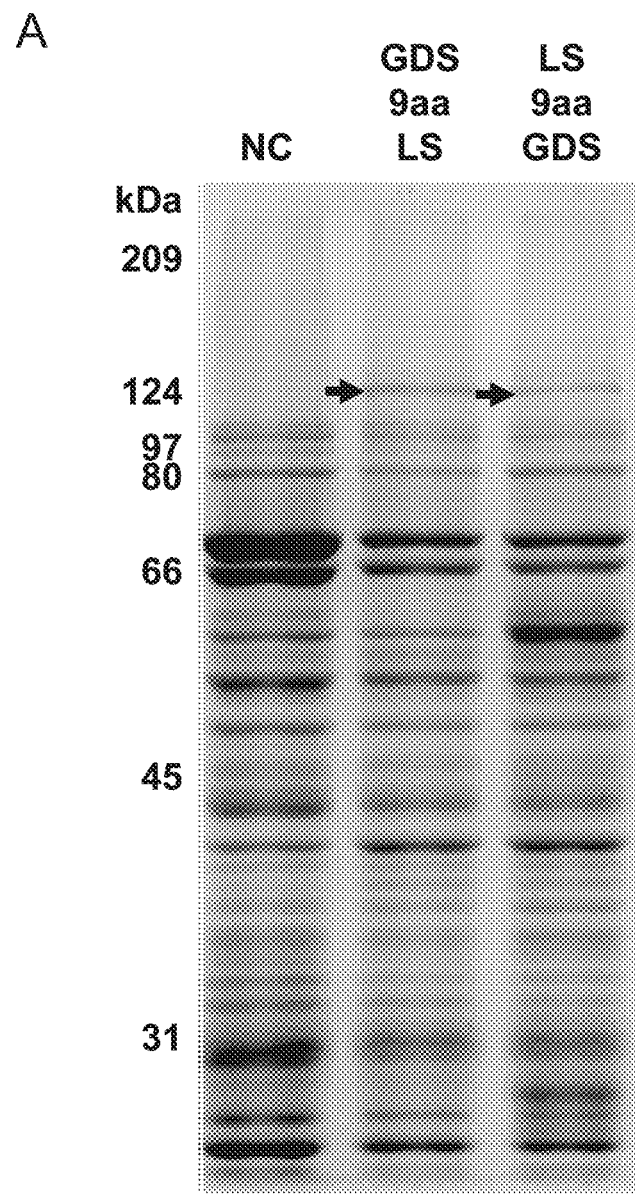
FIG. 9A shows the results of SDS-PAGE analysis of *E. coli* expressed recombinant proteins comprising N-terminal His-tagged versions of 2 fusion proteins comprising from the N-terminus, the GDS small subunit and large subunit fused to LS via a 9 amino acid-linker and a fusion protein comprising the same proteins but in the opposite orientation. NC, vector control; GDS9aaLS, geranyl diphosphate synthase (GDS) and limonene synthase (LS) fusion protein with a 9 amino acid-linker; LS9aaGDS, limonene synthase (LS) and geranyl diphosphate synthase (GDS) fusion protein with a 9 amino acid-linker.

T-DNA insertion was confirmed by PCR analyses of total DNA of T2 leaves (FIG. 6). Expression of mRNA from the integrated DsRed, GDS and LS were analyzed by RT-PCR (FIG. 7). Both GDS and LS enzyme activities were detected from T2 seeds in vitro by a coupling enzyme assay (FIG. 8). A reaction mixture containing transgenic seed extract catalyzed the enzymatic reactions of GDS and LS, i.e. producing limonene from IPP and DMAPP. These results suggest that peppermint GDS and LS expressed in *Camelina* were accumulated as catalytically active protein in the transgenic developing seeds in both TPGDSTPLS and GDSLS, although limonene was not detected in GDSLS transgenic seeds. GDS9aaLS and LS9aaGDS enzymes were expressed in *E. coli* host cells BL21(DE3)RIL containing pET28-GDS9aaLS (FIG. 30) and pET28-LS9aaGDS (FIG. 31). Both recombinant proteins were separated by SDS-PAGE and detected by Sypro-Ruby staining (Invitrogen) (FIG. 9A). Functional activity of the fusion GDS9aaLS protein was not detected using isopentenyl diphosphate (IPP) and dimethylallyl diphosphate (DMAPP) as substrates to produce limonene (FIG. 9B). Functional activity of the fusion LS9aaGDS protein was detected using isopentenyl diphosphate (IPP) and dimethylallyl diphosphate (DMAPP) as substrates to produce limonene (FIG. 9C).

TABLE E1

Primer sequences

| Name | Sequence | SEQ ID NO: |
|---|---|---|
| GSSfC | GGA TCC TTT CAT ATG CAG CCG TAC TGG GCC GCC AT | 39 |
| GSSr4 | TT GC GGC CGC TGA AGG ATC CGA ATA GCT CTA AGC C | 40 |
| GSLfC | GGA TCC TTT CAT ATG TTC GAT TTC GAC GGA TAC ATG CTC | 41 |
| GSLr2 | TT GC GGC CGC GAG AGG AGG AAG ATG GAA TCA ATT GTC | 42 |
| GSSr10aa | CCG GCC CTC GAT GCC GAG ATT GTT GGA GCT AGC CGC GTA AAG GCT CGG | 43 |
| 10aaGSLfC | AGC TCC AAC AAT CTC GGC ATC GAG GGC CGG TTC GAT TTC GAC GGA TAC ATG CTC | 44 |
| LSuf | GGA TCC AAACAT CAT AGA AAG AGA GTG GAA GAA AAG GAG | 45 |
| LSr | TT GC GGC CGC TCA TGC AAA GGG CTC GAA TAA GGT TG | 46 |
| fwdLSfC3 | GGA TCC TTT CAT ATG CAA CTC ACT ACC GAA AGA CGA TCC | 47 |
| fwdSacIMluISacI | TTCC AAA CAC ACG CGT AAA CAA CTT TAGCT | 48 |
| revSacIMluISacI | AA AGT TGT TTACG CGT G TGT TTG GAAAGCT | 49 |
| fwdMluIOP | TTT ACG CGT TAG TGT TTA TCT TTC TTG CTT TTC TGA AC | 50 |
| revNotIBamHINdeIOP | GC GGC CGC AGGA TCC TTT GCT AGC CAT ATG GGT TGA AGG TGA AGT TTA GGG TTT TGC | 51 |
| fwdNdeIBamHINotIOT | CAT ATG GCT AGC AAAGGA TCC TGC GGC CGC TGA GTA ATT CTG ATA TTA GAG GGA GC | 52 |
| revMluIOT | TTT ACG CGT TTG CTG AAA AAT GCC TAT GGG CTG ATG | 53 |
| fwdAscINP | TTT GG CGCG CC AAG CTT TCT TCA TCG GTG ATT GAT TCC | 54 |
| revNotIBamHINdeINP | GC GGC CGC AGGA TCC TTT GCT AGC CAT ATG TCG TGT ATG TTT TTA ATC TTG TTT GTA TTG | 55 |
| fwdNdeIBamHINotIGT | CAT ATG GCT AGC AAAGGA TCC TGC GGC CGC AGC CCT TTT TGT ATG TGC TAC C | 56 |
| revAscIGT | TTT GG CGCG CC AAG TCA TGA AGA ACC TGA TAA GAC GTC TTC | 57 |
| RuSfwd | GGA TCC TTT CAT ATG GCT TCT ATG ATA TCC TCT TCC GCT GTG | 58 |
| RuSrev | TTT CTC GAG TTA GTA GGA TTC TGG TGT GTG TGC AAT GAA ACT | 59 |
| revBamHIRuTP | AGG ATC CAT GCA CTT TAC TCT TCC ACC ATT GCT TG | 60 |
| fwdBamHIGDS | ATG GAT CCTCAG CCG TAC TGG GCC GCC AT | 61 |

TABLE E1-continued

Primer sequences

| Name | Sequence | SEQ ID NO: |
|---|---|---|
| fwdBamHILS | ATG GAT CCTCAA CTC ACT ACC GAA AGA CGA TCC | 62 |
| fwdBamHIEcoRIHindIII | GATCA GAATTC GAGCTC A GTCGAC A | 63 |
| revHindIIIEcoRIBamHI | AGCTT GTCGAC T GAGCTC GAATTC T | 64 |
| rev9aaGSLr2 | ACC TCC AGA ACC TCC TGA ACC TCC AGA ATT GTC CCT ATA AGC AAT ATA ATT GGC | 65 |
| fwd9aaLSfC3 | TCT GGA GGT TCA GGA GGT TCT GGA GGT ATG CAA CTC ACT ACC GAA AGA CGA TCC | 66 |
| rev9aaLSr | ACC TCC AGA ACC TCC TGA ACC TCC AGA TGC AAA GGG CTC GAA TAA GGT TG | 67 |
| fwd9aaGSSfC | TCT GGA GGT TCA GGA GGT TCT GGA GGT ATG CAG CCG TAC TGG GCC GCC AT | 68 |
| FDSf | GAA TTC TTT CAT ATG GCG GAT CTG AAA TCA ACC TTC C | 69 |
| FDSr | TTG CGG CCG CCT ACT TCT GCC TCT TGT AGA TCT TAG CCA | 70 |
| fwdBamHIEAS | ATG GAT CCA GCA TCA GCA GCA GTA GCC AAC | 71 |
| NtEASrc | ATA AGA ATG CGG CCG CCA GCT CAA ATT TTG ATG GAG TCC AC | 72 |

Example 2

Biosynthesis and Accumulation of Cyclic Monoterpene Hydrocarbon (4S)-Limonene and the Bicyclic Sesquiterpene Hydrocarbon 5-Epi-Aristolochene in *Camelina* Seed This example describes the biosynthesis and accumulation of the cyclic monoterpene hydrocarbon (4S)-limonene and the bicyclic sesquiterpene hydrocarbon 5-epi-aristolochene in *camelina* seed by expressing appropriate combinations of terpene biosynthetic enzymes.

The phrase "biosynthetically appropriate combination of enzymes" refers to a combination of terpene biosynthetic enzymes that facilitates the biosynthesis of a monoterpene or sesquiterpene of interest. Such combinations include a combination of: 1) a geranyl diphosphate synthase and a monoterpene synthase that catalyzes the formation of a monoterpene of interest, or 2) a combination of a farnesyl diphosphate synthase and a sesquiterpene synthase that catalyzes the formation of a sesquiterprene of interest. The phrase "a biosynthetically appropriate combination of nucleotide sequences" refers to nucleotide sequences that encode such biosynthetically appropriate combinations of enzymes.

Numerous monoterpene and sesquiterpene synthases that can be employed in the methods of the present invention to produce monoterpenes and sesquiterpenes of interest are known in the art, and are reviewed in Degenhardt et al. Phytochemistry 70:1621-1637 (2009).

Geranyl diphosphate synthase (peppermint) (Burke C. C., Wildung M. R. and Croteau R. (1999) *Proc Natl Acad Sci USA.*, 96, 13062-7) and (4S)-limonene synthase (peppermint) (Colby, S. M. Alonso, W. R., Katahira, E. J., McGarvey, D. J. & Croteau, R. *J. Biol. Chem.* 268, 23016-23024 (1993)) as well as farnesyl diphosphate synthase (*arabidopsis*) (Cunillera, N. et al. *J. Biol. Chem.* 271, 7774-7780 (1996)) and epi-aristolochene synthase (tobacco) (Wu, S. et al. *Plant Physiol.* 138, 1322-1333 (2005)) encoding cDNAs were constructed for either plastidic (expression vectors TPGDS TPLS and TPFDS TPEAS) or cytosolic (expression vectors GDS LS and FDS EAS) accumulation of enzymes behind seed-specific promoters (FIG. 32b) and introduced into *camelina* inflorescence by floral dip (Lu, C. & Kang, *J. Plant Cell Rep.* 27, 273-278 (2008)). Native transit peptides on the prenyltransferases and terpene synthases were replaced by the pea Rubisco small subunit transit peptide (Van den Broeck, G. et al. *Nature* 313, 358-363 (1985)).

While this example demonstrates the use of chloroplast transit peptides to target enzymes for the synthesis and accumulation of a monoterpene and a sesquiterpene of interest to plastids, expression of these enzymes in plastids via direct transformation of plastids with necessary coding sequences is also encompassed by the present invention.

Furthermore, while this example employs chloroplast transit peptide sequences, seeds contain a variety of other plastids as well, including, for example, proplastids, etioplasts, chromoplasts, leucoplasts, amyloplasts, and photoheterotrophic plastids. Consequently, plastid transit peptides that target peptides, polypeptides, or proteins to any of these types of plastids in seeds can also be employed in the methods of the present invention.

The geranyl diphosphate synthase from peppermint is a heterodimer, which was expressed as a fusion protein in *camelina* seed. Each reading frame was placed under the control of either the oleosin (Rowley et al. *Biochim. Biophys. Acta* 1345, 1-4 (1997)), napin (Josefsson et al. *J. Biol.*

Chem. 262, 12196-12201 (1987)), or glycinin (Nielsen et al. Plant Cell 1, 313-328 (1989)) promoter; any given promoter was used only once in an expression vector to avoid potential gene silencing. The effect of overexpression of the DXS (Estévez et al. Plant Physiol. 124, 95-104 (2000)) (expression vector TPGDS TPLS DXS), a gene encoding the enzyme 1-deoxy-D-xylulose 5-phosphate synthase that is involved in the formation of IPP and DMAPP via the non-mevalonate pathway in plastids, on terpene accumulation was also tested. The vectors contained the gene encoding the red-emitting fluorescent protein (DsRed) (Lu et al. Plant Cell Rep. 27, 273-278 (2008)), which facilitated transgenic seed identification under green light.

Six to seven weeks post floral dip, mature camelina seeds were harvested and fluorescent red, putative transgenic seeds, were extracted and analyzed by GC-MS for the presence of either mono- or sesquiterpenes. GC-MS analysis of TPGDS TPLS plants ((4S)-limonene biosynthetic enzymes directed to the plastid of camelina seed)) indicated that camelina that had been transformed with a geranyl diphosphate synthase cDNA from peppermint and a (4S)-limonene synthase cDNA from peppermint accumulates (4S)-limonene and minor amounts of four other similar monoterpene hydrocarbons in seed, whereas the wild type camelina seed is devoid of monoterpenes (FIG. 33a) Likewise, GC-MS analysis of TPFDS TPEAS plants (a farnesyl diphosphate synthase cDNA from arabidopsis and an epi-aristolochene synthase cDNA from tobacco directed to the plastid) indicated that, whereas wild type camelina seed is devoid of sesquiterpenes, camelina that had been transformed with sesquiterpene biosynthetic enzyme encoding cDNAs accumulated 5-epi-aristolochene plus minor quantities of nine other sesquiterpenes in seed (FIG. 33b). Functional expression of the transgenes was confirmed by RT-PCR and in vitro enzyme assay (FIGS. 35, 36).

Multiple transgenic events were achieved and analyzed with each vector construct tested. Typically, fifteen plants were transformed with each expression vector construct. A total of ca. 70-140 DsRed-positive seeds were obtained, representing 0.2-0.8% of total seeds produced in fifteen plants. Initial GC-MS analyses were carried out on extracts of individual Ti seeds. In subsequent generations, ten transgenic (red) seeds from each plant were combined for terpene extraction with subsequent GC-MS analysis. Only seeds from the T3 generation that were homozygous lines (produced >95% red seeds) were used for further analysis. The most productive monoterpene constructs yielded 1.5-3 mg (4S)-limonene per gram seed (TPGDS TPLS; (4S)-limonene biosynthetic enzymes directed to the plastid of camelina seed; FIG. 34a). When biosynthetic enzymes were directed to the cytosol (GDS LS), substantially less (4S)-limonene accumulated (0.065 mg g$^{-1}$ seed; FIG. 34b). Increasing the flux through the non-mevalonate pathway by over-expression of the non-mevalonate pathway gene DXS, as has been shown to be effective in other plants (Estévez et al. J. Biol. Chem. 276, 22901-22909 (2001)), doubled (4S)-limonene accumulation to 6 mg g$^{-1}$ seed (FIG. 34c). Corresponding constructs for sesquiterpene production resulted in the accumulation of 5-epi-aristolochene in both the plastid—(TPFDS TPEAS, 0.2-1.4 mg g$^{-1}$ seed) (FIG. 34d) and cytosol experiments (FDS EAS, 0.06-1.25 mg g$^{-1}$ seed) (FIG. 34e). In plants, (4S)-limonene is normally biosynthesized in plastid, and 5-epi-aristolochene is formed in the cytosol. In transgenic camelina seed, higher accumulation levels of (4S)-limonene were achieved in plastid and higher accumulation levels of 5-epi-aristolochene were also achieved in plastid. The activities of both the prenyltransferases and terpene synthases were tested in vitro in crude protein extracts prepared from camelina seed in order to examine whether the differences in terpene accumulation in the plastid and cytosol experiments were due to variations in enzyme activity. Both the plastidic and cytosolic accumulation experiments yielded similar ranges of GDS specific activity (TPGDS TPLS, 7-13.5 pmol min$^{-1}$ mg$^{-1}$ protein; GDS LS, 6.5-15 pmol min$^{-1}$ mg$^{-1}$ protein; FIG. 36a) and LS specific activity (TPGDS TPLS, 0.2-0.75 pmol min$^{-1}$ mg$^{-1}$ protein; GDS LS, 0.05-1.55 pmol min$^{-1}$ mg$^{-1}$ protein; FIG. 36b) Likewise, the plastidic and cytosolic accumulation experiments that compared constructs with and without the non-mevalonate pathway gene DXS yielded similar ranges of GDS specific activity (TPGDS TPLS, 12.5 pmol min$^{-1}$ mg$^{-1}$ protein; TPGDS TPLS DXS, 11.5 pmol min$^{-1}$ mg$^{-1}$ protein; FIG. 36c) and LS specific activity (TPGDS TPLS, 0.9 pmol min$^{-1}$ mg$^{-1}$ protein; TPGDS TPLS DXS, 1.1 pmol min$^{-1}$ mg$^{-1}$ protein; FIG. 36d).

Fusions between prenyltransferases and terpene synthase occur in nature, at least for formation of the diterpenes, the fusicoccins, in the plant pathogenic fungus Phomopsis amygdali (Toyomasu et al. Proc. Natl. Acad. Sci. USA 104, 3084-3088 (2007)). Fusion of farnesyl diphosphate synthase from Artemisia annua and 5-epi-aristolochene synthase from tobacco produced a functional chimera in E. coli. The $K_m$ values were unchanged in the fusion protein when compared to the individual enzymes, however, a more efficient conversion of IPP to 5-epi-aristolochene was achieved with the fusion protein (Brodelius et al. Eur. J. Biochem. 269, 3570-3577 (2002)). The geranyl diphosphate synthase expressed herein in camelina seed was a fusion of heteromonomers (Burke et al. Arch. Biochem. Biophys. 422, 52-60 (2004)). When fusions of geranyl diphosphate synthase and (4S)-limonene synthase were introduced into camelina, seed specific expression resulted in reduced quantities of (4S)-limonene when compared to experiments in which geranyl diphosphate synthase and (4S)-limonene synthase were produced as discrete enzymes (FIG. 37).

Since the terpene carbon skeleton can be oxygenated and further modified by addition of sugar moieties (Lücker et al. Plant J. 27, 315-324 (2001)), analyses for the presence of O-glycosylated monoterpene was also performed on camelina control- and transgenic seed. Total glycoside for T5 TPGDS TPLS seed was 1.54±0.54 mg/g (ca. ⅓ of total (4S)-limonene accumulated) based on LC-MS/MS using phenyl-β-D-glucopyranoside as standard. Although the exact position of glycosylation was not determined, the high-resolution mass spectra indicated that mono- and dihydroxylation of the monoterpene skeleton had occurred in camelina seed and facilitated O-glycosylation. Deglycosylation with 1 N HCl at 100° C. for 2 h resulted in formation of monohydroxylated (4S)-limonene and 4-isopropyltoluene (also called cymene, a constituent of oil of cumin and thyme), thereby confirming dihydroxylation of the hexene ring of (4S)-limonene.

Specialized cellular compartments have evolved to store terpenes in plants, such as the subcuticular space between trichome head cells and the cuticle that encloses them in herbaceous plant species (Gershenzon et al. Anal. Biochem. 200, 130-138 (1992)). Due to the high volatility of monoterpenes and the lack of a specialized storage compartment in camelina seed, head-space analysis of developing seed and mature, stored seed was carried out on (4S)-limonene-accumulating transgenic camelina to estimate yield loss due to release to the atmosphere. The amount of total volatile (4S)-limonene emitted during weeks 7 to 13 was calculated as 7.0 and 24.8 μg plant$^{-1}$, which corresponded to 0.24 and 0.84% of accumulated (4S)-limonene in mature seed, respectively (Table 1). Transgenic TPGDS TPLS plants monitored through the T5 generation demonstrated stability in (4S)-limonene accumulation (FIG. 38).

TABLE 1

(4S)-Limonene emission from TPGDS TPLS (plastid) developing *camelina* plant*

| Plant age (weeks) | TPGDS TPLS plastidic $T_4$ plant | | Wild type |
|---|---|---|---|
| | experiment 1 | experiment 2 | |
| | (ng limonene emitted plant$^{-1}$ hr$^{-1}$) | | |
| 7 | 0.0 | 0.0 | 0.0 |
| 8 | 2.6 | 0.0 | 0.0 |
| 9 | 17.2 | 78.9 | 0.0 |
| 10 | 10.6 | 68.6 | 0.0 |
| 11 | 7.5 | 0.0 | 0.0 |
| 12 | 4.0 | 0.0 | 0.0 |
| 13 | 0.0 | 0.0 | 0.0 |
| mature seed | 0.0 | 0.0 | 0.0 |

*The amount of total volatile (4S)-limonene emitted during weeks 7 to 13 was calculated as 7.0 and 24.8 µg plant$^{-1}$, which corresponded to 0.24 and 0.84% of accumulated (4S)-limonene in mature seed, respectively.

Taken together, the results presented herein demonstrate that *camelina* seed is a suitable synthetic biology platform for the production and accumulation of cyclic hydrocarbons that can function as components of biofuels. The plant is genetically tractable by floral dip, selection of transgenic seed is facilitated by florescence resulting from expression of the gene encoding DsRed in the transformation vector, and transgene expression is stable over at least generations. Importantly, loss of volatile terpenes during seed development and storage is minimal, and acid hydrolysis of terpene O-glucosides that are formed results in aromatic derivatives. These results should therefore be fully extrapolatable to seeds of other oil crops.

Cyclic terpenes are currently being considered as alternatives to diesel (Peralta-Yahya et al. *Nat. Commun.* 2, Article 483 (2011)). In this example, we demonstrate the production of cyclic mono- and sesquiterpenes as advanced biofuels in a nonfoodstuff oilseed crop. To the best of the inventor's knowledge, it has not been shown that cyclic terpene hydrocarbons can be stably over-produced and accumulated in an oilseed. To achieve industrial feasibility, we expect to increase terpene accumulation by optimizing flux through the biochemical pathway by altering gene dosage of prenyltransferase vs. terpene synthase to balance the difference in steady-state kinetics between these two classes of enzymes.

Materials and Methods

Cloning.

Total RNA was extracted from *Mentha piperita* (peppermint) and *Arabidopsis thaliana* (*Arabidopsis*) leaves using RNeasy plant mini kit (Qiagen). First-strand cDNAs were synthesized using SuperScript III (Invitrogen). Genomic DNA was extracted from *Nicotiana tabacum* (tobacco) leaves using DNeasy plant mini kit (Qiagen). Geranyl diphosphate synthase small subunit (GSS) and geranyl diphosphate synthase large subunit (GSL) have been cloned from the peppermint cDNAs with primers: GSSfC/GSSr4 and GSLfC/GSLr2, respectively (see Table E1 for primer sequences). A cDNA encoding the geranyl diphosphate synthase fusion protein (GDS) was generated by a 2-stage polymerase chain reaction (PCR) method (Burke et al. *Arch. Biochem. Biophys.* 422, 52-60 (2004)) using the GSS and GSL clones as templates by Phusion polymerase (New England BioLabs) with primers: GSSfC/GSSr10aa/10aaG-SLfC/GSLr2. GDS is comprised of GSS, a 10 amino acid linker (SSNNLGIEGR (SEQ ID NO:72)) and GSL. Limonene synthase (LS) has been cloned from the peppermint cDNAs with primers: LSuf/LSr and fwdLSfC3/LSr. Farnesyl diphosphate synthase (FDS) gene has been cloned from the *Arabidopsis* cDNA with primers: FDSf/FDSr. The 5-epi-aristolochene synthase (EAS) sequence was amplified from the tobacco DNA with primers: fwdBamHIEAS/NtEASrc.

Transformation Vectors.

The pNaMluIOleosin entry vector (OP-OT) contains a soybean oleosin promoter (OP) and a soybean oleosin terminator (OT). The pNaAscINapin entry vector (NP-GT) contains a rapeseed napin promoter (NP) and a soybean glycinin terminator (GT). A binary vector, pRS, was a kind gift from Dr. Jan Jaworski (Donald Danforth Plant Science Center, MO). The nucleotide sequence was modified as follows: The pRSe2 vector contains a *Discosoma* red fluorescent protein (DsRed) as a selection marker between the left and right border T-DNA repeat sequences. The pea Rubisco small subunit transit peptide (TP) was inserted into pNaMluIOleosin and pNaAscINapin, yielding pNaMluIOleosinTP (OP-TP-OT) and pNaAscINapinTP (NP-TP-GT) entry vectors, respectively. The cloned sequences of GDS, LS, FDS and EAS were inserted into the entry vectors. The nucleotide sequences of OP-TP-GDS-OT and NP-TP-LS-GT, OP-GDS-OT and NP-LS-GT, OP-FDS-OT and NP-EAS-GT, and OP-TP-FDS-OT and NP-TP-EAS-GT were inserted into pRSe2 and sequenced, yielding TPGDS TPLS (plastid), GDS LS (cytosol), FDS EAS (cytosol), and TPFDS TPEAS (plastid) *camelina* transformation vectors, respectively.

Fusion proteins of GDS and LS were constructed, which contained a nine amino acid linker (9aa, SGGSGGSGG (SEQ ID NO:35). The nucleotide sequences of OP-GDS-9aa-LS-OT, OP-TP-GDS-9aa-LS-OT, and OP-TP-LS-9aa-GDS-OT were inserted into pRSe2 and sequenced, yielding GDSLS fusion (cytosol), TPGDSLS fusion (plastid), TPLS-GDS fusion (plastid) *camelina* transformation vectors, respectively. The *Arabidopsis* DXS coding sequence with its own transit peptide was a kind gift from Dr. Ed Cahoon (University of Nebraska-Lincoln, Nebr.). It was ligated into the pRS binary vector, yielding pRSDXS. DXS expression is controlled by a soybean glycinin promoter. The nucleotide sequences of OP-TP-GDS-OT and NP-TP-LS-GT were inserted into pRSDXS and sequenced, yielding a TPGDS TPLS DXS (plastid) *camelina* transformation vector.

Camelina Plant Transformation.

The generated transformation vectors were transformed into *Agrobacterium tumefaciens* strain GV3101 (pMP90) using a freeze-thaw method (Weigel et al. *CSH Protoc.* doi:10.1101/pdb.prot4666 (2006)). Selection of transformed bacteria was carried out on YEP medium containing 10 gl$^{-1}$ Bacto-peptone, 5 gl$^{-1}$ yeast extract and 5 gl$^{-1}$ NaCl at pH 6.8 with 25 mgl$^{-1}$ rifampicin, 40 mgl$^{-1}$ gentamicin and 50 mgl$^{-1}$ kanamycin. The plasmid insertion was confirmed by PCR. Overnight preculture of the transformed bacteria was transferred into a 2 l flask containing 300 ml YEP medium with 50 mgl$^{-1}$ kanamycin and incubated at 28° C. for 24 hours. Cells were harvested by centrifugation at 4° C. at 5000 g for 10 min, and then resuspended in an infiltration medium consisting of 0.5× Murashige and Skoog medium with vitamins, 50 gl$^{-1}$ sucrose and 0.05% (v/v) Silwet L77 (Lehle Seeds, Round Rock, Tex.) to a final OD$_{600}$ of 1.0 to 1.5.

Wild-type *camelina* plant was grown in the Donald Danforth Plant Science Center green house. *Camelina* transformation was performed using a floral dip method (Lu et al. *Plant Cell Rep.* 27, 273-278 (2008)). *Camelina* plants were inoculated with the *Agrobacterium* suspension prepared as described above. One or two flowering *camelina* plants were placed into a vacuum desiccator and the inflorescences were immersed into the suspension in a 500 ml beaker. The suspension with the inflorescences was degassed under vacuum for 5 min. The inoculated plants were covered with plastic trays for 24 hours before returning to the greenhouse. Mature seeds of the transformed plants were illuminated with a green LED flashlight, and transgenic seeds identified based on their fluorescence visualized by a red-lens screen.

GC-MS Analysis of the Transgenic Seeds.

Ten transgenic mature seeds were ground with a glass rod, soaked overnight in diethyl ether at room temperature, and then finally shaken every 15 min for 2 hr. iso-Butylbenzene and hexadecane were added as an internal standard for (4S)-limonene and 5-epi-aristolochene analyses, respectively. The extract was concentrated under nitrogen and analyzed by GC-MS. GC-MS analyses were performed on an Agilent 7890A GC system equipped with a Phenomenex ZB-5MSi column (32.5 m×250 μm×0.25 μm) connected to a 5975C inert XL MSD mass spectrometer. Oven temperature for (4S)-limonene analysis was 50° C. for 3 min, raised to 80° C. at a rate of 10° C. min$^{-1}$, held for 3 min, raised again to 300° C. at 40° C. min$^{-1}$, and held for 3 min. Oven temperature for 5-epi-aristolochene analysis was 50° C. for 3 min, raised to 180° C. at a rate of 5° C. min$^{-1}$, raised to 300° C. at 40° C. min$^{-1}$, and held for 3 min. The (4S)-limonene and 5-epi-aristolochene concentrations were calculated using (4S)-limonene and valencene as standards (Sigma), respectively. Other monoterpenes and sesquiterpenes were assigned by comparison of their EI-MS spectra with those of the NIST library.

Enzyme Assay from *Camelina* Mature Seeds.

Total protein extract was prepared from dry mature seeds. Ca. 22 seeds (corresponding to ~20 mg) were ground in a 1.5 ml tube with a plastic homogenizer on ice for 3 min in 20 μl mg$^{-1}$ of extraction buffer containing 50 mM Tris-HCl pH 7.5, 100 mM NaCl, 10% (v/v) glycerol, 5 mM 2-mercaptoethanol and a protease inhibitor cocktail (Sigma). The protein extract was centrifuged at 15000 g for 30 min at 4° C. twice. 45 μl aliquots of the resulting supernatant were frozen in liquid nitrogen and stored at −80° C.

The enzyme activity of GDS was analyzed as follows: reactions were performed in a total volume of 1 ml adjusted to 50 mM Hepes pH 7.2, 10% (v/v) glycerol, 20 mM MgCl$_2$, 0.5 mM DTT and with 50 μg *E. coli* recombinant (4S)-limonene synthase purified from pET28-LS BL21(DE3) RIL, 2 nmol IPP, 2 nmol DMAPP and 45 μl *camelina* seed protein extract. The enzyme reaction was initiated by the addition of IPP and DMAPP, overlaid with hexane and incubated at 30° C. for 30 min to 4 hr. The enzyme activity of LS was analyzed as follows: reactions were performed in a total volume of 1 ml adjusted to 50 mM Hepes pH 7.2, 10% (v/v) glycerol, 20 mM MgCl$_2$, 0.5 mM DTT, 500 mM KCl and with 2 nmol GPP and 45 μl *camelina* seed protein extract. The enzyme reaction was initiated by the addition of GPP, overlaid with hexane and incubated at 30° C. for 1 hr to 8 hr. The reaction was stopped by chilling on ice followed by vigorous mixing. After adding the internal standard, enzymatically produced (4S)-limonene was extracted with hexane 3 times. The combined hexane extract was dehydrated by Na$_2$SO$_4$, concentrated and analyzed by GC-MS.

Head-Space Experiment of Volatile (4S)-Limonene.

Each week, the same individual plants of 7- to 13-week-old TPGDS TPLS (plastid) T4 and the same wild type plants were analyzed for terpene emission. A whole potted plant was enclosed in a plastic vacuum dessicator under fluorescent light. Air was aspirated by a small bench top vacuum pump at 2.5 in Hg for 8 hr. Activated charcoal (Sigma, 100-400 mesh) was placed both in the air-in and air-out valves in order to bind volatile compounds. After the incubation, the charcoal was washed with diethyl ether 5 times. After adding internal standard, the combined extract was concentrated under nitrogen gas and analyzed by GC-MS. The (4S)-limonene content was measured from the peak height of an ion of m/z 136. The volatile emission of mature seed on storage was also monitored (number of seeds produced per plant was ca. 1700). The total (4S)-limonene emission during seed development was estimated by integration of each time point from two individual cultivation periods.

LC-MS/MS Glycoside Analysis.

Approximately two grams of *camelina* seeds were homogenized and extracted with 100% methanol three times. The extracts were combined and evaporated under reduced pressure to dryness. The residue was dissolved in 50% methanol and analyzed by a HPLC (LC-20AD, Shimadzu) in tandem with a 4000 QTRAP mass spectrometer (Applied Biosystems). HPLC separation was carried out on a Phenomenex Gemini-NX c18 column (150×2 mm, 5 μm) using a linear gradient with a flow rate of 0.3 ml min$^{-1}$; solvent A was 5 mM ammonium acetate in water, and solvent B was 5 mM ammonium acetate in methanol. The glycosides were identified with precursor ion scan (m/z 161.0) and product ion scan (m/z 391.2) in negative ionization mode. The quantification was performed using phenyl-B-D-glucopyranoside as an internal standard by multiple reactions monitoring (MRM) scan.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES CITED

Alonso W. R., Rajaonarivony J. I., Gershenzon J. and Croteau R. (1992) Purification of 4S-limonene synthase, a monoterpene cyclase from the glandular trichomes of peppermint (*Mentha×piperita*) and spearmint (*Mentha spicata*). J Biol Chem., 267, 7582-7.

Burke C., Klettke K. and Croteau R. (2004) Heteromeric geranyl diphosphate synthase from mint: construction of a functional fusion protein and inhibition by bisphosphonate substrate analogs. *Arch. Biochem. Biophys.,* 422, 52-60.

Burke C. C., Wildung M. R. and Croteau R. (1999) Geranyl diphosphate synthase: cloning, expression, and characterization of this prenyltransferase as a heterodimer. *Proc Natl Acad Sci USA.,* 96, 13062-7.

Colby S. M., Alonso W. R., Katahira E. J., McGarvey D. J. and Croteau R. (1993) 4S-limonene synthase from the oil glands of spearmint (*Mentha spicata*). cDNA isolation, characterization, and bacterial expression of the catalytically active monoterpene cyclase. J Biol Chem., 268, 23016-24.

Ho S. N., Hunt H. D., Horton R. M., Pullen J. K. and Pease L. R. (1989) Site-directed mutagenesis by overlap extension using the polymerase chain reaction. *Gene,* 77, 51-9.

Lu C. and Kang J. (2008) Generation of transgenic plants of a potential oilseed crop *Camelina sativa* by *Agrobacterium*-mediated transformation. *Plant Cell Rep.,* 27, 273-8.

Weigel D. and Glazebrook J. (2006) Transformation of Agrobacterium Using the Freeze-Thaw Method. *Cold Spring Harb Protoc.,* doi:10.1101/pdb.prot4666

What is claimed is:

1. A method of producing and accumulating a monoterpene hydrocarbon, a sesquiterpene hydrocarbon, or a combination thereof, in seeds of *Camelina*, the method comprising the steps of:
   (a) transforming *Camelina* with a heterologous DNA construct, wherein said heterologous DNA construct comprises an enzyme-encoding nucleotide sequence encoding all, or a biosynthetically appropriate combination of, enzymes selected from the group consisting of a *Mentha* geranyl diphosphate synthase, a *Mentha* limonene synthase, an *Arabidopsis* farnesyl diphosphate synthase, and a *Nicotiana* 5-epi-aristolochene synthase, wherein said nucleotide sequence is operably linked for expression to a nucleotide sequence encoding Rubisco plastid transit peptide and to a promoter, wherein said promoter is an oleosin promoter, a napin promoter, or a glycinin promoter; and
   (b) obtaining a transgenic *Camelina* plant comprising the DNA construct of step (a), wherein seeds of said transgenic *Camelina* plant accumulate the monoterpene hydrocarbon limonene, the sesquiterpene hydrocarbon 5-epi-aristolochene, or a combination thereof, wherein the amount of limonene, 5-epi-aristolochene, or combination thereof, is at least 1.0 mg/g dry weight.

2. The method of claim 1, wherein the heterologous DNA construct further comprises a nucleotide sequence encoding an enzyme that catalyzes the biosynthesis of isopentenyl diphosphate and dimethylallyl diphosphate via the non-mevalonate pathway in plastids, wherein said nucleotide sequence further comprises a nucleotide sequence encoding RuBisCo small subunit transit peptide.

3. The method of claim 2, wherein said enzyme encoding nucleotide sequence encodes a 1-deoxy-xylulose 5-phosphate synthase enzyme comprising RuBisCo small subunit transit peptide.

4. The method of claim 3, further comprising expressing a nucleotide sequence encoding a selectable marker or a screenable marker that facilitates identification of transgenic seed, under the control of an operably linked promoter, wherein said promoter is an oleosin promoter, a napin promoter, or a glycinin promoter.

5. The method of claim 1, further comprising recovering said monoterpene hydrocarbon limonene, said sesquiterpene hydrocarbon 5-epi-aristolochene, or combination thereof, from seeds of said transgenic *Camelina* plant.

6. The transgenic *Camelina* plant that produces and accumulates the monoterpene hydrocarbon limonene, the sesquiterpene hydrocarbon 5-epi-aristolochene, or a combination thereof, produced by the method of claim 1.

7. A transgenic *Camelina* plant, cells of which comprise in their genome heterologous enzyme-encoding nucleotide sequences encoding all, or a biosynthetically appropriate combination of, enzymes selected from the group consisting of a *Mentha* geranyl diphosphate synthase, a *Mentha* limonene synthase, an *Arabidopsis* farnesyl diphosphate synthase, and a *Nicotiana* 5-epi-aristolochene synthase,
   wherein each of said nucleotide sequences is operably linked for expression to a nucleotide sequence encoding Rubisco plastid transit peptide and to a promoter, wherein said promoter is an oleosin promoter, a napin promoter, or a glycinin promoter,
   wherein said nucleotide sequences are coexpressed, and
   wherein said transgenic *Camelina* plant accumulates the monoterpene hydrocarbon limonene, the sesquiterpene hydrocarbon 5-epi-aristolochene, or a combination thereof, in seeds thereof in an amount of at least 1.0 mg/g dry weight.

8. The transgenic *Camelina* plant of claim 7, which further coexpresses a nucleotide sequence encoding an enzyme that catalyzes the biosynthesis of isopentenyl diphosphate and dimethylallyl diphosphate via the non-mevalonate pathway in plastids, wherein said nucleotide sequence comprises a nucleotide sequence encoding RuBisCo small subunit transit peptide.

9. The transgenic *Camelina* plant of claim 8, wherein said enzyme encoding nucleotide sequence encodes a 1-deoxy-xylulose 5-phosphate synthase enzyme comprising RuBisCo small subunit transit peptide.

10. The transgenic *Camelina* plant of claim 9, further comprising a nucleotide sequence encoding a selectable marker or a screenable marker that facilitates identification of transgenic seed, under the control of an operably linked promoter, wherein said promoter is an oleosin promoter, a napin promoter, or a glycinin promoter.

* * * * *

SEQUENCE LISTING

<160> NUMBER OF SEQ ID NOS: 72

<210> SEQ ID NO 1
<211> LENGTH: 313
<212> TYPE: PRT
<213> ORGANISM: Mentha x piperita

<400> SEQUENCE: 1

Met Ala Ile Asn Leu Ser His Ile Asn Ser Lys Thr Cys Phe Pro Leu
1               5                   10                  15

Lys Thr Arg Ser Asp Leu Ser Arg Ser Ser Ala Arg Cys Met Pro
            20                  25                  30

Thr Ala Ala Ala Ala Phe Pro Thr Ile Ala Thr Ala Ala Gln Ser
                35                  40                  45

Gln Pro Tyr Trp Ala Ala Ile Glu Ala Asp Ile Glu Arg Tyr Leu Lys
        50                  55                  60

Lys Ser Ile Thr Ile Arg Pro Pro Glu Thr Val Phe Gly Pro Met His
65                  70                  75                  80

His Leu Thr Phe Ala Ala Pro Ala Thr Ala Ala Ser Thr Leu Cys Leu
                85                  90                  95

Ala Ala Cys Glu Leu Val Gly Gly Asp Arg Ser Gln Ala Met Ala Ala
            100                 105                 110

Ala Ala Ala Ile His Leu Val His Ala Ala Ala Tyr Val His Glu His
            115                 120                 125

Leu Pro Leu Thr Asp Gly Ser Arg Pro Val Ser Lys Pro Ala Ile Gln
130                 135                 140

His Lys Tyr Gly Pro Asn Val Glu Leu Leu Thr Gly Asp Gly Ile Val
145                 150                 155                 160

Pro Phe Gly Phe Glu Leu Leu Ala Gly Ser Val Asp Pro Ala Arg Thr
                165                 170                 175

Asp Asp Pro Asp Arg Ile Leu Arg Val Ile Ile Glu Ile Ser Arg Ala
            180                 185                 190

Gly Gly Pro Glu Gly Met Ile Ser Gly Leu His Arg Glu Glu Glu Ile
            195                 200                 205

Val Asp Gly Asn Thr Ser Leu Asp Phe Ile Glu Tyr Val Cys Lys Lys
210                 215                 220

Lys Tyr Gly Glu Met His Ala Cys Gly Ala Ala Cys Gly Ala Ile Leu
225                 230                 235                 240

Gly Gly Ala Ala Glu Glu Ile Gln Lys Leu Arg Asn Phe Gly Leu
                245                 250                 255

Tyr Gln Gly Thr Leu Arg Gly Met Met Glu Met Lys Asn Ser His Gln
            260                 265                 270

Leu Ile Asp Glu Asn Ile Ile Gly Lys Leu Lys Glu Leu Ala Leu Glu
        275                 280                 285

Glu Leu Gly Gly Phe His Gly Lys Asn Ala Glu Leu Met Ser Ser Leu
            290                 295                 300

Val Ala Glu Pro Ser Leu Tyr Ala Ala
305                 310

<210> SEQ ID NO 2
<211> LENGTH: 297
<212> TYPE: PRT
<213> ORGANISM: Antirrhinum majus

<400> SEQUENCE: 2

Met Ala His Gly Leu Thr His Phe Asn Thr Lys Ser Gly Leu Phe Pro

```
                1               5                    10                      15
            Ser Ile Thr Lys Ser Lys Thr Thr Arg Pro Ser Thr Arg Pro Val Ile
                            20                   25                  30

Leu Ala Met Thr Arg Thr Gln Thr Tyr Arg Ala Thr Ile Glu Ser Asp
                            35                   40                  45

Ile Glu Ser Tyr Leu Lys Lys Ala Ile Pro Ile Arg Ala Pro Glu Ser
                50                       55                  60

Val Phe Glu Pro Met His His Leu Thr Phe Ala Ala Pro Arg Thr Ser
            65                       70                  75                  80

Ala Ser Ala Leu Cys Val Ala Ala Cys Glu Leu Val Gly Gly Asp Arg
                            85                   90                  95

Ser Asp Ala Met Ala Ala Ala Ala Val His Leu Met His Val Ala
                        100                 105                 110

Ala Tyr Thr His Glu Asn Leu Pro Leu Thr Asp Gly Pro Met Ser Lys
                        115                 120                 125

Ser Glu Ile Gln His Lys Phe Asp Pro Asn Ile Glu Leu Leu Thr Gly
                    130                 135                 140

Asp Gly Ile Ile Pro Phe Gly Leu Glu Leu Met Ala Arg Ser Met Asp
            145                 150                 155                 160

Pro Thr Arg Asn Asn Pro Asp Arg Ile Leu Arg Ala Ile Ile Glu Leu
                                165                 170                 175

Thr Arg Val Met Gly Ser Glu Gly Ile Val Glu Gly Gln Tyr His Glu
                            180                 185                 190

Leu Gly Leu Asn Gln Leu Asn Asp Leu Glu Leu Ile Glu Tyr Val Cys
                        195                 200                 205

Lys Lys Lys Glu Gly Thr Leu His Ala Cys Gly Ala Ala Cys Gly Ala
                    210                 215                 220

Ile Leu Gly Gly Cys Asp Glu Asp Lys Ile Glu Lys Leu Arg Arg Phe
            225                 230                 235                 240

Gly Leu Tyr Val Gly Thr Val Gln Gly Leu Leu Gly Lys Asn Arg Ser
                            245                 250                 255

Gly Phe Glu Gly Arg Ile Lys Glu Leu Lys Glu Leu Ala Val Lys Glu
                        260                 265                 270

Leu Glu Ser Phe Gly Gly Glu Lys Ile Glu Leu Ile Arg Gly Val Phe
                    275                 280                 285

Glu Leu Glu His Ser Leu Ala Gly Val
                    290                 295

<210> SEQ ID NO 3
<211> LENGTH: 308
<212> TYPE: PRT
<213> ORGANISM: Ricinus communis

<400> SEQUENCE: 3

Met Ala Gly Ala Leu Pro Tyr Ile Pro Gly Asn Pro Val Gly Arg Gly
            1               5                   10                  15

Val Phe Arg Arg Ser Phe Gly Tyr Gly Arg Gly Gly Ala Leu Phe Ser
                            20                  25                  30

Arg Arg Pro Val Ala Cys Val Met Ser Asn Ser Ser Lys Ile Asp Tyr
                        35                  40                  45

Trp Thr Cys Ile Asn Ala Asp Ile Glu Thr His Leu Lys Glu Ala Ile
                    50                  55                  60

Pro Val Arg Pro Val Val Phe Glu Pro Met His His Leu Thr
            65                  70                  75                  80
```

```
Phe Ala Ala Pro Arg Ser Phe Ala Pro Ala Leu Cys Ile Ala Ala Cys
                85                  90                  95
Glu Leu Val Gly Gly Ser Arg Asp Gln Ala Leu Ala Ala Ala Ser Ala
            100                 105                 110
Leu Arg Leu Met Ile Ala Ala Ala Phe Thr His Glu Asn Ile Pro Leu
        115                 120                 125
Thr Asp Arg Pro Arg Pro Ser Ala Arg Pro Met Phe His His Thr Phe
    130                 135                 140
Gly Pro Asn Ile Glu Leu Leu Thr Gly Asp Gly Met Ile Pro Phe Ala
145                 150                 155                 160
Phe Glu Leu Leu Ala Gln Leu Asn Asn Pro Ala Gln Asp Asn Ser Asp
                165                 170                 175
Arg Ile Leu Arg Val Met Ile Glu Ile Ser Arg Ala Met Gly Ser Gln
            180                 185                 190
Gly Met Val Glu Gly Gln Tyr Asn Glu Phe Gln Tyr Asp Gln Ser Val
        195                 200                 205
Gly Asp Glu Leu Phe His Val Ala Trp Leu Arg Asp Val Cys Lys Lys
    210                 215                 220
Lys Glu Gly Ala Ser His Ala Cys Ala Gly Ala Cys Gly Ala Ile Leu
225                 230                 235                 240
Gly Gly Gly Asn Glu Glu Ile Glu Lys Leu Arg Arg Tyr Gly Leu
                245                 250                 255
Tyr Val Gly Thr Ile Gln Gly Ile Tyr Asn Lys Val Glu Gly Asn Glu
                260                 265                 270
Glu Trp Ser Leu Lys Gly Val Asn Lys Leu Arg Asp Leu Ala Leu Lys
            275                 280                 285
Glu Leu Lys Asp Phe Asn Glu Glu Lys Val Arg Ala Ile Cys Ser
    290                 295                 300
Leu Val Glu Asn
305

<210> SEQ ID NO 4
<211> LENGTH: 236
<212> TYPE: PRT
<213> ORGANISM: Populus trichocarpa

<400> SEQUENCE: 4

Ser Tyr Trp Thr Ser Val Asn Asp Glu Ile Asp Ala His Leu Lys Gln
1               5                   10                  15
Ala Ile Pro Ile Arg Pro Pro Leu Ser Val Phe Glu Pro Met His His
            20                  25                  30
Leu Thr Phe Ala Ala Pro Arg Thr Thr Ala Pro Ala Leu Cys Ile Ala
        35                  40                  45
Ala Cys Glu Leu Val Gly Gly Asn Arg Asp Gln Ala Met Ala Ala Ala
    50                  55                  60
Ser Ala Leu Arg Leu Met His Ala Ala Ala Leu Thr His Glu His Ile
65                  70                  75                  80
Leu Ser Thr Gly Asn Arg Ala Arg Ile Gly His Ser Phe Gly Ser Asn
                85                  90                  95
Ile Glu Leu Leu Thr Gly Asp Gly Met Val Pro Phe Gly Leu Glu Leu
            100                 105                 110
Leu Ala Lys Ser Asp Asp Leu Thr Gln Asn Asn Ser Glu Arg Ile Leu
        115                 120                 125
Arg Val Ile Ile Glu Ile Thr Gln Ala Met Gly Ser Gln Gly Met Ala
    130                 135                 140
```

```
Leu Gly Gln Tyr Asn Gln Phe Gln His Gly Gln Ser Asp Tyr Ile Asp
145                 150                 155                 160

His Val Cys Lys Lys Glu Gly Glu Leu His Ser Cys Ala Gly Ala
                165                 170                 175

Val Gly Ala Ile Leu Gly Gly Thr Glu Glu Ile Glu Lys Leu
            180                 185                 190

Arg Arg Tyr Gly Leu Tyr Val Gly Leu Met Gln Gly Val Leu Ser Asn
                195                 200                 205

Trp Val Glu Arg Lys Glu Glu Val Ser Met Glu Lys Val Leu Asn Glu
                210                 215                 220

Leu Glu Asn Leu Ala Leu Lys Glu Leu Glu Gly Phe
225                 230                 235
```

<210> SEQ ID NO 5
<211> LENGTH: 306
<212> TYPE: PRT
<213> ORGANISM: Hevea brasiliensis

<400> SEQUENCE: 5

```
Met Ala Gly Ala Leu Ser Ser Thr Ile His Gly Asn Leu Ile Ala Arg
1               5                   10                  15

Ala Val Ser Ser Ser Asn Pro Lys His Pro Leu Phe Ser His Arg Pro
                20                  25                  30

Met Val Val Ala Met Ser Thr Asp Gln Ser Tyr Trp Ser Ser Val Asn
            35                  40                  45

Ala Asp Leu Asp Thr His Leu Lys Gln Ala Ile Pro Ile Arg Gln Pro
50                  55                  60

Leu Ala Val Phe Glu Pro Met Arg His Leu Ile Leu Ser Ala Pro Gln
65                  70                  75                  80

Thr Ser Ala Pro Ala Leu Cys Ile Ala Ala Cys Glu Leu Val Gly Gly
                85                  90                  95

His Arg Asn Gln Ala Met Ala Ala Ser Ala Leu Arg Leu Val His
                100                 105                 110

Ala Ser Ala Ser Thr His Glu Asn Leu Pro Leu Thr Asp Arg Pro Arg
            115                 120                 125

Pro Met Pro Arg Thr Arg Pro Thr Leu Tyr Gly Pro Asn Ile Glu Leu
130                 135                 140

Leu Ile Ala Asp Gly Ile Ile Pro Tyr Gly Phe Glu Leu Leu Ala Arg
145                 150                 155                 160

Asp Asp Asp Ala Ala Glu Asn Asn Ser Asn Arg Val Leu Arg Ala Ile
                165                 170                 175

Ile Glu Ile Ser Arg Ala Met Gly Ser Gln Gly Val Ile Glu Gly Gln
            180                 185                 190

Tyr Asn Glu Ser Gln Tyr Glu Glu Ser Glu Gly Glu Ile Phe His
                195                 200                 205

Val Gly Trp Leu Gln Asn Val Cys Arg Lys Glu Gly Thr Leu His
            210                 215                 220

Ala Cys Ala Gly Ala Cys Gly Ala Ile Leu Gly Gly Ser Glu Asp
225                 230                 235                 240

Glu Ile Glu Lys Leu Arg Arg Tyr Gly Leu Tyr Val Gly Met Val Gln
                245                 250                 255

Gly Ile Leu Ser Lys Val Asp Glu Arg Lys Glu Trp Pro Val Lys Glu
            260                 265                 270

Val Asn Lys Leu Arg Asp Leu Ala Leu Lys Glu Leu Lys Asp Phe Asn
```

```
            275                 280                 285
Gln Ala Lys Val Lys Thr Ile Ser Ile Leu Val Glu Thr Arg Phe Cys
    290                 295                 300

Asn Leu
305

<210> SEQ ID NO 6
<211> LENGTH: 279
<212> TYPE: PRT
<213> ORGANISM: Humulus lupulus

<400> SEQUENCE: 6

Met Ser Arg Thr His Glu Asn His His Val Pro Thr Ser Thr Ser Ile
1               5                   10                  15

Val Val Ser Ala Ser Ile Thr Ala Asp Ile Glu Ala His Leu Lys Gln
            20                  25                  30

Ser Ile Thr Leu Lys Pro Pro Leu Ser Val His Glu Pro Met Tyr Asn
        35                  40                  45

Leu Val Phe Ser Ala Pro Pro Asn Ser Ala Pro Ser Leu Cys Val Ala
    50                  55                  60

Ala Cys Glu Leu Val Gly Gly His Arg Ser Lys Ala Ile Ala Ala Ala
65                  70                  75                  80

Ser Ala Leu Arg Leu Leu His Ala Ala Asn Phe Thr His Glu His Leu
                85                  90                  95

Pro Leu Thr Asp Ser Pro Ser Pro Ser Pro Val Ile His Asn Ser Tyr
            100                 105                 110

Asp Pro Ser Ile Gln Leu Leu Met Pro Asp Ala Ile Leu Pro Leu Gly
        115                 120                 125

Phe Glu Leu Leu Ala Gln Ser Tyr Asn Pro Ala Gln Asn Asn Ser Asp
    130                 135                 140

Arg Val Leu Arg Val Ile Val Glu Phe Ala Arg Ala Phe Gly Ser Lys
145                 150                 155                 160

Gly Ile Leu Asp Gly Gln Tyr Arg Gln Arg Val Val Ser Ile Ser Asn
                165                 170                 175

Gly Asp Glu Val Asp Asn Ala Glu Arg Val Asp Cys Ser Gly Arg Glu
            180                 185                 190

Lys Glu Gly Lys Met His Ala Cys Ala Ala Cys Gly Ala Ile Leu
        195                 200                 205

Gly Asp Ala Asn Glu Glu Thr Glu Lys Leu Arg Thr Phe Gly Leu
    210                 215                 220

Tyr Val Gly Met Ile Gln Gly Tyr Ser Ile Lys Phe Met Arg Glu Arg
225                 230                 235                 240

Glu Glu Glu Lys Glu Ala Glu Arg Thr Ile Lys Glu Leu Arg Asn Leu
                245                 250                 255

Ala Leu Lys Glu Leu Glu His Phe His Gly Arg Lys Leu Glu Pro Ile
            260                 265                 270

Ser Ser Phe Ile Tyr Cys Leu
        275

<210> SEQ ID NO 7
<211> LENGTH: 279
<212> TYPE: PRT
<213> ORGANISM: Glycine max

<400> SEQUENCE: 7

Met Ser Arg Thr His Glu Asn His His Val Pro Thr Ser Thr Ser Ile
```

```
1               5                   10                  15
Val Val Ser Ala Ser Ile Thr Ala Asp Ile Glu Ala His Leu Lys Gln
            20                  25                  30

Ser Ile Thr Leu Lys Pro Pro Leu Ser Val His Glu Pro Met Tyr Asn
            35                  40                  45

Leu Val Phe Ser Ala Pro Pro Asn Ser Ala Pro Ser Leu Cys Val Ala
            50                  55                  60

Ala Cys Glu Leu Val Gly Gly His Arg Ser Lys Ala Ile Ala Ala Ala
65                      70                  75                  80

Ser Ala Leu Arg Leu Leu His Ala Ala Asn Phe Thr His Glu His Leu
            85                  90                  95

Pro Leu Thr Asp Ser Pro Ser Pro Ser Pro Val Ile His Asn Ser Tyr
            100                 105                 110

Asp Pro Ser Ile Gln Leu Leu Met Pro Asp Ala Ile Leu Pro Leu Gly
            115                 120                 125

Phe Glu Leu Leu Ala Gln Ser Tyr Asn Pro Ala Gln Asn Asn Ser Asp
            130                 135                 140

Arg Val Leu Arg Val Ile Val Glu Phe Ala Arg Ala Phe Gly Ser Lys
145                     150                 155                 160

Gly Ile Leu Asp Gly Gln Tyr Arg Gln Arg Val Val Ser Ile Ser Asn
            165                 170                 175

Gly Asp Glu Val Asp Asn Ala Glu Arg Val Asp Cys Ser Gly Arg Glu
            180                 185                 190

Lys Glu Gly Lys Met His Ala Cys Ala Ala Cys Gly Ala Ile Leu
            195                 200                 205

Gly Asp Ala Asn Glu Glu Thr Glu Lys Leu Arg Thr Phe Gly Leu
            210                 215                 220

Tyr Val Gly Met Ile Gln Gly Tyr Ser Ile Lys Phe Met Arg Glu Arg
225                     230                 235                 240

Glu Glu Glu Lys Glu Ala Glu Arg Thr Ile Lys Glu Leu Arg Asn Leu
            245                 250                 255

Ala Leu Lys Glu Leu Glu His Phe His Gly Arg Lys Leu Glu Pro Ile
            260                 265                 270

Ser Ser Phe Ile Tyr Cys Leu
            275

<210> SEQ ID NO 8
<211> LENGTH: 377
<212> TYPE: PRT
<213> ORGANISM: Mentha x piperita

<400> SEQUENCE: 8

Met Ser Ala Leu Val Asn Pro Val Ala Lys Trp Pro Gln Thr Ile Gly
1               5                   10                  15

Val Lys Asp Val His Gly Gly Arg Arg Arg Ser Arg Ser Thr Leu
            20                  25                  30

Phe Gln Ser His Pro Leu Arg Thr Glu Met Pro Phe Ser Leu Tyr Phe
            35                  40                  45

Ser Ser Pro Leu Lys Ala Pro Ala Thr Phe Ser Val Ser Ala Val Tyr
            50                  55                  60

Thr Lys Glu Gly Ser Glu Ile Arg Asp Lys Asp Pro Ala Pro Ser Thr
65                      70                  75                  80

Ser Pro Ala Phe Asp Phe Asp Gly Tyr Met Leu Arg Lys Ala Lys Ser
            85                  90                  95
```

```
Val Asn Lys Ala Leu Glu Ala Ala Val Gln Met Lys Glu Pro Leu Lys
            100                 105                 110

Ile His Glu Ser Met Arg Tyr Ser Leu Leu Ala Gly Gly Lys Arg Val
        115                 120                 125

Arg Pro Met Leu Cys Ile Ala Ala Cys Glu Leu Val Gly Gly Asp Glu
    130                 135                 140

Ser Thr Ala Met Pro Ala Ala Cys Ala Val Glu Met Ile His Thr Met
145                 150                 155                 160

Ser Leu Met His Asp Asp Leu Pro Cys Met Asp Asn Asp Leu Arg
                165                 170                 175

Arg Gly Lys Pro Thr Asn His Met Ala Phe Gly Glu Ser Val Ala Val
            180                 185                 190

Leu Ala Gly Asp Ala Leu Leu Ser Phe Ala Phe Glu His Val Ala Ala
            195                 200                 205

Ala Thr Lys Gly Ala Pro Pro Glu Arg Ile Val Arg Val Leu Gly Glu
            210                 215                 220

Leu Ala Val Ser Ile Gly Ser Glu Gly Leu Val Ala Gly Gln Val Val
225                 230                 235                 240

Asp Val Cys Ser Glu Gly Met Ala Glu Val Gly Leu Asp His Leu Glu
                245                 250                 255

Phe Ile His His His Lys Thr Ala Ala Leu Leu Gln Gly Ser Val Val
            260                 265                 270

Leu Gly Ala Ile Leu Gly Gly Gly Lys Glu Glu Glu Val Ala Lys Leu
            275                 280                 285

Arg Lys Phe Ala Asn Cys Ile Gly Leu Leu Phe Gln Val Val Asp Asp
290                 295                 300

Ile Leu Asp Val Thr Lys Ser Ser Lys Glu Leu Gly Lys Thr Ala Gly
305                 310                 315                 320

Lys Asp Leu Val Ala Asp Lys Thr Thr Tyr Pro Lys Leu Ile Gly Val
                325                 330                 335

Glu Lys Ser Lys Glu Phe Ala Asp Arg Leu Asn Arg Glu Ala Gln Glu
            340                 345                 350

Gln Leu Leu His Phe His Pro His Arg Ala Ala Pro Leu Ile Ala Leu
            355                 360                 365

Ala Asn Tyr Ile Ala Tyr Arg Asp Asn
            370                 375

<210> SEQ ID NO 9
<211> LENGTH: 377
<212> TYPE: PRT
<213> ORGANISM: Mentha haplocalyx var. piperascens

<400> SEQUENCE: 9

Met Ser Ala Leu Val Asn Pro Val Ala Lys Trp Pro Gln Thr Ile Gly
1               5                   10                  15

Ile Lys Asp Val His Gly Gly Arg Arg Arg Ser Arg Ser Thr Leu
            20                  25                  30

Phe Leu Ser His Pro Leu Arg Thr Glu Met Pro Phe Ser Leu Tyr Phe
            35                  40                  45

Ser Ser Pro Leu Lys Ala Pro Ala Thr Phe Ser Val Ser Ala Val Tyr
        50                  55                  60

Thr Lys Glu Gly Ser Glu Ile Arg Asp Lys Asp Pro Ala Pro Ser Thr
65                  70                  75                  80

Ser Pro Ala Phe Asp Phe Asp Gly Tyr Met Leu Arg Lys Ala Lys Ser
                85                  90                  95
```

Val Asn Lys Ala Leu Glu Ala Ala Val Gln Met Lys Glu Pro Leu Lys
            100                 105                 110

Ile His Glu Ser Met Arg Tyr Ser Leu Leu Ala Gly Gly Lys Arg Val
            115                 120                 125

Arg Pro Met Leu Cys Ile Ala Ala Cys Glu Leu Val Gly Gly Asp Glu
130                 135                 140

Ser Thr Ala Met Pro Ala Ala Cys Ala Val Glu Met Ile His Thr Met
145                 150                 155                 160

Ser Leu Met His Asp Asp Leu Pro Cys Met Asp Asn Asp Asp Leu Arg
                165                 170                 175

Arg Gly Lys Pro Thr Asn His Met Ala Phe Gly Glu Ser Val Ala Val
                180                 185                 190

Leu Ala Gly Asp Ala Leu Leu Ser Phe Ala Phe Glu His Val Ala Ala
            195                 200                 205

Ala Thr Lys Gly Ala Pro Pro Glu Arg Ile Val Arg Val Leu Gly Glu
210                 215                 220

Leu Ala Val Ser Val Gly Ser Glu Gly Leu Val Ala Gly Gln Val Val
225                 230                 235                 240

Asp Val Cys Ser Glu Gly Met Ala Glu Val Gly Leu Asp His Leu Glu
                245                 250                 255

Phe Ile His His His Lys Thr Ala Ala Leu Leu Gln Gly Ser Val Val
                260                 265                 270

Leu Gly Ala Ile Leu Gly Gly Gly Asn Glu Glu Glu Val Ala Lys Leu
            275                 280                 285

Arg Lys Phe Ala Asn Cys Ile Gly Leu Leu Phe Gln Val Val Asp Asp
290                 295                 300

Ile Leu Asp Val Thr Lys Ser Ser Lys Glu Leu Gly Lys Lys Ala Gly
305                 310                 315                 320

Lys Asp Leu Val Ala Asp Lys Thr Thr Tyr Pro Lys Leu Ile Gly Val
                325                 330                 335

Glu Lys Ser Met Glu Phe Ala Asp Arg Leu Asn Arg Glu Ala Gln Glu
                340                 345                 350

Gln Leu Leu His Phe His Pro His Arg Ala Ala Pro Leu Ile Ala Leu
            355                 360                 365

Ala Asn Tyr Ile Ala Tyr Arg Asp Asn
            370                 375

<210> SEQ ID NO 10
<211> LENGTH: 357
<212> TYPE: PRT
<213> ORGANISM: Catharanthus roseus

<400> SEQUENCE: 10

Met Arg Ser Asn Leu Cys His Pro Leu Lys Asn Gln Leu Pro Ile Ser
1               5                   10                  15

Phe Phe Leu Ser Gly Thr Ile Arg Lys Pro Ile Phe Ser Cys Ser Arg
            20                  25                  30

Leu Ser Ile Ser Ala Ile Ile Thr Lys Glu Gln Thr Gln Glu Glu Ser
            35                  40                  45

Glu Ser Lys Ser Lys Lys Glu Val Ala Phe Ser Ser Ser Ser Ser Phe
        50                  55                  60

Asp Phe Lys Ala Tyr Met Ile Gly Lys Ala Asn Ser Val Asn Lys Ala
65                  70                  75                  80

Leu Glu Asp Ala Val Leu Val Arg Glu Pro Leu Lys Ile His Glu Ser

```
                        85                  90                  95
Met Arg Tyr Ser Leu Leu Ala Gly Gly Lys Arg Val Arg Pro Met Leu
                100                 105                 110

Cys Ile Ala Ala Cys Glu Leu Phe Gly Gly Thr Glu Ser Val Ala Met
            115                 120                 125

Pro Ser Ala Cys Ala Val Glu Met Ile His Thr Met Ser Leu Met His
        130                 135                 140

Asp Asp Leu Pro Cys Met Asp Asn Asp Leu Arg Arg Gly Lys Pro
145                 150                 155                 160

Thr Asn His Lys Val Phe Gly Glu Asp Val Ala Val Leu Ala Gly Asp
                165                 170                 175

Ala Leu Leu Ala Phe Ala Phe Glu His Ile Ala Thr Ala Thr Lys Gly
                180                 185                 190

Val Ser Ser Glu Arg Ile Val Arg Val Val Gly Glu Leu Ala Lys Cys
                195                 200                 205

Ile Gly Ser Glu Gly Leu Val Ala Gly Gln Val Val Asp Val Cys Ser
                210                 215                 220

Glu Gly Ile Ala Asp Val Gly Leu Glu His Leu Glu Phe Ile His Ile
225                 230                 235                 240

His Lys Thr Ala Ala Leu Leu Glu Gly Ser Val Val Leu Gly Ala Ile
                245                 250                 255

Val Gly Gly Ala Asn Asp Glu Gln Ile Ser Lys Leu Arg Lys Phe Ala
                260                 265                 270

Arg Cys Ile Gly Leu Leu Phe Gln Val Asp Asp Ile Leu Asp Val
            275                 280                 285

Thr Lys Ser Ser Gln Glu Leu Gly Lys Thr Ala Gly Lys Asp Leu Val
                290                 295                 300

Ala Asp Lys Val Thr Tyr Pro Lys Leu Leu Gly Ile Asp Lys Ser Arg
305                 310                 315                 320

Glu Phe Ala Glu Lys Leu Asn Arg Glu Ala Gln Glu Gln Leu Ala Glu
                325                 330                 335

Phe Asp Pro Glu Lys Ala Ala Pro Leu Ile Ala Leu Ala Asn Tyr Ile
                340                 345                 350

Ala Tyr Arg Asp Asn
                355

<210> SEQ ID NO 11
<211> LENGTH: 371
<212> TYPE: PRT
<213> ORGANISM: Picrorhiza kurroa

<400> SEQUENCE: 11

Met Ser Leu Val Asn Ser Ile Thr Trp Ser Gln Thr Ser Ser Ile Leu
1               5                   10                  15

Asn Ile Gln Ser Asn Ile Ser Lys Lys Leu Thr Pro Phe Ser Ile Leu
                20                  25                  30

Pro His Pro Leu Thr Asn Asn Leu Pro Ile Ser Leu Phe Pro Asn Pro
            35                  40                  45

Lys Ser Asn Ile Ser Asn Ser Asn Thr Pro Leu Ser Ala Ile Leu Thr
        50                  55                  60

Lys Asp Gln Lys Pro Gln Asn Pro Thr Thr Pro Thr Phe Asp Phe
65                  70                  75                  80

Lys Ser Tyr Met Leu Gln Lys Ala Asp Ser Val Asn Lys Ala Leu Asp
                85                  90                  95
```

```
Asp Ser Ile Pro Leu Thr Glu Pro Leu Lys Ile Gln Glu Ser Met Arg
                100                 105                 110

Tyr Ser Leu Leu Ala Gly Gly Lys Arg Ile Arg Pro Met Leu Cys Ile
            115                 120                 125

Ala Ala Cys Glu Leu Val Gly Gly Asp Glu Ser Thr Ala Met Pro Ala
130                 135                 140

Ala Cys Ala Val Glu Met Val His Thr Met Ser Leu Met His Asp Asp
145                 150                 155                 160

Leu Pro Cys Met Asp Asn Asp Leu Arg Arg Gly Lys Pro Thr Asn
                165                 170                 175

His Lys Val Phe Thr Glu Asp Val Ala Val Leu Ala Gly Asp Ala Met
            180                 185                 190

Leu Ala Phe Ser Phe Glu His Val Ala Ser Leu Thr Lys Gly Val Cys
            195                 200                 205

Ser Glu Arg Ile Val Arg Val Ile Tyr Glu Leu Ala Lys Cys Val Gly
        210                 215                 220

Cys Glu Gly Leu Val Ala Gly Gln Val Val Asp Ile Cys Ser Glu Gly
225                 230                 235                 240

Met Asp Glu Val Gly Leu Glu His Leu Glu Phe Ile His Leu Asn Lys
                245                 250                 255

Thr Ala Ala Leu Leu Glu Gly Ser Val Val Leu Gly Ala Ile Leu Gly
            260                 265                 270

Gly Gly Ser Asp Glu Glu Val Glu Lys Leu Arg Asn Phe Ala Arg Cys
            275                 280                 285

Ile Gly Leu Leu Phe Gln Val Val Asp Asp Ile Leu Asp Val Thr Lys
        290                 295                 300

Ser Ser Lys Glu Leu Gly Lys Thr Ala Gly Lys Asp Leu Val Ala Asp
305                 310                 315                 320

Lys Thr Thr Tyr Pro Lys Leu Ile Gly Ile Glu Lys Ser Lys Glu Phe
                325                 330                 335

Ala Glu Arg Leu Asn Arg Glu Ala Lys Glu His Leu Ala Gly Phe Asp
            340                 345                 350

Gln Asn Lys Ala Ala Pro Leu Ile Ala Leu Ala Asp Tyr Ile Ala Tyr
            355                 360                 365

Arg Asp Asn
370

<210> SEQ ID NO 12
<211> LENGTH: 373
<212> TYPE: PRT
<213> ORGANISM: Ipomoea sp. kenyan

<400> SEQUENCE: 12

Met Ser Leu Ala Asn Pro Ser Thr Thr Trp Ala Lys Thr His Ser Phe
1               5                   10                  15

Cys Gly Arg Phe Arg Ser Arg Ser Leu Ile Arg Asn Asn Glu Phe Ser
            20                  25                  30

Ile Asn Leu Ser Ser Phe Pro Thr Ser Ile Arg Lys Pro Leu Tyr Tyr
        35                  40                  45

His Ser Cys Ser Ala Ile Leu Thr Lys Glu Gln Thr Gly Val Pro Gln
    50                  55                  60

Glu Glu Ser Glu Ser Glu Ser Glu Lys Lys Pro Ala Ala Ala Lys Leu
65                  70                  75                  80

Asp Phe Thr Ala Tyr Val Leu Gly Lys Ala Lys Ser Val Asn Lys Ala
                85                  90                  95
```

```
Leu Glu Gly Ala Val Leu Val Lys Glu Pro Leu Arg Ile His Glu Ser
                100                 105                 110

Met Arg Tyr Ser Leu Leu Ala Gly Gly Lys Arg Ile Arg Pro Met Leu
            115                 120                 125

Cys Ile Ala Ala Cys Glu Leu Val Gly Gly Asp Glu Glu Thr Ala Met
130                 135                 140

Pro Ala Ala Cys Ala Val Glu Met Ile His Thr Met Ser Leu Met His
145                 150                 155                 160

Asp Asp Leu Pro Cys Met Asp Asn Asp Leu Arg Arg Gly Lys Pro
                165                 170                 175

Thr Asn His Lys Val Tyr Gly Glu Asp Val Ala Val Leu Ala Gly Asp
            180                 185                 190

Ala Leu Leu Ala Phe Ala Phe Glu His Ile Ala Thr Ala Thr Lys Gly
            195                 200                 205

Ala Ser Ser Glu Lys Ile Val Arg Val Val Gly Glu Leu Ala Lys Ser
            210                 215                 220

Ile Gly Ala Glu Gly Leu Val Ala Gly Gln Val Val Asp Ile Cys Ser
225                 230                 235                 240

Glu Gly Ile Ser Asn Val Gly Leu Glu His Leu Glu Phe Ile His Leu
                245                 250                 255

His Lys Thr Ala Ala Leu Leu Gly Ser Val Val Leu Gly Ala Ile
            260                 265                 270

Leu Gly Gly Gly Thr Glu Glu Ile Ala Lys Leu Arg Lys Phe Ala
            275                 280                 285

Arg Asn Ile Gly Leu Leu Phe Gln Val Val Asp Asp Ile Leu Asp Val
290                 295                 300

Thr Lys Ser Ser Lys Glu Leu Gly Lys Thr Ala Gly Lys Asp Leu Val
305                 310                 315                 320

Ala Asp Lys Val Thr Tyr Pro Lys Leu Leu Gly Ile Gln Lys Ser Arg
                325                 330                 335

Glu Phe Ala Glu Gln Leu Asn Asn Glu Ala Gln Ala Gln Leu Ser Gly
            340                 345                 350

Phe Asp Gln Glu Lys Ala Ala Pro Leu Ile Ala Leu Ala Asn Tyr Ile
            355                 360                 365

Ala Tyr Arg Asp Asn
        370

<210> SEQ ID NO 13
<211> LENGTH: 351
<212> TYPE: PRT
<213> ORGANISM: Scoparia dulcis

<400> SEQUENCE: 13

Met Ser Leu Val Asn Pro Val Ser Thr Trp Pro Asn Pro Thr Arg Ser
1               5                   10                  15

Ser Val Phe Arg Pro Lys Pro Ala Ile Leu Asn Thr Thr His Leu Pro
            20                  25                  30

Ile Ser Phe Leu Phe Ala Gly Lys Pro Ile Ser Ala Val Leu Thr Lys
        35                  40                  45

Glu Tyr Ser His Gln Thr Ser Ser Thr Phe Asp Phe Lys Lys Tyr Met
    50                  55                  60

Leu Glu Lys Ala Ser Ser Val Asn Lys Ala Leu Glu Ser Ala Val Ser
65                  70                  75                  80

Leu Lys Glu Pro Leu Lys Ile His Glu Ser Met Arg Tyr Ser Leu Leu
```

```
Ala Gly Gly Lys Arg Val Arg Pro Met Leu Cys Leu Ala Ala Cys Glu
            100                 105                 110

Leu Val Gly Gly His Pro Ser Thr Ala Met Pro Ala Ala Cys Ser Ile
            115                 120                 125

Glu Met Ile His Thr Met Ser Leu Met His Asp Asp Leu Pro Cys Met
    130                 135                 140

Asp Asn Asp His Leu Arg Arg Gly His Pro Thr Asn His Ile Val Phe
145                 150                 155                 160

Gly Glu Asp Val Ala Val Leu Ala Gly Asp Ala Leu Leu Ala Tyr Ser
                165                 170                 175

Phe Glu Tyr Leu Ala Thr Ala Thr Glu Gly Val Leu Pro Glu Arg Ile
                180                 185                 190

Val Arg Val Ile Ala Glu Leu Ala Lys Cys Ile Arg Ser Glu Gly Leu
                195                 200                 205

Leu Ala Gly Gln Val Val Asp Ile Cys Ser Glu Gly Val Ser Glu Ile
            210                 215                 220

Gly Leu Glu His Leu Glu Tyr Ile His Leu His Lys Thr Ala Ala Leu
225                 230                 235                 240

Leu Glu Gly Ser Val Val Leu Gly Ala Ile Leu Gly Gly Gly Asn Asp
                245                 250                 255

Glu Glu Val Glu Arg Leu Arg Lys Phe Ala Arg Cys Ile Gly Leu Leu
            260                 265                 270

Phe Gln Val Val Asp Asp Ile Leu Asp Val Thr Lys Thr Ser Val Glu
        275                 280                 285

Leu Gly Lys Thr Ala Gly Lys Asp Leu Val Ala Asp Lys Thr Thr Tyr
    290                 295                 300

Pro Lys Leu Ile Gly Ile Glu Lys Ser Arg Glu Phe Ala Glu Lys Leu
305                 310                 315                 320

Asn Arg Glu Ala Gln Glu Gln Leu Val Gly Phe Asp Ser Asp Lys Ala
                325                 330                 335

Ala Pro Leu Ile Ala Leu Ala Asn Tyr Ile Ala Tyr Arg Glu Asn
            340                 345                 350

<210> SEQ ID NO 14
<211> LENGTH: 372
<212> TYPE: PRT
<213> ORGANISM: Antirrhinum majus

<400> SEQUENCE: 14

Met Ser Leu Val Asn Pro Ile Thr Thr Trp Ser Thr Thr Thr Thr Ser
1               5                   10                  15

Lys Ser Pro Lys Asn Val Gln Thr Thr Thr Arg Ser Arg Ser Ile Ile
            20                  25                  30

Leu Pro His Lys Ile Ser Leu Phe Pro Ser Asn Pro Lys Ser Lys Ser
            35                  40                  45

Lys Thr His Leu Arg Phe Ser Ile Ser Ser Ile Leu Thr Lys Asn Pro
    50                  55                  60

Gln Glu Ser Ser Gln Lys Thr Ser Lys Asp Pro Thr Phe Thr Leu Asp
65                  70                  75                  80

Phe Lys Thr Tyr Met Leu Glu Lys Ala Ser Ser Val Asn Lys Ala Leu
                85                  90                  95

Glu Gln Ala Val Leu Leu Lys Glu Pro Leu Lys Ile His Glu Ser Met
            100                 105                 110
```

-continued

```
Arg Tyr Ser Leu Leu Ala Gly Gly Lys Arg Val Arg Pro Met Leu Cys
            115                 120                 125

Ile Ala Ala Cys Glu Leu Val Gly Gly Leu Glu Ser Thr Ala Met Pro
130                 135                 140

Ser Ala Cys Ala Val Glu Met Ile His Thr Met Ser Leu Ile His Asp
145                 150                 155                 160

Asp Leu Pro Cys Met Asp Asn Asp Asp Leu Arg Arg Gly Lys Pro Thr
                165                 170                 175

Asn His Lys Ile Tyr Gly Glu Asp Val Ala Val Leu Ala Gly Asp Ala
            180                 185                 190

Leu Leu Ala Phe Ser Phe Glu His Val Ala Lys Ser Thr Lys Gly Val
        195                 200                 205

Ser Ser Asp Arg Ile Val Arg Val Ile Gly Glu Leu Ala Lys Cys Ile
210                 215                 220

Gly Ser Glu Gly Leu Val Ala Gly Gln Val Val Asp Ile Ser Ser Glu
225                 230                 235                 240

Gly Met Thr Glu Val Gly Leu Glu His Leu Glu Phe Ile His Val His
                245                 250                 255

Lys Thr Ala Ala Leu Leu Glu Ala Ser Val Val Leu Gly Ala Ile Val
            260                 265                 270

Gly Gly Ala Asp Asp Glu Asp Val Glu Lys Leu Arg Lys Phe Ala Arg
        275                 280                 285

Cys Ile Gly Leu Leu Phe Gln Val Val Asp Asp Ile Leu Asp Val Thr
290                 295                 300

Lys Ser Ser Gln Glu Leu Gly Lys Thr Ala Gly Lys Asp Leu Val Ala
305                 310                 315                 320

Asp Lys Thr Thr Tyr Pro Lys Leu Leu Gly Ile Glu Lys Ser Arg Glu
                325                 330                 335

Phe Ala Glu Lys Leu Asn Arg Glu Ala Gln Glu Gln Leu Glu Gly Phe
            340                 345                 350

Asp Ser Val Lys Ala Ala Pro Leu Ile Ala Leu Ala Asn Tyr Ile Ala
        355                 360                 365

Tyr Arg Asp Asn
    370

<210> SEQ ID NO 15
<211> LENGTH: 422
<212> TYPE: PRT
<213> ORGANISM: Arabidopsis thaliana

<400> SEQUENCE: 15

Met Leu Phe Thr Arg Ser Val Ala Arg Ile Ser Ser Lys Phe Leu Arg
1               5                   10                  15

Asn Arg Ser Phe Tyr Gly Ser Ser Gln Ser Leu Ala Ser His Arg Phe
            20                  25                  30

Ala Ile Ile Pro Asp Gln Gly His Ser Cys Ser Asp Ser Pro His Lys
        35                  40                  45

Gly Tyr Val Cys Arg Thr Thr Tyr Ser Leu Lys Ser Pro Val Phe Gly
    50                  55                  60

Gly Phe Ser His Gln Leu Tyr His Gln Ser Ser Ser Leu Val Glu Glu
65                  70                  75                  80

Glu Leu Asp Pro Phe Ser Leu Val Ala Asp Glu Leu Ser Leu Leu Ser
                85                  90                  95

Asn Lys Leu Arg Glu Met Val Leu Ala Glu Val Pro Lys Leu Ala Ser
            100                 105                 110
```

```
Ala Ala Glu Tyr Phe Phe Lys Arg Gly Val Gln Gly Lys Gln Phe Arg
            115                 120                 125

Ser Thr Ile Leu Leu Leu Met Ala Thr Ala Leu Asn Val Arg Val Pro
    130                 135                 140

Glu Ala Leu Ile Gly Glu Ser Thr Asp Ile Val Thr Ser Glu Leu Arg
145                 150                 155                 160

Val Arg Gln Arg Gly Ile Ala Glu Ile Thr Glu Met Ile His Val Ala
                165                 170                 175

Ser Leu Leu His Asp Asp Val Leu Asp Asp Ala Asp Thr Arg Arg Gly
            180                 185                 190

Val Gly Ser Leu Asn Val Val Met Gly Asn Lys Met Ser Val Leu Ala
            195                 200                 205

Gly Asp Phe Leu Leu Ser Arg Ala Cys Gly Ala Leu Ala Ala Leu Lys
            210                 215                 220

Asn Thr Glu Val Val Ala Leu Leu Ala Thr Ala Val Glu His Leu Val
225                 230                 235                 240

Thr Gly Glu Thr Met Glu Ile Thr Ser Ser Thr Glu Gln Arg Tyr Ser
                245                 250                 255

Met Asp Tyr Tyr Met Gln Lys Thr Tyr Tyr Lys Thr Ala Ser Leu Ile
            260                 265                 270

Ser Asn Ser Cys Lys Ala Val Ala Val Leu Thr Gly Gln Thr Ala Glu
            275                 280                 285

Val Ala Val Leu Ala Phe Glu Tyr Gly Arg Asn Leu Gly Leu Ala Phe
            290                 295                 300

Gln Leu Ile Asp Asp Ile Leu Asp Phe Thr Gly Thr Ser Ala Ser Leu
305                 310                 315                 320

Gly Lys Gly Ser Leu Ser Asp Ile Arg His Gly Val Ile Thr Ala Pro
                325                 330                 335

Ile Leu Phe Ala Met Glu Glu Phe Pro Gln Leu Arg Glu Val Val Asp
            340                 345                 350

Gln Val Glu Lys Asp Pro Arg Asn Val Asp Ile Ala Leu Glu Tyr Leu
            355                 360                 365

Gly Lys Ser Lys Gly Ile Gln Arg Ala Arg Glu Leu Ala Met Glu His
            370                 375                 380

Ala Asn Leu Ala Ala Ala Ile Gly Ser Leu Pro Glu Thr Asp Asn
385                 390                 395                 400

Glu Asp Val Lys Arg Ser Arg Arg Ala Leu Ile Asp Leu Thr His Arg
                405                 410                 415

Val Ile Thr Arg Asn Lys
            420

<210> SEQ ID NO 16
<211> LENGTH: 410
<212> TYPE: PRT
<213> ORGANISM: Chlamydomonas reinhardtii

<400> SEQUENCE: 16

Met Ser Leu Lys His Ala Leu Arg Gln Ala Gly Gly Leu Ile Ser Ala
1               5                   10                  15

Val Ala Ser Ser Ser Ser Ser Thr Gly Ala Val Ser Leu Phe Leu Asn
                20                  25                  30

Gly Ala Leu Asp Val Arg Pro Ala Leu His Arg Leu Phe Leu Thr Ala
            35                  40                  45

Ala Val Pro Gln Gly Tyr Ile Gln Thr Trp Ala Glu Val His Asp Arg
```

```
            50                  55                  60
Arg Val Glu Pro Phe Ser Val Gln Gln Glu Val Asp Val Ser
 65                  70                  75                  80

Glu Arg Leu Arg His Ser Val Thr Thr Gly Ile Pro Ala Leu Lys Thr
                 85                  90                  95

Ala Ala Glu Tyr Phe Phe Arg Arg Gly Ile Glu Gly Lys Arg Leu Arg
                100                 105                 110

Pro Thr Leu Ala Leu Leu Met Ser Ser Ala Leu Ser Pro Ala Ala Pro
                115                 120                 125

Ser Pro Glu Tyr Leu Gln Val Asp Thr Arg Pro Ala Ala Glu His Pro
                130                 135                 140

His Glu Met Arg Arg Arg Gln Gln Arg Leu Ala Glu Ile Ala Glu Leu
145                 150                 155                 160

Ile His Val Ala Ser Leu Leu His Asp Asp Val Ile Asp Asp Ala Gln
                165                 170                 175

Thr Arg Arg Gly Val Leu Ser Leu Asn Thr Ser Val Gly Asn Lys Thr
                180                 185                 190

Ala Ile Leu Ala Gly Asp Phe Leu Leu Ala Arg Ala Ser Val Thr Leu
                195                 200                 205

Ala Ser Leu Arg Asn Ser Glu Ile Val Glu Leu Met Ser Gln Val Leu
                210                 215                 220

Glu His Leu Val Ser Gly Glu Ile Met Gln Met Thr Ala Thr Ser Glu
225                 230                 235                 240

Gln Leu Leu Asp Leu Glu His Tyr Leu Ala Lys Thr Tyr Cys Lys Thr
                245                 250                 255

Ala Ser Leu Met Ala Asn Ser Ser Arg Ser Val Ala Val Leu Ala Gly
                260                 265                 270

Ala Ala Pro Glu Val Cys Asp Met Ala Trp Ser Tyr Gly Arg His Leu
                275                 280                 285

Gly Ile Ala Phe Gln Val Val Asp Asp Leu Leu Asp Leu Thr Gly Ser
                290                 295                 300

Ser Ser Val Leu Gly Lys Pro Ala Leu Asn Asp Met Arg Ser Gly Leu
305                 310                 315                 320

Ala Thr Ala Pro Val Leu Phe Ala Ala Gln Glu Pro Ala Leu Gln
                325                 330                 335

Ala Leu Ile Leu Arg Arg Phe Lys His Asp Gly Asp Val Thr Lys Ala
                340                 345                 350

Met Ser Leu Ile Glu Arg Thr Gln Gly Leu Arg Arg Ala Glu Glu Leu
                355                 360                 365

Ala Ala Gln His Ala Lys Ala Ala Asp Met Ile Arg Cys Leu Pro
370                 375                 380

Thr Ala Gln Ser Asp His Ala Glu Ile Ala Arg Glu Ala Leu Ile Gln
385                 390                 395                 400

Ile Thr His Arg Val Leu Thr Arg Lys Lys
                405                 410

<210> SEQ ID NO 17
<211> LENGTH: 266
<212> TYPE: PRT
<213> ORGANISM: Mentha x piperita

<400> SEQUENCE: 17

Met Gln Pro Tyr Trp Ala Ala Ile Glu Ala Asp Ile Glu Arg Tyr Leu
  1               5                  10                  15
```

```
Lys Lys Ser Ile Thr Ile Arg Pro Pro Glu Thr Val Phe Gly Pro Met
            20                  25                  30

His His Leu Thr Phe Ala Ala Pro Ala Thr Ala Ala Ser Thr Leu Cys
        35                  40                  45

Leu Ala Ala Cys Glu Leu Val Gly Gly Asp Arg Ser Gln Ala Met Ala
 50                  55                  60

Ala Ala Ala Ala Ile His Leu Val His Ala Ala Tyr Val His Glu
 65              70                  75                  80

His Leu Pro Leu Thr Asp Gly Ser Arg Pro Val Ser Lys Pro Ala Ile
                85                  90                  95

Gln His Lys Tyr Gly Pro Asn Val Glu Leu Leu Thr Gly Asp Gly Ile
            100                 105                 110

Val Pro Phe Gly Phe Glu Leu Leu Ala Gly Ser Val Asp Pro Ala Arg
            115                 120                 125

Thr Asp Asp Pro Asp Arg Ile Leu Arg Val Ile Ile Glu Ile Ser Arg
        130                 135                 140

Ala Gly Gly Pro Glu Gly Met Ile Ser Gly Leu His Arg Glu Glu
145                 150                 155                 160

Ile Val Asp Gly Asn Thr Ser Leu Asp Phe Ile Glu Tyr Val Cys Lys
                165                 170                 175

Lys Lys Tyr Gly Glu Met His Ala Cys Gly Ala Ala Cys Gly Ala Ile
            180                 185                 190

Leu Gly Gly Ala Ala Glu Glu Ile Gln Lys Leu Arg Asn Phe Gly
        195                 200                 205

Leu Tyr Gln Gly Thr Leu Arg Gly Met Met Glu Met Lys Asn Ser His
210                 215                 220

Gln Leu Ile Asp Glu Asn Ile Ile Gly Lys Leu Lys Glu Leu Ala Leu
225                 230                 235                 240

Glu Glu Leu Gly Gly Phe His Gly Lys Asn Ala Glu Leu Met Ser Ser
                245                 250                 255

Leu Val Ala Glu Pro Ser Leu Tyr Ala Ala
            260                 265

<210> SEQ ID NO 18
<211> LENGTH: 295
<212> TYPE: PRT
<213> ORGANISM: Mentha x piperita

<400> SEQUENCE: 18

Met Phe Asp Phe Asp Gly Tyr Met Leu Arg Lys Ala Thr Ser Val Asn
 1               5                  10                  15

Thr Ala Leu Glu Ala Ala Val Glu Met Lys Glu Pro Leu Lys Ile His
            20                  25                  30

Glu Ser Met Arg Tyr Ser Leu Leu Ala Gly Gly Lys Arg Val Arg Pro
        35                  40                  45

Ile Leu Cys Ile Ala Ala Cys Glu Leu Val Gly Gly Asp Glu Thr Thr
 50                  55                  60

Ala Met Pro Ala Ala Cys Ala Val Glu Met Ile His Thr Met Ser Leu
 65              70                  75                  80

Met His Asp Asp Leu Pro Cys Met Asp Asn Asp Leu Arg Arg Gly
                85                  90                  95

Lys Pro Thr Asn His Lys Val Phe Gly Glu Ser Thr Ala Val Leu Ala
            100                 105                 110

Gly Asp Ala Leu Leu Ser Phe Ala Phe Glu His Val Ala Ala Thr Thr
        115                 120                 125
```

Arg Gly Ala Pro Thr Glu Arg Ile Val Arg Val Leu Gly Glu Leu Ala
            130                 135                 140

Val Ser Ile Gly Ser Glu Gly Leu Val Ala Gly Gln Val Val Asp Ile
145                 150                 155                 160

Cys Ser Glu Gly Met Ala Glu Val Gly Leu Glu His Leu Glu Tyr Ile
                165                 170                 175

His His His Lys Thr Ala Ala Leu Leu Gln Gly Ser Val Val Leu Gly
            180                 185                 190

Ala Ile Leu Gly Gly Gly Glu Glu Val Ala Arg Leu Arg Lys
            195                 200                 205

Phe Ala Asn Cys Ile Gly Leu Leu Phe Gln Val Val Asp Asp Ile Leu
            210                 215                 220

Asp Val Thr Lys Ser Ser Lys Glu Leu Gly Lys Thr Ala Gly Lys Asp
225                 230                 235                 240

Leu Val Ala Asp Lys Thr Thr Tyr Pro Lys Leu Ile Gly Val Glu Lys
                245                 250                 255

Ser Lys Glu Phe Ala Asp Arg Leu Lys Arg Glu Ala Val Glu Gln Leu
            260                 265                 270

Leu His Phe His Pro His Arg Ala Ala Pro Leu Ile Ala Leu Ala Asn
            275                 280                 285

Tyr Ile Ala Tyr Arg Asp Asn
    290                 295

<210> SEQ ID NO 19
<211> LENGTH: 57
<212> TYPE: PRT
<213> ORGANISM: Pisum sativum

<400> SEQUENCE: 19

Met Ala Ser Met Ile Ser Ser Ala Val Thr Thr Val Ser Arg Ala
1               5                   10                  15

Ser Thr Val Gln Ser Ala Ala Val Ala Pro Phe Gly Gly Leu Lys Ser
                20                  25                  30

Met Thr Gly Phe Pro Val Lys Lys Val Asn Thr Asp Ile Thr Ser Ile
            35                  40                  45

Thr Ser Asn Gly Gly Arg Val Lys Cys
    50                  55

<210> SEQ ID NO 20
<211> LENGTH: 599
<212> TYPE: PRT
<213> ORGANISM: Mentha x piperita

<400> SEQUENCE: 20

Met Ala Leu Lys Val Phe Ser Gly Ala Met Gln Met Pro Ile Pro Ser
1               5                   10                  15

Lys Leu Thr Thr Tyr Leu Gln Pro Ser His Leu Asn Ser Ser Pro Lys
                20                  25                  30

Leu Leu Ser Asn Thr Lys Gly Thr Ser Arg Ser Arg Leu Arg Val Ser
            35                  40                  45

Cys Ser Ser Ser Gln Leu Thr Thr Glu Arg Arg Ser Gly Asn Tyr Asn
            50                  55                  60

Pro Ser Arg Trp Asp Val Asp Phe Ile Gln Thr Leu His Ser Asp Tyr
65                  70                  75                  80

Lys Asp Glu Lys His Ala Arg Arg Ala Ser Glu Leu Val Thr Leu Val
                85                  90                  95

```
Lys Met Glu Leu Glu Lys Glu Thr Asp Gln Ile Arg Gln Leu Glu Leu
                100                 105                 110

Ile Asp Asp Leu Gln Arg Met Gly Leu Ser Asp His Phe Gln Asn Glu
            115                 120                 125

Phe Lys Glu Ile Leu Ser Ser Val Tyr Leu Asp His Gly Tyr Tyr Lys
        130                 135                 140

Asn Pro Asp Pro Lys Glu Arg Asp Leu Tyr Ser Thr Ser Leu Ala
145                 150                 155                 160

Phe Arg Leu Leu Arg Glu His Gly Phe Gln Val Ala Gln Glu Val Phe
                165                 170                 175

Asp Ser Phe Lys Asn Glu Glu Gly Glu Phe Lys Glu Ser Leu Ser Asp
            180                 185                 190

Asp Thr Arg Gly Leu Leu Gln Leu Tyr Glu Ala Ser Phe Leu Leu Thr
        195                 200                 205

Glu Gly Glu Thr Thr Leu Glu Ser Ala Arg Glu Phe Ala Thr Lys Phe
    210                 215                 220

Leu Glu Glu Arg Val Asn Glu Gly Gly Asp Glu Asn Leu Leu Thr
225                 230                 235                 240

Arg Ile Ala Tyr Ser Leu Glu Ile Pro Leu His Trp Arg Ile Lys Arg
                245                 250                 255

Pro Asn Ala Pro Val Trp Ile Asp Ser Tyr Arg Lys Arg Pro Asn Met
            260                 265                 270

Asn Pro Val Val Leu Asp Leu Ala Ile Leu Asp Leu Asn Ile Val Gln
        275                 280                 285

Ala His Phe Gln Gln Glu Leu Lys Glu Ser Phe Arg Trp Trp Arg Asn
    290                 295                 300

Thr Gly Phe Val Glu Lys Leu Pro Phe Ala Arg Asp Arg Leu Val Glu
305                 310                 315                 320

Cys Tyr Phe Trp Asn Thr Gly Ile Ile Glu Pro Arg Gln His Ala Ser
                325                 330                 335

Ala Arg Ile Met Met Gly Lys Val Asn Ala Leu Ile Thr Val Ile Asp
            340                 345                 350

Asp Ile Tyr Asp Val Tyr Gly Thr Leu Glu Glu Leu Glu His Phe Thr
        355                 360                 365

Asp Leu Ile Arg Arg Trp Asp Ile Asp Ser Ile Asp Gln Leu Pro Asp
    370                 375                 380

Tyr Met Gln Leu Cys Phe Leu Ala Leu Asn Asn Phe Val Asp Glu Thr
385                 390                 395                 400

Ser Tyr Asp Val Met Lys Glu Lys Gly Val Asn Val Ile Pro Tyr Leu
                405                 410                 415

Arg Gln Ser Trp Val Asp Leu Ala Asp Lys Tyr Met Val Glu Ala Arg
            420                 425                 430

Trp Phe Tyr Gly Gly His Lys Pro Ser Leu Glu Glu Tyr Leu Glu Asn
        435                 440                 445

Ser Trp Met Ser Ile Ser Gly Pro Cys Met Leu Thr His Ile Phe Phe
    450                 455                 460

Arg Val Thr Asp Ser Phe Thr Lys Glu Thr Val Asp Ser Leu Tyr Lys
465                 470                 475                 480

Tyr His Asp Leu Val Arg Trp Ser Ser Phe Val Leu Arg Leu Ala Asp
                485                 490                 495

Asp Leu Gly Thr Ser Val Glu Glu Val Ser Arg Gly Asp Val Pro Lys
            500                 505                 510
```

```
Ser Leu Gln Cys Tyr Met Ser Asp Tyr Asn Ala Ser Glu Ala Ala
            515                 520                 525

Arg Lys His Val Lys Trp Leu Ile Ala Glu Val Trp Lys Lys Met Asn
530                 535                 540

Ala Glu Arg Val Ser Lys Asp Ser Pro Phe Gly Lys Asp Phe Ile Gly
545                 550                 555                 560

Cys Ala Val Asp Leu Gly Arg Met Ala Gln Leu Met Tyr His Asn Gly
            565                 570                 575

Asp Gly His Gly Thr Gln His Pro Ile Ile His Gln Gln Met Thr Ala
            580                 585                 590

Thr Leu Phe Glu Pro Phe Ala
            595

<210> SEQ ID NO 21
<211> LENGTH: 622
<212> TYPE: PRT
<213> ORGANISM: Cannabis sativa

<400> SEQUENCE: 21

Met Gln Cys Ile Ala Phe His Gln Phe Ala Ser Ser Ser Leu Pro
1               5                   10                  15

Ile Trp Ser Ser Ile Asp Asn Arg Phe Thr Pro Lys Thr Ser Ile Thr
            20                  25                  30

Ser Ile Ser Lys Pro Lys Pro Lys Leu Lys Ser Lys Ser Asn Leu Lys
        35                  40                  45

Ser Arg Ser Arg Ser Ser Thr Cys Tyr Ser Ile Gln Cys Thr Val Val
    50                  55                  60

Asp Asn Pro Ser Ser Thr Ile Thr Asn Asn Ser Asp Arg Arg Ser Ala
65                  70                  75                  80

Asn Tyr Gly Pro Pro Ile Trp Ser Phe Asp Phe Val Gln Ser Leu Pro
                85                  90                  95

Ile Gln Tyr Lys Gly Glu Ser Tyr Thr Ser Arg Leu Asn Lys Leu Glu
            100                 105                 110

Lys Asp Val Lys Arg Met Leu Ile Gly Val Glu Asn Ser Leu Ala Gln
        115                 120                 125

Leu Glu Leu Ile Asp Thr Ile Gln Arg Leu Gly Ile Ser Tyr Arg Phe
    130                 135                 140

Glu Asn Glu Ile Ile Ser Ile Leu Lys Glu Lys Phe Thr Asn Asn Asn
145                 150                 155                 160

Asp Asn Pro Asn Pro Asn Tyr Asp Leu Tyr Ala Thr Ala Leu Gln Phe
                165                 170                 175

Arg Leu Leu Arg Gln Tyr Gly Phe Glu Val Pro Gln Glu Ile Phe Asn
            180                 185                 190

Asn Phe Lys Asn His Lys Thr Gly Glu Phe Lys Ala Asn Ile Ser Asn
        195                 200                 205

Asp Ile Met Gly Ala Leu Gly Leu Tyr Glu Ala Ser Phe His Gly Lys
    210                 215                 220

Lys Gly Glu Ser Ile Leu Glu Glu Ala Arg Ile Phe Thr Thr Lys Cys
225                 230                 235                 240

Leu Lys Lys Tyr Lys Leu Met Ser Ser Asn Asn Asn Asn Met Thr
                245                 250                 255

Leu Ile Ser Leu Leu Val Asn His Ala Leu Glu Met Pro Leu Gln Trp
            260                 265                 270

Arg Ile Thr Arg Ser Glu Ala Lys Trp Phe Ile Glu Glu Ile Tyr Glu
        275                 280                 285
```

-continued

Arg Lys Gln Asp Met Asn Pro Thr Leu Leu Glu Phe Ala Lys Leu Asp
    290                 295                 300

Phe Asn Met Leu Gln Ser Thr Tyr Gln Glu Glu Leu Lys Val Leu Ser
305                 310                 315                 320

Arg Trp Trp Lys Asp Ser Lys Leu Gly Glu Lys Leu Pro Phe Val Arg
                325                 330                 335

Asp Arg Leu Val Glu Cys Phe Leu Trp Gln Val Gly Val Arg Phe Glu
            340                 345                 350

Pro Gln Phe Ser Tyr Phe Arg Ile Met Asp Thr Lys Leu Tyr Val Leu
        355                 360                 365

Leu Thr Ile Ile Asp Asp Met His Asp Ile Tyr Gly Thr Leu Glu Glu
    370                 375                 380

Leu Gln Leu Phe Thr Asn Ala Leu Gln Arg Trp Asp Leu Lys Glu Leu
385                 390                 395                 400

Asp Lys Leu Pro Asp Tyr Met Lys Thr Ala Phe Tyr Phe Thr Tyr Asn
                405                 410                 415

Phe Thr Asn Glu Leu Ala Phe Asp Val Leu Gln Glu His Gly Phe Val
            420                 425                 430

His Ile Glu Tyr Phe Lys Lys Leu Met Val Glu Leu Cys Lys His His
        435                 440                 445

Leu Gln Glu Ala Lys Trp Phe Tyr Ser Gly Tyr Lys Pro Thr Leu Gln
    450                 455                 460

Glu Tyr Val Glu Asn Gly Trp Leu Ser Val Gly Gly Gln Val Ile Leu
465                 470                 475                 480

Met His Ala Tyr Phe Ala Phe Thr Asn Pro Val Thr Lys Glu Ala Leu
                485                 490                 495

Glu Cys Leu Lys Asp Gly His Pro Asn Ile Val Arg His Ala Ser Ile
            500                 505                 510

Ile Leu Arg Leu Ala Asp Asp Leu Gly Thr Leu Ser Asp Glu Leu Lys
        515                 520                 525

Arg Gly Asp Val Pro Lys Ser Ile Gln Cys Tyr Met His Asp Thr Gly
    530                 535                 540

Ala Ser Glu Asp Glu Ala Arg Glu His Ile Lys Tyr Leu Ile Ser Glu
545                 550                 555                 560

Ser Trp Lys Glu Met Asn Asn Glu Asp Gly Asn Ile Asn Ser Phe Phe
                565                 570                 575

Ser Asn Glu Phe Val Gln Val Cys Gln Asn Leu Gly Arg Ala Ser Gln
            580                 585                 590

Phe Ile Tyr Gln Tyr Gly Asp Gly His Ala Ser Gln Asn Asn Leu Ser
        595                 600                 605

Lys Glu Arg Val Leu Gly Leu Ile Ile Thr Pro Ile Pro Met
    610                 615                 620

<210> SEQ ID NO 22
<211> LENGTH: 599
<212> TYPE: PRT
<213> ORGANISM: Mentha longifolia

<400> SEQUENCE: 22

Met Ala Leu Lys Val Phe Ser Val Ala Thr Gln Met Ala Ile Pro Ser
1               5                   10                  15

Lys Leu Thr Arg Cys Leu Gln Pro Ser His Leu Lys Ser Ser Pro Lys
            20                  25                  30

Leu Leu Ser Ser Thr Asn Ser Ser Ser Arg Ser Arg Leu Arg Val Tyr

-continued

```
                35                  40                  45
Cys Ser Ser Ser Gln Leu Thr Thr Glu Arg Arg Ser Gly Asn Tyr Asn
 50                  55                  60
Pro Ser Arg Trp Asp Val Glu Phe Ile Gln Ser Leu His Ser Asp Tyr
 65                  70                  75                  80
Glu Glu Asp Lys His Ala Ile Arg Ala Ser Glu Leu Val Thr Leu Val
                 85                  90                  95
Lys Met Glu Leu Glu Lys Glu Thr Asp His Ile Arg Gln Leu Glu Leu
                100                 105                 110
Ile Asp Asp Leu Gln Arg Met Gly Leu Ser Asp His Phe Gln Asn Glu
                115                 120                 125
Phe Lys Glu Ile Leu Ser Ser Ile Tyr Leu Asp His His Tyr Tyr Lys
130                 135                 140
Asn Pro Phe Pro Lys Glu Arg Asp Leu Tyr Ser Thr Ser Leu Ala
145                 150                 155                 160
Phe Arg Leu Leu Arg Glu His Gly Phe Gln Val Ala Gln Glu Val Phe
                165                 170                 175
Asp Ser Phe Lys Asn Glu Gly Glu Phe Lys Glu Ser Leu Ser Asp
                180                 185                 190
Asp Thr Arg Gly Leu Leu Gln Leu Tyr Glu Ala Ser Phe Leu Leu Thr
                195                 200                 205
Glu Gly Glu Thr Thr Leu Glu Ser Ala Arg Glu Phe Ala Thr Lys Phe
                210                 215                 220
Leu Glu Glu Arg Val Asn Glu Gly Gly Val Asp Gly Asp Leu Leu Thr
225                 230                 235                 240
Arg Ile Ala Tyr Ser Leu Asp Ile Pro Leu His Trp Arg Ile Lys Arg
                245                 250                 255
Pro Asn Ala Pro Ala Trp Ile Glu Trp Tyr Arg Lys Arg Pro Asp Met
                260                 265                 270
Asn Pro Val Val Leu Glu Leu Ala Ile Leu Asp Leu Asn Ile Val Gln
                275                 280                 285
Ala Gln Phe Gln Glu Glu Leu Lys Glu Ser Phe Arg Trp Trp Arg Asn
                290                 295                 300
Thr Gly Phe Val Glu Lys Leu Pro Phe Ala Arg Asp Arg Leu Val Glu
305                 310                 315                 320
Cys Tyr Phe Trp Asn Thr Gly Ile Ile Glu Pro Arg Gln His Ala Ser
                325                 330                 335
Ala Arg Ile Met Met Gly Lys Val Asn Ala Leu Ile Thr Val Ile Asp
                340                 345                 350
Asp Ile Tyr Asp Val Tyr Gly Thr Leu Glu Glu Leu Glu Gln Phe Thr
                355                 360                 365
Asp Leu Ile Arg Arg Trp Asp Ile Asn Ser Ile Asp Gln Leu Pro Asp
                370                 375                 380
Tyr Met Gln Leu Cys Phe Leu Ala Leu Asn Asn Phe Val Asp Asp Thr
385                 390                 395                 400
Ser Tyr Asp Val Met Lys Glu Lys Gly Val Asn Val Ile Pro Tyr Leu
                405                 410                 415
Arg Gln Ser Trp Val Asp Leu Ala Asp Lys Tyr Met Val Glu Ala Arg
                420                 425                 430
Trp Phe Tyr Gly Gly His Lys Pro Ser Leu Glu Glu Tyr Leu Glu Asn
                435                 440                 445
Ser Trp Gln Ser Ile Ser Gly Pro Cys Met Leu Thr His Ile Phe Phe
450                 455                 460
```

```
Arg Val Thr Asp Ser Phe Thr Lys Glu Thr Val Asp Ser Leu Tyr Lys
465                 470                 475                 480

Tyr His Asp Leu Val Arg Trp Ser Ser Phe Val Arg Leu Ala Asp
                485                 490                 495

Asp Leu Gly Thr Ser Val Glu Glu Val Ser Arg Gly Asp Val Pro Lys
            500                 505                 510

Ser Leu Gln Cys Tyr Met Ser Asp Tyr Asn Ala Ser Glu Ala Glu Ala
            515                 520                 525

Arg Lys His Val Lys Trp Leu Ile Ala Glu Val Trp Lys Lys Met Asn
            530                 535                 540

Ala Glu Arg Val Ser Lys Asp Ser Pro Phe Gly Lys Asp Phe Ile Gly
545                 550                 555                 560

Cys Ala Ala Asp Leu Gly Arg Met Ala Gln Leu Met Tyr His Asn Gly
                565                 570                 575

Asp Gly His Gly Thr Gln His Pro Ile Ile His Gln Gln Met Thr Arg
            580                 585                 590

Thr Leu Phe Glu Pro Phe Ala
            595
```

```
<210> SEQ ID NO 23
<211> LENGTH: 634
<212> TYPE: PRT
<213> ORGANISM: Picea sitchensis

<400> SEQUENCE: 23

Met Ser Pro Val Ser Ala Ile Pro Leu Ala Tyr Lys Leu Cys Leu Pro
1               5                   10                  15

Arg Ser Leu Ile Ser Ser Ser Arg Glu Leu Asn Pro Leu His Ile Thr
            20                  25                  30

Ile Pro Asn Leu Gly Met Cys Arg Arg Gly Lys Ser Met Ala Pro Ala
            35                  40                  45

Ser Met Ser Met Ile Leu Thr Ala Ala Val Ser Asp Asp Asp Arg Val
    50                  55                  60

Gln Arg Arg Arg Gly Asn Tyr His Ser Asn Leu Trp Asp Asp Asp Phe
65                  70                  75                  80

Ile Gln Ser Leu Ser Thr Pro Tyr Gly Glu Pro Ser Tyr Arg Glu Ser
                85                  90                  95

Ala Glu Arg Leu Lys Gly Glu Ile Lys Lys Met Phe Arg Ser Met Ser
            100                 105                 110

Lys Glu Asp Glu Glu Leu Ile Thr Pro Leu Asn Asp Leu Ile Gln Arg
            115                 120                 125

Leu Trp Met Val Asp Ser Val Glu Arg Leu Gly Ile Asp Arg His Phe
        130                 135                 140

Lys Asn Glu Ile Lys Ser Ala Leu Asp Tyr Val Tyr Ser Tyr Trp Asn
145                 150                 155                 160

Glu Lys Gly Ile Gly Cys Gly Arg Asp Ser Val Val Ala Asp Leu Asn
                165                 170                 175

Ser Thr Ala Leu Gly Phe Arg Thr Leu Arg Leu His Gly Tyr Asn Val
            180                 185                 190

Ser Ser Glu Val Leu Lys Val Phe Glu Asp Gln Asn Gly Gln Phe Ala
            195                 200                 205

Cys Ser Pro Ser Lys Thr Glu Gly Glu Ile Arg Ser Ala Leu Asn Leu
            210                 215                 220

Tyr Arg Ala Ser Leu Ile Ala Phe Pro Gly Glu Lys Val Met Glu Asp
```

-continued

```
            225                 230                 235                 240
        Ala Glu Ile Phe Ser Ser Arg Tyr Leu Lys Glu Ala Val Gln Lys Ile
                        245                 250                 255
        Pro Asp Cys Ser Leu Ser Gln Glu Ile Ala Tyr Ala Leu Glu Tyr Gly
                        260                 265                 270
        Trp His Thr Asn Met Pro Arg Leu Glu Ala Arg Asn Tyr Met Asp Val
                        275                 280                 285
        Phe Gly His Pro Ser Ser Pro Trp Leu Lys Lys Asn Lys Thr Gln Tyr
                        290                 295                 300
        Met Asp Gly Glu Lys Leu Leu Glu Leu Ala Lys Leu Glu Phe Asn Ile
        305                 310                 315                 320
        Phe His Ser Leu Gln Gln Glu Leu Gln Tyr Ile Ser Arg Trp Trp
                        325                 330                 335
        Lys Asp Ser Gly Leu Pro Lys Leu Ala Phe Ser Arg His Arg His Val
                        340                 345                 350
        Glu Tyr Tyr Thr Leu Gly Ser Cys Ile Ala Thr Asp Pro Lys His Arg
                        355                 360                 365
        Ala Phe Arg Leu Gly Phe Val Lys Thr Cys His Leu Asn Thr Val Leu
                        370                 375                 380
        Asp Asp Ile Tyr Asp Thr Phe Gly Thr Met Asp Glu Ile Glu Leu Phe
        385                 390                 395                 400
        Thr Glu Ala Val Arg Arg Trp Asp Pro Ser Glu Thr Glu Ser Leu Pro
                        405                 410                 415
        Asp Tyr Met Lys Gly Val Tyr Met Val Leu Tyr Glu Ala Leu Thr Glu
                        420                 425                 430
        Met Ala Gln Glu Ala Glu Lys Thr Gln Gly Arg Asp Thr Leu Asn Tyr
                        435                 440                 445
        Ala Arg Lys Ala Trp Glu Ile Tyr Leu Asp Ser Tyr Ile Gln Glu Ala
                        450                 455                 460
        Lys Trp Ile Ala Ser Gly Tyr Leu Pro Thr Phe Gln Glu Tyr Phe Glu
        465                 470                 475                 480
        Asn Gly Lys Ile Ser Ser Ala Tyr Arg Ala Ala Leu Thr Pro Ile
                        485                 490                 495
        Leu Thr Leu Asp Val Pro Leu Pro Glu Tyr Ile Leu Lys Gly Ile Asp
                        500                 505                 510
        Phe Pro Ser Arg Phe Asn Asp Leu Ala Ser Ser Phe Leu Arg Leu Arg
                        515                 520                 525
        Gly Asp Thr Arg Cys Tyr Lys Ala Asp Arg Ala Arg Gly Glu Glu Ala
                        530                 535                 540
        Ser Cys Ile Ser Cys Tyr Met Lys Asp Asn Pro Gly Ser Thr Glu Glu
        545                 550                 555                 560
        Asp Ala Leu Asn His Ile Asn Ser Met Ile Asn Glu Ile Ile Lys Glu
                        565                 570                 575
        Leu Asn Trp Glu Leu Leu Arg Pro Asp Ser Asn Ile Pro Met Pro Ala
                        580                 585                 590
        Arg Lys His Ala Phe Asp Ile Thr Arg Ala Leu His His Leu Tyr Lys
                        595                 600                 605
        Tyr Arg Asp Gly Phe Ser Val Ala Thr Lys Glu Thr Lys Ser Leu Val
                        610                 615                 620
        Ser Arg Met Val Leu Glu Pro Val Thr Leu
        625                 630

<210> SEQ ID NO 24
```

```
<211> LENGTH: 604
<212> TYPE: PRT
<213> ORGANISM: Perilla frutescens var. frutescens

<400> SEQUENCE: 24

Met Tyr Thr Gly Val Ile Met His Met Ala Ile Pro Ile Lys Pro Ala
1               5                   10                  15

His Tyr Leu His Asn Ser Gly Arg Ser Tyr Ala Ser Gln Leu Cys Gly
            20                  25                  30

Phe Ser Ser Thr Ser Thr Arg Ala Ala Ile Ala Arg Leu Pro Leu Cys
        35                  40                  45

Leu Arg Phe Arg Cys Ser Leu Gln Ala Ser Asp Gln Arg Arg Ser Gly
    50                  55                  60

Asn Tyr Ser Pro Ser Phe Trp Asn Ala Asp Tyr Ile Leu Ser Leu Asn
65                  70                  75                  80

Asn His Tyr Lys Glu Glu Ser Arg His Met Lys Arg Ala Gly Glu Leu
                85                  90                  95

Ile Val Gln Val Lys Met Val Met Gly Lys Glu Thr Asp Pro Val Val
            100                 105                 110

Gln Leu Glu Leu Ile Asp Asp Leu His Lys Leu Ala Leu Ser His His
        115                 120                 125

Phe Glu Lys Glu Ile Lys Glu Ile Leu Phe Asn Ile Ser Ile Tyr Asp
    130                 135                 140

His Lys Ile Met Val Glu Arg Asp Leu Tyr Ser Thr Ala Leu Ala Phe
145                 150                 155                 160

Arg Leu Leu Arg Gln Tyr Gly Phe Lys Val Pro Gln Glu Val Phe Asp
                165                 170                 175

Cys Phe Lys Asn Asp Asn Gly Glu Phe Lys Arg Ser Leu Ser Ser Asp
            180                 185                 190

Thr Lys Gly Leu Leu Gln Leu Tyr Glu Ala Ser Phe Leu Leu Thr Glu
        195                 200                 205

Gly Glu Met Thr Leu Glu Leu Ala Arg Glu Phe Ala Thr Ile Phe Leu
    210                 215                 220

Gln Glu Lys Leu Asn Asp Lys Thr Ile Asp Asp Asp Asp Ala Asp
225                 230                 235                 240

Thr Asn Leu Ile Ser Cys Val Arg His Ser Leu Asp Ile Pro Ile His
                245                 250                 255

Trp Arg Ile Gln Arg Pro Asn Ala Ser Trp Trp Ile Asp Ala Tyr Lys
            260                 265                 270

Arg Arg Ser His Met Asn Pro Leu Val Leu Glu Leu Ala Lys Leu Asp
        275                 280                 285

Leu Asn Ile Phe Gln Ala Gln Phe Gln Gln Glu Leu Lys Gln Asp Leu
    290                 295                 300

Gly Trp Trp Lys Asn Thr Cys Leu Ala Glu Lys Leu Pro Phe Thr Arg
305                 310                 315                 320

Asp Arg Leu Val Glu Cys Tyr Phe Trp Cys Thr Gly Ile Ile Gln Pro
                325                 330                 335

Leu Gln His Glu Asn Ala Arg Val Thr Leu Ala Lys Val Asn Ala Leu
            340                 345                 350

Ile Thr Thr Leu Asp Asp Ile Tyr Asp Val Tyr Gly Thr Leu Glu Glu
        355                 360                 365

Leu Glu Leu Phe Thr Glu Ala Ile Arg Arg Trp Asp Val Ser Ser Ile
    370                 375                 380

Asp His Leu Pro Asn Tyr Met Gln Leu Cys Phe Leu Ala Leu Asn Asn
```

Phe Val Asp Asp Thr Ala Tyr Asp Val Met Lys Glu Lys Asp Ile Asn
385                 390                 395                 400

Ile Ile Pro Tyr Leu Arg Lys Ser Trp Leu Asp Leu Ala Glu Thr Tyr
            405                 410                 415

Leu Val Glu Ala Lys Trp Phe Tyr Ser Gly His Lys Pro Asn Met Glu
                435                 440                 445

Glu Tyr Leu Asn Asn Ala Trp Ile Ser Ile Ser Gly Pro Val Met Leu
        450                 455                 460

Cys His Val Phe Phe Arg Val Thr Asp Ser Ile Thr Arg Glu Thr Val
465                 470                 475                 480

Glu Ser Leu Phe Lys Tyr His Asp Leu Ile Arg Tyr Ser Ser Thr Ile
                485                 490                 495

Leu Arg Leu Ala Asp Asp Leu Gly Thr Ser Leu Glu Glu Val Ser Arg
                500                 505                 510

Gly Asp Val Pro Lys Ser Ile Gln Cys Tyr Met Asn Asp Asn Asn Ala
                515                 520                 525

Ser Glu Glu Glu Ala Arg Arg His Val Arg Trp Leu Ile Ala Glu Thr
530                 535                 540

Trp Lys Lys Ile Asn Glu Val Trp Ser Ala Asp Ser Pro Phe Cys
545                 550                 555                 560

Lys Asp Phe Ile Ala Cys Ala Ala Asp Met Gly Arg Met Ala Gln Phe
                565                 570                 575

Met Tyr His Asn Gly Asp Gly His Gly Ile Gln Asn Pro Gln Ile His
                580                 585                 590

Gln Gln Met Thr Asp Ile Leu Phe Glu Gln Trp Leu
                595                 600

<210> SEQ ID NO 25
<211> LENGTH: 594
<212> TYPE: PRT
<213> ORGANISM: Rosmarinus officinalis

<400> SEQUENCE: 25

Met Phe Thr Ile Met Thr Ser Met Ala Ile Pro Met Lys Pro Val Lys
1               5                   10                  15

His Val His Asn Phe Ala Ala Arg Arg Asp Pro Lys Leu Arg Leu Ala
                20                  25                  30

Ser Pro Thr Cys Trp Arg Gln Ser Cys Ser Leu Lys Leu Thr Thr Asp
            35                  40                  45

Tyr Pro Cys Asp Gln Leu Gln Ser Thr Arg Arg Ser Gly Asn Tyr Lys
        50                  55                  60

Pro Thr Leu Trp Asp Phe Glu Arg Ile Gln Ser Leu Asn Ser Val Tyr
65                  70                  75                  80

Thr Glu Glu Lys Tyr Thr Thr Arg Ala Ser Glu Leu Val Val Gln Val
                85                  90                  95

Lys Lys Leu Leu Leu Leu Glu Ser Asn Trp Phe Leu Gln Leu Glu Leu
                100                 105                 110

Ile Asp Asp Leu Gln Lys Leu Gly Val Ser Tyr Arg Phe Asn His Glu
            115                 120                 125

Ile Asn Gln Ile Leu Asn Arg Ile Tyr Leu Glu Gln Lys Tyr Cys Asn
        130                 135                 140

Asn Ser Glu Arg Asp Leu Tyr Ser Thr Ala Leu Ala Phe Arg Leu Leu
145                 150                 155                 160

-continued

```
Arg Gln His Gly Leu Lys Val Ser Gln Asp Val Phe Asp Phe Phe Lys
                165                 170                 175
Asn Asp Glu Gly Glu Phe Glu Pro Asn Leu Gly Asp Asn Thr Lys Gly
            180                 185                 190
Leu Leu Gln Leu Tyr Glu Ala Ser Phe Leu Leu Thr Glu Gly Glu Met
        195                 200                 205
Ser Leu Glu Gln Ala Arg Val Phe Ser Thr Asn Leu Leu Gln Lys Lys
    210                 215                 220
Leu Asp Asp Gly Ile Met Asp Glu Tyr Leu Ser Ser Leu Val Arg Arg
225                 230                 235                 240
Ser Leu Glu Leu Pro Leu His Trp Ser Val Gln Arg Pro Asn Ser Arg
                245                 250                 255
Trp Leu Ile Asp Ala Tyr Thr Asn Arg Ser Asp Val Asn Pro Ile Leu
            260                 265                 270
Ile Glu Leu Ala Lys Leu Asp Phe Asn Ile Val Gln Ala Ser Tyr His
        275                 280                 285
Glu Glu Leu Lys Glu Val Ser Arg Trp Trp Lys Glu Thr Glu Leu Ala
    290                 295                 300
Glu Lys Leu Pro Phe Ala Arg Asp Arg Val Val Glu Asn Tyr Ile Trp
305                 310                 315                 320
Asn Val Gly Leu Leu Phe Gln Pro Gln Tyr Gly Tyr Pro Arg Ile Met
                325                 330                 335
Thr Thr Lys Leu Phe Ile Leu Ile Thr Val Ile Asp Asp Val Phe Asp
            340                 345                 350
Val Tyr Gly Thr Leu Glu Glu Thr Glu Leu Phe Lys Lys Ala Ile Leu
        355                 360                 365
Ser Trp Asp Val Glu Val Leu Asp Gln Leu Pro Asn Tyr Met Gln Ile
    370                 375                 380
Cys Tyr Met Ala Leu Asp Ser Phe Ile Asn Glu Met Ala Tyr His Val
385                 390                 395                 400
Leu Lys Glu Gln Gly Val Leu Ile Ile Gln Asp Leu Arg Lys Phe Trp
                405                 410                 415
Ala Asp Leu Cys Val Ala Tyr Ala Lys Glu Ala Glu Trp Tyr His Thr
            420                 425                 430
Gly His Lys Pro Thr Met Glu Glu Tyr Ile Asp Val Ala Trp Ile Ser
        435                 440                 445
Ile Ser Ala His Leu Ile Leu Ala His Val Phe Phe Leu Ile Thr Asn
    450                 455                 460
Pro Ile Gly Lys Glu Ala Ala Glu Ser Leu Arg Asn Tyr Asp Asp Ile
465                 470                 475                 480
Ile Arg Asn Ser Ala Met Ile Leu Arg Leu Ala Asp Asp Leu Gly Thr
                485                 490                 495
Ser Ser Tyr Glu Met Gln Arg Gly Asp Val Pro Lys Ala Val Glu Cys
            500                 505                 510
Tyr Met Asn Glu Met Gly Ala Ser Val Glu Ala Arg Glu His Val
        515                 520                 525
Lys Cys Met Ile Arg Glu Ala Trp Met Lys Thr Ser Ala Glu Arg Phe
    530                 535                 540
Lys Glu Ser Pro Phe Ser Lys Asp Phe Ile Arg Ser Ala Ala Asp Leu
545                 550                 555                 560
Gly Arg His Ala Gln Tyr Met Tyr Gln His Gly Asp Gly His Gly Ile
                565                 570                 575
Arg Asn Pro Gln Met Glu Glu Arg Ile Ser Thr Leu Ile Phe Gln Pro
```

```
                       580                 585                 590

Ile Asp

<210> SEQ ID NO 26
<211> LENGTH: 606
<212> TYPE: PRT
<213> ORGANISM: Citrus jambhiri

<400> SEQUENCE: 26

Met Ser Ser Cys Ile Asn Pro Ser Thr Leu Val Thr Ser Val Asn Ala
1               5                   10                  15

Phe Lys Cys Leu Pro Leu Ala Thr Asn Lys Ala Ala Ile Arg Ile Met
            20                  25                  30

Ala Lys Tyr Lys Pro Val Gln Cys Leu Ile Ser Ala Lys Tyr Asp Asn
        35                  40                  45

Leu Thr Val Asp Arg Arg Ser Ala Asn Tyr Gln Pro Ser Ile Trp Asp
    50                  55                  60

His Asp Phe Leu Gln Ser Leu Asn Ser Asn Tyr Thr Asp Glu Ala Tyr
65                  70                  75                  80

Lys Arg Arg Ala Glu Glu Leu Arg Gly Lys Val Lys Ile Ala Ile Lys
                85                  90                  95

Asp Val Ile Glu Pro Leu Asp Gln Leu Glu Leu Ile Asp Asn Leu Gln
            100                 105                 110

Arg Leu Gly Leu Ala His Arg Phe Glu Thr Glu Ile Arg Asn Ile Leu
        115                 120                 125

Asn Asn Ile Tyr Asn Asn Lys Asp Tyr Asn Trp Arg Lys Glu Asn
    130                 135                 140

Leu Tyr Ala Thr Ser Leu Glu Phe Arg Leu Leu Arg Gln His Gly Tyr
145                 150                 155                 160

Pro Val Ser Gln Glu Val Phe Asn Gly Phe Lys Asp Gln Gly Gly
                165                 170                 175

Phe Ile Cys Asp Asp Phe Lys Gly Ile Leu Ser Leu His Glu Ala Ser
            180                 185                 190

Tyr Tyr Ser Leu Glu Gly Glu Ser Ile Met Glu Glu Ala Trp Gln Phe
        195                 200                 205

Thr Ser Lys His Leu Lys Glu Val Met Ile Ser Lys Asn Met Glu Glu
    210                 215                 220

Asp Val Phe Val Ala Glu Gln Ala Lys Arg Ala Leu Glu Leu Pro Leu
225                 230                 235                 240

His Trp Lys Val Pro Met Leu Glu Ala Arg Trp Phe Ile His Ile Tyr
                245                 250                 255

Glu Arg Arg Glu Asp Lys Asn His Leu Leu Leu Glu Leu Ala Lys Met
            260                 265                 270

Glu Phe Asn Thr Leu Gln Ala Ile Tyr Gln Glu Glu Leu Lys Glu Ile
        275                 280                 285

Ser Gly Trp Trp Lys Asp Thr Gly Leu Gly Glu Lys Leu Ser Phe Ala
    290                 295                 300

Arg Asn Arg Leu Val Ala Ser Phe Leu Trp Ser Met Gly Ile Ala Phe
305                 310                 315                 320

Glu Pro Gln Phe Ala Tyr Cys Arg Arg Val Leu Thr Ile Ser Ile Ala
                325                 330                 335

Leu Ile Thr Val Ile Asp Asp Ile Tyr Asp Val Tyr Gly Thr Leu Asp
            340                 345                 350

Glu Leu Glu Ile Phe Thr Asp Ala Val Glu Arg Trp Asp Ile Asn Tyr
```

-continued

```
                355                 360                 365
Ala Leu Lys His Leu Pro Gly Tyr Met Lys Met Cys Phe Leu Ala Leu
370                 375                 380

Tyr Asn Phe Val Asn Glu Phe Ala Tyr Tyr Val Leu Lys Gln Gln Asp
385                 390                 395                 400

Phe Asp Leu Leu Leu Ser Ile Lys Asn Ala Trp Leu Gly Leu Ile Gln
                405                 410                 415

Ala Tyr Leu Val Glu Ala Lys Trp Tyr His Ser Lys Tyr Thr Pro Lys
                420                 425                 430

Leu Glu Glu Tyr Leu Glu Asn Gly Leu Val Ser Ile Thr Gly Pro Leu
                435                 440                 445

Ile Ile Thr Ile Ser Tyr Leu Ser Gly Thr Asn Pro Ile Ile Lys Lys
                450                 455                 460

Glu Leu Glu Phe Leu Glu Ser Asn Pro Asp Ile Val His Trp Ser Ser
465                 470                 475                 480

Lys Ile Phe Arg Leu Gln Asp Asp Leu Gly Thr Ser Ser Asp Glu Ile
                485                 490                 495

Gln Arg Gly Asp Val Pro Lys Ser Ile Gln Cys Tyr Met His Glu Thr
                500                 505                 510

Gly Ala Ser Glu Glu Val Ala Arg Gln His Ile Lys Asp Met Met Arg
                515                 520                 525

Gln Met Trp Lys Lys Val Asn Ala Tyr Thr Ala Asp Lys Asp Ser Pro
                530                 535                 540

Leu Thr Gly Thr Thr Thr Glu Phe Leu Leu Asn Leu Val Arg Met Ser
545                 550                 555                 560

His Phe Met Tyr Leu His Gly Asp Gly His Gly Val Gln Asn Gln Glu
                565                 570                 575

Thr Ile Asp Val Gly Phe Thr Leu Leu Phe Gln Pro Ile Pro Leu Glu
                580                 585                 590

Asp Lys His Met Ala Phe Thr Ala Ser Pro Gly Thr Lys Gly
                595                 600                 605

<210> SEQ ID NO 27
<211> LENGTH: 595
<212> TYPE: PRT
<213> ORGANISM: Toona sinensis

<400> SEQUENCE: 27

Met Ala Ser His Val Leu Ala Ser Leu Arg Ser Ala Ser Ala Arg Ile
1               5                   10                  15

Ser Thr Arg Leu Gln Ser Arg Ser Cys Ile Leu Ala Thr Ala Thr Ser
                20                  25                  30

Phe Ser Asn Gly Phe Val Ser Ala Ser Leu Val Gln Ser Met Ser Thr
                35                  40                  45

Thr Thr Gln Cys Asp Glu Ser Val Ala Arg Arg Ser Ala Asn Tyr Glu
50                  55                  60

Pro Pro Ile Trp Thr Tyr Asp Tyr Val Gln Ser Leu Arg Asn Pro Tyr
65                  70                  75                  80

Ala Gly Gly Ser Tyr Ala Lys Arg Ile Glu Lys Leu Lys Gly Asp Val
                85                  90                  95

Arg Val Met Leu Gln Lys Leu Val Asp Leu Asp Pro Leu His Gln Leu
                100                 105                 110

Glu Phe Ile Asp Thr Leu Gln Arg Leu Gly Val Ser Tyr His Tyr Gln
                115                 120                 125
```

-continued

Glu Gly Ile Lys Gly Ile Leu Asp Thr Val Tyr Asn Asn Tyr Met Gln
130                 135                 140

Lys Gln Glu Ser Leu Tyr Ala Val Ala Leu Gly Phe Arg Leu Phe Arg
145                 150                 155                 160

Gln His Gly Tyr His Ile Pro Ala Asp Ile Phe Ser Ser Phe Arg Asp
                165                 170                 175

Asp Lys Gly Asn Leu Lys Ser Cys Leu Gly Asp Asp Cys Arg Gly Ile
            180                 185                 190

Leu Ala Leu Tyr Glu Ala Ala His Leu Leu Val Glu Glu Glu Arg Asp
        195                 200                 205

Ile Phe Tyr Glu Ile Val Asn Phe Thr Thr Ala Tyr Leu Lys Glu Tyr
210                 215                 220

Val Lys His Asp Asn Asp Glu Tyr Leu Ser Ala Leu Val Asn His Ser
225                 230                 235                 240

Leu Glu Ile Pro Leu His Trp Arg Val Leu Arg Leu Glu Ala Arg Trp
                245                 250                 255

Phe Ile Gly Ala Tyr Glu Arg Ala Pro Asn Thr His Pro Ile Leu Leu
            260                 265                 270

Glu Phe Ala Lys Leu Asp Phe Asn Asp Val Gln Ala Thr His Gln Glu
        275                 280                 285

Asp Leu Lys Phe Met Ser Arg Trp Trp Lys Asn Thr Gly Leu Asp Arg
290                 295                 300

Glu Lys Met Asn Phe Ala Arg Asp Arg Ile Val Gln Asn Val Leu Trp
305                 310                 315                 320

Ser Leu Gly Ile Ile Phe Glu Pro Gln Phe Ala Tyr Cys Arg Arg Met
                325                 330                 335

Ser Val Lys Ala Tyr Ala Phe Ile Thr Leu Ile Asp Asp Val Tyr Asp
            340                 345                 350

Val Tyr Gly Thr Leu Asp Glu Leu Glu Leu Phe Thr Asp Ala Val Asp
        355                 360                 365

Arg Trp Asp Ala Thr Ala Ile Glu Lys Leu Pro Asp Tyr Met Lys Pro
370                 375                 380

Ile Phe Arg Thr Leu Tyr Thr Ser Ile Asn Asp Met Ala Leu Asp Ala
385                 390                 395                 400

Arg Lys Asp Arg Gly Val Asp Thr Arg Pro Phe Leu His Lys Ala Trp
                405                 410                 415

Ser Thr Leu Phe Asn Tyr Tyr Leu Met Glu Ala Lys Trp Phe Ser Asn
            420                 425                 430

Gly Tyr Met Pro Thr Tyr Lys Glu Tyr Met Asp Ile Ala Trp Phe Ser
        435                 440                 445

Val Gly Gly Pro Val Met Ile Val His Ser Tyr Cys Ala Ile Ala Asn
450                 455                 460

Pro Ala Thr Lys Glu Asn Met Glu Phe Phe Gln Glu Tyr Tyr Asp Ile
465                 470                 475                 480

Ile Arg Leu Cys Ser Thr Ile Leu Arg Phe Lys Asp Asp Met Gly Thr
                485                 490                 495

Ser Ser Asp Glu Leu Lys Arg Gly Asp Asn Pro Lys Ser Ile Gln Cys
            500                 505                 510

Tyr Met His Glu Ser Gly Val Ser Glu Lys Glu Ala Arg Gln His Leu
        515                 520                 525

Gly Asn Leu Ile Thr Glu Thr Trp Met Lys Val Asn Lys Asn Arg Ala
530                 535                 540

Glu Asn Pro His Leu Ser Asp Val Tyr Met Gly Ile Ala Ile Asn Met

```
                545                 550                 555                 560
           Ala Arg Met Ala Leu Cys Met Tyr Gln Phe Gly Asp Gly His Ala Val
                                565                 570                 575

Glu Ala His Ser Lys Asp Arg Val Leu Ser Leu Leu Ile Asn Pro Ile
                                580                 585                 590

Pro Cys Pro
                   595

<210> SEQ ID NO 28
<211> LENGTH: 606
<212> TYPE: PRT
<213> ORGANISM: Citrus limon

<400> SEQUENCE: 28

Met Ser Ser Cys Ile Asn Pro Ser Thr Leu Val Thr Ser Val Asn Ala
1               5                   10                  15

Phe Lys Cys Leu Pro Leu Ala Thr Asn Lys Ala Ala Ile Arg Ile Met
                20                  25                  30

Ala Lys Tyr Lys Pro Val Gln Cys Leu Ile Ser Ala Lys Tyr Asp Asn
            35                  40                  45

Leu Thr Val Asp Arg Arg Ser Ala Asn Tyr Gln Pro Ser Ile Trp Asp
        50                  55                  60

His Asp Phe Leu Gln Ser Leu Asn Ser Asn Tyr Thr Asp Glu Ala Tyr
65                  70                  75                  80

Lys Arg Arg Ala Glu Glu Leu Arg Gly Lys Val Lys Ile Ala Ile Lys
                85                  90                  95

Asp Val Ile Glu Pro Leu Asp Gln Leu Glu Leu Ile Asp Asn Leu Gln
            100                 105                 110

Arg Leu Gly Leu Ala His Arg Phe Glu Thr Glu Ile Arg Asn Ile Leu
        115                 120                 125

Asn Asn Ile Tyr Asn Asn Lys Asp Tyr Asn Trp Arg Lys Glu Asn
130                 135                 140

Leu Tyr Ala Thr Ser Leu Glu Phe Arg Leu Leu Arg Gln His Gly Tyr
145                 150                 155                 160

Pro Val Ser Gln Glu Val Phe Asn Gly Phe Lys Asp Asp Gln Gly Gly
                165                 170                 175

Phe Ile Cys Asp Asp Phe Lys Gly Ile Leu Ser Leu His Glu Ala Ser
            180                 185                 190

Tyr Tyr Ser Leu Glu Gly Glu Ser Ile Met Glu Glu Ala Trp Gln Phe
        195                 200                 205

Thr Ser Lys His Leu Lys Glu Val Met Ile Ser Lys Asn Met Glu Glu
    210                 215                 220

Asp Val Phe Val Ala Glu Gln Ala Lys Arg Ala Leu Glu Leu Pro Leu
225                 230                 235                 240

His Trp Lys Val Pro Met Leu Glu Ala Arg Trp Phe Ile His Ile Tyr
                245                 250                 255

Glu Arg Arg Glu Asp Lys Asn His Leu Leu Glu Leu Ala Lys Met
            260                 265                 270

Glu Phe Asn Thr Leu Gln Ala Ile Tyr Gln Glu Glu Leu Lys Glu Ile
        275                 280                 285

Ser Gly Trp Trp Lys Asp Thr Gly Leu Gly Glu Lys Leu Ser Phe Ala
    290                 295                 300

Arg Asn Arg Leu Val Ala Ser Phe Leu Trp Ser Met Gly Ile Ala Phe
305                 310                 315                 320
```

-continued

```
Glu Pro Gln Phe Ala Tyr Cys Arg Arg Val Leu Thr Ile Ser Ile Ala
                325                 330                 335

Leu Ile Thr Val Ile Asp Asp Ile Tyr Asp Val Tyr Gly Thr Leu Asp
            340                 345                 350

Glu Leu Glu Ile Phe Thr Asp Ala Val Glu Arg Trp Asp Ile Asn Tyr
        355                 360                 365

Ala Leu Lys His Leu Pro Gly Tyr Met Lys Met Cys Phe Leu Ala Leu
    370                 375                 380

Tyr Asn Phe Val Asn Glu Phe Ala Tyr Tyr Val Leu Lys Gln Gln Asp
385                 390                 395                 400

Phe Asp Leu Leu Leu Ser Ile Lys Asn Ala Trp Leu Gly Leu Ile Gln
                405                 410                 415

Ala Tyr Leu Val Glu Ala Lys Trp Tyr His Ser Lys Tyr Thr Pro Lys
            420                 425                 430

Leu Glu Glu Tyr Leu Glu Asn Gly Leu Val Ser Ile Thr Gly Pro Leu
        435                 440                 445

Ile Ile Thr Ile Ser Tyr Leu Ser Gly Thr Asn Pro Ile Ile Lys Lys
    450                 455                 460

Glu Leu Glu Phe Leu Glu Ser Asn Pro Asp Ile Val His Trp Ser Ser
465                 470                 475                 480

Lys Ile Phe Arg Leu Gln Asp Asp Leu Gly Thr Ser Ser Asp Glu Ile
                485                 490                 495

Gln Arg Gly Asp Val Pro Lys Ser Ile Gln Cys Tyr Met His Glu Thr
            500                 505                 510

Gly Ala Ser Glu Glu Val Ala Arg Gln His Ile Lys Asp Met Met Arg
        515                 520                 525

Gln Met Trp Lys Lys Val Asn Ala Tyr Thr Ala Asp Lys Asp Ser Pro
    530                 535                 540

Leu Thr Gly Thr Thr Thr Glu Phe Leu Leu Asn Leu Val Arg Met Ser
545                 550                 555                 560

His Phe Met Tyr Leu His Gly Asp Gly His Gly Val Gln Asn Gln Glu
                565                 570                 575

Thr Ile Asp Val Gly Phe Thr Leu Leu Phe Gln Pro Ile Pro Leu Glu
            580                 585                 590

Asp Lys His Met Ala Phe Thr Ala Ser Pro Gly Thr Lys Gly
        595                 600                 605

<210> SEQ ID NO 29
<211> LENGTH: 584
<212> TYPE: PRT
<213> ORGANISM: Ricinus communis

<400> SEQUENCE: 29

Met Glu Ile Val Phe Ser Ser Ser Leu Ser Ser Thr Leu Thr Val Thr
1               5                   10                  15

Lys Ile Leu Arg Ser Pro Arg His Ala Thr Thr Gly Asn Met Gln Asp
            20                  25                  30

Tyr Ser Arg Phe Pro Leu Phe Phe Thr Ile Ala Ser Arg Ser Asn Ala
        35                  40                  45

Ser Gln Ala Lys His Arg Arg Ser Ala Asn Tyr His Pro Thr Ile Trp
    50                  55                  60

Asp Pro Lys Ala Ile Glu Cys Leu Arg Thr Pro Tyr Thr Tyr Asp Gly
65                  70                  75                  80

Val His Gly Ala Arg Leu Gln Lys Leu Lys Asp Glu Val Arg Ser Leu
                85                  90                  95
```

Leu Thr Thr Phe Thr Lys Glu Pro Cys Gly Gln Leu Lys Leu Ile Asp
            100                 105                 110

Ser Met Gln Arg Leu Gly Val Ser Tyr His Phe Arg Glu Ile Glu
        115                 120                 125

Glu Ile Leu Asn Leu Val Glu Leu Asp Ser Asp Ser Asp Leu Tyr Thr
    130                 135                 140

Thr Ala Leu His Phe Arg Leu Leu Arg Gln His Gly Phe Thr Ile Ser
145                 150                 155                 160

Lys Glu Val Phe Glu Lys Phe Arg Asn Glu Asp Gly Lys Phe Lys Asp
                165                 170                 175

Ser Leu Lys Glu Asp Ile Leu Gly Leu Ser Leu Tyr Asp Ala Ser
            180                 185                 190

Tyr Leu Gly Met His Gly Glu His Ile Leu Glu Ala Lys Asp Phe
        195                 200                 205

Ser Thr Glu Gln Leu Lys Ser Leu Leu Gly Arg Ser Gln Gly Asp Ile
    210                 215                 220

Val Thr Tyr Gln Val Lys Gln Ala Leu Asp Val Pro Leu His Trp Arg
225                 230                 235                 240

Met Gln Arg Ile Glu Asn Arg Asn Tyr Ile Asn Ile Tyr Gln Lys Glu
                245                 250                 255

Asp Thr Asn Asn Leu Ala Leu Leu Glu Leu Ala Lys Leu Asp Tyr Asn
            260                 265                 270

Leu Val Gln Ser Val Tyr Gln Ile Glu Leu Lys Glu Leu Ala Arg Trp
        275                 280                 285

Trp Ile Ala Leu Gly Phe Arg Glu Lys Leu His Phe Ser Arg Asp Arg
    290                 295                 300

Leu Met Glu Asn Tyr Leu Trp Ser Met Gly Met Ile Phe Glu Pro His
305                 310                 315                 320

Phe Ser Lys Cys Arg Ile Tyr Leu Thr Lys Phe Ile Cys Ile Leu Ser
                325                 330                 335

Ser Ile Asp Asp Met Tyr Asp Ile Tyr Gly Ser Leu Asp Glu Leu Glu
            340                 345                 350

Leu Phe Thr Ser Ala Leu Lys Arg Trp Asp Pro Met Ala Leu Glu Glu
        355                 360                 365

Leu Pro Asp Tyr Met Lys Ile Cys Tyr Leu Ala Ile Leu Asn Phe Ala
    370                 375                 380

Ser Glu Leu Val Tyr Asp Val Leu Lys Glu Glu Gly Leu Tyr Thr Leu
385                 390                 395                 400

Pro Phe Ile Arg Asp Glu Trp Val Lys Leu Cys Gln Ala Tyr Leu Val
                405                 410                 415

Glu Ala Arg Trp Phe Asn Ser Gly Tyr Thr Pro Thr Phe Asp Glu Tyr
            420                 425                 430

Leu Glu Asn Ala Trp Ile Ser Val Gly Gly His Glu Ala Ile Val His
        435                 440                 445

Ala Cys Ala Leu Leu Gly His Thr Ser Thr Glu Asp Phe Gln Asn Phe
    450                 455                 460

Leu Lys His Gly Phe Glu Leu Ile Tyr Trp Ser Ser Leu Leu Val Arg
465                 470                 475                 480

Leu Asn Asp Asp Leu Gly Thr Ser Gln Ala Glu Ile Lys Arg Gly Asp
                485                 490                 495

Val Val Lys Ser Ile Gln Cys Tyr Met Ile Glu Lys Gly Val Ser Glu
            500                 505                 510

```
Lys Glu Ala Lys Asp His Val Lys Gly Leu Ile Ser His Ala Trp Lys
            515                 520                 525

Val Leu Asn Glu Glu Ser Val Lys Cys Ser Leu Ser Arg Ser Phe Val
        530                 535                 540

Asn Val Cys Leu Asn Met Thr Arg Thr Ala Gln Cys Ile Phe Gln Tyr
545                 550                 555                 560

Gly Asp Gly Ile Gly Thr Ser Ile Gly Val Thr Lys Asp Arg Leu Glu
                565                 570                 575

Phe Leu Ile Val Lys Pro Ile Leu
                580

<210> SEQ ID NO 30
<211> LENGTH: 599
<212> TYPE: PRT
<213> ORGANISM: Mentha x piperita

<400> SEQUENCE: 30

Met Ala Leu Lys Val Phe Ser Gly Ala Met Gln Met Pro Ile Pro Ser
1               5                   10                  15

Lys Leu Thr Thr Tyr Leu Gln Pro Ser His Leu Asn Ser Ser Pro Lys
            20                  25                  30

Leu Leu Ser Asn Thr Lys Gly Thr Ser Arg Ser Arg Leu Arg Val Ser
        35                  40                  45

Cys Ser Ser Ser Gln Leu Thr Thr Glu Arg Arg Ser Gly Asn Tyr Asn
50                  55                  60

Pro Ser Arg Trp Asp Val Asp Phe Ile Gln Thr Leu His Ser Asp Tyr
65                  70                  75                  80

Lys Asp Glu Lys His Ala Arg Arg Ala Ser Glu Leu Val Thr Leu Val
                85                  90                  95

Lys Met Glu Leu Glu Lys Glu Thr Asp Gln Ile Arg Gln Leu Glu Leu
            100                 105                 110

Ile Asp Asp Leu Gln Arg Met Gly Leu Ser Asp His Phe Gln Asn Glu
        115                 120                 125

Phe Lys Glu Ile Leu Ser Ser Val Tyr Leu Asp His Gly Tyr Tyr Lys
130                 135                 140

Asn Pro Asp Pro Lys Glu Glu Arg Asp Leu Tyr Ser Thr Ser Leu Ala
145                 150                 155                 160

Phe Arg Leu Leu Arg Glu His Gly Phe Gln Val Ala Gln Glu Val Phe
                165                 170                 175

Asp Ser Phe Lys Asn Glu Glu Gly Glu Phe Lys Glu Ser Leu Ser Asp
            180                 185                 190

Asp Thr Arg Gly Leu Leu Gln Leu Tyr Glu Ala Ser Phe Leu Leu Thr
        195                 200                 205

Glu Gly Glu Thr Thr Leu Glu Ser Ala Arg Glu Phe Ala Thr Lys Phe
210                 215                 220

Leu Glu Glu Arg Val Asn Glu Gly Gly Asp Glu Asn Leu Leu Thr
225                 230                 235                 240

Arg Ile Ala Tyr Ser Leu Glu Ile Pro Leu His Trp Arg Ile Lys Arg
                245                 250                 255

Pro Asn Ala Pro Val Trp Ile Asp Ser Tyr Arg Lys Arg Pro Asn Met
            260                 265                 270

Asn Pro Val Val Leu Asp Leu Ala Ile Leu Asp Leu Asn Ile Val Gln
        275                 280                 285

Ala His Phe Gln Gln Glu Leu Lys Glu Ser Phe Arg Trp Trp Arg Asn
290                 295                 300
```

Thr Gly Phe Val Glu Lys Leu Pro Phe Ala Arg Asp Arg Leu Val Glu
305                 310                 315                 320

Cys Tyr Phe Trp Asn Thr Gly Ile Ile Glu Pro Arg Gln His Ala Ser
                325                 330                 335

Ala Arg Ile Met Met Gly Lys Val Asn Ala Leu Ile Thr Val Ile Asp
                340                 345                 350

Asp Ile Tyr Asp Val Tyr Gly Thr Leu Glu Glu Leu His Phe Thr
            355                 360                 365

Asp Leu Ile Arg Arg Trp Asp Ile Asp Ser Ile Asp Gln Leu Pro Asp
            370                 375                 380

Tyr Met Gln Leu Cys Phe Leu Ala Leu Asn Asn Phe Val Asp Glu Thr
385                 390                 395                 400

Ser Tyr Asp Val Met Lys Glu Lys Gly Val Asn Val Ile Pro Tyr Leu
                405                 410                 415

Arg Gln Ser Trp Val Asp Leu Ala Asp Lys Tyr Met Val Glu Ala Arg
                420                 425                 430

Trp Phe Tyr Gly Gly His Lys Pro Ser Leu Glu Glu Tyr Leu Glu Asn
            435                 440                 445

Ser Trp Met Ser Ile Ser Gly Pro Cys Met Leu Thr His Ile Phe Phe
450                 455                 460

Arg Val Thr Asp Ser Phe Thr Lys Glu Thr Val Asp Ser Leu Tyr Lys
465                 470                 475                 480

Tyr His Asp Leu Val Arg Trp Ser Ser Phe Val Leu Arg Leu Ala Asp
                485                 490                 495

Asp Leu Gly Thr Ser Val Glu Glu Val Ser Arg Gly Asp Val Pro Lys
                500                 505                 510

Ser Leu Gln Cys Tyr Met Ser Asp Tyr Asn Ala Ser Glu Ala Glu Ala
            515                 520                 525

Arg Lys His Val Lys Trp Leu Ile Ala Glu Val Trp Lys Lys Met Asn
            530                 535                 540

Ala Glu Arg Val Ser Lys Asp Ser Pro Phe Gly Lys Asp Phe Ile Gly
545                 550                 555                 560

Cys Ala Val Asp Leu Gly Arg Met Ala Gln Leu Met Tyr His Asn Gly
                565                 570                 575

Asp Gly His Gly Thr Gln His Pro Ile Ile His Gln Gln Met Thr Ala
            580                 585                 590

Thr Leu Phe Glu Pro Phe Ala
        595

<210> SEQ ID NO 31
<211> LENGTH: 548
<212> TYPE: PRT
<213> ORGANISM: Mentha x piperita

<400> SEQUENCE: 31

Met Gln Leu Thr Thr Glu Arg Arg Ser Gly Asn Tyr Asn Pro Ser Arg
1               5                   10                  15

Trp Asp Val Asp Phe Ile Gln Thr Leu His Ser Asp Tyr Lys Asp Glu
                20                  25                  30

Lys His Ala Arg Arg Ala Ser Glu Leu Val Thr Leu Val Lys Met Glu
            35                  40                  45

Leu Glu Lys Glu Thr Asp Gln Ile Arg Gln Leu Glu Leu Ile Asp Asp
        50                  55                  60

Leu Gln Arg Met Gly Leu Ser Asp His Phe Gln Asn Glu Phe Lys Glu

```
                65                  70                  75                  80
Ile Leu Ser Ser Val Tyr Leu Asp His Gly Tyr Tyr Lys Asn Pro Asp
                    85                  90                  95

Pro Lys Glu Glu Arg Asp Leu Tyr Ser Thr Ser Leu Ala Phe Arg Leu
                100                 105                 110

Leu Arg Glu His Gly Phe Gln Val Ala Gln Val Phe Asp Ser Phe
            115                 120                 125

Lys Asn Glu Glu Gly Glu Phe Lys Glu Ser Leu Ser Asp Asp Thr Arg
            130                 135                 140

Gly Leu Leu Gln Leu Tyr Glu Ala Ser Phe Leu Leu Thr Glu Gly Glu
145                 150                 155                 160

Thr Thr Leu Glu Ser Ala Arg Glu Phe Ala Thr Lys Phe Leu Glu Glu
                165                 170                 175

Arg Val Asn Glu Gly Gly Gly Asp Glu Asn Leu Leu Thr Arg Ile Ala
                180                 185                 190

Tyr Ser Leu Glu Ile Pro Leu His Trp Arg Ile Lys Arg Pro Asn Ala
            195                 200                 205

Pro Val Trp Ile Asp Ser Tyr Arg Lys Arg Pro Asn Met Asn Pro Val
            210                 215                 220

Val Leu Asp Leu Ala Ile Leu Asp Leu Asn Ile Val Gln Ala His Phe
225                 230                 235                 240

Gln Gln Glu Leu Lys Glu Ser Phe Arg Trp Trp Arg Asn Thr Gly Phe
                245                 250                 255

Val Glu Lys Leu Pro Phe Ala Arg Asp Arg Leu Val Glu Cys Tyr Phe
                260                 265                 270

Trp Asn Thr Gly Ile Ile Glu Pro Arg Gln His Ala Ser Ala Arg Ile
            275                 280                 285

Met Met Gly Lys Val Asn Ala Leu Ile Thr Val Ile Asp Asp Ile Tyr
            290                 295                 300

Asp Val Tyr Gly Thr Leu Glu Glu Leu Glu His Phe Thr Asp Leu Ile
305                 310                 315                 320

Arg Arg Trp Asp Ile Asp Ser Ile Asp Gln Leu Pro Asp Tyr Met Gln
                325                 330                 335

Leu Cys Phe Leu Ala Leu Asn Asn Phe Val Asp Glu Thr Ser Tyr Asp
                340                 345                 350

Val Met Lys Glu Lys Gly Val Asn Val Ile Pro Tyr Leu Arg Gln Ser
            355                 360                 365

Trp Val Asp Leu Ala Asp Lys Tyr Met Val Glu Ala Arg Trp Phe Tyr
            370                 375                 380

Gly Gly His Lys Pro Ser Leu Glu Glu Tyr Leu Glu Asn Ser Trp Met
385                 390                 395                 400

Ser Ile Ser Gly Pro Cys Met Leu Thr His Ile Phe Phe Arg Val Thr
                405                 410                 415

Asp Ser Phe Thr Lys Glu Thr Val Asp Ser Leu Tyr Lys Tyr His Asp
                420                 425                 430

Leu Val Arg Trp Ser Ser Phe Val Leu Arg Leu Ala Asp Asp Leu Gly
            435                 440                 445

Thr Ser Val Glu Glu Val Ser Arg Gly Asp Val Pro Lys Ser Leu Gln
            450                 455                 460

Cys Tyr Met Ser Asp Tyr Asn Ala Ser Glu Ala Glu Ala Arg Lys His
465                 470                 475                 480

Val Lys Trp Leu Ile Ala Glu Val Trp Lys Lys Met Asn Ala Glu Arg
                485                 490                 495
```

```
Val Ser Lys Asp Ser Pro Phe Gly Lys Asp Phe Ile Gly Cys Ala Val
        500                 505                 510

Asp Leu Gly Arg Met Ala Gln Leu Met Tyr His Asn Gly Asp Gly His
        515                 520                 525

Gly Thr Gln His Pro Ile Ile His Gln Gln Met Thr Ala Thr Leu Phe
530                 535                 540

Glu Pro Phe Ala
545

<210> SEQ ID NO 32
<211> LENGTH: 57
<212> TYPE: PRT
<213> ORGANISM: Pisum sativum

<400> SEQUENCE: 32

Met Ala Ser Met Ile Ser Ser Ala Val Thr Thr Val Ser Arg Ala
1               5                   10                  15

Ser Thr Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys
    50                  55

<210> SEQ ID NO 33
<211> LENGTH: 607
<212> TYPE: PRT
<213> ORGANISM: Artificial Sequence
<220> FEATURE:
<223> OTHER INFORMATION: Pisum sativum RuBisCO small subunit transit
      peptide/limonene synthase fusion protein

<400> SEQUENCE: 33

Met Ala Ser Met Ile Ser Ser Ala Val Thr Thr Val Ser Arg Ala
1               5                   10                  15

Ser Thr Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Asp Pro Gln Leu Thr Thr
    50                  55                  60

Glu Arg Arg Ser Gly Asn Tyr Asn Pro Ser Arg Trp Asp Val Asp Phe
65                  70                  75                  80

Ile Gln Thr Leu His Ser Asp Tyr Lys Asp Glu Lys His Ala Arg Arg
                85                  90                  95

Ala Ser Glu Leu Val Thr Leu Val Lys Met Glu Leu Glu Lys Glu Thr
            100                 105                 110

Asp Gln Ile Arg Gln Leu Glu Leu Ile Asp Asp Leu Gln Arg Met Gly
        115                 120                 125

Leu Ser Asp His Phe Gln Asn Glu Phe Lys Glu Ile Leu Ser Ser Val
130                 135                 140

Tyr Leu Asp His Gly Tyr Tyr Lys Asn Pro Asp Pro Lys Glu Glu Arg
145                 150                 155                 160

Asp Leu Tyr Ser Thr Ser Leu Ala Phe Arg Leu Leu Arg Glu His Gly
                165                 170                 175

Phe Gln Val Ala Gln Glu Val Phe Asp Ser Phe Lys Asn Glu Glu Gly
            180                 185                 190
```

```
Glu Phe Lys Glu Ser Leu Ser Asp Asp Thr Arg Gly Leu Leu Gln Leu
            195                 200                 205

Tyr Glu Ala Ser Phe Leu Leu Thr Glu Gly Glu Thr Thr Leu Glu Ser
    210                 215                 220

Ala Arg Glu Phe Ala Thr Lys Phe Leu Glu Glu Arg Val Asn Glu Gly
225                 230                 235                 240

Gly Gly Asp Glu Asn Leu Leu Thr Arg Ile Ala Tyr Ser Leu Glu Ile
                245                 250                 255

Pro Leu His Trp Arg Ile Lys Arg Pro Asn Ala Pro Val Trp Ile Asp
            260                 265                 270

Ser Tyr Arg Lys Arg Pro Asn Met Asn Pro Val Val Leu Asp Leu Ala
    275                 280                 285

Ile Leu Asp Leu Asn Ile Val Gln Ala His Phe Gln Gln Glu Leu Lys
290                 295                 300

Glu Ser Phe Arg Trp Trp Arg Asn Thr Gly Phe Val Glu Lys Leu Pro
305                 310                 315                 320

Phe Ala Arg Asp Arg Leu Val Glu Cys Tyr Phe Trp Asn Thr Gly Ile
                325                 330                 335

Ile Glu Pro Arg Gln His Ala Ser Ala Arg Ile Met Met Gly Lys Val
            340                 345                 350

Asn Ala Leu Ile Thr Val Ile Asp Asp Ile Tyr Asp Val Tyr Gly Thr
    355                 360                 365

Leu Glu Glu Leu Glu His Phe Thr Asp Leu Ile Arg Arg Trp Asp Ile
370                 375                 380

Asp Ser Ile Asp Gln Leu Pro Asp Tyr Met Gln Leu Cys Phe Leu Ala
385                 390                 395                 400

Leu Asn Asn Phe Val Asp Glu Thr Ser Tyr Asp Val Met Lys Glu Lys
                405                 410                 415

Gly Val Asn Val Ile Pro Tyr Leu Arg Gln Ser Trp Val Asp Leu Ala
            420                 425                 430

Asp Lys Tyr Met Val Glu Ala Arg Trp Phe Tyr Gly His Lys Pro
    435                 440                 445

Ser Leu Glu Glu Tyr Leu Glu Asn Ser Trp Met Ser Ile Ser Gly Pro
    450                 455                 460

Cys Met Leu Thr His Ile Phe Phe Arg Val Thr Asp Ser Phe Thr Lys
465                 470                 475                 480

Glu Thr Val Asp Ser Leu Tyr Lys Tyr His Asp Leu Val Arg Trp Ser
                485                 490                 495

Ser Phe Val Leu Arg Leu Ala Asp Asp Leu Gly Thr Ser Val Glu Glu
            500                 505                 510

Val Ser Arg Gly Asp Val Pro Lys Ser Leu Gln Cys Tyr Met Ser Asp
    515                 520                 525

Tyr Asn Ala Ser Glu Ala Glu Arg Lys His Val Lys Trp Leu Ile
530                 535                 540

Ala Glu Val Trp Lys Lys Met Asn Ala Glu Arg Val Ser Lys Asp Ser
545                 550                 555                 560

Pro Phe Gly Lys Asp Phe Ile Gly Cys Ala Val Asp Leu Gly Arg Met
                565                 570                 575

Ala Gln Leu Met Tyr His Asn Gly Asp Gly His Gly Thr Gln His Pro
            580                 585                 590

Ile Ile His Gln Gln Met Thr Ala Thr Leu Phe Glu Pro Phe Ala
    595                 600                 605
```

<210> SEQ ID NO 34
<211> LENGTH: 10
<212> TYPE: PRT
<213> ORGANISM: Artificial Sequence
<220> FEATURE:
<223> OTHER INFORMATION: synthesized amino acid linker

<400> SEQUENCE: 34

```
Ser Ser Asn Asn Leu Gly Ile Glu Gly Arg
1               5                   10
```

<210> SEQ ID NO 35
<211> LENGTH: 629
<212> TYPE: PRT
<213> ORGANISM: Artificial Sequence
<220> FEATURE:
<223> OTHER INFORMATION: Pisum sativum RuBisCO small subunit transit
      peptide/geranyl diphosphate synthase small subunit/geranyl
      diphosphate large subunit fusion protein

<400> SEQUENCE: 35

```
Met Ala Ser Met Ile Ser Ser Ala Val Thr Thr Val Ser Arg Ala
1               5                   10                  15

Ser Thr Val Gln Ser Ala Ala Val Ala Pro Phe Gly Gly Leu Lys Ser
                20                  25                  30

Met Thr Gly Phe Pro Val Lys Lys Val Asn Thr Asp Ile Thr Ser Ile
            35                  40                  45

Thr Ser Asn Gly Gly Arg Val Lys Cys Met Asp Pro Gln Pro Tyr Trp
        50                  55                  60

Ala Ala Ile Glu Ala Asp Ile Glu Arg Tyr Leu Lys Lys Ser Ile Thr
65                  70                  75                  80

Ile Arg Pro Pro Glu Thr Val Phe Gly Pro Met His His Leu Thr Phe
                85                  90                  95

Ala Ala Pro Ala Thr Ala Ala Ser Thr Leu Cys Leu Ala Ala Cys Glu
                100                 105                 110

Leu Val Gly Gly Asp Arg Ser Gln Ala Met Ala Ala Ala Ala Ala Ile
            115                 120                 125

His Leu Val His Ala Ala Tyr Val His Glu His Leu Pro Leu Thr
        130                 135                 140

Asp Gly Ser Arg Pro Val Ser Lys Pro Ala Ile Gln His Lys Tyr Gly
145                 150                 155                 160

Pro Asn Val Glu Leu Leu Thr Gly Asp Gly Ile Val Pro Phe Gly Phe
                165                 170                 175

Glu Leu Leu Ala Gly Ser Val Asp Pro Ala Arg Thr Asp Asp Pro Asp
            180                 185                 190

Arg Ile Leu Arg Val Ile Ile Glu Ile Ser Arg Ala Gly Gly Pro Glu
        195                 200                 205

Gly Met Ile Ser Gly Leu His Arg Glu Glu Glu Ile Val Asp Gly Asn
    210                 215                 220

Thr Ser Leu Asp Phe Ile Glu Tyr Val Cys Lys Lys Lys Tyr Gly Glu
225                 230                 235                 240

Met His Ala Cys Gly Ala Ala Cys Gly Ala Ile Leu Gly Gly Ala Ala
                245                 250                 255

Glu Glu Glu Ile Gln Lys Leu Arg Asn Phe Gly Leu Tyr Gln Gly Thr
            260                 265                 270

Leu Arg Gly Met Met Glu Met Lys Asn Ser His Gln Leu Ile Asp Glu
        275                 280                 285
```

```
Asn Ile Ile Gly Lys Leu Lys Glu Leu Ala Leu Glu Glu Leu Gly Gly
        290                 295                 300

Phe His Gly Lys Asn Ala Glu Leu Met Ser Ser Leu Val Ala Glu Pro
305                 310                 315                 320

Ser Leu Tyr Ala Ala Ser Ser Asn Asn Leu Gly Ile Glu Gly Arg Phe
            325                 330                 335

Asp Phe Asp Gly Tyr Met Leu Arg Lys Ala Thr Ser Val Asn Thr Ala
            340                 345                 350

Leu Glu Ala Ala Val Glu Met Lys Glu Pro Leu Lys Ile His Glu Ser
        355                 360                 365

Met Arg Tyr Ser Leu Leu Ala Gly Gly Lys Arg Val Arg Pro Ile Leu
370                 375                 380

Cys Ile Ala Ala Cys Glu Leu Val Gly Gly Asp Glu Thr Thr Ala Met
385                 390                 395                 400

Pro Ala Ala Cys Ala Val Glu Met Ile His Thr Met Ser Leu Met His
                405                 410                 415

Asp Asp Leu Pro Cys Met Asp Asn Asp Asp Leu Arg Arg Gly Lys Pro
            420                 425                 430

Thr Asn His Lys Val Phe Gly Glu Ser Thr Ala Val Leu Ala Gly Asp
        435                 440                 445

Ala Leu Leu Ser Phe Ala Phe Glu His Val Ala Thr Thr Arg Gly
        450                 455                 460

Ala Pro Thr Glu Arg Ile Val Arg Val Leu Gly Glu Leu Ala Val Ser
465                 470                 475                 480

Ile Gly Ser Glu Gly Leu Val Ala Gly Gln Val Val Asp Ile Cys Ser
                485                 490                 495

Glu Gly Met Ala Glu Val Gly Leu Glu His Leu Glu Tyr Ile His His
            500                 505                 510

His Lys Thr Ala Ala Leu Leu Gln Gly Ser Val Val Leu Gly Ala Ile
        515                 520                 525

Leu Gly Gly Gly Gly Glu Glu Val Ala Arg Leu Arg Lys Phe Ala
        530                 535                 540

Asn Cys Ile Gly Leu Leu Phe Gln Val Val Asp Asp Ile Leu Asp Val
545                 550                 555                 560

Thr Lys Ser Ser Lys Glu Leu Gly Lys Thr Ala Gly Lys Asp Leu Val
                565                 570                 575

Ala Asp Lys Thr Thr Tyr Pro Lys Leu Ile Gly Val Glu Lys Ser Lys
            580                 585                 590

Glu Phe Ala Asp Arg Leu Lys Arg Glu Ala Val Glu Gln Leu Leu His
        595                 600                 605

Phe His Pro His Arg Ala Ala Pro Leu Ile Ala Leu Ala Asn Tyr Ile
610                 615                 620

Ala Tyr Arg Asp Asn
625

<210> SEQ ID NO 36
<211> LENGTH: 9
<212> TYPE: PRT
<213> ORGANISM: Artificial Sequence
<220> FEATURE:
<223> OTHER INFORMATION: synthesized amino acid linker

<400> SEQUENCE: 36

Ser Gly Gly Ser Gly Gly Ser Gly Gly
1               5
```

<210> SEQ ID NO 37
<211> LENGTH: 1186
<212> TYPE: PRT
<213> ORGANISM: Artificial Sequence
<220> FEATURE:
<223> OTHER INFORMATION: Pisum sativum RuBisCO small subunit transit peptide/limonene synthase/geranyl diphosphate synthase small subunit/geranyl disphosphate synthase large subunit fusion protein

<400> SEQUENCE: 37

```
Met Ala Ser Met Ile Ser Ser Ala Val Thr Thr Val Ser Arg Ala
1               5                   10                  15

Ser Thr Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Asp Pro Gln Leu Thr Thr
    50                  55                  60

Glu Arg Arg Ser Gly Asn Tyr Asn Pro Ser Arg Trp Asp Val Asp Phe
65                  70                  75                  80

Ile Gln Thr Leu His Ser Asp Tyr Lys Asp Glu Lys His Ala Arg Arg
                85                  90                  95

Ala Ser Glu Leu Val Thr Leu Val Lys Met Glu Leu Glu Lys Glu Thr
            100                 105                 110

Asp Gln Ile Arg Gln Leu Glu Leu Ile Asp Asp Leu Gln Arg Met Gly
        115                 120                 125

Leu Ser Asp His Phe Gln Asn Glu Phe Lys Glu Ile Leu Ser Ser Val
    130                 135                 140

Tyr Leu Asp His Gly Tyr Tyr Lys Asn Pro Asp Pro Lys Glu Glu Arg
145                 150                 155                 160

Asp Leu Tyr Ser Thr Ser Leu Ala Phe Arg Leu Leu Arg Glu His Gly
                165                 170                 175

Phe Gln Val Ala Gln Glu Val Phe Asp Ser Phe Lys Asn Glu Glu Gly
            180                 185                 190

Glu Phe Lys Glu Ser Leu Ser Asp Asp Thr Arg Gly Leu Leu Gln Leu
        195                 200                 205

Tyr Glu Ala Ser Phe Leu Leu Thr Glu Gly Glu Thr Thr Leu Glu Ser
    210                 215                 220

Ala Arg Glu Phe Ala Thr Lys Phe Leu Glu Glu Arg Val Asn Glu Gly
225                 230                 235                 240

Gly Gly Asp Glu Asn Leu Leu Thr Arg Ile Ala Tyr Ser Leu Glu Ile
                245                 250                 255

Pro Leu His Trp Arg Ile Lys Arg Pro Asn Ala Pro Val Trp Ile Asp
            260                 265                 270

Ser Tyr Arg Lys Arg Pro Asn Met Asn Pro Val Val Leu Asp Leu Ala
        275                 280                 285

Ile Leu Asp Leu Asn Ile Val Gln Ala His Phe Gln Gln Glu Leu Lys
    290                 295                 300

Glu Ser Phe Arg Trp Trp Arg Asn Thr Gly Phe Val Glu Lys Leu Pro
305                 310                 315                 320

Phe Ala Arg Asp Arg Leu Val Glu Cys Tyr Phe Trp Asn Thr Gly Ile
                325                 330                 335

Ile Glu Pro Arg Gln His Ala Ser Ala Arg Ile Met Met Gly Lys Val
            340                 345                 350

Asn Ala Leu Ile Thr Val Ile Asp Asp Ile Tyr Asp Val Tyr Gly Thr
```

```
            355                 360                 365
Leu Glu Glu Leu Glu His Phe Thr Asp Leu Ile Arg Arg Trp Asp Ile
    370                 375                 380

Asp Ser Ile Asp Gln Leu Pro Asp Tyr Met Gln Leu Cys Phe Leu Ala
385                 390                 395                 400

Leu Asn Asn Phe Val Asp Glu Thr Ser Tyr Asp Val Met Lys Glu Lys
                405                 410                 415

Gly Val Asn Val Ile Pro Tyr Leu Arg Gln Ser Trp Val Asp Leu Ala
            420                 425                 430

Asp Lys Tyr Met Val Glu Ala Arg Trp Phe Tyr Gly Gly His Lys Pro
        435                 440                 445

Ser Leu Glu Glu Tyr Leu Glu Asn Ser Trp Met Ser Ile Ser Gly Pro
    450                 455                 460

Cys Met Leu Thr His Ile Phe Phe Arg Val Thr Asp Ser Phe Thr Lys
465                 470                 475                 480

Glu Thr Val Asp Ser Leu Tyr Lys Tyr His Asp Leu Val Arg Trp Ser
                485                 490                 495

Ser Phe Val Leu Arg Leu Ala Asp Asp Leu Gly Thr Ser Val Glu Glu
            500                 505                 510

Val Ser Arg Gly Asp Val Pro Lys Ser Leu Gln Cys Tyr Met Ser Asp
        515                 520                 525

Tyr Asn Ala Ser Glu Ala Glu Ala Arg Lys His Val Lys Trp Leu Ile
    530                 535                 540

Ala Glu Val Trp Lys Lys Met Asn Ala Glu Arg Val Ser Lys Asp Ser
545                 550                 555                 560

Pro Phe Gly Lys Asp Phe Ile Gly Cys Ala Val Asp Leu Gly Arg Met
                565                 570                 575

Ala Gln Leu Met Tyr His Asn Gly Asp Gly His Gly Thr Gln His Pro
            580                 585                 590

Ile Ile His Gln Gln Met Thr Ala Thr Leu Phe Glu Pro Phe Ala Ser
        595                 600                 605

Gly Gly Ser Gly Gly Ser Gly Gly Met Gln Pro Tyr Trp Ala Ala Ile
    610                 615                 620

Glu Ala Asp Ile Glu Arg Tyr Leu Lys Lys Ser Ile Thr Ile Arg Pro
625                 630                 635                 640

Pro Glu Thr Val Phe Gly Pro Met His His Leu Thr Phe Ala Ala Pro
                645                 650                 655

Ala Thr Ala Ala Ser Thr Leu Cys Leu Ala Ala Cys Glu Leu Val Gly
            660                 665                 670

Gly Asp Arg Ser Gln Ala Met Ala Ala Ala Ile His Leu Val
        675                 680                 685

His Ala Ala Tyr Val His Glu His Leu Pro Leu Thr Asp Gly Ser
    690                 695                 700

Arg Pro Val Ser Lys Pro Ala Ile Gln His Lys Tyr Gly Pro Asn Val
705                 710                 715                 720

Glu Leu Leu Thr Gly Asp Gly Ile Val Pro Phe Gly Phe Glu Leu Leu
                725                 730                 735

Ala Gly Ser Val Asp Pro Ala Arg Thr Asp Pro Arg Ile Leu
            740                 745                 750

Arg Val Ile Ile Glu Ile Ser Arg Ala Gly Pro Glu Gly Met Ile
        755                 760                 765

Ser Gly Leu His Arg Glu Glu Ile Val Asp Gly Asn Thr Ser Leu
    770                 775                 780
```

```
Asp Phe Ile Glu Tyr Val Cys Lys Lys Tyr Gly Glu Met His Ala
785                 790                 795                 800

Cys Gly Ala Ala Cys Gly Ala Ile Leu Gly Gly Ala Ala Glu Glu Glu
                805                 810                 815

Ile Gln Lys Leu Arg Asn Phe Gly Leu Tyr Gln Gly Thr Leu Arg Gly
        820                 825                 830

Met Met Glu Met Lys Asn Ser His Gln Leu Ile Asp Glu Asn Ile Ile
            835                 840                 845

Gly Lys Leu Lys Glu Leu Ala Leu Glu Glu Leu Gly Gly Phe His Gly
        850                 855                 860

Lys Asn Ala Glu Leu Met Ser Ser Leu Val Ala Glu Pro Ser Leu Tyr
865                 870                 875                 880

Ala Ala Ser Ser Asn Asn Leu Gly Ile Glu Gly Arg Phe Asp Phe Asp
                885                 890                 895

Gly Tyr Met Leu Arg Lys Ala Thr Ser Val Asn Thr Ala Leu Glu Ala
                900                 905                 910

Ala Val Glu Met Lys Glu Pro Leu Lys Ile His Glu Ser Met Arg Tyr
            915                 920                 925

Ser Leu Leu Ala Gly Gly Lys Arg Val Arg Pro Ile Leu Cys Ile Ala
            930                 935                 940

Ala Cys Glu Leu Val Gly Gly Asp Glu Thr Thr Ala Met Pro Ala Ala
945                 950                 955                 960

Cys Ala Val Glu Met Ile His Thr Met Ser Leu Met His Asp Asp Leu
                965                 970                 975

Pro Cys Met Asp Asn Asp Asp Leu Arg Arg Gly Lys Pro Thr Asn His
                980                 985                 990

Lys Val Phe Gly Glu Ser Thr Ala  Val Leu Ala Gly Asp  Ala Leu Leu
            995                 1000                1005

Ser Phe  Ala Phe Glu His Val  Ala Ala Thr Thr Arg  Gly Ala Pro
    1010                1015                1020

Thr Glu  Arg Ile Val Arg Val  Leu Gly Glu Leu Ala  Val Ser Ile
    1025                1030                1035

Gly Ser  Glu Gly Leu Val Ala  Gly Gln Val Val Asp  Ile Cys Ser
    1040                1045                1050

Glu Gly  Met Ala Glu Val Gly  Leu Glu His Leu Glu  Tyr Ile His
    1055                1060                1065

His His  Lys Thr Ala Ala Leu  Leu Gln Gly Ser Val  Val Leu Gly
    1070                1075                1080

Ala Ile  Leu Gly Gly Gly Glu  Glu Glu Val Ala  Arg Leu Arg
    1085                1090                1095

Lys Phe  Ala Asn Cys Ile Gly  Leu Leu Phe Gln Val  Val Asp Asp
    1100                1105                1110

Ile Leu  Asp Val Thr Lys Ser  Ser Lys Glu Leu Gly  Lys Thr Ala
    1115                1120                1125

Gly Lys  Asp Leu Val Ala Asp  Lys Thr Thr Tyr Pro  Lys Leu Ile
    1130                1135                1140

Gly Val  Glu Lys Ser Lys Glu  Phe Ala Asp Arg Leu  Lys Arg Glu
    1145                1150                1155

Ala Val  Glu Gln Leu Leu His  Phe His Pro His Arg  Ala Ala Pro
    1160                1165                1170

Leu Ile  Ala Leu Ala Asn Tyr  Ile Ala Tyr Arg Asp  Asn
    1175                1180                1185
```

<210> SEQ ID NO 38
<211> LENGTH: 1186
<212> TYPE: PRT
<213> ORGANISM: Artificial Sequence
<220> FEATURE:
<223> OTHER INFORMATION: Pisum sativum RuBisCO small subunit transit peptide/geranyl diphosphate synthase small subunit/geranyl disphosphate synthase large subunit/limonene synthase fusion protein

<400> SEQUENCE: 38

```
Met Ala Ser Met Ile Ser Ser Ala Val Thr Thr Val Ser Arg Ala
1               5                   10                  15

Ser Thr Val Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Asp Pro Gln Pro Tyr Trp
    50                  55                  60

Ala Ala Ile Glu Ala Asp Ile Glu Arg Tyr Leu Lys Lys Ser Ile Thr
65                  70                  75                  80

Ile Arg Pro Pro Glu Thr Val Phe Gly Pro Met His His Leu Thr Phe
                85                  90                  95

Ala Ala Pro Ala Thr Ala Ala Ser Thr Leu Cys Leu Ala Ala Cys Glu
            100                 105                 110

Leu Val Gly Gly Asp Arg Ser Gln Ala Met Ala Ala Ala Ala Ala Ile
        115                 120                 125

His Leu Val His Ala Ala Tyr Val His Glu His Leu Pro Leu Thr
    130                 135                 140

Asp Gly Ser Arg Pro Val Ser Lys Pro Ala Ile Gln His Lys Tyr Gly
145                 150                 155                 160

Pro Asn Val Glu Leu Leu Thr Gly Asp Gly Ile Val Pro Phe Gly Phe
                165                 170                 175

Glu Leu Leu Ala Gly Ser Val Asp Pro Ala Arg Thr Asp Asp Pro Asp
            180                 185                 190

Arg Ile Leu Arg Val Ile Glu Ile Ser Arg Ala Gly Gly Pro Glu
        195                 200                 205

Gly Met Ile Ser Gly Leu His Arg Glu Glu Glu Ile Val Asp Gly Asn
    210                 215                 220

Thr Ser Leu Asp Phe Ile Glu Tyr Val Cys Lys Lys Tyr Gly Glu
225                 230                 235                 240

Met His Ala Cys Gly Ala Ala Cys Gly Ala Ile Leu Gly Gly Ala Ala
                245                 250                 255

Glu Glu Glu Ile Gln Lys Leu Arg Asn Phe Gly Leu Tyr Gln Gly Thr
            260                 265                 270

Leu Arg Gly Met Met Glu Met Lys Asn Ser His Gln Leu Ile Asp Glu
        275                 280                 285

Asn Ile Ile Gly Lys Leu Lys Glu Leu Ala Leu Glu Glu Leu Gly Gly
    290                 295                 300

Phe His Gly Lys Asn Ala Glu Leu Met Ser Ser Leu Val Ala Glu Pro
305                 310                 315                 320

Ser Leu Tyr Ala Ala Ser Ser Asn Asn Leu Gly Ile Glu Gly Arg Phe
                325                 330                 335

Asp Phe Asp Gly Tyr Met Leu Arg Lys Ala Thr Ser Val Asn Thr Ala
            340                 345                 350
```

-continued

```
Leu Glu Ala Ala Val Glu Met Lys Glu Pro Leu Lys Ile His Glu Ser
        355                 360                 365

Met Arg Tyr Ser Leu Leu Ala Gly Gly Lys Arg Val Arg Pro Ile Leu
    370                 375                 380

Cys Ile Ala Ala Cys Glu Leu Val Gly Gly Asp Glu Thr Thr Ala Met
385                 390                 395                 400

Pro Ala Ala Cys Ala Val Glu Met Ile His Thr Met Ser Leu Met His
                405                 410                 415

Asp Asp Leu Pro Cys Met Asp Asn Asp Leu Arg Arg Gly Lys Pro
                420                 425                 430

Thr Asn His Lys Val Phe Gly Glu Ser Thr Ala Val Leu Ala Gly Asp
        435                 440                 445

Ala Leu Leu Ser Phe Ala Phe Glu His Val Ala Ala Thr Thr Arg Gly
    450                 455                 460

Ala Pro Thr Glu Arg Ile Val Arg Val Leu Gly Glu Leu Ala Val Ser
465                 470                 475                 480

Ile Gly Ser Glu Gly Leu Val Ala Gly Gln Val Val Asp Ile Cys Ser
                485                 490                 495

Glu Gly Met Ala Glu Val Gly Leu Glu His Leu Glu Tyr Ile His His
                500                 505                 510

His Lys Thr Ala Ala Leu Leu Gln Gly Ser Val Val Leu Gly Ala Ile
        515                 520                 525

Leu Gly Gly Gly Gly Glu Glu Val Ala Arg Leu Arg Lys Phe Ala
    530                 535                 540

Asn Cys Ile Gly Leu Leu Phe Gln Val Val Asp Asp Ile Leu Asp Val
545                 550                 555                 560

Thr Lys Ser Ser Lys Glu Leu Gly Lys Thr Ala Gly Lys Asp Leu Val
                565                 570                 575

Ala Asp Lys Thr Thr Tyr Pro Lys Leu Ile Gly Val Glu Lys Ser Lys
                580                 585                 590

Glu Phe Ala Asp Arg Leu Lys Arg Glu Ala Val Glu Gln Leu Leu His
        595                 600                 605

Phe His Pro His Arg Ala Ala Pro Leu Ile Ala Leu Ala Asn Tyr Ile
    610                 615                 620

Ala Tyr Arg Asp Asn Ser Gly Ser Gly Gly Ser Gly Gly Met Gln
625                 630                 635                 640

Leu Thr Thr Glu Arg Arg Ser Gly Asn Tyr Asn Pro Ser Arg Trp Asp
                645                 650                 655

Val Asp Phe Ile Gln Thr Leu Ser Asp Tyr Lys Asp Glu Lys His
                660                 665                 670

Ala Arg Arg Ala Ser Glu Leu Val Thr Leu Val Lys Met Glu Leu Glu
        675                 680                 685

Lys Glu Thr Asp Gln Ile Arg Gln Leu Glu Leu Ile Asp Asp Leu Gln
    690                 695                 700

Arg Met Gly Leu Ser Asp His Phe Gln Asn Glu Phe Lys Glu Ile Leu
705                 710                 715                 720

Ser Ser Val Tyr Leu Asp His Gly Tyr Tyr Lys Asn Pro Asp Pro Lys
                725                 730                 735

Glu Glu Arg Asp Leu Tyr Ser Thr Ser Leu Ala Phe Arg Leu Leu Arg
        740                 745                 750

Glu His Gly Phe Gln Val Ala Gln Glu Val Phe Asp Ser Phe Lys Asn
    755                 760                 765

Glu Glu Gly Glu Phe Lys Glu Ser Leu Ser Asp Asp Thr Arg Gly Leu
```

-continued

```
            770                 775                 780
Leu Gln Leu Tyr Glu Ala Ser Phe Leu Leu Thr Glu Gly Glu Thr Thr
785                 790                 795                 800

Leu Glu Ser Ala Arg Glu Phe Ala Thr Lys Phe Leu Glu Glu Arg Val
                805                 810                 815

Asn Glu Gly Gly Gly Asp Glu Asn Leu Leu Thr Arg Ile Ala Tyr Ser
                820                 825                 830

Leu Glu Ile Pro Leu His Trp Arg Ile Lys Arg Pro Asn Ala Pro Val
                835                 840                 845

Trp Ile Asp Ser Tyr Arg Lys Arg Pro Asn Met Asn Pro Val Val Leu
                850                 855                 860

Asp Leu Ala Ile Leu Asp Leu Asn Ile Val Gln Ala His Phe Gln Gln
865                 870                 875                 880

Glu Leu Lys Glu Ser Phe Arg Trp Trp Arg Asn Thr Gly Phe Val Glu
                885                 890                 895

Lys Leu Pro Phe Ala Arg Asp Arg Leu Val Glu Cys Tyr Phe Trp Asn
                900                 905                 910

Thr Gly Ile Ile Glu Pro Arg Gln His Ala Ser Ala Arg Ile Met Met
                915                 920                 925

Gly Lys Val Asn Ala Leu Ile Thr Val Ile Asp Asp Ile Tyr Asp Val
                930                 935                 940

Tyr Gly Thr Leu Glu Glu Leu Glu His Phe Thr Asp Leu Ile Arg Arg
945                 950                 955                 960

Trp Asp Ile Asp Ser Ile Asp Gln Leu Pro Asp Tyr Met Gln Leu Cys
                965                 970                 975

Phe Leu Ala Leu Asn Asn Phe Val Asp Glu Thr Ser Tyr Asp Val Met
                980                 985                 990

Lys Glu Lys Gly Val Asn Val Ile Pro Tyr Leu Arg Gln Ser Trp Val
                995                 1000                1005

Asp Leu Ala Asp Lys Tyr Met Val Glu Ala Arg Trp Phe Tyr Gly
                1010                1015                1020

Gly His Lys Pro Ser Leu Glu Glu Tyr Leu Glu Asn Ser Trp Met
                1025                1030                1035

Ser Ile Ser Gly Pro Cys Met Leu Thr His Ile Phe Phe Arg Val
                1040                1045                1050

Thr Asp Ser Phe Thr Lys Glu Thr Val Asp Ser Leu Tyr Lys Tyr
                1055                1060                1065

His Asp Leu Val Arg Trp Ser Ser Phe Val Leu Arg Leu Ala Asp
                1070                1075                1080

Asp Leu Gly Thr Ser Val Glu Glu Val Ser Arg Gly Asp Val Pro
                1085                1090                1095

Lys Ser Leu Gln Cys Tyr Met Ser Asp Tyr Asn Ala Ser Glu Ala
                1100                1105                1110

Glu Ala Arg Lys His Val Lys Trp Leu Ile Ala Glu Val Trp Lys
                1115                1120                1125

Lys Met Asn Ala Glu Arg Val Ser Lys Asp Ser Pro Phe Gly Lys
                1130                1135                1140

Asp Phe Ile Gly Cys Ala Val Asp Leu Gly Arg Met Ala Gln Leu
                1145                1150                1155

Met Tyr His Asn Gly Asp Gly His Gly Thr Gln His Pro Ile Ile
                1160                1165                1170

His Gln Gln Met Thr Ala Thr Leu Phe Glu Pro Phe Ala
                1175                1180                1185
```

<210> SEQ ID NO 39
<211> LENGTH: 35
<212> TYPE: DNA
<213> ORGANISM: Artificial Sequence
<220> FEATURE:
<223> OTHER INFORMATION: PCR primer

<400> SEQUENCE: 39
ggatcctttc atatgcagcc gtactgggcc gccat                         35

<210> SEQ ID NO 40
<211> LENGTH: 35
<212> TYPE: DNA
<213> ORGANISM: Artificial Sequence
<220> FEATURE:
<223> OTHER INFORMATION: PCR primer

<400> SEQUENCE: 40
ttgcggccgc tgaaggatcc gaatagctct aagcc                         35

<210> SEQ ID NO 41
<211> LENGTH: 39
<212> TYPE: DNA
<213> ORGANISM: Artificial Sequence
<220> FEATURE:
<223> OTHER INFORMATION: PCR primer

<400> SEQUENCE: 41
ggatcctttc atatgttcga tttcgacgga tacatgctc                     39

<210> SEQ ID NO 42
<211> LENGTH: 37
<212> TYPE: DNA
<213> ORGANISM: Artificial Sequence
<220> FEATURE:
<223> OTHER INFORMATION: PCR primer

<400> SEQUENCE: 42
ttgcggccgc gagaggagga agatggaatc aattgtc                       37

<210> SEQ ID NO 43
<211> LENGTH: 48
<212> TYPE: DNA
<213> ORGANISM: Artificial Sequence
<220> FEATURE:
<223> OTHER INFORMATION: PCR primer

<400> SEQUENCE: 43
ccggccctcg atgccgagat tgttggagct agccgcgtaa aggctcgg           48

<210> SEQ ID NO 44
<211> LENGTH: 54
<212> TYPE: DNA
<213> ORGANISM: Artificial Sequence
<220> FEATURE:
<223> OTHER INFORMATION: PCR primer

<400> SEQUENCE: 44
agctccaaca atctcggcat cgagggccgg ttcgatttcg acggatacat gctc    54

<210> SEQ ID NO 45
<211> LENGTH: 39
<212> TYPE: DNA
<213> ORGANISM: Artificial Sequence
<220> FEATURE:

```
<223> OTHER INFORMATION: PCR primer

<400> SEQUENCE: 45
ggatccaaac atcatagaaa gagagtggaa gaaaaggag                          39

<210> SEQ ID NO 46
<211> LENGTH: 36
<212> TYPE: DNA
<213> ORGANISM: Artificial Sequence
<220> FEATURE:
<223> OTHER INFORMATION: PCR primer

<400> SEQUENCE: 46
ttgcggccgc tcatgcaaag ggctcgaata aggttg                             36

<210> SEQ ID NO 47
<211> LENGTH: 39
<212> TYPE: DNA
<213> ORGANISM: Artificial Sequence
<220> FEATURE:
<223> OTHER INFORMATION: PCR primer

<400> SEQUENCE: 47
ggatcctttc atatgcaact cactaccgaa agacgatcc                          39

<210> SEQ ID NO 48
<211> LENGTH: 30
<212> TYPE: DNA
<213> ORGANISM: Artificial Sequence
<220> FEATURE:
<223> OTHER INFORMATION: PCR primer

<400> SEQUENCE: 48
ttccaaacac acgcgtaaac aactttagct                                    30

<210> SEQ ID NO 49
<211> LENGTH: 30
<212> TYPE: DNA
<213> ORGANISM: Artificial Sequence
<220> FEATURE:
<223> OTHER INFORMATION: PCR primer

<400> SEQUENCE: 49
aaagttgttt acgcgtgtgt ttggaaagct                                    30

<210> SEQ ID NO 50
<211> LENGTH: 38
<212> TYPE: DNA
<213> ORGANISM: Artificial Sequence
<220> FEATURE:
<223> OTHER INFORMATION: PCR primer

<400> SEQUENCE: 50
tttacgcgtt agtgtttatc tttcttgctt ttctgaac                           38

<210> SEQ ID NO 51
<211> LENGTH: 57
<212> TYPE: DNA
<213> ORGANISM: Artificial Sequence
<220> FEATURE:
<223> OTHER INFORMATION: PCR primer

<400> SEQUENCE: 51
gcggccgcag gatcctttgc tagccatatg ggttgaaggt gaagtttagg gttttgc      57
```

<210> SEQ ID NO 52
<211> LENGTH: 56
<212> TYPE: DNA
<213> ORGANISM: Artificial Sequence
<220> FEATURE:
<223> OTHER INFORMATION: PCR primer

<400> SEQUENCE: 52
catatggcta gcaaaggatc ctgcggccgc tgagtaattc tgatattaga gggagc    56

<210> SEQ ID NO 53
<211> LENGTH: 36
<212> TYPE: DNA
<213> ORGANISM: Artificial Sequence
<220> FEATURE:
<223> OTHER INFORMATION: PCR primer

<400> SEQUENCE: 53
tttacgcgtt tgctgaaaaa tgcctattgg ctgatg    36

<210> SEQ ID NO 54
<211> LENGTH: 38
<212> TYPE: DNA
<213> ORGANISM: Artificial Sequence
<220> FEATURE:
<223> OTHER INFORMATION: PCR primer

<400> SEQUENCE: 54
tttggcgcgc caagctttct tcatcggtga ttgattcc    38

<210> SEQ ID NO 55
<211> LENGTH: 60
<212> TYPE: DNA
<213> ORGANISM: Artificial Sequence
<220> FEATURE:
<223> OTHER INFORMATION: PCR primer

<400> SEQUENCE: 55
gcggccgcag gatcctttgc tagccatatg tcgtgtatgt ttttaatctt gtttgtattg    60

<210> SEQ ID NO 56
<211> LENGTH: 52
<212> TYPE: DNA
<213> ORGANISM: Artificial Sequence
<220> FEATURE:
<223> OTHER INFORMATION: PCR primer

<400> SEQUENCE: 56
catatggcta gcaaaggatc ctgcggccgc agccctttt gtatgtgcta cc    52

<210> SEQ ID NO 57
<211> LENGTH: 41
<212> TYPE: DNA
<213> ORGANISM: Artificial Sequence
<220> FEATURE:
<223> OTHER INFORMATION: PCR primer

<400> SEQUENCE: 57
tttggcgcgc caagtcatga agaacctgat aagacgtctt c    41

<210> SEQ ID NO 58
<211> LENGTH: 42
<212> TYPE: DNA
<213> ORGANISM: Artificial Sequence
<220> FEATURE:
<223> OTHER INFORMATION: PCR primer

<400> SEQUENCE: 58
ggatcctttc atatggcttc tatgatatcc tcttccgctg tg                42

<210> SEQ ID NO 59
<211> LENGTH: 42
<212> TYPE: DNA
<213> ORGANISM: Artificial Sequence
<220> FEATURE:
<223> OTHER INFORMATION: PCR primer

<400> SEQUENCE: 59
tttctcgagt tagtaggatt ctggtgtgtg tgcaatgaaa ct                42

<210> SEQ ID NO 60
<211> LENGTH: 35
<212> TYPE: DNA
<213> ORGANISM: Artificial Sequence
<220> FEATURE:
<223> OTHER INFORMATION: PCR primer

<400> SEQUENCE: 60
aggatccatg cactttactc ttccaccatt gcttg                       35

<210> SEQ ID NO 61
<211> LENGTH: 29
<212> TYPE: DNA
<213> ORGANISM: Artificial Sequence
<220> FEATURE:
<223> OTHER INFORMATION: PCR primer

<400> SEQUENCE: 61
atggatcctc agccgtactg ggccgccat                              29

<210> SEQ ID NO 62
<211> LENGTH: 33
<212> TYPE: DNA
<213> ORGANISM: Artificial Sequence
<220> FEATURE:
<223> OTHER INFORMATION: PCR primer

<400> SEQUENCE: 62
atggatcctc aactcactac cgaaagacga tcc                         33

<210> SEQ ID NO 63
<211> LENGTH: 25
<212> TYPE: DNA
<213> ORGANISM: Artificial Sequence
<220> FEATURE:
<223> OTHER INFORMATION: PCR primer

<400> SEQUENCE: 63
gatcagaatt cgagctcagt cgaca                                  25

<210> SEQ ID NO 64
<211> LENGTH: 25
<212> TYPE: DNA
<213> ORGANISM: Artificial Sequence
<220> FEATURE:
<223> OTHER INFORMATION: PCR primer

<400> SEQUENCE: 64
agcttgtcga ctgagctcga attct                                  25

<210> SEQ ID NO 65
<211> LENGTH: 54

<212> TYPE: DNA
<213> ORGANISM: Artificial Sequence
<220> FEATURE:
<223> OTHER INFORMATION: PCR primer

<400> SEQUENCE: 65
acctccagaa cctcctgaac ctccagaatt gtccctataa gcaatataat tggc        54

<210> SEQ ID NO 66
<211> LENGTH: 54
<212> TYPE: DNA
<213> ORGANISM: Artificial Sequence
<220> FEATURE:
<223> OTHER INFORMATION: PCR primer

<400> SEQUENCE: 66
tctggaggtt caggaggttc tggaggtatg caactcacta ccgaaagacg atcc        54

<210> SEQ ID NO 67
<211> LENGTH: 50
<212> TYPE: DNA
<213> ORGANISM: Artificial Sequence
<220> FEATURE:
<223> OTHER INFORMATION: PCR primer

<400> SEQUENCE: 67
acctccagaa cctcctgaac ctccagatgc aaagggctcg aataaggttg        50

<210> SEQ ID NO 68
<211> LENGTH: 50
<212> TYPE: DNA
<213> ORGANISM: Artificial Sequence
<220> FEATURE:
<223> OTHER INFORMATION: PCR primer

<400> SEQUENCE: 68
tctggaggtt caggaggttc tggaggtatg cagccgtact gggccgccat        50

<210> SEQ ID NO 69
<211> LENGTH: 37
<212> TYPE: DNA
<213> ORGANISM: Artificial Sequence
<220> FEATURE:
<223> OTHER INFORMATION: PCR primer

<400> SEQUENCE: 69
gaattctttc atatggcgga tctgaaatca accttcc        37

<210> SEQ ID NO 70
<211> LENGTH: 39
<212> TYPE: DNA
<213> ORGANISM: Artificial Sequence
<220> FEATURE:
<223> OTHER INFORMATION: PCR primer

<400> SEQUENCE: 70
ttgcggccgc ctacttctgc ctcttgtaga tcttagcca        39

<210> SEQ ID NO 71
<211> LENGTH: 30
<212> TYPE: DNA
<213> ORGANISM: Artificial Sequence
<220> FEATURE:
<223> OTHER INFORMATION: PCR primer

<400> SEQUENCE: 71

```
atggatccag catcagcagc agtagccaac                                      30

<210> SEQ ID NO 72
<211> LENGTH: 41
<212> TYPE: DNA
<213> ORGANISM: Artificial Sequence
<220> FEATURE:
<223> OTHER INFORMATION: PCR primer

<400> SEQUENCE: 72
ataagaatgc ggccgccagc tcaaattttg atggagtcca c                         41
```